US012576131B2

(12) United States Patent
Stephan

(10) Patent No.: US 12,576,131 B2
(45) Date of Patent: Mar. 17, 2026

(54) ALTERING INFLAMMATORY STATES OF IMMUNE CELLS IN VIVO BY MODULATING CELLULAR ACTIVATION STATES

(71) Applicant: Fred Hutchinson Cancer Center, Seattle, WA (US)

(72) Inventor: Matthias Stephan, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 1164 days.

(21) Appl. No.: 16/963,119

(22) PCT Filed: Jan. 18, 2019

(86) PCT No.: PCT/US2019/014209
§ 371 (c)(1),
(2) Date: Jul. 17, 2020

(87) PCT Pub. No.: WO2019/143948
PCT Pub. Date: Jul. 25, 2019

(65) Prior Publication Data
US 2021/0046156 A1     Feb. 18, 2021

Related U.S. Application Data

(60) Provisional application No. 62/618,908, filed on Jan. 18, 2018.

(51) Int. Cl.
| | |
|---|---|
| *A61K 38/17* | (2006.01) |
| *A61K 9/14* | (2006.01) |
| *A61K 9/51* | (2006.01) |
| *A61K 31/7088* | (2006.01) |
| *A61K 38/45* | (2006.01) |
| *A61K 45/06* | (2006.01) |
| *C12N 15/11* | (2006.01) |

(52) U.S. Cl.
CPC .......... *A61K 38/1709* (2013.01); *A61K 9/146* (2013.01); *A61K 9/5146* (2013.01); *A61K 31/7088* (2013.01); *A61K 38/45* (2013.01); *A61K 45/06* (2013.01); *C12N 15/11* (2013.01); *C12Y 207/1101* (2013.01)

(58) Field of Classification Search
CPC ...... A61K 9/146; A61K 38/45; A61K 9/5153; A61K 47/54; A61K 99/0024; C12N 15/11; A61P 35/00
USPC ................... 514/44 A, 44 R; 536/23.1, 24.5; 435/6.1, 91.1, 91.31, 455, 458
See application file for complete search history.

(56) References Cited

U.S. PATENT DOCUMENTS

| | | |
|---|---|---|
| 4,078,052 A | 3/1978 | Papahadjopoulos |
| 4,224,179 A | 9/1980 | Schneider |
| 4,229,360 A | 10/1980 | Schneider et al. |
| 4,235,871 A | 11/1980 | Papahadjopoulos et al. |
| 4,241,046 A | 12/1980 | Papahadjopoulos et al. |
| 4,501,728 A | 2/1985 | Geho et al. |
| 4,737,323 A | 4/1988 | Martin et al. |
| 4,837,028 A | 6/1989 | Allen |
| 5,270,163 A | 12/1993 | Gold et al. |
| 5,756,122 A | 5/1998 | Thierry et al. |
| 6,011,138 A | 1/2000 | Reff et al. |
| 6,291,158 B1 | 9/2001 | Winter et al. |
| 6,291,161 B1 | 9/2001 | Lerner et al. |
| 6,346,248 B1 | 2/2002 | De Boer et al. |
| 6,491,916 B1 | 12/2002 | Bluestone et al. |
| 7,008,623 B1 | 3/2006 | Bonnefoy et al. |
| 7,332,586 B2 | 2/2008 | Franzen et al. |
| 7,378,504 B2 | 5/2008 | Graziano et al. |
| 7,498,177 B2 | 3/2009 | De La Fuente et al. |
| 7,531,624 B2 | 5/2009 | Banes et al. |
| 7,550,650 B2 | 6/2009 | Rapp et al. |
| 7,560,534 B2 | 7/2009 | Deo et al. |
| 7,829,693 B2 | 11/2010 | Kreutzer et al. |
| 8,008,438 B2 | 8/2011 | Boulter et al. |
| 8,378,082 B2 | 2/2013 | Fleener et al. |
| 8,440,431 B2 | 5/2013 | Voytas et al. |
| 8,518,437 B2 | 8/2013 | Tardi et al. |
| 8,663,599 B1 | 3/2014 | Sung et al. |
| 10,174,095 B2 | 1/2019 | Brogdon et al. |
| 10,188,749 B2 | 1/2019 | Stephan et al. |
| 10,189,906 B2 | 1/2019 | Lipp et al. |
| 10,392,446 B2 | 8/2019 | Stephan |
| 2002/0045235 A1 | 4/2002 | Karin et al. |
| 2003/0072794 A1 | 4/2003 | Boulikas |
| 2003/0166601 A1 | 9/2003 | Woodle et al. |
| 2004/0043401 A1 | 3/2004 | Sadelain et al. |
| 2004/0067587 A1 | 4/2004 | Trubetskoy et al. |

(Continued)

FOREIGN PATENT DOCUMENTS

| | | |
|---|---|---|
| CA | 2109924 A1 | 12/1992 |
| CA | 2325354 A1 | 10/1999 |

(Continued)

OTHER PUBLICATIONS

Li et al. (Inflammation, 39, 1704-1717, 2016). (Year: 2016).*
Phanse et al. (Acta Biomaterialia, 9(11), 8902-8909, 2013). (Year: 2013).*
Page et al (Oncogenes and Tumor Suppressers, Mol. Cancer Res., vol. 15, No. 9, pp. 1255-1264 (2017)), (Year: 3027).*

(Continued)

*Primary Examiner* — Jane J Zara

(74) *Attorney, Agent, or Firm* — Lee & Hayes, P.C.

(57) ABSTRACT

Systems and methods to modulate the activation state of immune cells in vivo are described. The systems and methods can be used to transform immunosuppressive macrophages that support cancer growth and metastasis into highly activated tumoricidal macrophages.

14 Claims, 56 Drawing Sheets

Specification includes a Sequence Listing.

(56)                  References Cited

U.S. PATENT DOCUMENTS

| | | | |
|---|---|---|---|
| 2004/0071654 A1 | 4/2004 | Anderson et al. | |
| 2005/0142114 A1 | 6/2005 | Gieseler et al. | |
| 2005/0214871 A1 | 9/2005 | Boon et al. | |
| 2007/0281897 A1 | 12/2007 | Karaolis | |
| 2008/0171061 A1 | 7/2008 | Nixon et al. | |
| 2009/0104229 A1 | 4/2009 | Voss | |
| 2009/0136917 A1 | 5/2009 | Szalay et al. | |
| 2009/0252725 A1 | 10/2009 | Harris et al. | |
| 2011/0189209 A1 | 8/2011 | Neville et al. | |
| 2011/0229556 A1 | 9/2011 | Irvine et al. | |
| 2012/0156135 A1 | 6/2012 | Farokhzad et al. | |
| 2012/0192298 A1 | 7/2012 | Weinstein et al. | |
| 2012/0207783 A1 | 8/2012 | Donnelly et al. | |
| 2013/0195881 A1 | 8/2013 | Singh et al. | |
| 2014/0227186 A1 | 8/2014 | Rademacher et al. | |
| 2014/0309177 A1 | 10/2014 | Perez-Pinera et al. | |
| 2015/0110858 A1 | 4/2015 | DeRosa et al. | |
| 2015/0246959 A1 | 9/2015 | Robbins et al. | |
| 2015/0283178 A1 | 10/2015 | June et al. | |
| 2016/0008399 A1 | 1/2016 | Stephan | |
| 2016/0067190 A1 | 3/2016 | Anderson et al. | |
| 2016/0083449 A1 | 3/2016 | Schmitt et al. | |
| 2016/0145348 A1 | 5/2016 | Stephan | |
| 2016/0175251 A1 | 6/2016 | Ostroff et al. | |
| 2016/0176969 A1 | 6/2016 | Bernett et al. | |
| 2016/0200828 A1 | 7/2016 | Tesar et al. | |
| 2016/0250258 A1 | 9/2016 | Delaney et al. | |
| 2016/0296471 A1 | 10/2016 | Bajpayee et al. | |
| 2017/0151339 A1 | 6/2017 | White et al. | |
| 2017/0224798 A1 | 8/2017 | Cooper et al. | |
| 2017/0283830 A1 | 10/2017 | Saltzman et al. | |
| 2017/0296676 A1 | 10/2017 | Stephan et al. | |
| 2018/0030153 A1 | 2/2018 | Stephan | |
| 2018/0258411 A1 | 9/2018 | Kadiyala et al. | |
| 2018/0369280 A1 | 12/2018 | Schmitt | |
| 2019/0111153 A1 | 4/2019 | Stephan et al. | |
| 2019/0269792 A1* | 9/2019 | Azab ................. | A61K 47/6939 |
| 2019/0330373 A1 | 10/2019 | Stephan | |
| 2020/0078313 A1* | 3/2020 | Roy ..................... | C08F 299/00 |
| 2020/0123219 A1 | 4/2020 | Stephan | |
| 2021/0128485 A1 | 5/2021 | Stephan | |
| 2023/0331804 A1 | 10/2023 | Stephan | |
| 2024/0285797 A1 | 8/2024 | Stephan et al. | |

FOREIGN PATENT DOCUMENTS

| | | |
|---|---|---|
| CN | 102851304 | 1/2013 |
| CN | 102851304 A | 1/2013 |
| EP | 4085137 A1 | 11/2022 |
| JP | S63503138 A | 11/1988 |
| JP | 2002544173 A | 12/2002 |
| JP | 2007504353 A | 3/2007 |
| JP | 2010501163 A | 1/2010 |
| JP | 2018515518 A | 6/2018 |
| JP | 2019511234 A | 4/2019 |
| WO | WO9307298 A1 | 4/1993 |
| WO | WO199601126 A1 | 1/1996 |
| WO | WO9957268 | 11/1999 |
| WO | WO1999056129 A1 | 11/1999 |
| WO | WO0072880 A2 | 12/2000 |
| WO | WO0232941 A2 | 4/2002 |
| WO | WO02076501 A2 | 10/2002 |
| WO | 2003054193 A2 | 7/2003 |
| WO | WO2003054193  * | 7/2003 |
| WO | WO2004076488 A1 | 9/2004 |
| WO | WO2005103083 A2 | 11/2005 |
| WO | 2006079176 A1 | 8/2006 |
| WO | WO2006079176  * | 8/2006 |
| WO | WO2006099875 A1 | 9/2006 |
| WO | WO2006125640 A2 | 11/2006 |
| WO | WO2006131953 A2 | 12/2006 |
| WO | WO2007042309 A2 | 4/2007 |
| WO | WO2008047242 A2 | 4/2008 |
| WO | WO2008074867 A2 | 6/2008 |
| WO | WO2008109806 | 9/2008 |
| WO | WO2008109806 A2 | 9/2008 |
| WO | WO2009146867 A1 | 12/2009 |
| WO | WO2011005799 A2 | 1/2011 |
| WO | WO2011039510 A2 | 4/2011 |
| WO | WO2011128642 A1 | 10/2011 |
| WO | 2011150240 A1 | 12/2011 |
| WO | WO2011154453 A1 | 12/2011 |
| WO | WO2012079000 | 6/2012 |
| WO | WO2012079000 A1 | 6/2012 |
| WO | WO2012092612 A1 | 7/2012 |
| WO | WO2012093258 | 7/2012 |
| WO | WO2012093258 A2 | 7/2012 |
| WO | WO2013106852 | 7/2013 |
| WO | WO2013174537 A1 | 11/2013 |
| WO | WO2014140376 A1 | 9/2014 |
| WO | WO2014153114 | 9/2014 |
| WO | WO2014153114 A1 | 9/2014 |
| WO | WO2014191527 | 12/2014 |
| WO | WO2014191527 A1 | 12/2014 |
| WO | WO2015042585 A1 | 3/2015 |
| WO | WO2015130728 A1 | 9/2015 |
| WO | WO2016145102 A1 | 9/2016 |
| WO | WO2016180778 A1 | 11/2016 |
| WO | WO2017031363 A2 | 2/2017 |
| WO | WO2017031367 A1 | 2/2017 |
| WO | WO2017112944 A1 | 6/2017 |
| WO | WO2017181110 A1 | 10/2017 |
| WO | WO2017201346 | 11/2017 |
| WO | WO2017201346 A1 | 11/2017 |
| WO | WO2018081459 A1 | 5/2018 |
| WO | WO2018102752 | 6/2018 |
| WO | WO2018102752 A1 | 6/2018 |
| WO | WO2018129270 | 7/2018 |
| WO | WO2018129270 A9 | 7/2018 |
| WO | WO2019143948 A1 | 7/2019 |
| WO | WO2019197600 A1 | 10/2019 |
| WO | WO2019213308 A1 | 11/2019 |
| WO | 2021138600 A1 | 7/2021 |

OTHER PUBLICATIONS

Andre et al (International Journal of Biochemistry and Cell Biology, vol. 85, pp. 166-174 (2017)) (Year: 2017).*

Bi et al (Breast Cancer Res., vol. 13, R111, pp. 1-14 (2011)) (Year: 2011).*

Phanse et al (Acta Biomaterials, vol. 9, pp. 8902-8909 (2013)) (Year: 2013).*

European Office Action mailed Oct. 12, 2022 for European Patent Application No. 22199369.4, a foreign counterpart to U.S. Pat. No. 10,188,749, 1 page.

Indian Office Action mailed Oct. 7, 2022 for Indian Patent Application No. 201817039265, a foreign counterpart to U.S. Pat. No. 10,188,749, 5 pages.

Japanese Office Action mailed Aug. 9, 2022 for Japanese Application No. 2019-536560, a foreign counterpart to U.S. Pat. No. 11,440,945, 9 pages.

Office Action for U.S. Appl. No. 16/222,942, mailed on Sep. 7, 2022, Stephan, "Compositions and Methods to Program Therapeutic Cells Using Targeted Nucleic Acid Nanocarrier", 6 pages.

Shirakura, et al, "T-cell receptor gene therapy targeting melanoma-associated antigen-A4 inhibits human tumor growth in non-obese diabetic/SCID/ycnull mice", Cancer Science, vol. 103, No. 1, 2012, pp. 17-25.

Arimilli, et al., "Refolding and Reconstitution of Functionally Active Complexes of Human Leukocyte Antigen DR2 and Myelin Basic Protein Peptide from Recombinant Alpha and Beta Polypeptide Chains," Bio. Chem., vol. 270, No. 2, 1995, pp. 971-977.

Arnold, et al., "A critical role for suppressor of cytokine signalling 3 in promoting M1 macrophage activation and function in vitro and in vivo," Immunology, vol. 141, No. 1, 2013, pp. 96-110.

Bai, et al., "Enhancement of the in vivo persistence and antitumor efficacy of CD19 chimeric antigen receptor T cells through the delivery of modified TERT mRNA," Cell Discov., vol. 1, 2015, 15 pages.

Barnes, et al., "Multiple Regulatory Domains of IRF-5 Control Activation, Cellular Localization, and Induction of Chemokines

(56) References Cited

OTHER PUBLICATIONS

That Mediate Recruitment of T Lymphocytes," Molecular and Cellular Biology, vol. 22, No. 16, 2002, pp. 5721-5740.

Bodmer, et al., "Nomenclature for factors of the HLA system, 1994," Tissue Antigens, vol. 4, 1994, pp. 1-18.

Boissel,, et al., "Assembly and Characterization of megaTALs for Hyperspecific Genome Engineering Applications," Methods Mol. .Biol., vol. 1239, 2015, pp. 171-196.

Boulikas, et al., "Nuclear localization signals (NLS)," Crit. Rev. Eukaryot Gene Expr., vol. 3, No. 3, 1993, pp. 193-227.

Bowman & Joyce, "Therapeutic targeting of tumor-associated macrophages and microglia in glioblastoma," Immunotherapy, vol. 6, No. 6, 2014, pp. 663-666.

Butler, et al., "CXCR3+ monocytes/macrophages are required for establishment of pulmonary metastases," Scientific Reports, vol. 7, 2017, 9 pages.

Butowski, et al., "Orally administered colony stimulating factor 1 receptor inhibitor PLX3397 in recurrent glioblastoma: an Ivy Foundation Early Phase Clinical Trials Consortium phase II study," Neuro-Oncology, vol. 18, No. 4, 2016, pp. 557-564.

Cardinanos and Bradley, "Generation of an inducible and optimized piggyBac transposon system," Nucleic Acids Res., vol. 35, No. 35, 2007, pp. 1-8.

Chaloin, et al., "Design of Carrier Peptide-Oligonucleotide Conjugates with Rapid Membrane Translocation and Nuclear Localization Properties," Biochem. Biophys. Res. Commun., vol. 243, No. 2, 1998, pp. 601-608.

Chang, et al., "The Small Ubiquitin-like Modifier-Deconjugating Enzyme Sentrin-Specific Peptidase 1 Switches IFN Regulatory Factor 8 from a Repressor to an Activator during Macrophage Activation," Journal of Immunology, vol. 189, No. 7, 2012, pp. 3548-3556.

Chao, et al., "The CD47-SIRPalpha pathway in cancer immune evasion and potential therapeutic implications," Current Opinion in Immunology, vol. 24, No. 2, 2012, pp. 225-232.

Chavez-Galan, et al., "Much More than M1 and M2 Macrophages, There are also CD169+ and TCR+ Macrophages," Frontiers in Immunology, vol. 6, 2015, 15 pages.

Chen, et al., "Insights into interferon regulatory factor activation from the crystal structure of dimeric IRF5," Nature Structural & Molecular Biology, vol. 15, No. 11, 2008, pp. 1213-1220.

Office Action Dated Aug. 5, 2020 for Chilean Patent Application No. 02905-2018, 13 pages.

Cline, "Perspectives for gene therapy: Inserting new genetic information into mammalian cells by physical techniques and viral vectors," Pharmacol. Ther., vol. 29, No. 1, 1985, pp. 69-92.

Office Action Dated Oct. 26, 2020 for Colombian Patent Application No. NC2018/0012099, 19 pages.

Office Action Dated Jul. 7, 2020 for Colombian Patent Application No. NC2018/0012099, 9 pages.

Cohen, et al., "Interaction between Interferon Consensus Sequence-binding Protein and COP9/Signalosome Subunit CSN2 (Trip15)," Journal of Biological Chemistry, vol. 275, No. 50, 2000, pp. 39081-39089.

Cokol, et al., "Finding nuclear localization signals," EMBO Rep, vol. 1, No. 5, 2000, pp. 44-415.

Collas and Alestrom, "Nuclear localization signal of SV40 T antigen directs import of plasmid DNA into sea urchin male pronuclei in vitro," Mol. Reprod. Devel., vol. 45, 1996, pp. 431-438.

Collas, et al., "Nuclear localization signals: a driving force for nuclear transport of plasmid DNA in zebrafish," Biochem. Cell Biol., vol. 75, No. 5, 1997, pp. 633-640.

Collas, et al., "The nuclear localization sequence of the SV40 T antigen promotes transgene uptake and expression in zebrafish embryo nuclei," Transgenic Res., vol. 5, No. 6, 1996, pp. 451-458.

Copeland, et al., "Acute Inflammatory Response to Endotoxin in Mice and Humans," Clinical and Diagnostic Laboratory Immunology, vol. 12, No. 1, 2005, pp. 60-67.

Copolovici, et al., "Cell-penetrating peptides: design, synthesis, and applications," ACS Nano., vol. 8, No. 3, 2014, pp. 1972-1994.

Costa, et al., "Generation of sensory hair cells by genetic programming with a combination of transcription factors," Development, vol. 142, No. 11, 2015, pp. 1948-1959.

Cotten, et al., "Receptor-Mediated Transport of DNA into Eukaryotic Cells," Methods Enzymol., vol. 217, 1993, pp. 618-644.

Cox, et al., "Therapeutic genome editing: prospects and challenges," Nat. Med., vol. 21, No. 2, 2015, pp. 121-131.

Cribbs, et al., "Simplified production and concentration of lentiviral vectors to achieve high transduction in primary human T cells," BMC Biotechnol., vol. 13, No. 98, 2013, 8 pages.

Debs, et al., "Targeting of anti-Thy 1.1 monoclonal antibody conjugated liposomes in Thy 1.1 mice after intravenous administration," Biochimica et Biophysica Acta, vol. 901, 1987, pp. 183-190.

Derossi, et al., "Cell Internalization of the Third Helix of the Antennapedia Homeodomain Is Receptor-independent," J. Biol. Chem., vol. 271, No. 30, 1996, pp. 18188-18193.

Desai, et al., "Interaction of nanoparticles and cell-penetrating peptides with skin for transdermal drug delivery," Mol. Membr. Biol., vol. 27, No. 7, 2010, 19 pages.

Dingwall, et al., "Nuclear targeting sequences—a consensus?" Trends Biochem. Sci., vol. 16, No. 12, 1991, pp. 471-481.

Dow, et al., "Intravenous Cytokine Gene Delivery by LipidDNA Complexes Controls the Growth of Established Lung Metastases," Human Gene Therapy, vol. 10, 1999, pp. 2961-2972.

Dror, et al., "Identification of IRF-8 and IRF-1 target genes in activated macrophages," Molecular Immunology, vol. 44, No. 4, 2007, pp. 338-346.

Duguid, et al., "A physicochemical approach for predicting the effectiveness of peptide-based gene delivery systems for use in plasmid-based gene therapy," Biophys. J., vol. 74, No. 6, 1998, pp. 2802-2814.

Duluc, et al., "Tumor-associated leukemia inhibitory factor and IL-6 skew monocyte differentiation into tumor-associated macrophage-like cells," Blood, vol. 110, No. 13, 2007, pp. 4319-4330.

Ebert, et al., "Lymphocyte apoptosis: induction by gene transfer techniques," Gene Therapy, vol. 4, 1997, pp. 296-302.

Office Action Dated May 29, 2020 for European Patent Application No. 17783314.2, 4 pages.

Extended European Search Report Dated Aug. 23, 2019 for European Patent Application No. 17783314.2, 25 pages.

Eun, et al., "LPS potentiates nucleotide-induced inflammatory gene expression in macrophages via the upregulation of P2Y2 receptor," International Immunopharmacology, vol. 18, No. 2, 2014, pp. 270-276.

Foreman, et al., "Activation of Interferon Regulatory Factor 5 by Site Specific Phosphorylation," PLoS One, vol. 7, No. 3, 2012, 12 pages.

Fremont, et al., "Structures of an MHC Class II Molecule with Covalently Bound Single Peptides," Science, vol. 272, No. 5264, 1996, pp. 1001-1004.

Fritz, et al., "Depletion of tumor-associated macrophages slows the growth of chemically induced mouse lung adenocarcinomas," Frontiers in Immunology, vol. 5, No. 587, 2014, 11 pages.

Gabrilovich & Nagaraj, "Myeloid-derived suppressor cells as regulators of the immune system," Nature Reviews Immunology, vol. 9, No. 3, 2009, pp. 162-174.

Geall, et al., "Nonviral delivery of self-amplifying RNA vaccines," PNAS, vol. 109, No. 36, 2012, pp. 14604-14609.

Gocheva, et al., "IL-4 induces cathepsin protease activity in tumor-associated macrophages to promote cancer growth and invasion," Genes & Development, vol. 24, 2010, pp. 241-255.

Gordon & Taylor, "Monocyte and macrophage heterogeneity," Nature Reviews Immunology, vol. 5, No. 12, 2005, pp. 953-964.

Office Action Dated Feb. 2, 2021 in Chilean Application No. 02905-2018, 15 pages.

Columbian Office Action mailed Aug. 1, 2023 for Columbian Application No. NC2020/0015686, a foreign counterpart to U.S. Pat. No. 10/188,749, 28 pages.

Japanese Office Action mailed Aug. 18, 2023 for Japanese Patent Application No. 2022-102442, a foreign counterpart to U.S. Pat. No. 10/188,749, 8 pages.

(56) References Cited

OTHER PUBLICATIONS

Office Action Dated Nov. 9, 2021 for Chinese Patent Application No. 201780023532.9, 6 pages.

Office Action Dated Nov. 1, 2021 for Israel Patent Application No. 262361, 12 pages.

Office Action Dated Oct. 15, 2021 in Korean Application No. 10-2018-7032542, 3 pages.

Office Action Dated Sep. 21, 2021 for Mexican Patent Application No. MX/a/2018/012556, 6 pages.

Office Action Dated Sep. 20, 2021 for U.S. Appl. No. 16/222,942, 15 Pages.

Office Action Dated Jan. 17, 2022 for Chinese Patent Application No. 201880005741.5, 9 pages.

Office Action mailed Dec. 7, 2021 for Japanese Patent Application No. 2019-536560, 7 pages.

Office Action Dated Jan. 7, 2022 in U.S. Appl. No. 16/474,503, 7 Pages.

Stauss, et al., "WT1-specific T cell receptor gene therapy Improving TCR fuction in transduced T cells", Blood Cells Mol. Dis., vol. 40, 2008, pp. 113-116.

Australian Office Action mailed May 9, 2022 for Australian Patent Application No. 2017250295, a foreign counterpart to U.S. Pat. No. 10,188,749, 3 pages.

Chinese Office Action mailed Apr. 26, 2022 for Chinese Patent Application No. 201780023532.9, a foreign counterpart to U.S. Pat. No. 10,188,749, 5 pages.

Chinese Office Action mailed May 16, 2022 for Chinese Patent Application No. 201980009095.4, a foreign counterpart to U.S. Appl. No. 16/963,119, 7 pages.

Columbian Action mailed Mar. 3, 2022 for Columbian Patent Application No. NC2020/0015686, a foreign counterpart to U.S. Pat. No. 10,188,749, 3 pages.

Columbian Office Action mailed Apr. 19, 2022 for Columbian Patent Application No. NC2018/0012099, a foreign counterpart to U.S. Pat. No. 10,188,749, 9 pages.

Costa Rican Office Action mailed Apr. 7, 2022 for Costa Rican Patent Application No. 2018-503, a foreign counterpart to U.S. Pat. No. 10,188,749, 11 pages.

Partial European Search Report mailed Mar. 24, 2022 for European Patent Application No. 19795782.2, 21 pages.

Korean Office Action mailed Mar. 4, 2022 for Korean Patent Application No. 10-2018-7032542, a foreign counterpart to U.S. Pat. No. 10,188,749, 12 pages.

Japanese Office Action mailed Jun. 6, 2023 for Japanese Patent Application No. 2020-561067, a foreign counterpart to U.S. Appl. No. 17/044,779, 14 pages.

Stromnes, et al., "T cells engineered against a native antigen can surmount immunologic and physical barriers to treat pancreatic ductal adenocarcinoma," Cancer Cell, vol. 28, No. 5, 2015, pp. 638-652.

Surdziel, et al., "Multidimensional pooled shRNA screens in human THP-1 cells identify candidate modulators of macrophage polarization," PLoS One, vol. 12, No. 8, 2017, 20 pages.

Szoka, "Comparative properties and methods of preparation of lipid vesicles (liposomes)," Ann. Rev. Biophys. Bioeng., vol. 9, 1980, pp. 467-508.

Szoka, Francis, "Comparative Properties and Methods of Preparation of Lipid Vesicles (Liposomes)," Annual Review of Biophysics and Bioengineering, vol. 9, 1980, pp. 467-508.

Takeda, et al., "Differential activation and antagonistic function of HIF-alpha isoforms in macrophages are essential for No homeostasis," Genes & Dev., vol. 24, 2010, pp. 491-501.

Tap, et al., "Structure-Guided Blockade of CSF1R Kinase in Tenosynovial Giant-Cell Tumor," The New England Journal of Medicine, vol. 373, 2015, pp. 428-437.

Tarrant, Jacqueline, "Blood Cytokines as Biomarkers of In Vivo Toxicity in Preclinical Safety Assessment: Considerations for Their Use," Toxicological Sciences, vol. 117, No. 1, 2010, pp. 4-16.

Tejera, et al., "FoxO1 controls effector-to-memory transition and maintenance of functional CD8 T cell memory," J. Immunol., vol. 191, No. 1, 2013, pp. 187-199.

Themeli et al., "Generation of tumor-targeted human T lymphocytes from induced pluripotent stem cells for cancer therapy," Nat. Biotechnol., vol. 31, 2013, pp. 928-933.

Thompson, et al., "Therapeutic Targeting of IRFs: Pathway-Dependence or Structure-Based?," Front. Immunol., vol. 9, 2018, 13 pages.

Thurber, et al., "Antibody tumor penetration: Transport opposed by systemic and antigen-mediated clearance," Advanced Drug Delivery Reviews, vol. 60, No. 12, 2008, pp. 1421-1434.

Tousignant, et al., "Comprehensive Analysis of the Acute Toxicities Induced by Systemic Administration of Cationic Lipid:Plasmid DNA Complexes in Mice," Human Gene Therapy, vol. 22, 2000, pp. 2493-2513.

Uhrbom, et al., "Dissecting tumor maintenance requirements using bioluminescence imaging of cell proliferation in a mouse glioma model," Nature Medicine, vol. 10, No. 11, 2004, pp. 1257-1260.

Ushio, et al., "Crucial roles of macrophages in the pathogenesis of autoimmune disease," World Journal of Immunology, vol. 7, No. 1, 2017, 8 pages.

Varga, et al., "Highly Dynamic Transcriptional Signature of Distinct Macrophage Subsets during Sterile Inflammation, Resolution, and Tissue Repair," Journal of Immunology, vol. 196, No. 11, 2016, pp. 4771-4782.

Wang, et al., "Highly efficient homology-driven genome editing in human T cells by combining zinc-finger nuclease mRNA and AAV6 donor delivery," Nucleic Acids Res., vol. 44, No. 3, 2016, 9 pages.

Wang, et al., "Tumor-associated macrophages provide a suitable microenvironment for non-small lung cancer invasion and progression," Lung Cancer, vol. 74, No. 2, 2011, pp. 188-196.

White, et al., "Interferon Regulatory Factor 8 (IRF8) Impairs Induction of Interferon Induced with Tetratricopeptide Repeat Motif (IFIT) Gene Family Members," Journal of Biological Chemistry, vol. 291, No. 26, 2016, pp. 13535-13545.

Wurm, et al., "Ectopic expression of HOXC6 blocks myeloid differentiation and predisposes to malignant transformation," Exp. Hematol., vol. 42, No. 2, 2014, pp. 114-125.

Xia, et al, "Polyglutamic Acid Based Polyanionic Shielding System for Polycationic Gene Carriers," Chinese Journal of Polymer Science, vol. 34, No. 3, Zhongguo Huaxuehui, CN, 2016, pp. 316-323.

Yang and Huang, "Overcoming the inhibitory effect of serum on lipofection by increasing the charge ratio of cationic liposome to DNA," Gene Therapy, vol. 4, 1997, pp. 950-960.

Zhang, et al., "MicroRNA-31 negatively regulates peripherally derived regulatory T-cell generation by repressing retinoic acid-inducible protein 3," Nat. Commun., vol. 6, No. 7639 2015, 12 pages.

Zhang, et al.,"The Isolation and Characterization of Murine Macrophages," Curr. Protoc. Immunol., vol. 83, No. 1, 2008, 18 pages.

Zhong, et. al., "Direct Cytoplasmic Delivery and Nuclear Targeting Delivery of HPMA-MT Conjugates in a Microtubules Dependent Fashion," Mol. Pharm., vol. 13, 2016, pp. 3069-3079.

Zhu, et al., "Systemic Gene Expression After Intravenous DNA Delivery into Adult Mice," Science, vol. 261, 1993, 4 pages.

Chinese Office Action mailed Jul. 11, 2022 for Chinese Patent Application No. 201980029594.X, a foreign counterpart to U.S. Appl. No. 17/044,779, 14 pages.

Chinese Office Action mailed Jul. 28, 2022 for Chinese Patent Application No. 201780023532.9, a foreign counterpart to U.S. Pat. No. 10,188,749, 3 pages.

The Extended European Search Report mailed Jun. 24, 2022 for European Patent Application No. 19795782.2 20 pages.

Korean Office Action mailed Jun. 21, 2022 for Korean Patent Application No. 10-2018-7032542, a foreign counterpart to U.S. Pat. No. 10,188,749, 7 pages.

Extended European Search Report dated Jul. 10, 2023 for European Patent Application No. 19740957.6, 8 pages.

Office Action Dated May 8, 2021 for Chinese Patent Application No. 201980029594.X, 1 page.

(56)        References Cited

OTHER PUBLICATIONS

Office Action Dated Aug. 6, 2021 for European Patent Application No. 17783314.2, 3 pages.
Extended European Search Report Dated Dec. 2, 2020 for European Patent Application No. 18735984.9, 9 pages.
Robbins, et al., "A Pilot Trial Using Lymphocytes Genetically Engineered with an NY-ES0-1-Reactive T-cell Receptor: Long-term Follow-up and Correlates with Response," Clinical Cancer Research, vol. 21, No. 5, 2015, 10 pages.
Mantovani, Alberto, and Massimo Locati. "Tumor-associated macrophages as a paradigm of macrophage plasticity, diversity, and polarization: lessons and open questions." Arteriosclerosis, thrombosis, and vascular biology 33.7 (2013): 1478-1483.
Chang Foreman, Hui-Chen, et al. "Activation of interferon regulatory factor 5 by site specific phosphorylation." PLoS One 7.3 (2012): e33098.
Chinese Office Action mailed Nov. 22, 2022 for Chinese Patent Application No. 201980009095.4, a foreign counterpart to U.S. Appl. No. 16/963,119, 3 pages.
Japanese Office Action mailed Nov. 29, 2022 for Japanese Patent Application No. 2020-539806.
Miao, Xiaoyuan, Xiangfeng Leng, and Qiu Zhang. "The current state of nanoparticle-induced macrophage polarization and reprogramming research." International Journal of Molecular Sciences 18.2 (2017): 336.
Zhu, et al, "Targeting of Tumor-Associated macrophages made possible by PEG-Scheddable, mannose-modified nanoparticles", Sep. 3, 2013, vol. 10, No. 9, pp. 3525-3530.
Chinese Office Action mailed Mar. 16, 2023 for Chinese Patent Application No. 201980029594.X, a foreign counterpart to U.S. Appl. No. 17/044,779, 14 pages.
Extended European Search Report mailed Mar. 15, 2023 for European Patent Application No. 22199369.4, 13 pages.
Office Action Dated May 25, 2021 for Chinese Patent Application No. 201880005741.5, 7 pages.
Office Action Dated May 31, 2021 for Eurasian Patent Application No. 201892326, 31 pages.
Harris, et al., "Tissue-specific gene delivery via nanoparticle coating," Biomaterials, vol. 31, 2010, pp. 998-1006.
Office Action Dated Jun. 1, 2021 for Japanese Patent Application No. 2018-553912, 4 pages.
Kurosaki, et al., "gamma-Polyglutamic acid-coated vectors for effective and safe gene therapy," Journal of Controlled Release, vol. 14, 2009, pp. 404-410.
Shmueli, et al., "Electrostatic Surface Modifications to Improve Gene Delivery," Expert Opin. Drug Deliv., vol. 7, No. 4, 2010, pp. 535-550.
Trubetskoy, et al., "Recharging cationic DNA Complexes with highly charged polyanions for in vitro and in vivo gene delivery," Gene Therapy, vol. 10, 2003, pp. 261-271.
Grandjean, et al., "High-level transgene expression by homologous recombination-mediated gene transfer," Nucleic Acids Research, vol. 39, No. 15 e104, 2011, 15 pages.
Green, et al, "Chemoattractant Signaling between Tumor Cells and Macrophages Regulates Cancel Cell Migration, Metastasis and Neovascularization," PLOS ONE, vol. 4, No. 8, 2009, pp. 1-15.
Heath, et al., "Antibody-targeted liposomes: Increase in specific toxicity of methotrexate-gamma-aspartate," PNAS, vol. 80, 1983, pp. 1377-1381.
Heikkinen, et al., "Safety of MF59-adjuvanated A/H1N1 influenza vaccine in pregnancy: a comparative cohort study," Am. J. Obstet. Gynecol., vol. 207, No. 3, 2012, pp. 187.e1-187.e8.
Hope, et al., "Generation of multilamellar and unilamellar phospholipid vesicles," Chem. Phys. Lip., vol. 40, No. 2-4, 1986, pp. 89-107.
Office Action Dated Jan. 31, 2019 for Israeli Application No. 262361, 4 pages.
Invitation to Pay Fees Dated Apr. 9, 2019 for International Application No. PCT/US2019/014209, 4 Pages.

Invitation to Pay Fees Dated Aug. 6, 2019 for International Application No. PCT/US2019/030263, 3 pages.
Kacherovsky, et al., "Combination of Sleeping Beauty transposition and chemically induced dimerization selection for robust production of engineered cells," Nucleic Acids Research, vol. 40, No. 11e85, 2012, 10 pages.
Kim, et al., "The transcription factor Foxo1 controls central-memory CD8+ T cell responses to infection," Immunity, vol. 39, No. 1, 2013, pp. 286-297.
Kobayashi, et al., "A new cloning and expression system yields and validates TCRs from blood lymphocytes of patients with cancer within 10 days," Nat. Med., vol. 19, No. 11, 2013, pp. 1542-1546.
Koh, et al., "A practical approach to immunotherapy of hepatocellular carcinoma using T cells redirected against hepatitis B virus," Mol. Ther. Nucleic Acids, vol. 2, 2013, 9 pages.
Kozono, et al., "Production of soluble MHC class II proteins with covalently bound single peptides," Nature, vol. 369, No. 154, 1994, pp. 151-154.
Kurosaki, et al, "Secure Splenic Delivery of Plasmid DNA and Its Application to DNA Vaccine," Biological & Pharmaceutical Bulletin, vol. 36, No. 11, 2013, pp. 1800-1806.
Kurosaki, et al, "Ternary Complexes of pDNA, Polyethylenimine, and y-polyglutamic acid for gene delivery systems," Biomaterials, vol. 30, No. 14, 2009, pp. 2846-2853.
Lin, et al, "CCL21 Cancer Immunotherapy," Cancers, vol. 6, No. 2, 2014, pp. 1098-1110.
Liu, et al., "Affinity-Tuned ErbB2 or EGFR Chimeric Antigen Receptor T Cells Exhibit an Increased Therapeutic Index against Tumors in Mice," Cancer Res., vol. 75, No. 17, 2015, pp. 3596-3607.
Liu, et al., "Cell-penetrating peptide-mediated delivery of TALEN proteins via bioconjugation for genome engineering," PLoS One, vol. 9, No. 1, 2014, 7 pages.
Liu, et al., "Improved cell-penetrating zinc-finger nuclease proteins for precision genome engineering," Mol. Ther. Nucleic Acids, vol. 4, 2015, 9 pages.
Loeffler and Behr, "Gene transfer into primary and established mammalian cell lines with lipopolyamine-coated DNA," Methods Enzymol., vol. 217, 1993, pp. 599-618.
Lopez-Pelaez, et. al., "Protein kinase IKKB-catalyzed phosphorylation of IRF5 at Ser462 induces its dimerization and nuclear translocation in myeloid cells," PNAS, vol. 111, No. 49, 2014, pp. 17432-17437.
Mangraviti, et al., "Polymeric nanoparticles for nonviral gene therapy extend brain tumor survival in vivo," ACS Nano., vol. 9, No. 2, 2015, pp. 1236-1249.
Nag, et al., "Functionally Active Recombinant Alpha and Beta Chain-Peptide Complexes of Human Major Histocompatibility Class II Molecules," J. Biol. Chem., vol. 271, No. 17, 1996, pp. 10413-10418.
Nag, et al., "Stimulation of T cells by antigenic peptide complexed with isolated chains of major histocompatibility complex class II molecules," PNAS, vol. 90, No. 4, 1993, pp. 1604-1608.
Narayanan, et al., "Mimicking cellular transport mechanism in stem cells through endosomal escape of new peptide-coated quantum dots," Sci. Rep., vol. 3, 2013, 6 pages.
ClinicalTrials.gov [Internet]. Bethesda (MD): National Library of Medicine (US). Mar. 30, 2012—. Identifier NCT01567891, CT Antigen TCR-redirected T Cells for Ovarian Cancer; Mar. 16, 2012; [about 10 screens]. Available from: https://clinicaltrials.gov/ct2/show/NCT01567891.
ClinicalTrials.gov [Internet]. Bethesda (MD): National Library of Medicine (US). Jul. 13, 2012—. Identifier NCT01640301, Laboratory-Treated T Cells in Treating Patients With High-Risk Relapsed Acute Myeloid Leukemia, Myelodysplastic Syndrome, or Chronic Myelogenous Leukemia Previously Treated With Donor Stem Cell Transplant; [about 11 screens]. Available from: https://clinicaltrials.gov/ct2/show/NCT01640301.
ClinicalTrials.gov [Internet]. Bethesda (MD): National Library of Medicine (US). May 3, 2017—Identifier NCT03139370, Safety and Efficacy of MAGE-A3/A6 T Cell Receptor Engineered T Cells (KITE-718) in HLA-DPB1*04:01 Positive Adults With Advanced Cancers; [about 9 screens]. Available from: https://clinicaltrials.gov/ct2/show/NCT03139370.

(56)     References Cited

OTHER PUBLICATIONS

Nicolle, et al., "Specific tolerance to an acetylcholine receptor epitope induced in vitro in myasthenia gravis CD4+ lymphocytes by soluble major histocompatibility complex class II-peptide complexes," J. Clin. Invest., 1994, vol. 93, No. 4, pp. 1361-1369.

Nielsen & Schmid, "Macrophages as Key Drivers of Cancer Progression and Metastasis," Mediators of Inflammation, vol. 2017, 2017, 11 pages.

Nywening, et al., "Targeting tumour-associated macrophages with CCR2 inhibition in combination with Folfirinox in patients with borderline resectable and locally advanced pancreatic cancer: a single-centre, open-label, dose-finding, non-randomised, phase 1b trial," Lancet Oncology, vol. 17, No. 5, 2016, pp. 651-662.

Office Action Dated Feb. 8, 2017 for U.S. Appl. No. 14/776,661, 13 pages.

Office Action Dated May 15, 2018 for U.S. Appl. No. 15/594,344, 13 pages.

Office Action Dated Aug. 14, 2018 for U.S. Appl. No. 15/672,106, 15 pages.

Odegaard, et al., "Macrophage-specific PPARGamma controls alternative activation and improves insulin resistance," Nature, vol. 447, 2007, pp. 1116-1120.

Olweus, "Manufacture of CAR-T cells in the body," Nature Biotechnology, vol. 35, 2017, pp. 520-521.

Online Mendelian Inheritance in Man, OMIM. Johns Hopkins University, Baltimore, MD. MIM No. 607218: Sep. 30, 2019. World Wide Web URL: https://omim.org/entry/607218.

Orcutt, et al., "Engineering an antibody with picomolar affinity to DOTA chelates of multiple radionuclides for pretargeted radioimmunotherapy and imaging," Nucl. Med. Biol., vol. 38, No. 2, 2011, pp. 223-233.

Invitation to Pay Additional Fees Dated Mar. 20, 2018 for International Application No. PCT/US2018/012507, 3 pages.

Search Report and Written Opinion Dated Oct. 11, 2019 for International Application No. PCT/US2019/030263, 18 pages.

Search Report and Written Opinion Dated May 25, 2018 for International Application No. PCT/US2018/012507, 27 pages.

Search Report and Written Opinion Dated Jun. 3, 2019 for International Application No. PCT/US2019/014209, 22 pages.

Search Report and Written Opinion Dated Jul. 31, 2017 for International Application No. PCT/US2017/027767, 17 pages.

Pene, et al., "IgE production by normal human lymphocytes is induced by interleukin 4 and suppressed by interferons gamma and alpha and prostaglandin E2," PNAS USA, vol. 85, No. 18, 1988, pp. 6880-6884.

Philip, et al., "In Vivo Gene Delivery," J. Biol. Chem., vol. 268, No. 22, 1993, pp. 16087-16090.

Pollard, "Tumour-educated macrophages promote tumour progression and metastasis," Nat. Rev. Cancer, vol. 4, No. 1, 2004, pp. 71-78.

Pyonteck, et al., "CSF-1R inhibition alters macrophage polarization and blocks glioma progression," Nat. Med., vol. 19, No. 10, 2013, pp. 1264-1272.

Quabius & Krupp, "Synthetic mRNAs for manipulating cellular phenotypes: an overview," New Biotechnology, vol. 32, No. 1, 2015, pp. 229-235.

Quail, et al., "The tumor microenvironment underlies acquired resistance to CSF-1R inhibition in gliomas," Science, vol. 352, 2016, 17 pages.

Rector, et al., "Detection and characterization of monoclonal antibodies specific to IgE receptors on human lymphocytes by flow cytometry.," Immunology, vol. 55, No. 3, 1985, pp. 481-488.

Ren, et al, "Constructions of Polycation-Based Non-Viral DNA Nanoparticles and Polyanion Multilayers via Layer-by-layer Self-Assembly," Macromolecular Rapid Communications, vol. 26, No. 20, 2005, pp. 1633-1638.

Ren, et al., "IKKBeta is an IRF5 kinase that instigates inflammation," PNAS USA, vol. 111, No. 49, 2014, pp. 17438-17443.

Rhode, et al., "Single-chain MHC class II molecules induce T cell activation and apoptosis," J. Immunol., vol. 157, No. 11, 1996, pp. 4885-4891.

Robbins, et al., "Single and Dual Amino Acid Substitutions in TCR CDRs Can Enhance Antigen-Specific T Cell Functions," J. Immunol., vol. 180, No. 9, 2008, pp. 6116-6131.

Rocher & Singla, "SMAD-PI3K-Akt-mTOR Pathway Mediates BMP-7 Polarization of Monocytes into M2 Macrophages," PLoS One, vol. 8, No. 12, 2013, 9 pages.

Ronchetti, et al., "GILZ as a Mediator of the Anti-Inflammatory Effects of Glucocorticoids," Front. Endocrinol., vol. 6, No. 170, 2015, 6 pages.

Roszer, Tamas, "Understanding the Mysterious M2 Macrophage through Activation Markers and Effector Mechanisms," Mediators of Inflammation, vol. 2015, 2015, 17 pages.

Ryzhakov, et al., "Activation and Function of Interferon Regulatory Factor 5," Journal of Interferon & Cytokine Research, vol. 35, No. 2, 2015, pp. 71-78.

Sahin, et al., "mRNA-based therapeutics—developing a new class of drugs," Nature Reviews Drug Discovery, vol. 13, 2014, pp. 759-780.

Satoh, et al., "The Jmjd3-Irf4 axis regulates M2 macrophage polarization and host responses against helminth infection," Nature Immunology, vol. 11, 2010, pp. 936-944.

Schumann, et al., "Generation of knock-in primary human T cells using Cas9 ribonucleoproteins," PNAS, vol. 112, No. 22, 2015, pp. 10437-10442.

Sharma, et al., "Antigen-specific therapy of experimental allergic encephalomyelitis by soluble class II major histocompatibility complex-peptide complexes," PNAS, vol. 88, 1991, pp. 11465-11469.

Sharma, et al., "Computational study of the activated O(H) state in the catalytic mechanism of cytochrome c oxidase," PNAS, vol. 110, No. 42, 2013, pp. 16844-16849.

Sherr, et al., "Binding the low affinity Fc epsilon R on B cells suppresses ongoing human IgE synthesis.," Journal of Immunology, vol. 142, No. 2, 1989, pp. 481-489.

Sica & Bronte, "Altered macrophage differentiation and immune dysfunction in tumor development," Journal of Clinical Investigation, vol. 117, No. 5, 2007, pp. 1155-1166.

Sica & Mantovani, "Macrophage plasticity and polarization: in vivo veritas," Journal of Clinical Investigation, vol. 122, No. 3, pp. 787-795.

Sierra-Filardi, et al., "Activin A skews macrophage polarization by promoting a proinflammatory phenotype and inhibiting the acquisition of anti-inflammatory macrophage markers," Blood, vol. 117, No. 19, 2011, pp. 5092-5101.

Smith, et al, "In situ programming of leukaemia-specific T cells using synthetic DNA nanocarriers," Nature Nanotechnology, vol. 12, No. 8, 2017, pp. 813-820.

Spack, et al., "Preclinical and Pharmacological Studies of AG284, a Soluble HLA-DR2:Myelin Basic Protein Peptide Complex for the Treatment of Multiple Sclerosis," CNS Drug Rev., vol. 4, No. 225, 1998, pp. 1527-3458.

Search Report and Written Opinion Dated Jul. 28, 2014 in International Application No. PCT/US2014/029137, 12 pages.

Stephan, et al., "Enhancing Cell therapies from the Outside In: Cell Surface Engineering Using Synthetic Nanomaterials," Nano Today, vol. 6, No. 3, 2011, 28 pages.

Stephan, et al., "Biopolymer implants enhance the efficacy of adoptive T-cell therapy," Nature Biotechnology, vol. 33, No. 1, 2015, pp. 97-101.

Office Action Dated Dec. 15, 2020 for European Patent Application No. 17783314.2, 4 pages.

Canadian Office Action mailed May 12, 2023 for Canadian Patent Application No. 3,020,857, a foreign counterpart to U.S. Pat. No. 10,188,749, 5 pages.

Japanese Office Action mailed Apr. 11, 2023 for Japanese Application No. 2019-536560, a foreign counterpart to U.S. Pat. No. 11,440,945, 8 pages.

Office Action for U.S. Appl. No. 16/510,646, mailed on May 19, 2023, 18 Pages.

Martin, et al., "The Design of Cationic Lipids for Gene Delivery," Curr. Pharm. Des., vol. 11, No. 3, 2005, pp. 375-394.

(56)                 References Cited

OTHER PUBLICATIONS

Maruyama, et al., "Lipid composition is important for highly efficient target binding and retention of immunoliposomes," PNAS, vol. 87, 1990, pp. 5744-5748.

Mi, et al., "Characterization of a class of cationic peptides able to facilitate efficient protein transduction in vitro and in vivo," Mol. Ther., vol. 2, No. 4, 2000, pp. 338-347.

Moffett, et al, "Hit-and-run programming of therapeutic cytoreagents using mRNA nanocarriers," Nature Communications, vol. 8, No. 1, 2017, pp. 1-13.

Moffett, et. al., "Hit-and-run programming of therapeutic cytoreagents using mRNA nanocarriers," Nature Communications, vol. 8, No. 1, 2017, 13 pages.

Moffett, "Hit-and-run Programming of Therapeutic Cytoreagents using mRNA Nanocarriers," Nature Communications, vol. 8, No. 1, 2017, 13 pages.

Hambardzumyan, et al., "Modeling Adult Gliomas UsingRCAS/t-va Technology," Transl. Oncol., vol. 2, No. 2, 2009, pp. 89-95.

Tambardzumyan, et al., "The role of microglia and macrophages in glioma maintenance and progression," Nature Neuroscience, vol. 19, 2016, pp. 20-27.

Hoet, et al., "Generation of high-affinity human antibodies by combining donor-derived and synthetic complementarity-determining-region diversity," Nature Biotechnology, vol. 23, No. 3, 2005, pp. 344-348.

Jablonski, et al., "Novel Markers to Delineate Murine M1 and M2 Macrophages," PLoS One, vol. 10, No. 12, 2015, 25 pages.

Jain & Stylianopoulos, "Delivering nanomedicine to solid tumors," Nature Reviews Clinical Oncology, vol. 7, 2010, pp. 653-664.

Kariko, et al., "Incorporation of Pseudouridine Into mRNA Yields Superior Nonimmunogenic Vector With Increased Translational Capacity and Biological Stability," Molecular Therapy, vol. 16, No. 11, 2008, pp. 1833-1840.

Komohara, et al., "Clinical significance of macrophage heterogeneity in human malignant tumors," Cancer Science, vol. 105, No. 1, 2013, pp. 1-8.

Korczeniewska & Barnes, "The COP9 Signalosome Interacts with and Regulates Interferon Regulatory Factor 5 Protein Stability," Molecular and Celluar Biology, vol. 33, No. 6, 2013, pp. 1124-1138.

Krausgruber, et al., "IRF5 promotes inflammatory macrophage polarization and TH1-TH17 responses," Nature Immunology, vol. 12, No. 3, 2011, pp. 231-238.

Kurosaki, et al., "Ternary Complexes of pDNA, Polyethylenimine, and γ-polyglutamic acid for gene delivery systems," Biomaterials, vol. 30, No. 14, 2009, pp. 2846-2853.

Li, et al., "Bioelectric modulation of macrophage polarization," Scientific Reports, vol. 6, 2016, 12 pages.

Li, et al., "IL-21 Modulates Release of Proinflammatory Cytokines in LPS-Stimulated Macrophages through Distinct Signaling Pathways," Mediators of Inflammation, vol. 2013, 2013, 12 pages.

Liao, et al., "Preservation of tumor-host immune interactions with luciferase-tagged imaging in a murine model of ovarian cancer," Journal for Immuno Therapy of Cancer, vol. 3, No. 16, 2015, 9 pages.

Lin, et al., "A CRM1-dependent Nuclear Export Pathway Is Involved in the Regulation of IRF-5 Subcellular Localization," Journal of Biological Chemistry, vol. 280, No. 4, 2005, pp. 3088-3095.

Lin, et al., "Selective DNA Binding and Association with the CREB Binding Protein Coactivator Contribute to Differential Activation of Alpha/Beta Interferon Genes by Interferon Regulatory Factors 3 and 7," Molecular and Cellular Biology, vol. 20, No. 17, 2000, pp. 6342-6353.

Lin, et al., "Virus-Dependent Phosphorylation of the IRF-3 Transcription Factor Regulates Nuclear Translocation, Transactivation Potential, and Proteasome-Mediated Degradation," Molecular and Cellular Biology, vol. 18, No. 5, 1998, pp. 2986-2996.

Mann, et al., "Advances in Radiotherapy for Glioblastoma," Frontiers in Neurology, vol. 8, No. 748, 2017, 11 pages.

Mantovani, et al., "Tumour-associated macrophages as treatment targets in oncology," Nature Reviews Clinical Oncology, vol. 14, 2017, pp. 399-416.

Massimino, et al., "IRF5 is a target of BCR-ABL kinase activity and reduces CML cell proliferation," Carcinogenesis, vol. 35, No. 5, 2014, pp. 1132-1143.

Murakami, et al., "Human ERG-2 protein is a phosphorylated DNA-binding protein-a distinct member of the ets family," Oncogene, vol. 8, No. 6, 1993, pp. 1559-1566.

Columbian Office Action mailed Sep. 1, 2023 for Columbian Patent Applicatin No. NC2018/0012099, a foreign counterpart to U.S. Pat. No. 10,188,749, 24 pages.

Li, et al., "Nanoparticle-Delivered IRF5 siRNA Facilitates M1 to M2 Transition, Reduces Demyelination and Neurofilament Loss, and Promotes Functional Recovery After Spinal Cord Injury in Mice", Inflammation, vol. 39, No. 5, Jul. 19, 2016, pp. 1704-1717.

Schlake, et al., "mRNA: A Novel Avenue to Antibody Therapy?", Molecular Therapy, vol. 27, No. 4, Apr. 2019, pp. 773-784.

Deisting, et al., "Impact of Diverse Impact of Divers Immune Evasion Mechanisms of Cancer Cells on T Cells Engaged by EpCAM/CD3-Bispecific Antibody Construct AMG 110", PLOS ONE, vol. 10, No. 10, Jan. 1, 2015, pp. 1-16.

Krishnan, et al., "Predicting life expectancy in patients with advanced incurable cancer: a review", The Journal of Supportive Oncology, vol. 11, 2013, pp. 68-74.

National Cancer Institute, "What is Cancer?", retrieved on Sep. 23, 2024, at <<www.cancer.gov/about-cancer/understanding/what-is-cancer>>, NIH, May 28, 2016, pp. 1-10.

Aljabali, et al., "Nanomaterials and Their Impact on the Immune System", Int J Mol Sci., 2023, 24, 2008, 26 pages.

Amorós-Pérez, et al., "State of the Art in CAR-T Cell Therapy for Solid Tumors: Is There a Sweeter Future?," Cells, vol. 13, No. 9, 725, 2024, 22 pages.

Australian Office Action Dated Feb. 15, 2024 for Australian Application No. 2019210188, 4 pages.

Barbesti, et al, "A simplified flow cytometry method of CD4 and CD8 cell counting based on thermoresistant reagents: implications for large scale monitoring of HIV-infected patients in resource-limited settings", Cytometry Part B (Clinical Cytometry) 64B: 43-51, 2005, pp. 1-2.

Baulu et al., "TCR-engineered T cell therapy in solid tumors: State of the art and perspectives", Sci Adv, vol. 9, No. 7, 15 pages.

Office Action Dated Jan. 4, 2024 for Canadian Patent Application No. 3,162,629, 3 pages.

Office Action Dated Feb. 9, 2024 for Canadian Application No. 3,049,244, 5 pages.

Office Action Dated Mar. 1, 2024 for Canadian Application No. 3,088,122, 8 pages.

Chistiakov, et al., "The Impact of interferon-regulatory factors to macrophage differetiation and polarization into M1 and M2", Immunobiology, vol. 223, No. 1, 2017, pp. 101-111.

NCI Thesaurus entry for "DMXAA"; available at ncithesaurus.nci. nih.gov/ncitbrowser/pages/concept_details.jsf?dictionary=NCI_ Thesaurus&version=22.01e&code=C2504&ns=ncit&type=synonym &key=null&b=1&n=0&vse=null; last accessed Mar. 16, 2022.

Durymanov, et al., "Non-viral Delivery of Nucleic Acids: Insight Into Mechanisms of Overcoming Intracellular Barriers", Front Pharmacol., vol. 9, No. 971, 2018, 15 pages.

European Office Action Dated Feb. 16, 2024 for European Application No. 22199369.4, 4 pages.

Office Action Dated Jan. 10, 2024 for European Application No. 19795782.2, 9 pages.

Office Action for European Application No. 18735984.9, Dated Apr. 25, 2024, 9 pages.

NCI Thesaurus entry for "Hiltonol"; available at ncithesaurus.nci. nih.gov/ncitbrowser/pages/concept_details.jsf?dictionary=NCI_ Thesaurus&version=22.01e&code=C1198&ns=ncit&type=synonym &key=1569668399&b=1&n=0&vse=1; last accessed Mar. 16, 2022.

Office Action Dated Dec. 31, 2023 for Israeli Application No. 300282, 10 pages.

Office Action for Israeli Application No. 276122, Dated May 1, 2024, 4 pages.

(56) References Cited

OTHER PUBLICATIONS

NCI Thesaurus entry for "Imiquimod"; available at ncithesaurus. nci.nih.gov/ncitbrowser/pages/concept_details.jsf?dictionary=NCI_ Thesaurus&version=22.01e&code=C1431&ns=ncit&type=synonym &key=265972622&b=1&n=0&vse=null; last accessed Mar. 16, 2022.

Japanese Office Action Dated Nov. 30, 2021 in Japanese Application No. 2018-553912, 2 pages.

Office Action for Japanese Application No. 2022-102442, Dated Apr. 23, 2024, 6 pages.

Kaye. "Cytomegalovirus (CMV) Infection" retrieved Jul. 3, 2024, at <<https://www.merckmanuals.com/home/infections/herpesvirus-infections/cytomegalovirus-cmv-infection>> Year: 2018, 3 pgs.

Office Action Dated Feb. 21, 2024 for Korean Application No. 10-2023-7019209, 6 pages.

Office Action Dated Mar. 1, 2024 for Korean Application No. 10-2020-7022164, 13 pages.

Office Action for Korean Application No. 10-2020-7034074, Dated May 31, 2024, 12 pages.

Li, "Poly(I-glutamic acid)-anticancer drug conjugates", Advanced Drug Delivery Reviews, vol. 54, Issue 5, Sep. 13, 2002, pp. 695-713.

Liao-Chan, et al., "Quantitative Assessment of Antibody Internalization with Novel Monoclonal Antibodies against Alexa Fluorophores" PLoS One, 2015, vol. 10, No. 4, 15 pages.

Lin, et al., "Angiopoietin-Like Proteins Stimulate HSC Development Through Direct Interaction with Notch", Blood Journal, 2013, pp. 1-5.

NCI Thesaurus entry for "MPLAI"; available at ncithesaurus.nci. nih.gov/ncitbrowser/pages/concept_details.jsf?dictionary=NCI_ Thesaurus&version=22.01e&code=C87754&ns=ncit&type=synonym &key=null&b=1&n=0&vse=null; last accessed Mar. 16, 2022.

National Cancer Institute. "Cancer Treatment", Retrieved Jul. 2, 2024, at <<https://www.cancer.gov/about-cancer/treatment>>, 2023, 1 pg.

Office Action for U.S. Appl. No. 18/053,283, mailed on Nov. 9, 2023, 12 pages.

Office Action for U.S. Appl. No. 18/053,283, mailed on Apr. 18, 2024, 13 Pages.

Office Action for U.S. Appl. No. 17/044/779, mailed on Jul. 16, 2024, 22 Pages.

Invitation to Pay Additional Fees Dated Apr. 8, 2021 for International Application No. PCT/US2020/067729, 4 Pages.

Search Report and Written Opinion Dated Jun. 3, 2021 for International Application No. PCT/US2020/067729, 23 pages.

Pereira, "Biosynthesis of highly pure poly-γ-glutamic acid for biomedical applications", J Mater Sci Mater Med., Jul. 2012, vol. 23, No. 7, pp. 1583-1591.

Philip, et al., "In vivo gene delivery. Efficient transfection of T lymphocytes in adult mice," J Biol Chem, 1993, vol. 268, No. 22, pp. 16087-16090.

Prodhomme, et al., "Multivalent Conjugates of Poly-ç-D-glutamic Acid from Bacillus licheniformis with Antibody F(abc) and Glycopeptide Ligands", Bioconjugate Chem, 2003, pp. 1148-1155.

Entry from AcronymFinder.com for "PSCA"; available at www. acronymfinder.com/Prostate-Stem-Cell-Antigen-(PSCA). html; last accessed Mar. 16, 2022.

Entry from AcronymFinder.com for "PSMA"; available at https:// www.acronymfinder.com/Prostate_Specific-Membrane- Antigen-(PSMA).html; last accessed Mar. 16, 2022.

Ren, et al., "Co-administration of a DNA vaccine encoding the prostate specific membrane antigen and CpG oligodeoxynucleotides suppresses tumor growth", J Transl Med, vol. 2, No. 29, 2004, 10 pages.

Ren, et al., "Construction of Polycation-Based Non-Viral DNA Nanoparticles and Polyanion Multilayers via Layer-byLayer Self-Assembly", Macromolecular rapid communications, Jul. 10, 2005, pp. 1633-1638.

NCI Thesaurus entry for "ROR1"; available at ncithesaurus.nci.nih. gov/ncitbrowser/pages/concept_details.jsf?dictionary=NCI_Thesaurus &version=22.01e&code=C29879&ns=ncit&type=synonym&key= n1959117208&b=1&n=0&vse=null; last accessed Mar. 16, 2022.

Office Action for Russian Application No. 2022120799, Dated Apr. 25, 2024, 14 pages.

Search Report for European Application No. 20911288.7, Dated May 14, 2024, 12 pages.

Office Action for U.S. Appl. No. 16/510,646, Dated Dec. 6, 2023, 18 Pages.

Wang, et al., "Challenges in the development and establishment of exosome-based drug delivery systems", J Control Release., vol. 329, 2020, pp. 894-906.

Wild, et al, "Exendin-4-Based Radiopharmaceuticals for Glucagon-like Peptide-1 Receptor PET/CT and SPECT/CT", Journal of Nuclear Medicine, Jul. 2010, pp. 1-17.

Zhao, et al., "Exosomes as drug carriers for cancer therapy and challenges regarding exosome uptake", Biomed Pharmacother, vol. 128, No. 110237, 2020, 9 pages.

Zheng, et al., "Harnessing Exosomes for the Development of Brain Drug Delivery Systems". Bioconjugate Chem., vol. 30, 2019, pp. 994-1005.

* cited by examiner

FIG. 1A

Nanoparticle with IVT mRNA cargo

Transcription factor controlling
macrophage phenotype

Tumor injection

I.P. injection of NPs for 9 weeks, 2 doses/week, 50 µg/dose

D 0      D 14      D 77

Biodistribution after i.p. administration

Mice received 6 doses (50 μg mRNA /dose)
of (1) PBS; (2) GFP-NPs; (3) IRF5-NPs

FIG. 5D

| Parameter | Unit | PBS | GFP-NPs | IRF5-NPs |
|---|---|---|---|---|
| WBC | K/uL | 4.24 | 3.18 | 2.14 |
| RBC | M/uL | 9.13 | 8.83 | 7.95 |
| HGB | g/dL | 14.36 | 13.8 | 11.95 |
| NEUCT | /uL | 303.2 | 246 | 115.4 |
| LYMCT | /uL | 3849 | 2830 | 1960 |
| MONCT | /uL | 53.5 | 60.8 | 68 |
| EOSCT | /uL | 66.4 | 55.4 | 25.2 |
| BASCT | /uL | 0 | 0 | 0 |
| ALP | U/L | 99.4 | 99.4 | 62.4 |
| ALT | U/L | 45.75 | 41 | 54.25 |
| AST | U/L | 116 | 116 | 149.8 |
| BUN | mg/dL | 34.2 | 30.6 | 25.6 |

Tumor-free lung

Lung with established
tumor lesions

○  PBS (ms=27)
△  GFP-NPs (ms=28)          ] P<0.0001
✕  IRF5-NPs (ms=35)          ] P<0.0001

PBS            GFP-NPs            IRF5-NPs

FIG. 6I

T2-MRI          H&E (See FIG. 7B)

DAPI     GFP (glioma cells)     Anti-CD68 (Macrophages)     Composite

Tumor-free
brain tissue                    Glioma

Intravenous injections of
IRF5-NPs; 30 µg/dose

THP1-Lucia ISG (interferon-stimulated genes) express the secreted luciferase Lucia reproter gene under the control of an IRF-inducible promoter.

Untransfected (MFI: 92 ± 13)
GFP-NPs (MFI: 421 ± 126)
huIRF5-NPs (MFI: 1,008 ± 206)

FIG. 9

| Antibody Specificity | Clone | Isotype | Dilution | Dye | Supplier | Catalog# |
|---|---|---|---|---|---|---|
| Myeloid Panel | | | | | | |
| CD45 | 30-F11 | Rat IgG2b, κ | 1:800 | eFluor 450 | eBioscience | 48-0451 |
| MHC I-A/I-E | M5/114.15.2 | Rat IgG2b, κ | 1:400 | AlexaFluor700 | Biolegend | 107622 |
| CD11b | M1/70 | Rat IgG2b, κ | 1:200 | APC | BD Biosciences | 557657 |
| CD11C | N418 | Arm Ham IgG | 1:200 | PE-CF594 | BD Biosciences | 562454 |
| Ly6C | HK1.4 | Rat IgG2a, κ | 1:200 | PerCP-Cy5.5 | eBioscience | 45-4932 |
| Ly6G | 1A8 | Rat IgG2a, κ | 1:200 | APC-Cy7 | Biolegend | 127624 |
| CD38 | 90/CD38 | Rat IgG2a, κ | 1:200 | BUV395 | BD Biosciences | 740245 |
| CD206 | C0682C2 | Rat IgG2a, κ | 1:200 | PE-Dazzle 594 | Biolegend | 141732 |
| Live/Dead Fixable Green | - | - | 1:800 | FITC | Life Technologies | L23101 |
| Lymphoid Panel | | | | | | |
| CD45 | 30-F11 | Rat IgG2b, κ | 1:800 | eFluor 450 | eBioscience | 48-0451 |
| CD335 (Nkp46) | 29A1.4 | Rat IgG2a, κ | 1:200 | BUV737 | BD | 565085 |
| CD4 | RM4-5 | Rat IgG2a, κ | 1:400 | PerCP-Cy5.5 | Biolegend | 100540 |
| CD44 | IM7 | Rat IgG2b, κ | 1:400 | PE-CF594 | BD | 562464 |
| CD49B | HMa2 | Ham IgG | 1:200 | BUV395 | BD | 740250 |
| CD62L | MEL-14 | Rat IgG2a, κ | 1:200 | APC-Cy7 | Biolegend | 104428 |
| CD8 | 53-6.7 | Rat IgG2a, κ | 1:400 | APC | Biolegend | 100712 |
| TCR-β chain | B20.6 | Rat IgG2b, κ | 1:400 | PE | Biolegend | 127908 |
| Live/Dead Fixable Green | - | - | 1:800 | FITC | Life Technologies | L23101 |
| Other antibodies | | | | | | |
| F4/80 | BM8 | Rat IgG2a, κ | 1:400 | PE | eBioscience | 12-4801 |
| 7AAD | - | - | 1:400 | - | Biolegend | 420404 |
| Trustain fcX | 93 | Rat IgG2a, κ | 1:400 | - | Biolegend | 101320 |

FIG. 10

>Human IRF5 Isoform 1 (UniProt Accession Q13568-1)
MNQSIPVAPTPPRRVRLKPWLVAQVNSCQYPGLQWVVNGEKKLFCIPWRHATRHGPSQDGDNTIF
KAWAKETGKYTEGVDEADPAKWKANLRCALNKSRDFRLIYDGPRDMPPQPYKIYEVCSNGPAPT
DSQPPEDYSFGAGEEEEEEEELQRMLPSLSLTEDVKWPPTLQPPTLRPPTLQPPTLQPPVVLGPP
APDPSPLAPPPGNPAGFRELLSEVLEPGPLPASLPPAGEQLLPDLLISPHMLPLTDLEIKFQYRGRP
PRALTISNPHGCRLFYSQLEATQEQVELFGPISLEQVRFPSPEDIPSDKQRFYTNQLLDVLDRGLIL
QLQGQDLYAIRLCQCKVFWSGPCASAHDSCPNPIQREVKTKLFSLEHFLNELILFQKGQTNTPPPF
EIFFCFGEEWPDRKPREKKLITVQVVPVAARLLLEMFSGELSWSADSIRLQISNPDLKDRMVEQFKE
LHHIWQSQQRLQPVAQAPPGAGLGVGQGPWPMHPAGMQ(SEQ ID NO: 1)

>Human IRF5 Isoform 2 (UniProt Accession Q13568-2)
MNQSIPVAPTPPRRVRLKPWLVAQVNSCQYPGLQWVVNGEKKLFCIPWRHATRHGPSQDGDNTIF
KAWAKETGKYTEGVDEADPAKWKANLRCALNKSRDFRLIYDGPRDMPPQPYKIYEVCSNGPAPT
DSQPPEDYSFGAGEEEEEEEELQRMLPSLSLTDAVQSGPHMTPYSLLKEDVKWPPTLQPPTLRPP
TLQPPTLQPPVVLGPPAPDPSPLAPPPGNPAGFRELLSEVLEPGPLPASLPPAGEQLLPDLLISPHM
LPLTDLEIKFQYRGRPPRALTISNPHGCRLFYSQLEATQEQVELFGPISLEQVRFPSPEDIPSDKQR
FYTNQLLDVLDRGLILQLQGQDLYAIRLCQCKVFWSGPCASAHDSCPNPIQREVKTKLFSLEHFLN
ELILFQKGQTNTPPPFEIFFCFGEEWPDRKPREKKLITVQVVPVAARLLLEMFSGELSWSADSIRLQI
SNPDLKDRMVEQFKELHHIWQSQQRLQPVAQAPPGAGLGVGQGPWPMHPAGMQ (SEQ ID NO:
2)

>Human IRF5 Isoform 3 (UniProt Accession Q13568-3)
MNQSIPVAPTPPRRVRLKPWLVAQVNSCQYPGLQWVVNGEKKLFCIPWRHATRHGPSQDGDNTIF
KAWAKETGKYTEGVDEADPAKWKANLRCALNKSRDFRLIYDGPRDMPPQPYKIYEVCSNGPAPT
DSQPPEDYSFGAGEEEEEEEELQRMLPSLSLTDAVQSGPHMTPYSLLKEDVKWPPTLQPPTLQPP
VVLGPPAPDPSPLAPPPGNPAGFRELLSEVLEPGPLPASLPPAGEQLLPDLLISPHMLPLTDLEIKF
QYRGRPPRALTISNPHGCRLFYSQLEATQEQVELFGPISLEQVRFPSPEDIPSDKQRFYTNQLLDVL
DRGLILQLQGQDLYAIRLCQCKVFWSGPCASAHDSCPNPIQREVKTKLFSLEHFLNELILFQKGQTN
TPPPFEIFFCFGEEWPDRKPREKKLITVQVVPVAARLLLEMFSGELSWSADSIRLQISNPDLKDRMV
EQFKELHHIWQSQQRLQPVAQAPPGAGLGVGQGPWPMHPAGMQ (SEQ ID NO: 3)

>Human IRF5 Isoform 4 (UniProt Accession Q13568-4)
MNQSIPVAPTPPRRVRLKPWLVAQVNSCQYPGLQWVVNGEKKLFCIPWRHATRHGPSQDGDNTIF
KAWAKETGKYTEGVDEADPAKWKANLRCALNKSRDFRLIYDGPRDMPPQPYKIYEVCSNGPAPT
DSQPPEDYSFGAGEEEEEEEELQRMLPSLSLTEDVKWPPTLQPPTLQPPVVLGPPAPDPSPLAPP
PGNPAGFRELLSEVLEPGPLPASLPPAGEQLLPDLLISPHMLPLTDLEIKFQYRGRPPRALTISNPH
GCRLFYSQLEATQEQVELFGPISLEQVRFPSPEDIPSDKQRFYTNQLLDVLDRGLILQLQGQDLYAI
RLCQCKVFWSGPCASAHDSCPNPIQREVKTKLFSLEHFLNELILFQKGQTNTPPPFEIFFCFGEEW
PDRKPREKKLITVQVVPVAARLLLEMFSGELSWSADSIRLQISNPDLKDRMVEQFKELHHIWQSQQ
RLQPVAQAPPGAGLGVGQGPWPMHPAGMQ (SEQ ID NO: 4)

>Human IRF5 Isoform 5 (UniProt Accession Q13568-5)
MNQSIPVAPTPPRRVRLKPWLVAQVNSCQYPGLQWVVNGEKKLFCIPWRHATRHGPSQDGDNTIF
KAWAKETGKYTEGVDEADPAKWKANLRCALNKSRDFRLIYDGPRDMPPQPYKIYEVCSNGPAPT
DSQPPEDYSFGAGEEEEEEEELQRMLPSLSLTVTDLEIKFQYRGRPPRALTISNPHGCRLFYSQLE
ATQEQVELFGPISLEQVRFPSPEDIPSDKQRFYTNQLLDVLDRGLILQLQGQDLYAIRLCQCKVFWS
GPCASAHDSCPNPIQREVKTKLFSLEHFLNELILFQKGQTNTPPPFEIFFCFGEEWPDRKPREKKLI
TVQVVPVAARLLLEMFSGELSWSADSIRLQISNPDLKDRMVEQFKELHHIWQSQQRLQPVAQAPP
GAGLGVGQGPWPMHPAGMQ (SEQ ID NO: 5)

FIG. 10 CONT.

>Human IRF5 Isoform 6 (UniProt Accession Q13568-6)
MNQSIPVAPTPPRRVRLKPWLVAQVNSCQYPGLQWVNGEKKLFCIPWRHATRHGPSQDGDNTIF
KAWAKETGKYTEGVDEADPAKWKANLRCALNKSRDFRLIYDGPRDMPPQPYKIYETPSPLRITLLV
QERRRKKRKSCRGCCQA (SEQ ID NO: 6)

>Murine IRF5 protein (pI=5.19, Mw = 56005, UniProt Accession P56477)
MNHSAPGIPPPPRRVRLKPWLVAQVNSCQYPGLQWVNGEKKLFYIPWRHATRHGPSQDGDNTIF
KAWAKETGKYTEGVDEADPAKWKANLRCALNKSRDFQLFYDGPRDMPPQPYKIYEVCSNGPAPT
ESQPTDDYVLGEEEEEEEEELQRMLPGLSITEPALPGPPNAPYSLPKEDTKWPPALQPPVGLGPP
VPDPNLLAPPSGNPAGFRQLLPEVLEPGPLASSQPPTEPLLPDLLISPHMLPLTDLEIKFQYRGRAP
RTLTISNPQGCRLFYSQLEATQEQVELFGPVTLEQVRFPSPEDIPSDKQRFYTNQLLDVLDRGLILQ
LQGGQDLYAIRLCQCKVFWSGPCALAHGSCPNPIQREVKTKLFSLEQFLNELILFQKGQTNTPPPFEI
FFCFGEEWPDVKPREKKLITVQVVPVAARLLLEMFSGELSWSADSIRLQISNPDLKDHMVEQFKEL
HHLWQSQQQLQPMVQAPPVAGLDASQGPWPMHPVGMQ (SEQ ID NO: 7)

>Human IRF1 (UniProt Accession P10914)
MPITRMRMRPWLEMQINSNQIPGLIWINKEEMIFQIPWKHAAKHGWDINKDACLFRSWAIHTGRYK
AGEKEPDPKTWKANFRCAMNSLPDIEEVKDQSRNKGSSAVRVYRMLPPLTKNQRKERKSKSSRD
AKSKAKRKSCGDSSPDTFSDGLSSSTLPDDHSSYTVPGYMQDLEVEQALTPALSPCAVSSTLPDW
HIPVEVVPDSTSDLYNFQVSPMPSTSEATTDEDEEGKLPEDIMKLLEQSEWQPTNVDGKGYLLNEP
GVQPTSVYGDFSCKEEPEIDSPGGDIGLSLQRVFTDLKNMDATWLDSLLTPVRLPSIQAIPCAP
(SEQ ID NO: 8)

>Human IRF3 isoform 1 (UniProt Accession Q14653-1)
MGTPKPRILPWLVSQLDLGQLEGVAWVNKSRTRFRIPWKHGLRQDAQQEDFGIFQAWAEATGAY
VPGRDKPDLPTWKRNFRSALNRKEGLRLAEDRSKDPHDPHKIYEFVNSGVGDFSQPDTSPDTNG
GGSTSDTQEDILDELLGNMVLAPLPDPGPPSLAVAPEPCPQPLRSPSLDNPTPFPNLGPSENPLKR
LLVPGEEWEFEVTAFYRGRQVFQQTISCPEGLRLVGSEVGDRTLPGWPVTLPDPGMSLTDRGVM
SYVRHVLSCLGGGLALWRAGQWLWAQRLGHCHTYWAVSEELLPNSGHGPDGEVPKDKEGGVF
DLGPFIVDLITFTEGSGRSPRYALWFCVGESWPQDQPWTKRLVMVKVVPTCLRALVEMARVGGA
SSLENTVDLHISNSHPLSLTSDQYKAYLQDLVEGMDFQGPGES (SEQ ID NO: 9)

>Human IRF7 isoform A (UniProt Accession Q92985-1)
MALAPERAAPRVLFGEWLLGEISSGCYEGLQWLDEARTCFRVPWKHFARKDLSEADARIFKAWAV
ARGRWPPSSRGGGPPPEAETAERAGWKTNFRCALRSTRRFVMLRDNSGDPADPHKVYALSREL
CWREGPGTDQTEAEAPAAVPPPQGGPPGPFLAHTHAGLQAPGPLPAPAGDKGDLLLQAVQQSCL
ADHLLTASWGADPVPTKAPGEGQEGLPLTGACAGGPGLPAGELYGWAVETTPSPGPQPAALTTG
EAAAPESPHQAEPYLSPSPSACTAVQEPSPGALDVTIMYKGRTVLQKVVGHPSCTFLYGPPDPAV
RATDPQQVAFPSPAELPDQKQLRYTEELLRHVAPGLHLELRGPQLWARRMGKCKVYWEVGGPP
GSASPSTPACLLPRNCDTPIFDFRVFFQELVEFRARQRRGSPRYTIYLGFGQDLSAGRPKEKSLVL
VKLEPWLCRVHLEGTQREGVSSLDSSSLSLCLSSANSLYDDIECFLMELEQPA (SEQ ID NO: 10)

>Human IRF8 (UniProt Accession Q02556)
MCDRNGGRRLRQWLIEQIDSSMYPGLIWENEEKSMFRIPWKHAGKQDYNQEVDASIFKAWAVFK
GKFKEGDKAEPATWKTRLRCALNKSPDFEEVTDRSQLDISEPYKVYRIVPEEEQKCKLGVATAGC
VNEVTEMECGRSEIDELIKEPSVDDYMGMIKRSPSPPEACRSQLLPDWWAQQPSTGVPLVTGYTT
YDAHHSAFSQMVISFYYGGKLVGQATTTCPEGCRLSLSQPGLPGTKLYGPEGLELVRFPPADAIPS
ERQRQVTRKLFGHLERGVLLHSSRQGVFVKRLCQGRVFCSGNAVVCKGRPNKLERDEVVQVFDT
SQFFRELQQFYNSQGRLPDGRVVLCFGEEFPDMAPLRSKLILVQIEQLYVRQLAEEAGKSCGAGS
VMQAPEEPPPDQVFRMFPDICASHQRSFFRENQQITV (SEQ ID NO: 11)

FIG. 10 CONT.

>Murine IRF1 (UniProt Accession P15314)
MPITRMRMRPWLEMQINSNQIPGLIWINKEEMIFQIPWKHAAKHGWDINKDACLFRSWAIHTGRYK
AGEKEPDPKTWKANFRCAMNSLPDIEEVKDQSRNKGSSAVRVYRMLPPLTRNQRKERKSKSSRD
TKSKTKRKLCGDVSPDTFSDGLSSSTLPDDHSSYTTQGYLGQDLDMERDITPALSPCVVSSSLSE
WHMQMDIIPDSTTDLYNLQVSPMPSTSEAATDEDEEGKIAEDLMKLFEQSEWQPTHIDGKGYLLNE
PGTQLSSVYGDFSCKEEPEIDSPRGDIGIGIQHVFTEMKNMDSIMVMDSLLGNSVRLPPSIQAIPCA
P (SEQ ID NO: 12)

>Murine IRF3 (UniProt Accession P70671)
METPKPRILPWLVSQLDLGQLEGVAWLDESRTRFRIPWKHGLRQDAQMADFGIFQAWAEASGAY
TPGKDKPDVSTWKRNFRSALNRKEVLRLAADNSKDPYDPHKVYEFVTPGARDFVHLGASPDTNG
KSSLPHSQENLPKLFDGLILGPLKDEGSSDLAIVSDPSQQLPSPNVNNFLNPAPQENPLKQLLAEEQ
WEFEVTAFYRGRQVFQQTLFCPGGLRLVGSTADMTLPWQPVTLPDPEGFLTDKLVKEYVGQVLK
GLGNGLALWQAGQCLWAQRLGHSHAFWALGEEELLPDSGRGPDGEVHKDKDGAVFDLRPFVADLI
AFMEGSGHSPRYTLWFCMGEMWPQDQPWVKRLVMVKVVPTCLKELLEMAREGGASSLKTVDLH
ISNSQPISLTSDQYKAYLQDLVEDMDFQATGNI (SEQ ID NO: 13)

>Murine IRF7 (UniProt Accession P70434)
MAEVRGVQRVLFGDWLLGEVSSGQYEGLQWLNEARTVFRVPWKHFGRRDLDEEDAQIFKAWAV
ARGRWPPSGVNLPPPEAEAAERRERRGWKTNFRCALHSTGRFILRQDNSGDPVDPHKVYELSRE
LGSTVGPATENREEVSLSNALPTQGVSPGSFLARENAGLQTPSPLLSSDAGDLLLQVLQYSHILES
ESGADPVPPQAPGQEQDRVYEEPYAAWQVEAVPSPRPQQPALTERSLGFLDVTIMYKGRTVLQA
VVGHPRCVFLYSPMAPAVRTSEPQPVIFPSPAELPDQKQLHYTETLLQHVSPGLQLELRGPSLWAL
RMGKCKVYWEVGSPMGTTGPSTPPQLLERNRHTPIFDFSTFFRELEEFRARRRQGSPHYTIYLGF
GQDLSAGRPKEKTLILVKLEPWVCKAYLEGVQREGVSSLDSSSLGLCLSSTNSLYEDIEHFLMDLG
QWP (SEQ ID NO: 14)

>Murine IRF7/IRF3 5(D) protein (pI=4.72, MW = 58456)
MAEVRGVQRVLFGDWLLGEVSSGQYEGLQWLNEARTVFRVPWKHFGRRDLDEEDAQIFKAWAV
ARGRWPPSGVNLPPPEAEAAERRERRGWKTNFRCALHSTGRFILRQDNSGDPVDPHKVYELSRE
LGSTVGPATENREEVSLSNALPTQGVSPGSFLARENAGLQTPSPLLSSDAGDLLLQVLQYSHILES
ESGADPVPPQAPGQEQDRVYEEPYAAWQVEAVPSPRPQQPALTERSLGFLDVTKLFDGLILGPLK
DEGSSDLAIVSDPSQQLPSPNVNNFLNPAPQENPLKQLLAEEQWEFEVTAFYRGRQVFQQTLFCP
GGLRLVGSTADMTLPWQPVTLPDPEGFLTDKLVKEYVGQVLKGLGNGLALWQAGQCLWAQRLG
HSHAFWALGEEELLPDSGRGPDGEVHKDKDGAVFDLRPFVADLIAFMEGSGHSPRYTLWFCMGEM
WPQDQPWVKRLVMVKVVPTCLKELLEMAREGGASSLKTVDLHIDNDQPIDLDDDQYKAYLQDLVE
DMDFQATGNI (SEQ ID NO: 15)

>Murine IRF8 (UniProt Accession P23611)
MCDRNGGRRLRQWLIEQIDSSMYPGLIWENDEKTMFRIPWKHAGKQDYNQEVDASIFKAWAVFK
GKFKEGDKAEPATWKTRLRCALNKSPDFEEVTDRSQLDISEPYKVYRIVPEEEQKCKLGVAPAGC
MSEVPEMECGRSEIEELIKEPSVDEYMGMTKRSPSPPEACRSQILPDWWVQQPSAGLPLVTGYAA
YDTHHSAFSQMVISFYYGGKLVGQATTTCLEGCRLSLSQPGLPKLYGPDGLEPVCFPTADTIPSER
QRQVTRKLFGHLERGVLLHSNRKGVFVKRLCQGRVFCSGNAVVCKGRPNKLERDEVVQVFDTNQ
FIRELQQFYATQSRLPDSRVVLCFGEEFPDTVPLRSKLILVQVEQLYARQLVEEAGKSCGAGSLMP
ALEEPQPDQAFRMFPDICTSHQRPFFRENQQITV (SEQ ID NO: 16)

FIG. 10 CONT.

>Murine IRF8 (K310R) protein (pI= 6.38, MW = 48265)
MCDRNGGRRLRQWLIEQIDSSMYPGLIWENDEKTMFRIPWKHAGKQDYNQEVDASIFKAWAVFK
GKFKEGDKAEPATWKTRLRCALNKSPDFEEVTDRSQLDISEPYKVYRIVPEEEQKCKLGVAPAGC
MSEVPEMECGRSEIEELIKEPSVDEYMGMTKRSPSPPEACRSQILPDWWVQQPSAGLPLVTGYAA
YDTHHSAFSQMVISFYYGGKLVGQATTTCLEGCRLSLSQPGLPKLYGPDGLEPVCFPTADTIPSER
QRQVTRKLFGHLERGVLLHSNRKGVFVKRLCQGRVFCSGNAVVCKGRPNRLERDEVVQVFDTNQ
FIRELQQFYATQSRLPDSRVVLCFGEEFPDTVPLRSKLILVQVEQLYARQLVEEAGKSCGAGSLMP
ALEEPQPDQAFRMFPDICTSHQRPFFRENQQITV (SEQ ID NO: 17)

>Human IKKβ isoform 1 (UniProt Accession O14920-1)
MSWSPSLTTQTCGAWEMKERLGTGGFGNVIRWHNQETGEQIAIKQCRQELSPRNRERWCLEIQI
MRRLTHPNVVAARDVPEGMQNLAPNDLPLLAMEYCQGGDLRKYLNQFENCCGLREGAILTLLSDI
ASALRYLHENRIIHRDLKPENIVLQQGEQRLIHKIIDLGYAKELDQGSLCTSFVGTLQYLAPELLEQQK
YTVTVDYWSFGTLAFECITGFRPFLPNWQPVQWHSKVRQKSEVDIVVSEDLNGTVKFSSSLPYPN
NLNSVLAERLEKWLQLMLMWHPRQRGTDPTYGPNGCFKALDDILNLKLVHILNMVTGTIHTYPVTE
DESLQSLKARIQQDTGIPEEDQELLQEAGLALIPDKPATQCISDGKLNEGHTLDMDLVFLFDNSKITY
ETQISPRPQPESVSCILQEPKRNLAFFQLRKVWGQVVWHSIQTLKEDCNRLQQGQRAAMMNLLRNN
SCLSKMKNSMASMSQQLKAKLDFFKTSIQIDLEKYSEQTEFGITSDKLLLAWREMEQAVELCGREN
EVKLLVERMMALQTDIVDLQRSPMGRKQGGTLDDLEEQARELYRRLREKPRDQRTEGDSQEMVR
LLLQAIQSFEKKVRVIYTQLSKTVVCKQKALELLPKVEEVVSLMNEDEKTVVRLQEKRQKELWNLLK
IACSKVRGPVSGSPDSMNASRLSQPGGQLMSQPSTASNSLPEPAKKSEELVAEAHNLCTLLENAIQD
TVREQDQSFTALDWSWLQTEEEEHSCLEQAS (SEQ ID NO: 18)

>Human IKKβ isoform 2 (UniProt Accession O14920-2)
MFSGGCHSPGFGRPSPAFPAPGSPPPAPRPCRQETGEQIAIKQCRQELSPRNRERWCLEIQIMRR
LTHPNVVAARDVPEGMQNLAPNDLPLLAMEYCQGGDLRKYLNQFENCCGLREGAILTLLSDIASAL
RYLHENRIIHRDLKPENIVLQQGEQRLIHKIIDLGYAKELDQGSLCTSFVGTLQYLAPELLEQQKYTVT
VDYWSFGTLAFECITGFRPFLPNWQPVQWHSKVRQKSEVDIVVSEDLNGTVKFSSSLPYPNNLNS
VLAERLEKWLQLMLMWHPRQRGTDPTYGPNGCFKALDDILNLKLVHILNMVTGTIHTYPVTEDESL
QSLKARIQQDTGIPEEDQELLQEAGLALIPDKPATQCISDGKLNEGHTLDMDLVFLFDNSKITYETQI
SPRPQPESVSCILQEPKRNLAFFQLRKVWGQVVWHSIQTLKEDCNRLQQGQRAAMMNLLRNNSCL
SKMKNSMASMSQQLKAKLDFFKTSIQIDLEKYSEQTEFGITSDKLLLAWREMEQAVELCGRENEVK
LLVERMMALQTDIVDLQRSPMGRKQGGTLDDLEEQARELYRRLREKPRDQRTEGDSQEMVRLLL
QAIQSFEKKVRVIYTQLSKTVVCKQKALELLPKVEEVVSLMNEDEKTVVRLQEKRQKELWNLLKIAC
SKVRGPVSGSPDSMNASRLSQPGGQLMSQPSTASNSLPEPAKKSEELVAEAHNLCTLLENAIQDTV
REQDQSFTALDWSWLQTEEEEHSCLEQAS (SEQ ID NO: 19)

>Human IKKβ isoform 3 (UniProt Accession O14920-3)
MSWSPSLTTQTCGAWEMKERLGTGGFGNVIRWHNQETGEQIAIKQCRQELSPRNRERWCLEIQI
MRRLTHPNVVAARDVPEGMQNLAPNDLPLLAMEYCQGGDLRKYLNQFENCCGLREGAILTLLSDI
ASALRYLHENRIIHRDLKPENIVLQQGEQRLIHKIIDLGYAKELDQGSLCTSFVGTLQYLAPELLEQQK
YTVTVDYWSFGTLAFECITGFRPFLPNWQPVQCVRMWPGTVAHSCNPSTLGGRGRWIS (SEQ ID
NO: 20)

FIG. 10 CONT.

>Human IKKβ isoform 4 (UniProt Accession O14920-4)
MSSDGTIRLTHPNVVAARDVPEGMQNLAPNDLPLLAMEYCQGGDLRKYLNQFENCCGLREGAILT
LLSDIASALRYLHENRIIHRDLKPENIVLQQGEQRLIHKIIDLGYAKELDQGSLCTSFVGTLQYLAPELL
EQQKYTVTVDYWSFGTLAFECITGFRPFLPNWQPVQWHSKVRQKSEVDIVVSEDLNGTVKFSSSL
PYPNNLNSVLAERLEKWLQLMLMWHPRQRGTDPTYGPNGCFKALDDILNLKLVHILNMVTGTIHTY
PVTEDESLQSLKARIQQDTGIPEEDQELLQEAGLALIPDKPATQCISDGKLNEGHTLDMDLVFLFDN
SKITYETQISPRPQPESVSCILQEPKRNLAFFQLRKVWGQVWHSIQTLKEDCNRLQQGQRAAMMN
LLRNNSCLSKMKNSMASMSQQLKAKLDFFKTSIQIDLEKYSEQTEFGITSDKLLLAWREMEQAVEL
CGRENEVKLLVERMMALQTDIVDLQRSPMGRKQGGTLDDLEEQARELYRRLREKPRDQRTEGDS
QEMVRLLLQAIQSFEKKVRVIYTQLSKTVVCKQKALELLPKVEEVVSLMNEDEKTVVRLQEKRQKEL
WNLLKIACSKVRGPVSGSPDSMNASRLSQPGQLMSQPSTASNSLPEPAKKSEELVAEAHNLCTLL
ENAIQDTVREQDQSFTALDWSWLQTEEEEHSCLEQAS (SEQ ID NO: 21)

>Murine IKK β protein (pI=6.20, MW=84387.61, GenBank Accession no. NP_034676.1)
MSWSPSLPTQTCGAWEMKERLGTGGFGNVIRWHNQATGEQIAIKQCRQELSPKNRDRWCLEIQI
MRRLNHPNVVAARDVPEGMQNLAPNDLPLLAMEYCQGGDLRRYLNQFENCCGLREGAVLTLLSD
IASALRYLHENRIIHRDLKPENIVLQQGEKRLIHKIIDLGYAKELDQGSLCTSFVGTLQYLAPELLEQQ
KYTVTVDYWSFGTLAFECITGFRPFLPNWQPVQWHSKVRQKSEVDIVVSEDLNGAVKFSSSLPFP
NNLNSVLAERLEKWLQLMLMWHPRQRGTDPQYGPNGCFRALDDILNLKLVHVLNMVTGTVHTYP
VTEDESLQSLKTRIQEDTGILETDQELLQEAGLVLLPDKPATQCISDSKTNEGLTLDMDLVFLFDNSK
INYETQITPRPQPESVSCILQEPKRNLSFFQLRKVWGQVWHSIQTLKEDCNRLQQGQRAAMMSLL
RNNSCLSKMKNAMASTAQQLKAKLDFFKTSIQIDLEKYKEQTEFGITSDKLLLAWREMEQAVEQCG
RENDVKHLVERMMALQTDIVDLQRSPMGRKQGGTLDDLEEQARELYRRLREKPRDQRTEGDSQE
MVRLLLQAIQSFEKKVRVIYTQLSKTVVCKQKALELLPKVEEVVSLMNEDERTVVRLQEKRQKELW
NLLKIACSKVRGPVSGSPDSMNVSRLSHPGQLMSQPSSACDSLPESDKKSEELVAEAHALCSRLE
SALQDTVKEQDRSFTVTA (SEQ ID NO: 22)

FIG. 10 CONT.

>Human IRF5 isoform 1 cds
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGGTCTGCTCCAATGGC
CCTGCTCCCACAGACTCCCAGCCCCCTGAGGATTACTCTTTTGGTGCAGGAGAGGAGGAGGA
AGAAGAGGAAGAGCTGCAGAGGATGTTGCCAAGCCTGAGCCTCACAGAGGATGTCAAGTGGC
CGCCCACTCTGCAGCCGCCCACTCTGCGGCCGCCTACTCTGCAGCCGCCCACTCTGCAGCC
GCCCGTGGTGCTGGGTCCCCCTGCTCCAGACCCCAGCCCCCTGGCTCCTCCCCCTGGCAAC
CCTGCTGGCTTCAGGGAGCTTCTCTCTGAGGTCCTGGAGCCTGGGCCCCTGCCTGCCAGCCT
GCCCCCTGCAGGCGAACAGCTCCTGCCAGACCTGCTGATCAGCCCCCACATGCTGCCTCTGA
CCGACCTGGAGATCAAGTTTCAGTACCGGGGGCGGCCACCCCGGGCCCTCACCATCAGCAAC
CCCCATGGCTGCCGGCTCTTCTACAGCCAGCTGGAGGCCACCCAGGAGCAGGTGGAACTCTT
CGGCCCCATAAGCCTGGAGCAAGTGCGCTTCCCCAGCCCTGAGGACATCCCCAGTGACAAGC
AGCGCTTCTACACGAACCAGCTGCTGGATGTCCTGGACCGCGGGCTCATCCTCCAGCTACAG
GGCCAGGACCTTTATGCCATCCGCCTGTGTCAGTGCAAGGTGTTCTGGAGCGGGCCTTGTGC
CTCAGCCCATGACTCATGCCCCAACCCCATCCAGCGGGAGGTCAAGACCAAGCTTTTCAGCC
TGGAGCATTTTCTCAATGAGCTCATCCTGTTCCAAAAGGGCCAGACCAACACCCCACCACCCT
TCGAGATCTTCTTCTGCTTTGGGGAAGAATGGCCTGACCGCAAACCCCGAGAGAAGAAGCTCA
TTACTGTACAGGTGGTGCCTGTAGCAGCTCGACTGCTGCTGGAGATGTTCTCAGGGGAGCTAT
CTTGGTCAGCTGATAGTATCCGGCTACAGATCTCAAACCCAGACCTCAAAGACCGCATGGTGG
AGCAATTCAAGGAGCTCCATCACATCTGGCAGTCCCAGCAGCGGTTGCAGCCTGTGGCCCAG
GCCCCTCCTGGAGCAGGCCTTGGTGTTGGCCAGGGGCCCTGGCCTATGCACCCAGCTGGCA
TGCAATAA (SEQ ID NO: 23)

FIG. 10 CONT.

>Human IRF5 isoform 2 cds
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGGTCTGCTCCAATGGC
CCTGCTCCCACAGACTCCCAGCCCCCTGAGGATTACTCTTTTGGTGCAGGAGAGGAGGAGGA
AGAAGAGGAAGAGCTGCAGAGGATGTTGCCAAGCCTGAGCCTCACAGATGCAGTGCAGTCTG
GCCCCCACATGACACCCTATTCTTTACTCAAAGAGGATGTCAAGTGGCCGCCCACTCTGCAGC
CGCCCACTCTGCGGCCGCCTACTCTGCAGCCGCCCACTCTGCAGCCGCCCGTGGTGCTGGG
TCCCCCTGCTCCAGACCCCAGCCCCCTGGCTCCTCCCCCTGGCAACCCTGCTGGCTTCAGGG
AGCTTCTCTCTGAGGTCCTGGAGCCTGGGCCCCTGCCTGCCAGCCTGCCCCCTGCAGGCGAA
CAGCTCCTGCCAGACCTGCTGATCAGCCCCCACATGCTGCCTCTGACCGACCTGGAGATCAA
GTTTCAGTACCGGGGGCGGCCACCCCGGGCCCTCACCATCAGCAACCCCATGGCTGCCGG
CTCTTCTACAGCCAGCTGGAGGCCACCCAGGAGCAGGTGGAACTCTTCGGCCCCATAAGCCT
GGAGCAAGTGCGCTTCCCCAGCCCTGAGGACATCCCCAGTGACAAGCAGCGCTTCTACACGA
ACCAGCTGCTGGATGTCCTGGACCGCGGGCTCATCCTCCAGCTACAGGGCCAGGACCTTTAT
GCCATCCGCCTGTGTCAGTGCAAGGTGTTCTGGAGCGGGCCTTGTGCCTCAGCCCATGACTC
ATGCCCCAACCCCATCCAGCGGGAGGTCAAGACCAAGCTTTTCAGCCTGGAGCATTTTCTCAA
TGAGCTCATCCTGTTCCAAAAGGGCCAGACCAACACCCCACCACCCTTCGAGATCTTCTTCTG
CTTTGGGGAAGAATGGCCTGACCGCAAACCCCGAGAGAAGAAGCTCATTACTGTACAGGTGG
TGCCTGTAGCAGCTCGACTGCTGCTGGAGATGTTCTCAGGGGAGCTATCTTGGTCAGCTGATA
GTATCCGGCTACAGATCTCAAACCCAGACCTCAAAGACCGCATGGTGGAGCAATTCAAGGAG
CTCCATCACATCTGGCAGTCCCAGCAGCGGTTGCAGCCTGTGGCCCAGGCCCCTCCTGGAGC
AGGCCTTGGTGTTGGCCAGGGGCCCTGGCCTATGCACCCAGCTGGCATGCAATAA (SEQ ID
NO: 24)

FIG. 10 CONT.

>Human IRF5 isoform 3 cds (GenBank Accession U51127)
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGGGAAGGCCAACCTGCGCTGTGCCCTTAACAAGAGCCGGGACTTCCGCCTCATCTA
CGACGGGCCCCGGGACATGCCACCTCAGCCCTACAAGATCTACGAGGTCTGCTCCAATGGCC
CTGCTCCCACAGACTCCCAGCCCCCTGAGGATTACTCTTTTGGTGCAGGAGAGGAGGAGGAA
GAAGAGGAAGAGCTGCAGAGGATGTTGCCAAGCCTGAGCCTCACAGATGCAGTGCAGTCTGG
CCCCCACATGACACCCTATTCTTTACTCAAAGAGGATGTCAAGTGGCCGCCCACTCTGCAGCC
GCCCACTCTGCAGCCGCCCGTGGTGCTGGGTCCCCCTGCTCCAGACCCCAGCCCCCTGGCT
CCTCCCCCTGGCAACCCTGCTGGCTTCAGGGAGCTTCTCTCTGAGGTCCTGGAGCCTGGGCC
CCTGCCTGCCAGCCTGCCCCCTGCAGGCGAACAGCTCCTGCCAGACCTGCTGATCAGCCCCC
ACATGCTGCCTCTGACCGACCTGGAGATCAAGTTTCAGTACCGGGGGCGGCCACCCCGGGCC
CTCACCATCAGCAACCCCCATGGCTGCCGGCTCTTCTACAGCCAGCTGGAGGCCACCCAGGA
GCAGGTGGAACTCTTCGGCCCCATAAGCCTGGAGCAAGTGCGCTTCCCCAGCCCTGAGGACA
TCCCCAGTGACAAGCAGCGCTTCTACACGAACCAGCTGCTGGATGTCCTGGACCGCGGGCTC
ATCCTCCAGCTACAGGGCCAGGACCTTTATGCCATCCGCCTGTGTCAGTGCAAGGTGTTCTGG
AGCGGGCCTTGTGCCTCAGCCCATGACTCATGCCCCAACCCCATCCAGCGGGAGGTCAAGAC
CAAGCTTTTCAGCCTGGAGCATTTTCTCAATGAGCTCATCCTGTTCCAAAAGGGCCAGACCAA
CACCCCACCACCCTTCGAGATCTTCTTCTGCTTTGGGGAAGAATGGCCTGACCGCAAACCCCG
AGAGAAGAAGCTCATTACTGTACAGGTGGTGCCTGTAGCAGCTCGACTGCTGCTGGAGATGTT
CTCAGGGGAGCTATCTTGGTCAGCTGATAGTATCCGGCTACAGATCTCAAACCCAGACCTCAA
AGACCGCATGGTGGAGCAATTCAAGGAGCTCCATCACATCTGGCAGTCCCAGCAGCGGTTGC
AGCCTGTGGCCCAGGCCCCTCCTGGAGCAGGCCTTGGTGTTGGCCAGGGGCCCTGGCCTAT
GCACCCAGCTGGCATGCAATAA (SEQ ID NO: 25)

FIG. 10 CONT.

>Human IRF5 isoform 4 cds (GenBank Accession nos. AY504946 or AY504947)
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGGTCTGCTCCAATGGC
CCTGCTCCCACAGACTCCCAGCCCCCTGAGGATTACTCTTTTGGTGCAGGAGAGGAGGAGGA
AGAAGAGGAAGAGCTGCAGAGGATGTTGCCAAGCCTGAGCCTCACAGAGGATGTCAAGTGGC
CGCCCACTCTGCAGCCGCCCACTCTGCAGCCGCCCGTGGTGCTGGGTCCCCCTGCTCCAGA
CCCCAGCCCCCTGGCTCCTCCCCCTGGCAACCCTGCTGGCTTCAGGGAGCTTCTCTCTGAGG
TCCTGGAGCCTGGGCCCCTGCCTGCCAGCCTGCCCCCTGCAGGCGAACAGCTCCTGCCAGA
CCTGCTGATCAGCCCCCACATGCTGCCTCTGACCGACCTGGAGATCAAGTTTCAGTACCGGG
GGCGGCCACCCCGGGCCCTCACCATCAGCAACCCCCATGGCTGCCGGCTCTTCTACAGCCA
GCTGGAGGCCACCCAGGAGCAGGTGGAACTCTTCGGCCCCATAAGCCTGGAGCAAGTGCGC
TTCCCCAGCCCTGAGGACATCCCCAGTGACAAGCAGCGCTTCTACACGAACCAGCTGCTGGA
TGTCCTGGACCGCGGGCTCATCCTCCAGCTACAGGGCCAGGACCTTTATGCCATCCGCCTGT
GTCAGTGCAAGGTGTTCTGGAGCGGGCCTTGTGCCTCAGCCCATGACTCATGCCCCAACCCC
ATCCAGCGGGAGGTCAAGACCAAGCTTTTCAGCCTGGAGCATTTTCTCAATGAGCTCATCCTG
TTCCAAAAGGGCCAGACCAACACCCCACCACCCTTCGAGATCTTCTTCTGCTTTGGGGAAGAA
TGGCCTGACCGCAAACCCCGAGAGAAGAAGCTCATTACTGTACAGGTGGTGCCTGTAGCAGC
TCGACTGCTGCTGGAGATGTTCTCAGGGGAGCTATCTTGGTCAGCTGATAGTATCCGGCTACA
GATCTCAAACCCAGACCTCAAAGACCGCATGGTGGAGCAATTCAAGGAGCTCCATCACATCTG
GCAGTCCCAGCAGCGGTTGCAGCCTGTGGCCCAGGCCCCTCCTGGAGCAGGCCTTGGTGTT
GGCCAGGGGCCCTGGCCTATGCACCCAGCTGGCATGCAATAA (SEQ ID NO: 26)

>Human IRF5 isoform 5 cds
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGGTCTGCTCCAATGGC
CCTGCTCCCACAGACTCCCAGCCCCCTGAGGATTACTCTTTTGGTGCAGGAGAGGAGGAGGA
AGAAGAGGAAGAGCTGCAGAGGATGTTGCCAAGCCTGAGCCTCACAGTGACCGACCTGGAGA
TCAAGTTTCAGTACCGGGGGCGGCCACCCCGGGCCCTCACCATCAGCAACCCCCATGGCTGC
CGGCTCTTCTACAGCCAGCTGGAGGCCACCCAGGAGCAGGTGGAACTCTTCGGCCCCATAAG
CCTGGAGCAAGTGCGCTTCCCCAGCCCTGAGGACATCCCCAGTGACAAGCAGCGCTTCTACA
CGAACCAGCTGCTGGATGTCCTGGACCGCGGGCTCATCCTCCAGCTACAGGGCCAGGACCTT
TATGCCATCCGCCTGTGTCAGTGCAAGGTGTTCTGGAGCGGGCCTTGTGCCTCAGCCCATGA
CTCATGCCCCAACCCCATCCAGCGGGAGGTCAAGACCAAGCTTTTCAGCCTGGAGCATTTTCT
CAATGAGCTCATCCTGTTCCAAAAGGGCCAGACCAACACCCCACCACCCTTCGAGATCTTCTT
CTGCTTTGGGGAAGAATGGCCTGACCGCAAACCCCGAGAGAAGAAGCTCATTACTGTACAGG
TGGTGCCTGTAGCAGCTCGACTGCTGCTGGAGATGTTCTCAGGGGAGCTATCTTGGTCAGCT
GATAGTATCCGGCTACAGATCTCAAACCCAGACCTCAAAGACCGCATGGTGGAGCAATTCAAG
GAGCTCCATCACATCTGGCAGTCCCAGCAGCGGTTGCAGCCTGTGGCCCAGGCCCCTCCTGG
AGCAGGCCTTGGTGTTGGCCAGGGGCCCTGGCCTATGCACCCAGCTGGCATGCAATAA (SEQ
ID NO: 27)

FIG. 10 CONT.

>Human IRF5 isoform 6 cds
ATGAACCAGTCCATCCCAGTGGCTCCCACCCCACCCCGCCGCGTGCGGCTGAAGCCCTGGCT
GGTGGCCCAGGTGAACAGCTGCCAGTACCCAGGGCTTCAATGGGTCAACGGGGAAAAGAAAT
TATTCTGCATCCCCTGGAGGCATGCCACAAGGCATGGTCCCAGCCAGGACGGAGATAACACC
ATCTTCAAGGCCTGGGCCAAGGAGACAGGGAAATACACCGAAGGCGTGGATGAAGCCGATCC
GGCCAAGTGGAAGGCCAACCTGCGCTGTGCCCTTAACAAGAGCCGGGACTTCCGCCTCATCT
ACGACGGGCCCCGGGACATGCCACCTCAGCCCTACAAGATCTACGAGACTCCCAGCCCCCTG
AGGATTACTCTTTTGGTGCAGGAGAGGAGGAGGAAGAAGAGGAAGAGCTGCAGAGGATGTTG
CCAAGCCTGA (SEQ ID NO: 28)

>Murine IRF5 cds (1494nt)
ATGAATCATAGTGCACCCGGGATCCCTCCTCCTCCAAGACGAGTACGCCTCAAGCCCTGGTTG
GTAGCTCAAGTCAACTCATGCCAATACCCTGGGCTTCAGTGGGTGAACGGTGAGAAGAAATTG
TTTTATATCCCATGGCGACACGCAACAAGACATGGCCCATCACAGGATGGAGATAACACCATA
TTTAAGGCATGGGCAAAGGAAACAGGAAAGTACACTGAGGGCGTTGATGAGGCCGATCCTGC
AAAATGGAAAGCAAATTTGCGATGCGCTCTCAATAAATCACGAGATTTCCAACTCTTTTACGAC
GGCCCAAGGGACATGCCACCACAACCTTATAAAATCTACGAGGTATGTTCCAACGGTCCAGCC
CCAACTGAATCCCAGCCTACTGACGACTATGTCCTTGGAGAAGAGGAGGAAGAAGAAGAGGA
GGAACTTCAGCGGATGTTGCCTGGGTTGTCCATAACTGAGCCTGCCTTGCCAGGACCCCCTAA
TGCACCATACTCCCTTCCCAAAGAAGATACAAAATGGCCCCCCGCATTGCAACCCCCCGTTGG
TTTGGGACCACCTGTGCCCGACCCAAATCTCTTGGCCCCACCAAGCGGTAACCCAGCCGGAT
TTCGACAACTTCTGCCCGAAGTCCTTGAGCCAGGTCCCTTGGCCTCTTCTCAGCCCCCTACAG
AACCTCTGCTCCCCGATCTCTTGATATCTCCCCACATGCTTCCCTTGACTGATTTGGAGATAA
AATTTCAGTATCGCGGCCGAGCTCCCAGAACACTGACTATATCAAATCCCCAAGGTTGCCGCC
TGTTTTACAGTCAGTTGGAGGCAACTCAGGAGCAAGTAGAGCTCTTTGGGCCAGTTACTCTGG
AGCAGGTGAGATTCCCTAGTCCAGAGGACATACCAAGCGATAAGCAAAGATTTTACACAAATC
AACTTCTGGATGTACTTGATCGAGGTTTGATCCTTCAGTTGCAGGGCCAAGATTTGTATGCCAT
TCGACTCTGTCAATGCAAGGTATTTTGGAGCGGCCCATGTGCCCTTGCTCATGGCAGCTGCCC
TAATCCCATCCAAAGAGAAGTAAAGACTAAACTTTTCAGCCTGGAACAATTTCTCAACGAACTC
ATTCTGTTTCAAAAAGGTCAGACCAACACACCCCCTCCTTTCGAGATTTTCTTCTGCTTCGGCG
AAGAGTGGCCTGATGTGAAGCCCCGCGAAAAAAAGCTTATCACCGTTCAAGTGGTACCCGTCG
CAGCCAGGCTCCTTCTTGAAATGTTTAGCGGTGAACTCTCATGGTCCGCTGACAGTATCCGGC
TCCAAATATCAAACCCTGATCTTAAAGACCACATGGTAGAACAGTTTAAAGAACTCCACCACC
TGTGGCAATCCCAACAGCAGCTCCAGCCAATGGTTCAAGCTCCTCCAGTCGCTGGGCTGGAC
GCCTCACAAGGACCCTGGCCCATGCACCCCGTCGGGATGCAGTAA (SEQ ID NO: 29)

FIG. 10 CONT.

>Human IRF1 cds
ATGCCCATCACTCGGGATGCGGCATGAGAGACCCTGGCTAGAGATGCAGATTAATTCCAACCAAATC
CCGGGGCTCATCTGGATTAATAAAGAGGAGATGATCTTCCAGATCCCATGGAAGCATGCTGCC
AAGCATGGCTGGGACATCAACAAGGATGCCTGTTGTTCCGGAGCTGGGCCATTCACACAGG
CCGATACAAAGCAGGGGAAAGGAGCCAGATCCCAAGACGTGGAAGGCCAACTTTCGCTGTG
CCATGAACTCCCTGCCAGATATCGAGGAGGTGAAAGACCAGAGACCAGGAGGCAGCTCA
GCTGTGCGAGTGTACCGGATGCTTCCACCTCTCACCAGAGACCAGAGAAAGAAGAAGTCG
AAGTCCAGCCGAGATGCTAAGAGCAAGGCCAAGAGGAAGTCATGTGGGGATTCCAGCCCTGA
TACCTTCTCTGATGGACTACAGCAGCTCCACTCTGCCTGATGACCACAGCAGCTACACAGTTCC
AGGCTACATGCCAGGACTTGGAGGTGGAGCAGGCCCTGACTCCAGCACTGTCGCCCATGTGCTG
TCAGCAGCACTCTCCCCGACTGGCACATCCCAGTGGAAGTTGTGCCGGACAGCACCAGTGAT
CTGTACAACTTCCAGGTGTCACCCATGCCCTCCACCTCTGAAGCTACAACAGATGAGGATGAG
GAAGGGAAATTACCTGAGGACATCATGAAGCTCTTGGAGCAGTCGGAGTGGCAGCCAACAAA
CGTGGATGGGAAGGGGTACCTACTCAATGAACCTGGAGTCCAGCCACCTCTGTCTATGGAG
ACTTTAGCTGTAAGGAGGAGCCAGAAATTGACAGCCCAGGGGGGATATTGGGCTGAGTCTA
CAGCGGTGTCTTCACAGATCTGAAGAACATGGATGCCACCTGGCCACCTGGCTGCTGACCCC
AGTCCGGTTGCCCTCCATCCAGGCCATTCCC
TGTGCACCGTAG (SEQ ID NO: 30)

FIG. 10 CONT.

\>Human IRF3 isoform 1 cds (NM_001571.5)
ATGGGAACCCCAAAGCCACGGATCCTGCCCTGGCTGGTGTCGCAGCTGGACCTGGGGCAACT
GGAGGGCGTGGCCTGGGTGAACAAGAGCCGCACG
CGCTTCCGCATCCCTTGGAAGCACGGC
CTACGGCAGGATGCACAGCAGGAGGATTTCGGAATCTTCCAGGCCTGGGCCGAGGCCACTGG
TGCATATGTTCCCGGGAGGGATAAGCCAGACCTGCCAACCTGGAAGAGGAATTTCCGCTCTG
CCCTCAACCGCAAAGAAGGGTTGCGTTTAGCAGAGGACCGGAGCAAGGACCCTCACGACCCA
CATAAAATCTACGAGTTTGTGAACTCAGGAGTTGGGGACTTTTCCCAGCCAGACACCTCTCCG
GACACCAATGGTGGAGGCAGTACTTCTGATACCCAGGAAGACATTCTGGATGAGTTACTGGGT
AACATGGTGTTGGCCCCACTCCCAGATCCGGGACCCCCAAGCCTGGCTGTAGCCCCTGAGCC
CTGCCCTCAGCCCCTGCGGAGCCCCAGCTTGGACAATCCCACTCCCTTCCCAAACCTGGGGC
CCTCTGAGAACCCACTGAAGCGGCTGTTGGTGCCGGGGGAAGAGTGGGAGTTCGAGGTGAC
AGCCTTCTACCGGGGCCGCCAAGTCTTCCAGCAGACCATCTCCTGCCCGGAGGGCCTGCGG
CTGGTGGGGTCCGAAGTGGGAGACAGGACGCTGCCTGGATGGCCAGTCACACTGCCAGACC
CTGGCATGTCCCTGACAGACAGGGGAGTGATGAGCTACGTGAGGCATGTGCTGAGCTGCCTG
GGTGGGGGACTGGCTCTCTGGCGGGCCGGGCAGTGGCTCTGGGCCCAGCGGCTGGGGCAC
TGCCACACATACTGGGCAGTGAGCGAGGAGCTGCTCCCCAACAGCGGGCATGGGCCTGATG
GCGAGGTCCCCAAGGACAAGGAAGGAGGCGTGTTTGACCTGGGGCCCTTCATTGTAGATCTG
ATTACCTTCACGGAAGGAAGCGGACGCTCACCACGCTATGCCCTCTGGTTCTGTGTGGGGGA
GTCATGGCCCCAGGACCAGCCGTGGACCAAGAGGCTCGTGATGGTCAAGGTTGTGCCCACGT
GCCTCAGGGCCTTGGTAGAAATGGCCCGGGTAGGGGGTGCCTCCTCCCTGGAGAATACTGTG
GACCTGCACATTTCCAACAGCCACCCACTCTCCCTCACCTCCGACCAGTACAAGGCCTACCTG
CAGGACTTGGTGGAGGGCATGGATTTCCAGGGCCCTGGGGAGAGCTGA (SEQ ID NO: 31)

\>Human IRF7 isoform A cds (NM_001572.3)
ATGGCCTTGGCTCCTGAGAGGGCAGCCCCACGCGTGCTGTTCGGAGAGTGGCTCCTTGGAGA
GATCAGCAGCGGCTGCTATGAGGGGCTGCAGTGGCTGGACGAGGCCCGCACCTGTTTCCGC
GTGCCCTGGAAGCACTTCGCGCGCAAGGACCTGAGCGAGGCCGACGCGCGCATCTTCAAGG
CCTGGGCTGTGGCCCGCGGCAGGTGGCCGCCTAGCAGCAGGGGAGGTGGCCCGCCCCCCG
AGGCTGAGACTGCGGAGCGCGCCGGCTGGAAAACCAACTTCCGCTGCGCACTGCGCAGCAC
GCGTCGCTTCGTGATGCTGCGGGATAACTCGGGGGGACCCGGCCGACCCGCACAAGGTGTAC
GCGCTCAGCCGGGAGCTGTGCTGGCGAGAAGGCCCAGGCACGGACCAGACTGAGGCAGAG
GCCCCGCAGCTGTCCCACCACCACAGGGTGGGCCCCCAGGGCCATTCCTGGCACACACAC
ATGCTGGACTCCAAGCCCCAGGCCCCCTCCCTGCCCCAGCTGGTGACAAGGGGGACCTCCT
GCTCCAGGCAGTGCAACAGAGCTGCCTGGCAGACCATCTGCTGACAGCGTCATGGGGGGGCA
GATCCAGTCCCAACCAAGGCTCCTGGAGAGGGACAAGAAGGGCTTCCCCTGACTGGGGCCTG
TGCTGGAGGCCCAGGGCTCCCTGCTGGGGAGCTGTACGGGTGGGCAGTAGAGACGACCCCC
AGCCCCGGGCCCCAGCCCGCGGCACTAACGACAGGCGAGGCCGCGGCCCCAGAGTCCCCG
CACCAGGCAGAGCCGTACCTGTCACCCTCCCCAAGCGCCTGCACCGCGGTGCAAGAGCCCA
GCCCAGGGGCGCTGGACGTGACCATCATGTACAAGGGCCGCACGGTGCTGCAGAAGGTGGT
GGGACACCCGAGCTGCACGTTCCTATACGGCCCCCAGACCCAGCTGTCCGGGCCACAGAC
CCCCAGCAGGTAGCATTCCCCAGCCCTGCCGAGCTCCCGGACCAGAAGCAGCTGCGCTACA
CGGAGGAACTGCTGCGGCACGTGGCCCCTGGGTTGCACCTGGAGCTTCGGGGGCCACAGCT
GTGGGCCCGGCGCATGGGCAAGTGCAAGGTGTACTGGGAGGTGGGCGGACCCCCAGGCTCC
GCCAGCCCCTCCACCCCAGCCTGCCTGCTGCCTCGGAACTGTGACACCCCCATCTTCGACTT
CAGAGTCTTCTTCCAAGAGCTGGTGGAATTCCGGGCACGGCAGCGCCGTGGCTCCCCACGCT
ATACCATCTACCTGGGCTTCGGGCAGGACCTGTCAGCTGGGAGGCCCAAGGAGAAGAGCCTG
GTCCTGGTGAAGCTGGAACCCTGGCTGTGCCGAGTGCACCTAGAGGGCACGCAGCGTGAGG
GTGTGTCTTCCCTGGATAGCAGCAGCCTCAGCCTCTGCCTGTCCAGCGCCAACAGCCTCTAT
GACGACATCGAGTGCTTCCTTATGGAGCTGGAGCAGCCCGCCTAG (SEQ ID NO: 32)

FIG. 10 CONT.

>Human IRF8 cds
ATGTGTGACCGGAATGGTGGTCGGCGGCTTCGACAGTGGCTGATCGAGCAGATTGACAGTAG
CATGTATCCAGGACTGATTTGGGAGAATGAGGAGAAGAGCATGTTCCGGATCCCTTGGAAACA
CGCTGGCAAGCAAGATTATAATCAGGAAGTGGATGCCTCCATTTTTAAGGCCTGGGCAGTTTT
TAAAGGGAAGTTTAAAGAAGGGGACAAAGCTGAACCAGCCACTTGGAAGACGAGGTTACGCT
GTGCTTTGAATAAGAGCCCAGATTTTGAGGAAGTGACGGACCGGTCCCAACTGGACATTTCCG
AGCCATACAAAGTTTACCGAATTGTTCCTGAGGAAGAGCAAAAATGCAAACTAGGCGTGGCAA
CTGCTGGCTGCGTGAATGAAGTTACAGAGATGGAGTGCGGTCGCTCTGAAATCGACGAGCTG
ATCAAGGAGCCTTCTGTGGACGATTACATGGGGATGATCAAAAGGAGCCCTTCCCCGCCGGA
GGCCTGTCGGAGTCAGCTCCTTCCAGACTGGTGGGCGCAGCAGCCCAGCACAGGCGTGCCG
CTGGTGACGGGGTACACCACCTACGACGCGCACCATTCAGCATTCTCCCAGATGGTGATCAG
CTTCTACTATGGGGGCAAGCTGGTGGGCCAGGCCACCACCACCTGCCCCGAGGGCTGCCGC
CTGTCCCTGAGCCAGCCTGGGCTGCCCGGCACCAAGCTGTATGGGCCCGAGGGCCTGGAGC
TGGTGCGCTTCCCGCCGGCCGACGCCATCCCCAGCGAGCGACAGAGGCAGGTGACGCGGAA
GCTGTTCGGGCACCTGGAGCGCGGGGTGCTGCTGCACAGCAGCCGGCAGGGCGTGTTCGTC
AAGCGGCTGTGCCAGGGCCGCGTGTTCTGCAGCGGCAACGCCGTGGTGTGCAAAGGCAGGC
CCAACAAGCTGGAGCGTGATGAGGTGGTCCAGGTCTTCGACACCAGCCAGTTCTTCCGAGAG
CTGCAGCAGTTCTATAACAGCCAGGGCCGGCTTCCTGACGGCAGGGTGGTGCTGTGCTTTGG
GGAAGAGTTTCCGGATATGGCCCCCTTGCGCTCCAAACTCATTCTCGTGCAGATTGAGCAGCT
GTATGTCCGGCAACTGGCAGAAGAGGCTGGGAAGAGCTGTGGAGCCGGCTCTGTGATGCAG
GCCCCCGAGGAGCCGCCGCCAGACCAGGTCTTCCGGATGTTTCCAGATATTTGTGCCTCACA
CCAGAGATCATTTTTCAGAGAAAACCAACAGATCACCGTCTAA (SEQ ID NO: 33)

>Murine IRF1 cds (NM_001159396.1)
ATGCCAATCACTCGAATGCGGATGAGACCCTGGCTAGAGATGCAGATTAATTCCAACCAAATC
CCAGGGCTGATCTGGATCAATAAAGAAGAGATGATCTTCCAGATTCCATGGAAGCACGCTGCT
AAGCACGGCTGGGACATCAACAAGGATGCCTGTCTGTTCCGGAGCTGGGCCATTCACACAGG
CCGATACAAAGCAGGAGAAAAAGAGCCAGATCCCAAGACATGGAAGGCAAACTTCCGTTGTG
CCATGAACTCCCTGCCAGACATCGAGGAAGTGAAGGATCAGAGTAGGAACAAGGGCAGCTCT
GCTGTGCGGGTGTACCGGATGCTGCCACCCCTCACCAGGAACCAGAGGAAAGAGAGAAAGTC
CAAGTCCAGCCGAGACACTAAGAGCAAAACCAAGAGGAAGCTGTGTGGAGATGTTAGCCCGG
ACACTTTCTCTGATGGACTCAGCAGCTCTACCCTACCTGATGACCACAGCAGTTACACCACTC
AGGGCTACCTGGGTCAGGACTTGGATATGGAAAGGGACATAACTCCAGCACTGTCACCGTGT
GTCGTCAGCAGCAGTCTCTCTGAGTGGCATATGCAGATGGACATTATACCAGATAGCACCACT
GATCTGTATAACCTACAGGTGTCACCCATGCCTTCCACCTCCGAAGCCGCAACAGACGAGGAT
GAGGAAGGGAAGATAGCCGAAGACCTTATGAAGCTCTTTGAACAGTCTGAGTGGCAGCCGAC
ACACATCGATGGCAAGGGATACTTGCTCAATGAGCCAGGGACCCAGCTCTCTTCTGTCTATGG
AGACTTCAGCTGCAAAGAGGAACCAGAGATTGACAGCCCTCGAGGGGACATTGGGATAGGCA
TACAACATGTCTTCACGGAGATGAAGAATATGGACTCCATCATGTGGATGGACAGCCTGCTGG
GCAACTCTGTGAGGCTGCCGCCCTCTATTCAGGCCATTCCTTGTGCACCATAG (SEQ ID NO:
34)

FIG. 10 CONT.

>Murine IRF3 cds (NM_016849.4)
ATGGAAACCCCGAAACCGCGGATTTTGCCCTGGCTGGTGTCACAGCTGGACCTGGGGCAGCT
GGAAGGCGTGGCCTGGCTGGACGAGAGCCGAACGAGGTTCAGGATCCCGTGGAAGCATGGC
CTACGGCAGGACGCACAGATGGCTGACTTTGGCATCTTCCAGGCCTGGGCAGAAGCCAGTGG
TGCCTACACCCCGGGGAAGGATAAGCCGGACGTGTCAACCTGGAAGAGGAATTTCCGGTCAG
CCCTGAACCGGAAAGAAGTGTTGCGGTTAGCTGCTGACAATAGCAAGGACCCTTATGACCCTC
ATAAAGTGTATGAGTTTGTGACTCCAGGGGCGCGGGACTTCGTACATCTGGGTGCCTCTCCTG
ACACCAATGGCAAAAGCAGCCTGCCTCACTCCCAGGAAAACCTACCGAAGTTATTTGATGGCC
TGATCTTGGGGCCCCTCAAAGATGAGGGGTCCTCAGATCTGGCTATTGTTTCTGATCCTTCTC
AACAACTGCCAAGCCCCAATGTGAACAACTTCCTAAACCCTGCACCCCAAGAAAATCCACTGA
AGCAGCTGCTAGCTGAGGAACAATGGGAGTTCGAGGTGACCGCCTTCTACCGAGGCCGCCAG
GTCTTCCAGCAGACACTCTTTTGCCCGGGGGGCCTGCGGCTGGTGGGCAGCACAGCTGACAT
GACACTGCCCTGGCAGCCAGTCACCCTGCCCGATCCTGAGGGGTTTCTGACGGACAAGCTTG
TGAAGGAGTACGTGGGGCAGGTGCTCAAAGGGCTGGGCAATGGGCTGGCACTGTGGCAGGC
TGGGCAGTGCCTCTGGGCCCAGCGCCTAGGCCACTCCCACGCCTTCTGGGCTCTGGGGGAG
GAGCTGCTTCCAGACAGTGGGCGAGGGCCTGATGGAGAGGTCCACAAGGACAAGGACGGAG
CCGTGTTCGACCTCAGGCCCTTCGTGGCAGATCTGATTGCCTTCATGGAAGGAAGTGGACACT
CCCCACGCTACACTCTGTGGTTCTGCATGGGGGAAATGTGGCCCCAGGACCAGCCATGGGTC
AAGAGGCTTGTGATGGTCAAGGTTGTTCCTACATGTCTTAAGGAGCTGTTAGAGATGGCCCGG
GAAGGGGGAGCCTCTTCACTGAAAACCGTGGACTTGCACATCTCCAACAGCCAGCCTATCTCC
CTTACCTCTGACCAGTACAAGGCCTACCTCCAGGACTTGGTGGAGGACATGGACTTCCAGGC
CACTGGAAATATCTGA (SEQ ID NO: 35)

>Murine IRF7 cds (NM_016850.3)
ATGGCTGAAGTGAGGGGGGTCCAGCGAGTGCTGTTTGGAGACTGGCTATTGGGGGAGGTCAG
CAGCGGCCAGTACGAGGGGCTGCAGTGGCTGAACGAGGCTCGCACAGTCTTCCGCGTACCC
TGGAAGCATTTCGGTCGTAGGGATCTGGATGAAGAAGATGCACAGATCTTCAAGGCCTGGGCT
GTGGCCCGAGGGAGGTGGCCACCTAGTGGAGTTAACCTGCCACCCCCAGAGGCTGAGGCTG
CTGAGCGAAGAGAGCGAAGAGGCTGGAAGACCAACTTCCGCTGTGCACTCCACAGCACAGGG
CGTTTTATCTTGCGCCAAGACAATTCAGGGGATCCAGTTGATCCGCATAAGGTGTACGAACTT
AGCCGGGAGCTTGGATCTACTGTGGGCCCAGCCACGGAAAATAGGGAAGAAGTGAGCCTCAG
CAATGCTCTGCCCACACAGGGTGTGTCCCCAGGATCATTTCTGGCAAGAGAAAATGCTGGGCT
CCAAACCCCAAGCCCTCTGCTTTCTAGTGATGCCGGGGACCTCTTGCTTCAGGTTCTGCAGTA
CAGCCACATACTGGAATCCGAGTCTGGGGCAGACCCCGTCCCACCACAGGCTCCTGGCCAGG
AGCAAGACCGTGTTTACGAGGAACCCTATGCAGCATGGCAGGTGGAAGCTGTCCCCAGTCCC
AGGCCTCAACAGCCAGCTCTCACCGAGCGCAGCCTTGGGTTCCTGGATGTGACCATCATGTA
CAAGGGCCGCACAGTGCTACAGGCAGTGGTGGGGCACCCCAGATGCGTGTTCCTGTACAGC
CCCATGGCCCCAGCAGTAAGAACTTCAGAGCCCCAGCCGGTGATCTTTCCCAGTCCTGCTGA
GCTCCCAGATCAGAAGCAGCTGCACTACACAGAGACGCTTCTCCAGCATGTGTCTCCCGGCC
TTCAGCTGGAGCTTCGAGGACCGTCACTGTGGGCCCTGCGTATGGGCAAGTGCAAGGTGTAC
TGGGAGGTAGGCAGCCCTATGGGCACTACCGGCCCCTCCACCCCACCCCAGCTGCTGGAGC
GCAACCGCCACACCCCCATCTTCGACTTCAGCACTTTCTTCCGAGAACTGGAGGAGTTTCGGG
CTCGGAGGCGGCAAGGGTCACCACACTACACCATCTACCTGGGTTTTGGGCAAGACTTGTCA
GCAGGGAGGCCCAAGGAGAAGACCCTGATCCTGGTGAAGCTGGAGCCATGGGTATGCAAGG
CATACCTGGAGGGCGTGCAGCGTGAGGGTGTGTCCTCCCTGGACAGCAGCAGTCTCGGCTTG
TGCTTGTCTAGCACCAACAGTCTCTACGAAGACATCGAACACTTCCTCATGGACCTGGGTCAG
TGGCCTTGA (SEQ ID NO: 36)

FIG. 10 CONT.

>Murine IRF-7/IRF-3 5(D) cds (1578 nt)
ATGGCCGAAGTTCGAGGAGTACAGCGCGTGCTGTTTGGGGACTGGTTGCTTGGTGAAGTCTC
TTCTGGTCAGTATGAAGGCCTGCAATGGCTTAATGAGGCACGCACAGTTTTTCGAGTGCCATG
GAAACACTTCGGTAGGCGCGATCTCGACGAAGAGGATGCCCAGATTTTCAAGGCATGGGCAG
TCGCACGGGGCAGGTGGCCCCCTTCAGGCGTAAATTTGCCCCCCCCAGAGGCTGAAGCTGCT
GAACGCAGAGAACGCCGGGGATGGAAGACTAACTTTCGATGTGCCCTTCACAGTACAGGCAG
GTTCATCTTGCGGCAGGATAATAGTGGCGACCCTGTAGACCCACACAAGGTTTATGAGCTGAG
CCGGGAGCTTGGCTCAACAGTCGGTCCTGCAACCGAGAACAGAGAAGAGGTGTCCTTGTCTA
ACGCCCTCCCAACTCAGGGTGTGTCTCCCGGTAGCTTCCTGGCACGCGAAAACGCTGGACTC
CAAACCCCCTCCCCACTGTTGTCCAGTGATGCCGGTGATCTTCTCCTTCAGGTGCTCCAATAC
TCCCATATACTGGAGAGCGAGTCAGGGGCTGATCCCGTGCCCCCTCAAGCTCCTGGACAGGA
ACAAGATCGCGTCTACGAGGAGCCATATGCTGCCTGGCAGGTCGAGGCTGTGCCATCACCTC
GGCCTCAACAGCCCGCTCTCACCGAGCGCTCACTTGGGTTTTTGGATGTCACTAAACTTTTCG
ACGGCCTGATACTTGGCCCATTGAAGGACGAGGGATCATCCGATCTTGCCATAGTAAGTGACC
CATCACAGCAGTTGCCCTCACCAAACGTCAACAACTTCCTCAATCCAGCTCCCCAGGAGAACC
CCCTCAAACAGCTTCTCGCAGAAGAGCAATGGGAGTTTGAGGTGACTGCTTTCTATAGAGGTA
GGCAGGTGTTCCAACAAACTCTGTTTTGCCCCGGAGGTCTGCGCCTTGTAGGTAGCACCGCA
GACATGACACTTCCCTGGCAACCTGTGACACTTCCCGATCCTGAGGGATTTCTCACAGATAAA
CTCGTTAAGGAATATGTGGGGCAAGTACTCAAAGGTCTGGGCAATGGGTTGGCCCTTTGGCAA
GCTGGTCAATGTCTCTGGGCTCAACGACTCGGGCACTCACATGCTTTTTGGGCTCTTGGCGAG
GAGCTGCTCCCCGACAGCGGGCGCGGACCTGACGGGGAGGTTCATAAGGACAAAGACGGCG
CCGTATTTGATCTTAGACCCTTCGTGGCAGATCTGATCGCTTTCATGGAAGGATCAGGTCATAG
CCCCAGGTACACACTTTGGTTTTGCATGGGTGAAATGTGGCCTCAGGACCAACCTTGGGTCAA
GCGCTTGGTCATGGTTAAGGTGGTTCCCACTTGCCTCAAAGAGTTGTTGGAGATGGCTAGGGA
AGGTGGGGCTTCCTCACTGAAAACCGTAGATCTCCACATTGATAATGATCAGCCTATAGATTT
GGACGACGACCAATACAAAGCTTATCTCCAGGACCTGGTTGAAGATATGGACTTTCAGGCTAC
AGGTAACATCTAA (SEQ ID NO: 37)

FIG. 10 CONT.

>Murine IRF8 cds (SEQ ID NO: 38)
ATGTGTGACAGGAACGGCGGTAGAAGACTGAGACAGTGGCTGATCGAGCAAATTGACAGCTC
AATGTACCCTGGGTTGATATGGGAAAACGATGAAAAGACAATGTTCAGAATACCCTGGAAGCA
CGCTGGAAAGCAGGATTACAACCAGGAAGTGGACGCCAGTATTTTTAAGGCTTGGGCTGTCTT
CAAAGGGAAGTTTAAAGAGGGCGACAAAGCAGAGCCAGCAACCTGGAAAACCCGCTTGAGGT
GTGCACTCAATAAGTCACCCGACTTCGAGGAAGTCACTGACCGCAGTCAATTGGACATATCAG
AACCATACAAAGTCTACAGGATAGTCCCCGAAGAAGAGCAGAAATGCAAACTCGGTGTAGCAC
CTGCTGGCTGTATGAGTGAAGTGCCTGAAATGGAATGCGGCAGATCAGAAATCGAAGAACTCA
TAAAAGAACCAAGTGTAGATGAGTATATGGGAATGACCAAAAGATCCCCATCCCCCCCAGAAG
CCTGTCGGAGCCAAATCTTGCCTGACTGGTGGGTACAGCAACCCTCCGCCGGACTTCCCCTT
GTGACAGGCTATGCCGCTTACGATACTCATCACAGCGCTTTTAGCCAGATGGTTATTTCCTTC
TATTATGGAGGAAAACTGGTCGGCCAAGCCACAACCACCTGCCTCGAGGGGTGTCGCTTGAG
TTTGAGTCAACCCGGTCTTCCCAAACTCTATGGCCCCGATGGGCTTGAACCTGTCTGCTTTCC
CACTGCTGATACTATTCCCTCAGAGAGACAACGACAAGTCACCCGAAAATTGTTTGGCCACCT
CGAGAGGGGAGTACTCTTGCACTCTAACAGGAAGGGTGTCTTTGTGAAACGCCTCTGTCAAGG
TAGGGTATTCTGTTCTGGAAATGCAGTTGTTTGCAAAGGCAGGCCTAACAAACTGGAACGGGA
TGAAGTCGTACAAGTGTTCGATACCAATCAGTTTATTCGGGAGTTGCAGCAGTTTTACGCTACA
CAAAGTCGCCTCCCTGACAGTCGGGTTGTGTTGTGCTTCGGGGAGGAGTTTCCCGACACTGT
ACCCCTCCGAAGCAAACTCATACTGGTACAGGTAGAACAACTTTATGCCAGGCAACTGGTGGA
AGAGGCCGGTAAGTCCTGTGGCGCAGGATCCCTGATGCCAGCCCTGGAAGAGCCCCAGCCT
GACCAAGCATTTAGGATGTTTCCCGACATTTGTACCTCACACCAGAGGCCTTTTTTCCGCGAAA
ACCAGCAGATAACCGTGTAA (SEQ ID NO: 38)

>Murine IRF8 K310R cds (1275 nt)
ATGTGTGACAGGAACGGCGGTAGAAGACTGAGACAGTGGCTGATCGAGCAAATTGACAGCTC
AATGTACCCTGGGTTGATATGGGAAAACGATGAAAAGACAATGTTCAGAATACCCTGGAAGCA
CGCTGGAAAGCAGGATTACAACCAGGAAGTGGACGCCAGTATTTTTAAGGCTTGGGCTGTCTT
CAAAGGGAAGTTTAAAGAGGGCGACAAAGCAGAGCCAGCAACCTGGAAAACCCGCTTGAGGT
GTGCACTCAATAAGTCACCCGACTTCGAGGAAGTCACTGACCGCAGTCAATTGGACATATCAG
AACCATACAAAGTCTACAGGATAGTCCCCGAAGAAGAGCAGAAATGCAAACTCGGTGTAGCAC
CTGCTGGCTGTATGAGTGAAGTGCCTGAAATGGAATGCGGCAGATCAGAAATCGAAGAACTCA
TAAAAGAACCAAGTGTAGATGAGTATATGGGAATGACCAAAAGATCCCCATCCCCCCCAGAAG
CCTGTCGGAGCCAAATCTTGCCTGACTGGTGGGTACAGCAACCCTCCGCCGGACTTCCCCTT
GTGACAGGCTATGCCGCTTACGATACTCATCACAGCGCTTTTAGCCAGATGGTTATTTCCTTC
TATTATGGAGGAAAACTGGTCGGCCAAGCCACAACCACCTGCCTCGAGGGGTGTCGCTTGAG
TTTGAGTCAACCCGGTCTTCCCAAACTCTATGGCCCCGATGGGCTTGAACCTGTCTGCTTTCC
CACTGCTGATACTATTCCCTCAGAGAGACAACGACAAGTCACCCGAAAATTGTTTGGCCACCT
CGAGAGGGGAGTACTCTTGCACTCTAACAGGAAGGGTGTCTTTGTGAAACGCCTCTGTCAAGG
TAGGGTATTCTGTTCTGGAAATGCAGTTGTTTGCAAAGGCAGGCCTAACAGACTGGAACGGGA
TGAAGTCGTACAAGTGTTCGATACCAATCAGTTTATTCGGGAGTTGCAGCAGTTTTACGCTACA
CAAAGTCGCCTCCCTGACAGTCGGGTTGTGTTGTGCTTCGGGGAGGAGTTTCCCGACACTGT
ACCCCTCCGAAGCAAACTCATACTGGTACAGGTAGAACAACTTTATGCCAGGCAACTGGTGGA
AGAGGCCGGTAAGTCCTGTGGCGCAGGATCCCTGATGCCAGCCCTGGAAGAGCCCCAGCCT
GACCAAGCATTTAGGATGTTTCCCGACATTTGTACCTCACACCAGAGGCCTTTTTTCCGCGAAA
ACCAGCAGATAACCGTGTAA (SEQ ID NO: 39)

FIG. 10 CONT.

>Human IKKβ isoform 1 cds
ATGAGCTGGTCACCTTCCCTGACAACGCAGACATGTGGGGCCTGGGAAATGAAAGAGCGCCT
TGGGACAGGGGGATTTGGAAATGTCATCCGATGGCACAATCAGGAAACAGGTGAGCAGATTG
CCATCAAGCAGTGCCGGCAGGAGCTCAGCCCCCGGAACCGAGAGCGGTGGTGCCTGGAGAT
CCAGATCATGAGAAGGCTGACCCACCCCAATGTGGTGGCTGCCCGAGATGTCCCTGAGGGGA
TGCAGAACTTGGCGCCCAATGACCTGCCCCTGCTGGCCATGGAGTACTGCCAAGGAGGAGAT
CTCCGGAAGTACCTGAACCAGTTTGAGAACTGCTGTGGTCTGCGGGAAGGTGCCATCCTCAC
CTTGCTGAGTGACATTGCCTCTGCGCTTAGATACCTTCATGAAAACAGAATCATCCATCGGGA
TCTAAAGCCAGAAAACATCGTCCTGCAGCAAGGAGAACAGAGGTTAATACACAAAATTATTGAC
CTAGGATATGCCAAGGAGCTGGATCAGGGCAGTCTTTGCACATCATTCGTGGGGACCCTGCA
GTACCTGGCCCCAGAGCTACTGGAGCAGCAGAAGTACACAGTGACCGTCGACTACTGGAGCT
TCGGCACCCTGGCCTTTGAGTGCATCACGGGCTTCCGGCCCTTCCTCCCCAACTGGCAGCCC
GTGCAGTGGCATTCAAAAGTGCGGCAGAAGAGTGAGGTGGACATTGTTGTTAGCGAAGACTTG
AATGGAACGGTGAAGTTTTCAAGCTCTTTACCCTACCCCAATAATCTTAACAGTGTCCTGGCT
GAGCGACTGGAGAAGTGGCTGCAACTGATGCTGATGTGGCACCCCCGACAGAGGGGCACGG
ATCCCACGTATGGGCCCAATGGCTGCTTCAAGGCCCTGGATGACATCTTAAACTTAAAGCTGG
TTCATATCTTGAACATGGTCACGGGCACCATCCACACCTACCCTGTGACAGAGGATGAGAGTC
TGCAGAGCTTGAAGGCCAGAATCCAACAGGACACGGGCATCCCAGAGGAGGACCAGGAGCT
GCTGCAGGAAGCGGGCCTGGCGTTGATCCCCGATAAGCCTGCCACTCAGTGTATTTCAGACG
GCAAGTTAAATGAGGGCCACACATTGGACATGGATCTTGTTTTTCTCTTTGACAACAGTAAAAT
CACCTATGAGACTCAGATCTCCCCACGGCCCCAACCTGAAAGTGTCAGCTGTATCCTTCAAGA
GCCCAAGAGGAATCTCGCCTTCTTCCAGCTGAGGAAGGTGTGGGGCCAGGTCTGGCACAGCA
TCCAGACCCTGAAGGAAGATTGCAACCGGCTGCAGCAGGGACAGCGAGCCGCCATGATGAAT
CTCCTCCGAAACAACAGCTGCCTCTCCAAAATGAAGAATTCCATGGCTTCCATGTCTCAGCAG
CTCAAGGCCAAGTTGGATTTCTTCAAAACCAGCATCCAGATTGACCTGGAGAAGTACAGCGAG
CAAACCGAGTTTGGGATCACATCAGATAAACTGCTGCTGGCCTGGAGGGAAATGGAGCAGGC
TGTGGAGCTCTGTGGGCGGGAGAACGAAGTGAAACTCCTGGTAGAACGGATGATGGCTCTGC
AGACCGACATTGTGGACTTACAGAGGAGCCCCATGGGCCGGAAGCAGGGGGGAACGCTGGA
CGACCTAGAGGAGCAAGCAAGGGAGCTGTACAGGAGACTAAGGGAAAAACCTCGAGACCAGC
GAACTGAGGGTGACAGTCAGGAAATGGTACGGCTGCTGCTTCAGGCAATTCAGAGCTTCGAG
AAGAAAGTGCGAGTGATCTATACGCAGCTCAGTAAAACTGTGGTTTGCAAGCAGAAGGCGCTG
GAACTGTTGCCCAAGGTGGAAGAGGTGGTGAGCTTAATGAATGAGGATGAGAAGACTGTTGTC
CGGCTGCAGGAGAAGCGGCAGAAGGAGCTCTGGAATCTCCTGAAGATTGCTTGTAGCAAGGT
CCGTGGTCCTGTCAGTGGAAGCCCGGATAGCATGAATGCCTCTCGACTTAGCCAGCCTGGGC
AGCTGATGTCTCAGCCCTCCACGGCCTCCAACAGCTTACCTGAGCCAGCCAAGAAGAGTGAA
GAACTGGTGGCTGAAGCACATAACCTCTGCACCCTGCTAGAAAATGCCATACAGGACACTGTG
AGGGAACAAGACCAGAGTTTCACGGCCCTAGACTGGAGCTGGTTACAGACGGAAGAAGAAGA
GCACAGCTGCCTGGAGCAGGCCTCATGA (SEQ ID NO: 40)

FIG. 10 CONT.

>Human IKKβ isoform 2 cds
ATGTTTTCAGGGGGGGTGTCATAGCCCCGGGTTTGGCCGCCCCAGCCCCGCCTTCCCCGCCCC
GGGGAGCCCGCCCCCTGCCCCGCGTCCCTGCCGACAGGAAACAGGTGAGCAGATTGCCATC
AAGCAGTGCCGGCAGGAGCTCAGCCCCCGGAACCGAGAGCGGTGGTGCCTGGAGATCCAGA
TCATGAGAAGGCTGACCCACCCCAATGTGGTGGCTGCCCGAGATGTCCCTGAGGGGATGCAG
AACTTGGCGCCCAATGACCTGCCCCTGCTGGCCATGGAGTACTGCCAAGGAGGAGATCTCCG
GAAGTACCTGAACCAGTTTGAGAACTGCTGTGGTCTGCGGGAAGGTGCCATCCTCACCTTGCT
GAGTGACATTGCCTCTGCGCTTAGATACCTTCATGAAAACAGAATCATCCATCGGGATCTAAA
GCCAGAAACATCGTCCTGCAGCAAGGAGAACAGAGGTTAATACACAAAATTATTGACCTAGG
ATATGCCAAGGAGCTGGATCAGGGCAGTCTTTGCACATCATTCGTGGGGACCCTGCAGTACCT
GGCCCCAGAGCTACTGGAGCAGCAGAAGTACACAGTGACCGTCGACTACTGGAGCTTCGGCA
CCCTGGCCTTTGAGTGCATCACGGGCTTCCGGCCCTTCCTCCCCAACTGGCAGCCCGTGCAG
TGGCATTCAAAAGTGCGGCAGAAGAGTGAGGTGGACATTGTTGTTAGCGAAGACTTGAATGGA
ACGGTGAAGTTTTCAAGCTCTTTACCCTACCCCAATAATCTTAACAGTGTCCTGGCTGAGCGA
CTGGAGAAGTGGCTGCAACTGATGCTGATGTGGCACCCCCGACAGAGGGGCACGGATCCCA
CGTATGGGCCCAATGGCTGCTTCAAGGCCCTGGATGACATCTTAAACTTAAAGCTGGTTCATA
TCTTGAACATGGTCACGGGCACCATCCACACCTACCCTGTGACAGAGGATGAGAGTCTGCAGA
GCTTGAAGGCCAGAATCCAACAGGACACGGGCATCCCAGAGGAGGACCAGGAGCTGCTGCA
GGAAGCGGGCCTGGCGTTGATCCCCGATAAGCCTGCCACTCAGTGTATTTCAGACGGCAAGT
TAAATGAGGGCCACACATTGGACATGGATCTTGTTTTTCTCTTTGACAACAGTAAAATCACCT
ATGAGACTCAGATCTCCCCACGGCCCCAACCTGAAAGTGTCAGCTGTATCCTTCAAGAGCCCA
AGAGGAATCTCGCCTTCTTCCAGCTGAGGAAGGTGTGGGGCCAGGTCTGGCACAGCATCCAG
ACCCTGAAGGAAGATTGCAACCGGCTGCAGCAGGGACAGCGAGCCGCCATGATGAATCTCCT
CCGAAACAACAGCTGCCTCTCCAAAATGAAGAATTCCATGGCTTCCATGTCTCAGCAGCTCAA
GGCCAAGTTGGATTTCTTCAAAACCAGCATCCAGATTGACCTGGAGAAGTACAGCGAGCAAAC
CGAGTTTGGGATCACATCAGATAAACTGCTGCTGGCCTGGAGGGAAATGGAGCAGGCTGTGG
AGCTCTGTGGGCGGGAGAACGAAGTGAAACTCCTGGTAGAACGGATGATGGCTCTGCAGACC
GACATTGTGGACTTACAGAGGAGCCCCATGGGCCGGAAGCAGGGGGGAACGCTGGACGACC
TAGAGGAGCAAGCAAGGGAGCTGTACAGGAGACTAAGGGAAAAACCTCGAGACCAGCGAACT
GAGGGTGACAGTCAGGAAATGGTACGGCTGCTGCTTCAGGCAATTCAGAGCTTCGAGAAGAA
AGTGCGAGTGATCTATACGCAGCTCAGTAAAACTGTGGTTTGCAAGCAGAAGGCGCTGGAACT
GTTGCCCAAGGTGGAAGAGGTGGTGAGCTTAATGAATGAGGATGAGAAGACTGTTGTCCGGC
TGCAGGAGAAGCGGCAGAAGGAGCTCTGGAATCTCCTGAAGATTGCTTGTAGCAAGGTCCGT
GGTCCTGTCAGTGGAAGCCCGGATAGCATGAATGCCTCTCGACTTAGCCAGCCTGGGCAGCT
GATGTCTCAGCCCTCCACGGCCTCCAACAGCTTACCTGAGCCAGCCAAGAAGAGTGAAGAAC
TGGTGGCTGAAGCACATAACCTCTGCACCCTGCTAGAAAATGCCATACAGGACACTGTGAGGG
AACAAGACCAGAGTTTCACGGCCCTAGACTGGAGCTGGTTACAGACGGAAGAAGAAGAGCAC
AGCTGCCTGGAGCAGGCCTCATGA (SEQ ID NO: 41)

FIG. 10 CONT.

>Human IKKβ isoform  cds
ATGAGCTGGTCACCTTCCCTGACAACGCAGACATGTGGGGCCTGGGAAATGAAAGAGCGCCT
TGGGACAGGGGGGATTTGGAAATGTCATCCGATGGCACAATCAGGAAACAGGTGAGCAGATTG
CCATCAAGCAGTGCCGGCAGGAGCTCAGCCCCCGGAACCGAGAGCGGTGGTGCCTGGAGAT
CCAGATCATGAGAAGGCTGACCCACCCCAATGTGGTGGCTGCCCGAGATGTCCCTGAGGGGA
TGCAGAACTTGGCGCCCAATGACCTGCCCCTGCTGGCCATGGAGTACTGCCAAGGAGGAGAT
CTCCGGAAGTACCTGAACCAGTTTGAGAACTGCTGTGGTCTGCGGGAAGGTGCCATCCTCAC
CTTGCTGAGTGACATTGCCTCTGCGCTTAGATACCTTCATGAAAACAGAATCATCCATCGGGA
TCTAAAGCCAGAAAACATCGTCCTGCAGCAAGGAGAACAGAGGTTAATACACAAATTATTGAC
CTAGGATATGCCAAGGAGCTGGATCAGGGCAGTCTTTGCACATCATTCGTGGGGACCCTGCA
GTACCTGGCCCCAGAGCTACTGGAGCAGCAGAAGTACACAGTGACCGTCGACTACTGGAGCT
TCGGCACCCTGGCCTTTGAGTGCATCACGGGCTTCCGGCCCTTCCTCCCCAACTGGCAGCCC
GTGCAGTGCGTAAGAATGTGGCCGGGTACAGTGGCTCACTCCTGTAATCCCAGCACTTTGGG
AGGCCGAGGCAGGTGGATCAGTTGA (SEQ ID NO: 42)

>Human IKKβ isoform 4 cds
ATGTCATCCGATGGCACAATCAGGCTGACCCACCCCAATGTGGTGGCTGCCCGAGATGTCCC
TGAGGGGATGCAGAACTTGGCGCCCAATGACCTGCCCCTGCTGGCCATGGAGTACTGCCAAG
GAGGAGATCTCCGGAAGTACCTGAACCAGTTTGAGAACTGCTGTGGTCTGCGGGAAGGTGCC
ATCCTCACCTTGCTGAGTGACATTGCCTCTGCGCTTAGATACCTTCATGAAAACAGAATCATC
CATCGGGATCTAAAGCCAGAAAACATCGTCCTGCAGCAAGGAGAACAGAGGTTAATACACAAA
ATTATTGACCTAGGATATGCCAAGGAGCTGGATCAGGGCAGTCTTTGCACATCATTCGTGGGG
ACCCTGCAGTACCTGGCCCCAGAGCTACTGGAGCAGCAGAAGTACACAGTGACCGTCGACTA
CTGGAGCTTCGGCACCCTGGCCTTTGAGTGCATCACGGGCTTCCGGCCCTTCCTCCCCAACT
GGCAGCCCGTGCAGTGGCATTCAAAAGTGCGGCAGAAGAGTGAGGTGGACATTGTTGTTAGC
GAAGACTTGAATGGAACGGTGAAGTTTTCAAGCTCTTTACCCTACCCCAATAATCTTAACAGTG
TCCTGGCTGAGCGACTGGAGAAGTGGCTGCAACTGATGCTGATGTGGCACCCCCGACAGAGG
GGCACGGATCCCACGTATGGGCCCAATGGCTGCTTCAAGGCCCTGGATGACATCTTAAACTTA
AAGCTGGTTCATATCTTGAACATGGTCACGGGCACCATCCACACCTACCCTGTGACAGAGGAT
GAGAGTCTGCAGAGCTTGAAGGCCAGAATCCAACAGGACACGGGCATCCCAGAGGAGGACCA
GGAGCTGCTGCAGGAAGCGGGCCTGGCGTTGATCCCCGATAAGCCTGCCACTCAGTGTATTT
CAGACGGCAAGTTAAATGAGGGCCACACATTGGACATGGATCTTGTTTTTCTCTTTGACAACAG
TAAAATCACCTATGAGACTCAGATCTCCCCACGGCCCCAACCTGAAAGTGTCAGCTGTATCCT
TCAAGAGCCCAAGAGGAATCTCGCCTTCTTCCAGCTGAGGAAGGTGTGGGGCCAGGTCTGGC
ACAGCATCCAGACCCTGAAGGAAGATTGCAACCGGCTGCAGCAGGGACAGCGAGCCGCCAT
GATGAATCTCCTCCGAAACAACAGCTGCCTCTCCAAAATGAAGAATTCCATGGCTTCCATGTCT
CAGCAGCTCAAGGCCAAGTTGGATTTCTTCAAAACCAGCATCCAGATTGACCTGGAGAAGTAC
AGCGAGCAAACCGAGTTTGGGATCACATCAGATAAACTGCTGCTGGCCTGGAGGGAAATGGA
GCAGGCTGTGGAGCTCTGTGGGCGGGAGAACGAAGTGAAACTCCTGGTAGAACGGATGATGG
CTCTGCAGACCGACATTGTGGACTTACAGAGGAGCCCCATGGGCCGGAAGCAGGGGGGAAC
GCTGGACGACCTAGAGGAGCAAGCAAGGGAGCTGTACAGGAGACTAAGGGAAAAACCTCGAG
ACCAGCGAACTGAGGGTGACAGTCAGGAAATGGTACGGCTGCTGCTTCAGGCAATTCAGAGC
TTCGAGAAGAAAGTGCGAGTGATCTATACGCAGCTCAGTAAAACTGTGGTTTGCAAGCAGAAG
GCGCTGGAACTGTTGCCCAAGGTGGAAGAGGTGGTGAGCTTAATGAATGAGGATGAGAAGAC
TGTTGTCCGGCTGCAGGAGAAGCGGCAGAAGGAGCTCTGGAATCTCCTGAAGATTGCTTGTA
GCAAGGTCCGTGGTCCTGTCAGTGGAAGCCCGGATAGCATGAATGCCTCTCGACTTAGCCAG
CCTGGGCAGCTGATGTCTCAGCCCTCCACGGCCTCCAACAGCTTACCTGAGCCAGCCAAGAA
GAGTGAAGAACTGGTGGCTGAAGCACATAACCTCTGCACCCTGCTAGAAAATGCCATACAGGA
CACTGTGAGGGAACAAGACCAGAGTTTCACGGCCCTAGACTGGAGCTGGTTACAGACGGAAG
AAGAAGAGCACAGCTGCCTGGAGCAGGCCTCATGA (SEQ ID NO: 43)

FIG. 10 CONT.

>Human IKKβ isoform 4 cds
ATGTCATCCGATGGCACAATCAGGCTGACCCACCCCAATGTGGTGGCTGCCCGAGATGTCCC
TGAGGGGATGCAGAACTTGGCGCCCAATGACCTGCCCCTGCTGGCCATGGAGTACTGCCAAG
GAGGAGATCTCCGGAAGTACCTGAACCAGTTTGAGAACTGCTGTGGTCTGCGGGAAGGTGCC
ATCCTCACCTTGCTGAGTGACATTGCCTCTGCGCTTAGATACCTTCATGAAAACAGAATCATC
CATCGGGATCTAAAGCCAGAAAACATCGTCCTGCAGCAAGGAGAACAGAGGTTAATACACAAA
ATTATTGACCTAGGATATGCCAAGGAGCTGGATCAGGGCAGTCTTTGCACATCATTCGTGGGG
ACCCTGCAGTACCTGGCCCCAGAGCTACTGGAGCAGCAGAAGTACACAGTGACCGTCGACTA
CTGGAGCTTCGGCACCCTGGCCTTTGAGTGCATCACGGGCTTCCGGCCCTTCCTCCCCAACT
GGCAGCCCGTGCAGTGGCATTCAAAAGTGCGGCAGAAGAGTGAGGTGGACATTGTTGTTAGC
GAAGACTTGAATGGAACGGTGAAGTTTTCAAGCTCTTTACCCTACCCCAATAATCTTAACAGTG
TCCTGGCTGAGCGACTGGAGAAGTGGCTGCAACTGATGCTGATGTGGCACCCCCGACAGAGG
GGCACGGATCCCACGTATGGGCCCAATGGCTGCTTCAAGGCCCTGGATGACATCTTAAACTTA
AAGCTGGTTCATATCTTGAACATGGTCACGGGCACCATCCACACCTACCCTGTGACAGAGGAT
GAGAGTCTGCAGAGCTTGAAGGCCAGAATCCAACAGGACACGGGCATCCCAGAGGAGGACCA
GGAGCTGCTGCAGGAAGCGGGCCTGGCGTTGATCCCCGATAAGCCTGCCACTCAGTGTATTT
CAGACGGCAAGTTAAATGAGGGCCACACATTGGACATGGATCTTGTTTTTCTCTTTGACAACAG
TAAAATCACCTATGAGACTCAGATCTCCCCACGGCCCCAACCTGAAAGTGTCAGCTGTATCCT
TCAAGAGCCCAAGAGGAATCTCGCCTTCTTCCAGCTGAGGAAGGTGTGGGGCCAGGTCTGGC
ACAGCATCCAGACCCTGAAGGAAGATTGCAACCGGCTGCAGCAGGGACAGCGAGCCGCCAT
GATGAATCTCCTCCGAAACAACAGCTGCCTCTCCAAAATGAAGAATTCCATGGCTTCCATGTCT
CAGCAGCTCAAGGCCAAGTTGGATTTCTTCAAAACCAGCATCCAGATTGACCTGGAGAAGTAC
AGCGAGCAAACCGAGTTTGGGATCACATCAGATAAACTGCTGCTGGCCTGGAGGGAAATGGA
GCAGGCTGTGGAGCTCTGTGGGCGGGAGAACGAAGTGAAACTCCTGGTAGAACGGATGATGG
CTCTGCAGACCGACATTGTGGACTTACAGAGGAGCCCCATGGGCCGGAAGCAGGGGGGAAC
GCTGGACGACCTAGAGGAGCAAGCAAGGGAGCTGTACAGGAGACTAAGGGAAAAACCTCGAG
ACCAGCGAACTGAGGGTGACAGTCAGGAAATGGTACGGCTGCTGCTTCAGGCAATTCAGAGC
TTCGAGAAGAAAGTGCGAGTGATCTATACGCAGCTCAGTAAAACTGTGGTTTGCAAGCAGAAG
GCGCTGGAACTGTTGCCCAAGGTGGAAGAGGTGGTGAGCTTAATGAATGAGGATGAGAAGAC
TGTTGTCCGGCTGCAGGAGAAGCGGCAGAAGGAGCTCTGGAATCTCCTGAAGATTGCTTGTA
GCAAGGTCCGTGGTCCTGTCAGTGGAAGCCCGGATAGCATGAATGCCTCTCGACTTAGCCAG
CCTGGGCAGCTGATGTCTCAGCCCTCCACGGCCTCCAACAGCTTACCTGAGCCAGCCAAGAA
GAGTGAAGAACTGGTGGCTGAAGCACATAACCTCTGCACCCTGCTAGAAAATGCCATACAGGA
CACTGTGAGGGAACAAGACCAGAGTTTCACGGCCCTAGACTGGAGCTGGTTACAGACGGAAG
AAGAAGAGCACAGCTGCCTGGAGCAGGCCTCATGA (SEQ ID NO: 43)

FIG. 10 CONT.

>Murine IKKβ cds (2217 nt)
ATGAGCTGGTCACCGTCCCTCCCAACCCAGACATGTGGAGCCTGGGAAATGAAAGAACGCCT
GGGGACCGGGGGGATTTGGAAACGTCATCCGGTGGCACAATCAGGCGACAGGTGAACAGATC
GCCATCAAGCAATGCCGACAGGAGCTCAGCCCAAAGAACAGAGACCGCTGGTGCCTCGAAAT
CCAGATCATGAGAAGGCTGAACCATCCCAATGTGGTGGCTGCCCGGGATGTCCCAGAGGGGA
TGCAGAACCTGGCACCCAATGATTTGCCACTGCTGGCCATGGAGTACTGCCAAGGAGGAGAT
CTCCGAAGATACTTGAACCAGTTCGAGAACTGCTGTGGCCTGCGGGAAGGAGCTGTCCTTAC
CCTGCTGAGTGACATCGCATCGGCTCTTAGATACCTTCACGAAAACAGAATCATCCATCGAGA
CCTGAAGCCAGAAAACATCGTTCTGCAGCAAGGAGAGAAAGATTAATACACAAAATTATTGAT
CTAGGATATGCCAAGGAGCTGGATCAGGGCAGTCTGTGCACGTCATTTGTGGGGACTCTGCA
ATACCTGGCGCCAGAGCTTCTGGAGCAGCAGAAGTACACCGTGACCGTTGACTACTGGAGCT
TCGGCACCCTGGCCTTCGAGTGCATCACTGGCTTCCGGCCCTTCCTCCCTAACTGGCAGCCT
GTGCAGTGGCACTCCAAAGTCCGGCAGAAGAGCGAAGTGGACATCGTTGTTAGTGAAGACTT
GAATGGAGCAGTGAAGTTTTCAAGTTCGCTACCCTTCCCCAATAATCTTAACAGTGTCTTGGCT
GAACGGCTGGAGAAGTGGCTGCAGCTGATGCTTATGTGGCACCCTCGGCAAAGGGGCACGG
ATCCCCAGTATGGCCCCAACGGCTGCTTCAGAGCCCTGGATGACATCTTGAACTTGAAGCTGG
TTCATGTCTTGAACATGGTCACAGGCACCGTTCACACATACCCCGTGACGGAGGATGAGAGTC
TGCAGAGCTTAAAAACCAGAATCCAGGAAGACACGGGGATCCTGGAGACAGACCAGGAGCTG
CTGCAAGAGGCAGGGCTGGTGCTGCTCCCTGACAAGCCTGCTACTCAGTGCATCTCAGACAG
CAAGACAAACGAGGGCCTCACGTTGGACATGGATCTTGTTTTTCTCTTTGACAACAGTAAAATC
AACTATGAGACTCAGATCACCCCCCGACCCCAACCGGAAAGTGTCAGCTGTATCCTTCAGGAG
CCCAAGCGGAACCTCTCCTTCTTCCAGCTGAGGAAAGTGTGGGGCCAAGTCTGGCACAGCAT
CCAGACGCTGAAGGAAGACTGTAACCGGCTGCAGCAGGGACAGCGAGCAGCCATGATGAGT
CTCCTCCGGAATAACAGCTGCCTCTCTAAGATGAAGAACGCCATGGCCTCCACGGCCCAGCA
GCTCAAGGCCAAGCTGGACTTCTTCAAAACCAGCATCCAGATCGACCTGGAGAAGTATAAAGA
GCAGACCGAGTTTGGGATCACCTCAGATAAATTGCTGCTGGCTTGGCGGGAGATGGAGCAGG
CTGTGGAGCAGTGTGGGCGGGAGAATGACGTGAAGCATCTAGTAGAGCGGATGATGGCACTG
CAGACTGACATTGTGGACCTGCAGAGGAGCCCGATGGGTCGGAAGCAGGGGGGCACCCTGG
ATGACCTAGAGGAACAAGCGAGGGAGCTCTACCGAAGACTCAGGGAGAAGCCAAGAGACCAA
AGGACAGAAGGTGACAGCCAGGAGATGGTACGGCTGCTGCTTCAGGCAATCCAAAGCTTTGA
GAAGAAGTTCGGGTGATTTATACACAGCTCAGTAAGACCGTGGTTTGTAAGCAGAAGGCACT
GGAGTTGCTGCCCAAGGTAGAAGAGGTAGTGAGCCTTATGAACGAGGACGAGAGGACCGTGG
TCCGGCTTCAGGAGAAGCGGCAGAAGGAACTCTGGAACCTCCTGAAGATCGCCTGTAGCAAA
GTCCGAGGTCCCGTGAGTGGAAGCCCAGACAGCATGAATGTGTCTCGACTCAGTCACCCTGG
TCAGCTAATGTCCCAGCCTTCCAGTGCCTGTGACAGCTTACCTGAATCAGACAAGAAAAGTGA
AGAACTGGTGGCCGAAGCCCACGCCCTCTGCTCCCGGCTAGAAAGTGCGCTGCAGGACACTG
TGAAGGAGCAAGACAGAAGCTTCACGGTAACCGCCTGATAA (SEQ ID NO: 44)

FIG. 10 CONT.

>Human glucocorticoid-induced leuzine zipper (GILZ) isoform 1 (UniProt Accession Q99576-1)

MNTEMYQTPMEVAVYQLHNFSISFFSSLLGGDVVSVKLDNSASGASVVAIDNKIEQAMDL
VKNHLMYAVREEVEILKEQIRELVEKNSQLERENTLLKTLASPEQLEKFQSCLSPEEPAP
ESPQVPEAPGGGSAV (SEQ ID NO: 110)

>Human glucocorticoid-induced leuzine zipper (GILZ) cds (GenBank Accession no.
NM_004089.3)

ATGAACACCGAAATGTATCAGACCCCCATGGAGGTGGCCGGTCTACCAGCTGCACAATTTCTCC
ATCTCCTTCTTCTCTTCTCTGCTTGGAGGGGATGTGGTTTCCGTTAAGCTGGACAACAGTGCCT
CCGGAGCCAGCGTGGTGGCCATAGACAACAAGATCGAACAGGCCATGGATCTGGTGAAGAAT
CATCTGATGTATGCTGTGAGAGAGAGGTGGAGATCCTGAAGGAGCAGATCCGAGAGCTGGT
GGAGAAGAACTCCCAGCTAGAGCGTGAGAACACCCTGTTGAAGACCCTGGCAAGCCCAGAGC
AGCTGGAGAAGTTCCAGTCTGTCTGAGCCCTGAAGAGCCAGCTCCCGAATCCCCACAAGTG
CCCGAGGCCCCTGGTGGTTCTGCGGGTGTAA (SEQ ID NO: 111)

FIG. 11

| Description | Protein SEQ ID NO | CDS SEQ ID NO | Notes |
|---|---|---|---|
| Human IRF5 isoform 1 | 1 | 23 | UniProt Accession Q13568-1.<br>The isoform is identical to 'variant 2' or 'isoform b' (GenBank Accession NM032643) or 'variant 6' (GenBank Accession AY693666).<br>Mutations at amino acid residues S156, S158 and/or T160 mimicking phosphorylation localizes the protein to the nucleus. |
| Human IRF5 isoform 2 | 2 | 24 | UniProt Accession Q13568-2.<br>The isoform is identical to 'variant 5' (GenBank Accession AY693665).<br>Mutations at amino acid residues T10, S158, S309, S317, S451, and/or S462 renders the protein constitutively active. |
| Human IRF5 isoform 3 | 3 | 25 | UniProt Accession Q13568-3.<br>The isoform is identical to 'isoform a' or 'variant 1' (GenBank Accession U51127).<br>Mutations at amino acid residues S156, S158 and/or T160 mimicking phosphorylation localizes the protein to the nucleus. |
| Human IRF5 isoform 4 | 4 | 26 | UniProt Accession Q13568-4.<br>The isoform is identical to 'variant 3' or 'variant 4' (GenBank Accession nos. AY504946 or AY504947, respectively).<br>Mutations at amino acid residues S425, S427, S430, and/or S436 mimicking phosphorylation renders the protein constitutively active. |
| Human IRF5 isoform 5 | 5 | 27 | UniProt Accession Q13568-5. |
| Human IRF5 isoform 6 | 6 | 28 | UniProt Accession Q13568-6. |
| Murine IRF5 | 7 | 29 | UniProt Accession P56477. |
| Human IRF1 | 8 | 30 | UniProt Accession P10914. |
| Human IRF3 isoform 1 | 9 | 31 | UniProt Accession Q14653-1. |
| Human IRF7 isoform A | 10 | 32 | UniProt Accession Q92985-1. |
| Human IRF8 | 11 | 33 | UniProt Accession Q02556. |
| Murine IRF1 | 12 | 34 | UniProt Accession P15314. |
| Murine IRF3 | 13 | 35 | UniProt Accession P70671. |
| Murine IRF7 | 14 | 36 | UniProt Accession P70434. |

FIG. 11 CONT.

| Description | Protein SEQ ID NO | CDS SEQ ID NO | Notes |
|---|---|---|---|
| Murine IRF7/IRF3 5(D) | 15 | 37 | Mouse fusion protein with 5 AA residues in the IRF3 association domain changed to D to constitutively activate as described in the present disclosure. |
| Murine IRF8 | 16 | 38 | UniProt Accession P23611. |
| Murine IRF8 K310R | 17 | 39 | Mutant mouse IRF8 with mutation that affects SUMO binding and renders IRF8 constitutively active as described in the present disclosure. |
| Human IKKbeta isoform 1 | 18 | 40 | UniProt Accession O14920. |
| Human IKKbeta isoform 2 | 19 | 41 | UniProt Accession O14920-2. |
| Human IKKbeta isoform 3 | 20 | 42 | UniProt Accession O14920-3. |
| Human IKKbeta isoform 4 | 21 | 43 | UniProt Accession O14920-4. |
| Murine IKKbeta | 22 | 44 | GenBank Accession no. NP_034676.1 |
| Human glucocorticoid-induced leucine zipper (GILZ) isoform 1 | 110 | 111 | UniProt Accession Q99576-1. |

ALTERING INFLAMMATORY STATES OF IMMUNE CELLS IN VIVO BY MODULATING CELLULAR ACTIVATION STATES

CROSS-REFERENCE TO RELATED APPLICATIONS

This application is a U.S. National Phase Application based on International Pat. Application No. PCT/US2019/014209, filed Jan. 18, 2019, which claims the benefit of priority to U.S. Provisional Pat. Application No. 62/618,908, filed Jan. 18, 2018, both of which are incorporated by reference herein in their entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2BD3077 ST25.txt. The text file is 145 KB, was created on Jun. 22, 2020, and is being submitted electronically via EFS-Web.

FIELD OF THE DISCLOSURE

The current disclosure provides systems and methods to modulate the activation state of immune cells in vivo. The systems and methods can be used to transform immunosuppressive macrophages that support cancer growth and metastasis into highly activated tumoricidal macrophages.

BACKGROUND OF THE DISCLOSURE

A number of adverse physiological conditions are associated with immune system activation (e.g., autoimmune disorders) or immune system suppression (e.g., cancer). For example, macrophages are key immune effector cells that infiltrate cancerous tissue in high numbers. Within the tumor microenvironment, however, macrophages undergo a switch from an activated tumoricidal state to an immunosuppressive phenotype that actually facilitates tumor growth and metastasis. Pollard, Nat Rev Cancer 4, 71-78 (2004); Mantovani, et al., Nat Rev Clin Oncol (2017).

Understanding that immunosuppressed macrophages within the tumor microenvironment facilitate cancer growth and metastasis, much effort has been devoted to developing therapies that target immunosuppressive tumor-associated macrophages (TAMs). Many efforts to address TAMs have focused on killing the TAMs to alleviate immunosuppression in the tumor microenvironment. With this approach, however, the TAMs are simply replaced with newly-arriving macrophages at the tumor environment. Moreover, even when successful at killing some TAMs, most therapeutics developed to date have not been able to sufficiently penetrate into the tumor microenvironment. While some small molecule drugs and antibodies have shown some success, these approaches have suppressed all macrophages in the body, inducing dangerous side effects. Bowman & Joyce, Immunotherapy 6, 663-666 (2014). Thus, as is understood by everyone affected by cancer, more effective treatment strategies with fewer side effects are greatly needed.

SUMMARY OF THE DISCLOSURE

The current disclosure provides systems and methods to modulate the function of immune cells in vivo. In particular embodiments, the systems and methods are used to reverse the immunosuppressive, tumor supporting state of tumor-associated macrophages (TAMs) and turn these TAMs into highly activated, tumor cell-killing macrophages. Thus, the systems and methods disclosed herein do not simply aim to kill TAMs, but instead redirects their activity from tumor-promoting to tumor-destroying. In particular embodiments, the systems and methods are used as a therapeutic to induce the killing of cancer cells and/or to reduce or prevent the growth or development of new cancer cells. Data disclosed herein shows that these systems and methods are able to completely eradicate and suppress ovarian cancer, a notoriously difficult cancer type to control.

The systems and methods disclosed herein can be used to alter the immunosuppressive state in a tumor, providing a mechanism to restructure the tumor microenvironment. In these embodiments, a restructured tumor microenvironment can render a tumor more susceptible to a companion treatment, such as a vaccine, a chimeric antigen receptor (CAR) therapy, and/or chemotherapy.

Importantly, the systems and methods disclosed herein can be used locally at the tumor microenvironment obviating the need to resort to systemic treatments that globally disrupt immune system homeostasis. Moreover, particular embodiments have been optimized to successfully infiltrate the tumor microenvironment.

Particular embodiments alter the activation states of immune cells in vivo by utilizing a particle to deliver nucleotides encoding activation regulators, such as transcription factors. A particularly useful particle has a positive core and a neutral or negatively-charged surface and delivers nucleotides encoding the transcription factor interferon-regulatory factor 5 (IRF5) in combination with the kinase IKKβ. A particle size of <130 nm ensures tumor infiltration. Moreover, the particles can include a TAM targeting ligand to direct more selective uptake of the particles by TAMs. As one example, TAMs express CD206, a cellular surface receptor that can be targeted by including mannose on the surface of the particles.

BRIEF DESCRIPTION OF THE FIGURES

Many of the figures submitted herein are better understood in color. Applicants consider the color versions of the drawings as part of the original submission and reserve the right to present color images of the drawings in later proceedings.

Figure 1A:
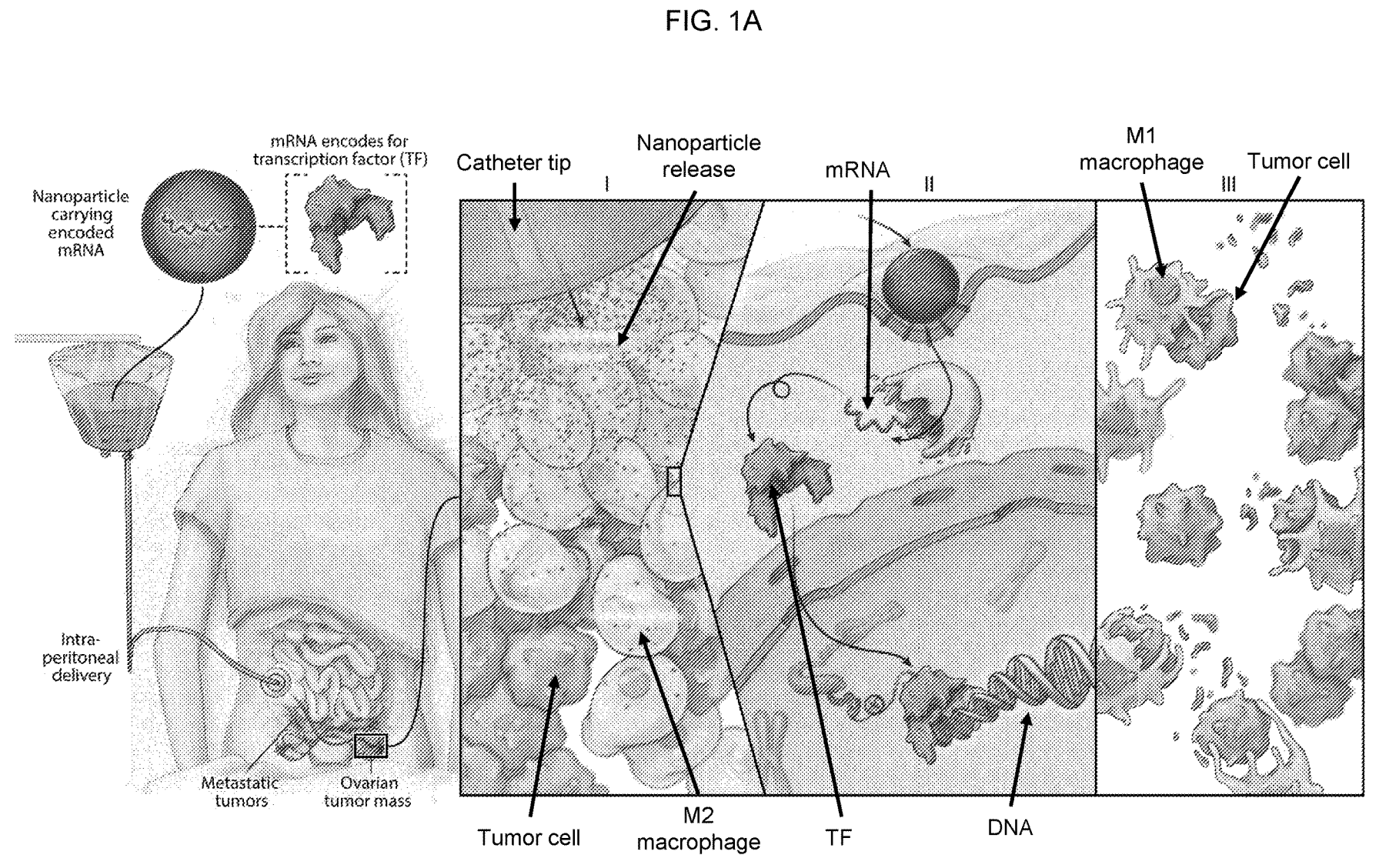

FIGS. 1A, 1B. Scheme to genetically transform tumor-associated macrophages (TAMs) into tumoricidal cells using targeted mRNA nanoparticles. (FIG. 1A) An injectable nanocarrier was developed to deliver in vitro transcribed mRNA encoding M1-polarizing transcription factors as a new method to rationally reprogram TAMs for therapeutic purposes without causing systemic toxicity. Illustrated is the first planned clinical application, designed to treat ovarian cancer patients with repeated intraperitoneal infusions of mRNA nanoparticles. (FIG. 1B) Scheme to genetically reprogram intracranial TAMs into tumoricidal macrophages using targeted mRNA nanoparticles.

(FIG. 2A) Design of macrophage-targeted polymeric NPs formulated with mRNAs encoding key regulators of macrophage polarization. The particles consist of a PbAE-mRNA polyplex core coated with a layer of PGA-Di-mannose, which targets the particles to mannose receptors (CD206) expressed by M2-like macrophages. Also depicted is the synthetic mRNA encapsulated in the NP, which is engineered to encode the reprogramming transcription factors. (FIG. 2B) Transmission electron microscopy of a population of NPs (scale bar 200 nm) and a single NP (inset, scale bar 50 nm). (FIG. 2C) Size distributions of NPs, measured using a NanoSight NS300 instrument. (FIG. 2D) NPs demonstrated high transfection (46%) of bone marrow-derived macrophages (BMDMs) after 1 h exposure. (FIG. 2E) Gene-transfer efficiencies into bone marrow derived macrophages (BM DM) measured by flow cytometry 24 hours after nanoparticle transfection. (FIG. 2F) Relative viability of NP transfected and untransfected macrophages (assessed by staining with Annexin V and PI). N.s.; non-significant. (FIG. 2G) Expression kinetics of codon-optimized IRF5 mRNA (blue, left Y axis) and endogenous IRF5 mRNA (black, right Y axis) measured by qRT-PCR, n=3 for each time point. (FIG. 2H) Timelines depicting NP transfection protocols and culture conditions for the BMDMs used in FIGS. 2I-2K. (FIG. 2I) Gene expression profiles of IRF5/IKKβ NP-transfected macrophages compared to signature M1 cells stimulated with the Toll-like Receptor 6 agonist MPLA. Results are depicted as a Volcano plot that shows the distribution of the fold changes in gene expression. M1 signature genes are indicated. P value of overlap between IRF5/IKKβ NP-transfected macrophages and the M1 signature gene set was determined by GSEA. (FIG. 2J) Heat map of M1 signature gene expression in macrophages cultured in IL-4 versus cells cultured in IL-4 and transfected with IRF5/IKKβ NPs. (FIG. 2K) Box plots showing mean counts for indicated genes and S.E.M.

(FIG. 4A) Time lines and dosing regimens. Arrows indicate time of I.P. injection. (FIG. 4B) Sequential bioluminescence imaging of tumor growth in control and treated mice. (FIG. 4C) Kaplan-Meier survival curves for treated versus control mice. Statistical analysis was performed using the log-rank test. (FIG. 4D) Flow cytometric quantitation of in vivo transfection rates in different immune cell subpopulations 48 hours after a single i.p. dose of D-mannose-coated NPs carrying GFP mRNA as a control: macrophages (CD45+, CD11b+, MHCII+, CD11c−, Ly6C−/low, Ly6G−), monocytes (CD45+, CD11b+, MHCII+, CD11c−, Ly6C+, Ly6G−), neutrophils (CD45+, CD11b+, MHCII+, CD11c−, Ly6G+), CD4+ T cells (CD45+, TCR-β chain+, CD4+, CD8−), CD8+ T cells (CD45+, TCR-β chain+, CD4−, CD8+), and natural killer cells (CD45+, TCR-β chain−, CD49b+) were measured. (FIG. 4E) Flow cytometric analysis of macrophage phenotypes in the peritoneum of mice with disseminated ID8 ovarian cancer. Animals were either treated with 4 doses of IRF5/IKKβ NPs or PBS. (FIG. 4F) Box plots summarizing relative percent (left panel) and absolute numbers (right panel) of Ly6C−, F4/80+, and CD206+ (M2-like) macrophages. (FIG. 4G) Corresponding numbers for Ly6C−, F4/80+, and CD206− (M1-like) macrophages. (FIG. 4H) Representative hematoxylin and eosin-stained sections of ovarian tumor-infiltrated mesenteries isolated from PBS controls (top panel) or IRF5/IKKβ NP-treated animals (bottom panel; scale bar 100 μm). 10-fold magnifications of representative malignant lesions are shown on the right (scale bar 50 μm). (FIG. 4I) Luminex assay measuring cytokines produced by isolated peritoneal macrophages from each treatment group. CD11b+, F4/80+ peritoneal macrophages were isolated by fluorescence activated cell sorting, and cultured ex vivo. After 24 hours, cell culture supernatants were collected. In parallel experiments, FACS-sorted CD11b+, F4/80+ peritoneal macrophages were directly analyzed by pRT-PCR to determine expression levels of four master regulators of the macrophage phenotypes (SerpinB2, Retnla, Ccl11, and Ccl5). Results are summarized as box plots in FIG. 4J.

FIGS. 5A-5F. Macrophage-programming mRNA nanocarriers are highly biocompatible and safe for repeated dosing. (FIG. 5A) In vivo biodistribution of macrophage-targeted IRF5/IKKβ NPs following i.p. administration. NP-delivered (codon optimized) mRNA was detected by qPCR 24 hours after a single injection of particles containing 50 μg mRNA. (FIG. 5B) Schematic representation of the experimental timeline. *Twenty-four hours after the last dose, mice were euthanized by $CO_2$ inhalation. Blood was collected through retro-orbital bleeding into heparin coated tubes for serum chemistry and complete blood count. Necrospy was performed for histological analysis of liver, spleen, pancreas, mesentery and omentum, stomach, and urinary bladder. (FIG. 5C) Representative hematoxylin and eosin-stained sections of various organs isolated from controls or NP-treated animals. Scale bar, 100 μm. Lesions found in the NP-treated animals are shown and described here based on analysis by a Comparative Pathologist. The relevant findings for each numbered image is: [1] Discrete foci of cellular infiltrates largely composed of mononuclear cells admixed with a few granulocytes; Mild extramedullary hematopoiesis. [2] In a few locally extensive areas, hepatocytes are mild to moderately swollen. [3] Moderate myeloid (predominant), erythroid and megakaryocyte hyperplasia within the red pulp. [4] Mild hypocellularity of the white pulp. [5] Within the mesentery, there are moderate, multifocal infiltrates of macrophages, lymphocytes, plasma cells and granulocytes. [6] Mild to moderate infiltrates of macrophages admixed with lymphocytes, plasma cells and granulocytes; Mild dissociation of the acini and acinar loss; Mild diffuse loss of zymogen granules from the acinar cells. [7] Dense aggregates of lymphocytes admixed with macrophages around fat tissue. [8] Mild multifocal vacuolar degeneration of the chief and parietal cells within the gastric mucosa. (FIG. 5D) Serum chemistry and blood counts. (FIGS. 5E, 5F) Luminex assay measurements of serum IL-6 (FIG. 5E) and TNF-α (FIG. 5F) cytokines 4 or 8 days after a single i.p. injection of IRF5/IKKβ NPs.

FIGS. 6A-6I. Intravenously infused IRF5/IKKβ nanoparticles can control tumor metastases in the lung. (FIG. 6A) In vivo biodistribution of macrophage-targeted IRF5/IKKβ NPs following i.v. administration. Codon-optimized mRNA was measured by qPCR 24 hours after a single i.v. injection of particles containing 50 μg mRNA. (FIGS. 6B-6H) C57BL/6 albino mice were injected via tail vein with $1 \times 10^6$ B16F10 firefly luciferase-expressing melanoma cells to establish lung metastases. After 7 days, animals were randomly assigned to either the IRF5/IKKβ NP treatment group, the control GFP NP group, or the PBS control. (FIG. 6B) Time lines and dosing regimens. (FIG. 6C) Confocal microscopy of healthy lungs (left panel) and B16F10 tumor-infiltrated lungs (right panel). Infiltrating macrophage populations fluoresce in green. (FIG. 6D) Sequential bioluminescence tumor imaging. (FIG. 6E) Kaplan-Meier survival curves for each treatment group. ms indicates median survival. Statistical analysis was performed using the log-rank test, and P<0.05 was considered significant. (FIG. 6F) Representative photographs (top row) and micrographs of lungs containing B16F10 melanoma metastases representing each group following 2 weeks of treatment. (FIG. 6G) Counts of lung tumor foci. (FIG. 6H) Phenotypic characterization of monocyte/macrophage populations in bronchoalveolar lavage from each treatment group. (FIG. 6I) Summary of the relative percentages of suppressive and activated macrophages.

(FIG. 7A) T2 MRI scan, and histological staining following initiation of a PDGFβ-driven glioma in RCAS-PDGF-B/Nestin-Tv-a; Ink4a/Arf−/−; Pten−/− transgenic mice on post-induction day 21. (FIG. 7B) Confocal microscopy of CD68+ TAMs infiltrating the glioma margin. Scale bar 300 μm. (FIG. 7C) Flow cytometry analysis of macrophage (F4/80+, CD11b+) populations in healthy brain tissue versus glioma. (FIGS. 7D-7E) Kaplan-Meier survival curves of mice with established gliomas receiving IRF5/IKKβ treatments as a monotherapy (FIG. 7D) or combined with brain tumor radiotherapy (FIG. 7E). Time lines and dosing regimens are shown on top. Ms, median survival. Statistical analysis was performed using the log-rank test, and P<0.05 was considered statistically significant. (FIG. 7F) Sequential bioluminescence imaging of tumor progression.

(FIG. 8A) Time line and culture conditions to differentiate the human THP-1 monocytic cell line into suppressive M2-like macrophages. (FIG. 8B) Bioluminescent imaging of M2-differentiated THP1-Lucia cells cultured in 24 wells and transfected with indicated concentrations of NPs carrying human IRF5/IKKβ mRNA versus control GFP mRNA. Levels of IRF-induced Lucia luciferase were determined 24 hours after transfection using Quanti-Luc. (FIG. 8C) Summary of bioluminescent counts. (FIGS. 8D-8E) Differences in IL-1β cytokine secretion (FIG. 8D) and surface expression (FIG. 8E) of the M1-macrophage marker CD80.

FIG. 9. List of antibodies used in myeloid and lymphoid immunophenotyping panels described in Example 1.

FIG. 10 provides exemplary sequences supporting the disclosure (SEQ ID NOs: 1-44, 110, and 111). The identities of SEQ ID NOs: 1-44, 110, and 111 are described in FIG. 11. Regarding SEQ ID NO: 15 particularly, the fusion protein includes the DBD (DNA binding domain) and CAD (constitutively active domain) of murine IRF7 and the NES (Nuclear Export Signal) and IRF association domains of murine IRF3. The IRF association domain includes Asp mutations at four serine and one threonine residues in the N terminal region, conferring constitutive activation and translocation of the fusion protein (Lin R et al. (1998) supra). Regarding SEQ ID NO: 17 particularly, a SUMO (small ubiquitin-like modifier) binding site in murine IRF8 is at Lysine (K) 310. Binding of SUMO 2/3 prevents IRF-8 from engaging and activating IRF8 responsive genes. Mutation of the K310 residue prevents SUMO binding to IRF8, leading to an increase in IRF8 specific gene transcription 2-5 fold (Chang T-H et al. The Journal of Immunology (2012) 189(7): 3548-3556).

FIG. 11 provides a SEQ ID NO: key of exemplary protein sequences and encoding nucleotide sequences.

DETAILED DESCRIPTION

Figure 1B:
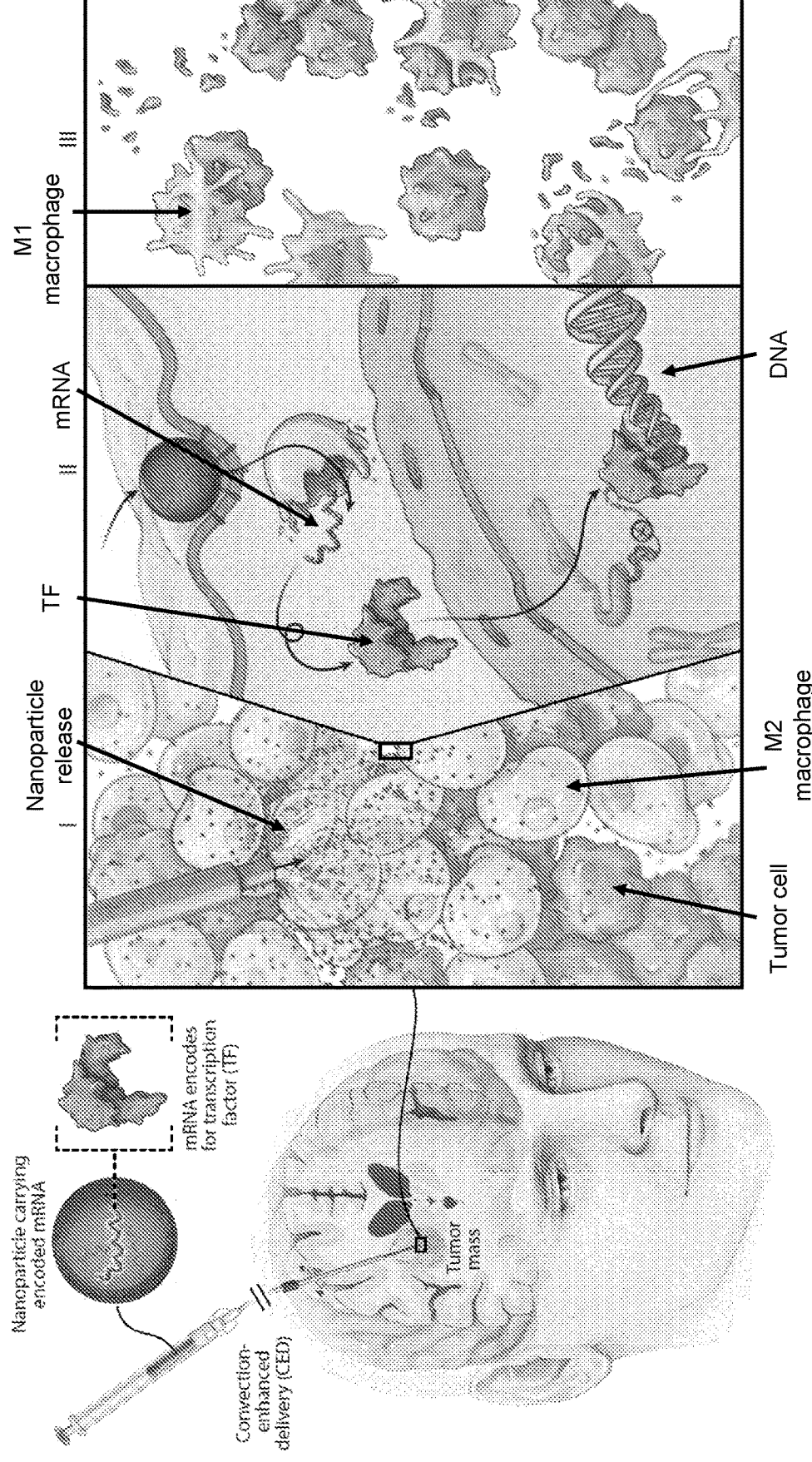

A number of adverse physiological conditions are associated with immune system activation (e.g., autoimmune disorders) or immune system suppression (e.g., cancer). For example, macrophages are key immune effector cells that infiltrate cancerous tissue in high numbers. However, within an immunosuppressive tumor milieu, they undergo a switch from an activated tumoricidal state to an immunosuppressive phenotype, which facilitates tumor growth and metastasis. These tumor-associated immunosuppressed macrophages (TAMs) are associated with poor prognosis (Komohara Y et al. (2014) Cancer science 105(1): 1-8). They induce angiogenesis, lymphogenesis, and stroma remodeling. They also play a key role in promoting tumor invasion and metastasis through secretion of the enzymes plasmin, uPA, matrix metalloproteinases (MMPs) and cathepsin B (Komohara, Y et al. (2016) Advanced drug delivery reviews 99: 180-185; Gocheva V et al. (2010) Genes Dev 24: 241-255; Wang R et al. (2011) Lung Cancer 74: 188-196). Apart from mediating tumor growth and progression, TAMs can also interact with other immune cells and suppress innate and adaptive antitumor immune responses.

Several small molecule drugs focus on blocking the localization of TAM-precursor cells to tumors by targeting the pathways involved in cell recruitment or expansion (i.e. inhibitors of the CSF-1/CSF-1R pathway (Pyon; teck et al. Nat Med 19, 1264-1272 (2013); Tap et al. N Engl J Med 373, 428-437 (2015)) or the CCL2 pathway (Nywening, et al. Lancet Oncol 17, 651-662 (2016)). These approaches require repeated systemic exposure to large doses of the small molecule drugs. Furthermore, clinical trials of these drugs showed low responses unless they were combined with cytoreductive therapies. Nywening, et al. Lancet Oncol 17, 651-662 (2016); Butowski et al. Neuro Oncol 18, 557-564 (2016). Furthermore, these small molecule approaches do not actively promote macrophage anti-tumor activity.

Conventional nanocarriers such as liposomes have been formulated with bisphosphonates or other antiproliferative agents to systemically destroy macrophages within a tumor (i.e. liposomal-clodronate) (Fritz et al., Front Immunol 5, 587 (2014)). Oncolytic viruses have also been used to deliver siRNA to silence immune-evasion pathways within tumors and indirectly promote phagocytosis of TAMs. (Chao et al., Curr Opin Immunol 24, 225-232 (2012)). The macrophages that are destroyed using these approaches, however, are naturally replaced by newly-arriving macrophages that similarly become immunosuppressive.

Antibodies have been developed to induce functional activation of TAMs. These approaches utilize antibodies to target defined antigen types within the tumor. Mantovani, et al., Nat Rev Clin Oncol (2017) Success of these antibodies, however, is limited by their low tumor penetration and heterogeneous distribution. Thurber et al., Adv Drug Deliv Rev 60, 1421-1434 (2008). They also do not address tumor escape variants that lack the antigen targeted by the antibody.

None of the described approaches directly and effectively reprogram TAMs to become activated tumoricidal macrophages, as disclosed herein. The systems and methods disclosed herein are significantly innovative because they allow the reprogramming of TAMs to become tumor-clearing macrophages while simultaneously reducing the tumor-promoting TAM burden. Currently, no other method exists that allow physicians to rationally reprogram TAMs for these therapeutic purposes. Mantovani, et al., Nat Rev Clin Oncol (2017); Gabrilovich & Nagaraj, Nat Rev Immunol 9, 162-174 (2009). This in and of itself can provide therapeutic benefit in the treatment of tumors. By modulating or restructuring the tumor microenvironment, the current disclosure also renders tumors more susceptible to other treatment types, such as vaccines, immunotherapies (e.g., CAR), and/or chemotherapies.

Particular embodiments utilize particles to provide cells with nucleotides encoding genes encoding activation regulators such as transcription factors (e.g., Interferon Regulatory Factors (IRFs)) and/or kinases (e.g., IKKβ). These activation regulators regulate macrophage polarization (FIG. 1). Macrophage polarization is a highly dynamic process through which the physiological activity of macrophages changes. As indicated, in most tumors, TAMs exhibit an immunosuppressed phenotype which can be an "M2" phenotype. By contrast, activated macrophages can exhibit an "M1" phenotype which results in tumor cell killing. Particular embodiments disclosed herein reverse the polarization of tumor-promoting TAMs into tumor-killing macrophages. This effect ameliorates the immunosuppressive milieu within the tumors by inducing inflammatory cytokines, activating other immune cells, and phagocytosing tumor cells.

"Macrophage activation" refers to the process of altering the phenotype or function of a macrophage from (i) an inactivated state to an activated state; (ii) a non-activated state to an activated state; (iii) an activated state to a more activated state; or (iv) an inactivated state to a non-activated state. An inactivated state means an immunosuppressed phenotype that facilitates tumor growth and metastasis. A non-activated state means that the macrophage neither facilitates tumor growth or metastasis nor promotes the killing of tumor cells. Activated means that the macrophage exhibits tumoricidal activity. In particular embodiments, the activated state results in an M1 phenotype as described more fully below. In particular embodiments, the inactivated state results in an M2 phenotype, also as described more fully below.

"Macrophage inactivation" refers to the process of altering the phenotype or function of a macrophage from (i) an activated state to a less activated state; (ii) an activated state to a non-activated state; (iii) an activated state to an inactivated state; or (iv) a non-activated state to an inactivated state. In particular embodiments, the inactivated state is M2. In particular embodiments, the activated state is M1.

In particular embodiments, one benefit of the disclosed systems and methods is that patients can be spared from systemic toxicities because inflammation induced by treatment remains localized at the treatment site. To achieve this benefit, locally infused particles target TAMs in the tumor milieu, (2) deliver nucleotides that selectively reprogram signaling pathways that control macrophage polarization, and (3) are completely degradable locally by physiological pathways (Sahin et al., Nat Rev Drug Discov 13, 759-780 (2014)).

Achieving high expression of exogenous nucleotides in solid tumors is challenging in vivo. Before the current disclosure, nucleotide delivery systems based on viruses or conventional nanocarriers such as liposomes were limited by their restricted diffusion within tumor tissue. Jain & Stylianopoulos, Nat Rev Clin Oncol 7, 653-664 (2010). To circumvent this barrier, particular embodiments utilize nanoparticles (NPs) with enhanced diffusivity so that the NPs deliver nucleotides to a large population of TAMs within a tumor. Particular embodiments utilize NPs <130 nm in size that carry a neutral surface charge. Particular embodiments can further include a targeting ligand attached to the surface of the NP. For example, di-mannose can be attached to the NP surface to enable more selective targeting to the mannose receptor (CD206) expressed on the TAM cell surface. Other TAM cell surface receptors that can be targeted include early growth response protein 2 (Egr2), CD163, CD23, interleukin (IL)27RA, CLEC4A, CD1a, CD1b, CD93, CD226, IL13-Ra1, IL-4r, IL-1R type II, decoy IL-1R type II, IL-10r, macrophage scavenging receptors A and B, Ym-1, Ym-2, Low density receptor-related protein 1 (LRP1), IL-6r, CXCR1/2, and PD-L1.

In particular embodiments, systems and methods disclosed herein include administering particles to a subject in need thereof. The particles are directed to macrophages present in tumors in the subject and are designed to be internalized by the macrophages. Once internalized, the particles further deliver one or more nucleotides having sequences that encode IRF5 and IKKβ. The one or more nucleotides modify the macrophages to express IRF5 and IKKβ. Without being bound by theory, the IKKβ kinase activates the IRF5 transcription factor by phosphorylation. Activated IRF5 then causes expression of type I interferon (IFN) genes, inflammatory cytokines, including tumor necrosis factor (TNF), IL-6, IL-12 and IL-23, and tumor suppressors. In M2 macrophages that have internalized one or more nucleotides encoding IRF5 and IKKβ, the expression of the aforementioned genes through IRF5 action leads to a phenotypic or functional switch of the macrophages from an M2 phenotype to an M1 phenotype, which enables the macrophages to kill or otherwise trigger the destruction of tumor cells, thereby treating cancer. In particular embodiments, the particles are internalized in the macrophages by phagocytosis. In particular embodiments, the particles are internalized in the macrophages by ligand-mediated endocytosis (e.g., CD-206-mediated endocytosis). In particular embodiments, delivery of the particles including the IRF5 and IKKβ genes into macrophages can include, e.g., (1) binding to the macrophages, (2) internalization of the particles by the macrophages, (3) escape from endocytic vesicles into the cytoplasm after internalization, (4) release of the one or more nucleotides, which (5) can be transported into the nucleus of the macrophages and (6) transcribed to deliver genes for expressing IRF5 and IKKβ.

Aspects of the disclosure are now described in more detail as follows: (1) macrophages and macrophage phenotypes; (2) cellular pathways to affect macrophage polarization; (3) nucleotides encoding activation regulators; (4) particles to deliver nucleotides; (5) targeting ligands to more selectively deliver nucleotides; (6) pharmaceutical compositions including particles; (7) methods of use; and (8) experimental examples.

(1) Macrophages and Macrophage Phenotypes. "Macrophage" refers to a white blood cell of the immune system differentiated from bone marrow derived monocytes. Macrophages are characterized by their phagocytic activity and their antigen presentation capacity. Macrophages are key players in both the innate and adaptive immune responses. Phenotypically macrophages express the surface marker F4/80 (Ly71) and may also express other surface markers such as CDIIb (Macl), CDIIc, CD14, CD40 or CD68.

Macrophages play an important role in both innate and adaptive immunity by activating T lymphocytes. In cancer, macrophages are one of the major populations of infiltrating leukocytes associated with solid tumors (Gordon S & Taylor P R (2005) Nature Reviews Immunology 5(12): 953-964). They can be recruited to the tumor site from surrounding tissues or by the tumor itself through the secretion of chemotactic molecules. Macrophages participate in immune responses to tumors in a polarized manner depending on their phenotype. "Phenotype" is used herein to refer to the physical attributes or biochemical characteristics of a cell as a result of the interaction of its genotype and the environment and can include functions of a cell.

Macrophages that activate Th1 T lymphocytes provide an inflammatory response and are often denoted as having an M1-polarized or "classically activated" phenotype. Macrophages in an activated state (i.e. M1 macrophages or macrophages having an M1 phenotype), also referred to as "killer macrophages," inhibit cell proliferation, cause tissue damage, mediate resistance to pathogens, and possess strong tumoricidal activity. These macrophages can increase expression of mediators that are responsible for antigen presentation and costimulation; promoting infiltration of neutrophils to a tumor area leading to neutrophil-targeted tumor regression. An M1 phenotype can also be evidenced by increased antigen presentation as compared to a relevant control condition. In particular embodiments, an M1 phenotype can be evidenced by M1 macrophage production of reactive oxygen species (ROS) and nitric oxide (NO). NO has anti-proliferative effects integral for protection against pathogens and aberrant cells like tumor cells. In particular embodiments, an M1 phenotype can be evidenced by a pro-inflammatory state that induces Th1 immunity through the production of cytokines such as IL-12. In particular embodiments, macrophages in an activated state are classically activated macrophages that can phagocytose pathogens.

Beyond function, an M1 phenotype can also be evidenced by surface markers expressed by the macrophages; factors, proteins, or compounds produced by the macrophages upon polarization; or genes induced by the macrophages upon polarization. M1 polarization can lead to a phenotype evidenced by expression of CD80, CD86, iNOS, suppressor of cytokine signaling 3 (SOCS3), TNFα, IL-1, IL-6, IL-12, IL-23, Type I IFN, CXCL1, CXCL2, CXCL3, CXCL5, CXCL8, CXCL9, and CXCL10. In particular embodiments, an M1 phenotype includes an increase in expression of CD80. In particular embodiments, an M1 phenotype includes CD206−, MHCII+, CD11c−, and CD11b+.

On the other hand, macrophages that activate Th2 T lymphocytes provide an anti-inflammatory response and are often denoted as having an "M2" phenotype. Macrophages that are in an inactivated state (i.e. M2 macrophages or macrophages having an M2 phenotype), also referred to as "repair macrophages," are involved in metazoan parasites containment, cell proliferation, tissue repair, tumor progression, anti-inflammation pathways, and immunosuppression. An M2 phenotype can reduce antigen presentation and decrease phagocytosis as compared to a relevant control condition. An M2 phenotype can also be evidenced by, for example, expression of one or more of arginase 1 (Arg1 (arginase activity is associated with pro-proliferative effects and tissue repair responses)), IL-10, TGF-β, PPARγ, KLF4, CD206 (MRC1), Dectin-1 (a signaling non-TLR pattern-recognition receptor), DC-SIGN (C-type lectin), scavenger receptor A, scavenger receptor B-1, CD163 (high affinity scavenger receptor for the hemoglobin-haptoglobin complex), chemokine receptors CCR2, CXCR1, and CXCR2, YM1 (chitinase 3-like 3), and Fizz1; and secretion of the chemokines CCL17, CCL22 and CCL24. In particular embodiments, macrophages in an inactivated state promote metastasis and/or resistance to chemotherapy. In particular embodiments, an M2 phenotype includes CD206+, MHCII−, CD11c+, and CD11b$^{low}$.

Table 1 provides particular combinations of criteria that can be used to distinguish an M1 phenotype from M2 phenotypes (including sub-phenotypes designated as M2a, M2b, M2c and M2d).

TABLE 1

Exemplary Criteria to Categorize Macrophage Phenotypes.

| | M1 | M2a | M2b | M2c | M2d |
|---|---|---|---|---|---|
| Stimulation/ Activation | IFN-γ LPS GM-CSF | IL-4 IL-13 Fungal and Helminth infection | ICs IL-1R | IL-10 TGF-β GCs | IL-6 LIF Adenosine |
| Marker Expression | CD86 CD80 CD68 MHC II IL-1R TLR2 TLR4 iNOS SOCS3 CD28 Gpr18 Fpr2 CD64 | CD163 CD23 MHC II SR MMR/CD206 CD200R TGM2 DecoyR IL-1R II Mouse only: Ym½ Fizz1 Arg-1 | CD86 MHC II | CD163 TLR1 TLR8 | VEGF |
| Cytokine secretion | TNF IL-1β IL-6 IL-12 IL-23 | IL-10 TGF-β IL-1ra | IL-1 IL-6 IL-10 TNFα | IL-10 TGF-β | IL-10 IL-12 TNFα TGFβ |
| Chemokine secretion | CCL10 CCL11 CCL5 CCL8 CCL9 CCL2 CCL3 CCL4 | CCL17 CCL22 CCL24 | CCL1 | CCR2 | CCL5 CXCL10 CXCL16 |

Adapted from Röszer T (2015) Mediators Inflamm 2015, 816460 and Duluc D et al. (2007) Blood 110: 4319-4330. Arg-1, arginase-1; Fizz1, resistin-like molecule-alpha (Retnl-alpha); GCs, glucocorticoids; ICs, immune complexes; IL1-ra, IL-1 receptor antagonist; LIF, leukocyte inhibitory factor; TGM2, transglutaminase 2; TGF-β, transforming growth factor-beta; TNFα, tumor necrosis factor alpha; TLR, Toll-like receptor; MMR (CD206), macrophage mannose receptor; iNOS, inducible nitric oxide synthase; SR, scavenger receptor; SOCS3, suppressor of cytokine signaling 3; VEGF, vascular endothelial growth factor; Ym1 (also known as chitinase-3-like protein-3 (Chi3l3)).

Assays to assess macrophage phenotype can take advantage of the different molecular signatures particular to the M1 or M2 phenotype. A commonly accepted marker profile for M1 macrophages is CD80+, whereas M2-macrophages can be characterized as CD163+. Thus, flow cytometry can be performed to assess for these markers. Driving macrophages towards a M1 type and away from a M2 type can also be assessed by measuring an increase of the IL-12/IL-10 ratio or the CD163−/CD163+ macrophage ratio. In particular embodiments, M1 versus M2 morphology can be assessed by light microscopy. In particular embodiments, phagocytosis assays may be used in conjunction with other assays to assess whether a macrophage is M1 type or M2 phenotype. Phagocytosis assays of different macrophage populations may be performed by incubating an entity to be phagocytosed with macrophages at a concentration that is consistent with their normalized total surface area per cell. The entity to be phagocytosed may be added to macrophage cultures. The entity to be phagocytosed may be, for example, labeled with a fluorescent label. Phagocytosis index may be determined by the median total fluorescence intensity measured per macrophage. Quantification of phagocytosis may be by, for example, flow cytometry. Tumor cell killing assays may also be utilized. In particular embodiments, an M1 phenotype includes reduced expression of signature M2 macrophage genes including SerpinB2 (inhibitor of urokinase-type plasminogen activator), CCL2 (C—C motif chemokine ligand 2), CCL11 (C—C motif chemokine ligand 11), and Retnla (resistin like alpha; Fizz1). In particular embodiments, an M1 phenotype includes increased expression of M1 differentiation genes including CCL5 (C—C motif chemokine ligand 5).

Gene expression (e.g., M1 expression of CD80, CD86 and/or other genes noted above) can be measured by assays well known to a skilled artisan. Methods to measure gene expression include NanoString nCounter® expression assays (NanoString Technologies, Inc., Seattle, WA), Northern blots, dot blots, microarrays, serial analysis of gene expression (SAGE), RNA-seq, and quantitative RT-PCR. Methods to measure gene expression products, e.g., protein level, include ELISA (enzyme linked immunosorbent assay), western blot, FACS, radioimmunological assay (RIA), sandwich assay, fluorescent in situ hybridization (FISH), immunohistological staining, immunoelectrophoresis, immunoprecipitation, and immunofluorescence using detection reagents such as an antibody or protein binding agents.

(2) Cellular Pathways to Affect Macrophage Polarization. Polarization of a macrophage towards an activated or inactivated phenotype results from macrophage interaction with a number of different molecules or environments. For example, M1 macrophage polarization is triggered by stimuli including Toll-like receptor (TLR) ligands (e.g. lipopolysaccharide (LPS), muramyl dipeptide, lipoteichoic acid, imiquimod, CpG), IFNα, TNFα, and macrophage colony-stimulating factor (GM-CSF). M2 polarized macrophages can be divided into subsets, depending on the stimuli that initiates the polarization: the M2a subtype is elicited by IL-4, IL-13 or fungal and helminth infections; M2b is elicited by IL-1 receptor ligands, immune complexes and LPS; M2c is elicited by IL-10, TGF-β and glucocorticoids; and M2d is elicited by IL-6 and adenosine. M2 macrophage polarization may also be triggered by IL-21, GM-CSF, complement components, and apoptotic cells. Macrophage polarization is also modulated by local microenvironmental conditions such as hypoxia.

The aforementioned molecules and environments affect macrophage polarization by triggering different intracellular signaling pathways involving transcription factors. Transcription factors that are involved in both M1 and M2 polarization include IRFs, signal transducers and activators of transcription (STAT), SOCS3 proteins, and nuclear factor kappa-light-chain-enhancer of activated B cells (NFκB). Mitogen-activated protein kinases (MAPK) also play a role in directing macrophage function towards either the M1 or M2 phenotype.

The IRF/STAT pathways, activated by such stimuli as IFNs and TLR signaling as discussed above, polarize macrophages to the M1 activation state via STAT1. On the other hand, such stimuli as IL-4 and IL-13 skew macrophages toward the M2 activation state via STAT6 (Sica A & Bronte V (2007) J Clin Invest 117: 1155-1166). These signaling events thus result in either the promotion of an inflammatory immune response and tumoricidal activity, as in the case of M1 macrophage polarization, or in the promotion of an immunosuppressive protumor response, as in the case of M2 macrophage polarization.

Some intracellular molecules implicated in the induction of an M1 phenotype include the G-protein coupled receptor, P2Y(2)R, which plays a role in inducing NO via NOS2 (Eun S Y et al. (2014) Int Immunopharmacol 18: 270-276); SOCS3, which activates NFκB/PI-3 kinase pathways to produce NO (Arnold C E et al. (2014) Immunology 141: 96-110); and growth and differentiation factor Activin A, which promotes M1 markers and down-regulates IL-10 (Sierra-Filardi E et al. (2011) Blood 117: 5092-5101).

Other intracellular molecules involved in induction of the M1 phenotype include IRFs. IRFs are a group of transcription factors with diverse roles, including virus-mediated activation of IFN, and modulation of cell growth, differentiation, apoptosis, and immune system activity. Members of the IRF family are characterized by a conserved N-terminal DNA-binding domain containing tryptophan (W) repeats.

IRF5 is a transcription factor that possesses a helix-turn-helix DNA-binding motif and mediates virus- and IFN-induced signaling pathways. It acts as a molecular switch that controls whether macrophages will promote or inhibit inflammation. IRF5 activates type I IFN genes, inflammatory cytokines, including TNF, IL-6, IL-12 and IL-23, and tumor suppressors as well as Th1 and Th17 responses. It is encoded by the human IRF5 gene located at chromosome 7q32 (OMIM ID 607218). It is appreciated that several isoforms/transcriptional variants of IRF5 exist. In particular embodiments, isoforms of human IRF5 include isoform 1 (UniProt Accession Q13568-1, SEQ ID NO: 1), isoform 2 (UniProt Accession Q13568-2, SEQ ID NO: 2), isoform 3 (UniProt Accession Q13568-3, SEQ ID NO: 3), isoform 4 (UniProt Accession Q13568-4, SEQ ID NO: 4), isoform 5 (UniProt Accession Q13568-5, SEQ ID NO: 5) and isoform 6 (UniProt Accession Q13568-6, SEQ ID NO: 6). In particular embodiments, isoforms of human IRF5 include isoform 1 encoded by a nucleotide sequence shown in SEQ ID NO: 23, isoform 2 encoded by a nucleotide sequence shown in SEQ ID NO: 24, isoform 3 encoded by a nucleotide sequence shown in SEQ ID NO: 25, isoform 4 encoded by a nucleotide sequence shown in SEQ ID NO: 26, isoform 5 encoded by a nucleotide sequence shown in SEQ ID NO: 27 and isoform 6 encoded by a nucleotide sequence shown in SEQ ID NO: 28. In particular embodiments, murine IRF5 includes an amino acid sequence shown in SEQ ID NO: 7. In particular embodiments, murine IRF5 is encoded by a nucleotide sequence shown in SEQ ID NO: 29. M1 macrophages have been shown to upregulate IRF5.

IRF1 and IRF8 also play critical roles in the development and function of myeloid cells, including activation of macrophages by proinflammatory signals such as IFN-γ. Dror N et al. (2007) Mol Immunol. 44(4):338-346. In particular embodiments, human IRF1 includes an amino acid sequence shown in SEQ ID NO: 8. In particular embodiments, human IRF1 is encoded by a nucleotide sequence shown in SEQ ID NO: 30. In particular embodiments, murine IRF1 includes an amino acid sequence shown in SEQ ID NO: 12. In particular embodiments, murine IRF1 is encoded by a nucleotide sequence shown in SEQ ID NO: 34. In particular embodiments, human IRF8 includes an amino acid sequence shown in SEQ ID NO: 11. In particular embodiments, human IRF8 is encoded by a nucleotide sequence shown in SEQ ID NO: 33. In particular embodiments, murine IRF8 includes an amino acid sequence shown in SEQ ID NO: 16. In particular embodiments, murine IRF8 is encoded by a nucleotide sequence shown in SEQ ID NO: 38.

IRF3 is a homolog of IRF1 and IRF2. It contains several functional domains including a NES, a DBD, a C-terminal IRF association domain and several regulatory phosphorylation sites. IRF3 is found in an inactive cytoplasmic form that upon serine/threonine phosphorylation forms a complex with CREB Binding Protein, a transcriptional coactivator. This complex translocates to the nucleus and activates the transcription of IFN-α and -β, as well as other interferon-induced genes. In particular embodiments, isoforms of human IRF3 include isoform 1 (UniProt Accession Q14653-1), isoform 2 (UniProt Accession Q14653-2), isoform 3 (UniProt Accession Q14653-3), isoform 4 (UniProt Accession Q14653-4), and isoform 5 (UniProt Accession Q14653-5). In particular embodiments, human IRF3 isoform 1 includes an amino acid sequence shown in SEQ ID NO: 9. In particular embodiments, human IRF3 isoform 1 is encoded by a nucleotide sequence shown in SEQ ID NO: 31. In particular embodiments, murine IRF3 includes an amino acid sequence shown in SEQ ID NO: 13. In particular embodiments, murine IRF3 is encoded by a nucleotide sequence shown in SEQ ID NO: 35.

IRF7 has been shown to play a role in the transcriptional activation of type I IFN genes. In particular embodiments, isoforms of human IRF7 include isoform A (UniProt Accession Q92985-1), isoform B (UniProt Accession Q92985-2), isoform C (UniProt Accession Q92985-3), and isoform D (UniProt Accession Q92985-4). In particular embodiments, human IRF7 isoform A includes an amino acid sequence shown in SEQ ID NO: 10. In particular embodiments, human IRF7 isoform A is encoded by a nucleotide sequence shown in SEQ ID NO: 32. In particular embodiments, murine IRF7 includes an amino acid sequence shown in SEQ ID NO: 14. In particular embodiments, murine IRF7 is encoded by a nucleotide sequence shown in SEQ ID NO: 36.

One or more IRF mutants that contribute to IRF activation may also be used. For example: phosphomimetic mutants of human variant 3/variant 4 of IRF5 (isoform 4, SEQ ID NO: 4) that substitute amino acid residues S425, S427, S430, S436 with residues mimicking phosphorylation, such as aspartic acid residues (Chen W et al. (2008) Nat Struct Mol Biol. 15(11): 1213-1220); phosphomimetic mutants of human variant 5 of IRF5 (isoform 2, SEQ ID NO: 2) that substitute amino acid residues T10, S158, S309, S317, S451, and/or S462 with residues mimicking phosphorylation, such as aspartic acid residues (Chang Foreman H-C et al. infra); mutation of human IRF5 isoform a (variant 1, isoform 3, SEQ ID NO: 3) and isoform b (variant 2, isoform 1, SEQ ID NO: 1) residues S156, S158 and T160 to residues mimicking phosphorylation, such as aspartic acid residues, for constitutive nuclear accumulation of IRF5 (Lin R et al. (2005) J Biol Chem 280(4): 3088-3095); and IRF3 phosphomimetic mutants that substitute amino acid residue S396 of IRF3 with residues mimicking phosphorylation, such as aspartic acid (Chen W et al. infra). In particular embodiments, a fusion protein of murine IRF7/IRF3 includes Asp (D) mutations at four serine and one threonine residues in the IRF3 association domains (SEQ ID NO: 15), conferring constitutive activation and translocation of the fusion protein (Lin R et al. (1998) supra; Lin et al. (2000) Molecular and Cellular Biology 20: 6342-6353). In particular embodiments, a fusion protein of murine IRF7/IRF3 including D mutations at four serine and one threonine residues in the IRF3 association domains is encoded by a nucleotide sequence shown in SEQ ID NO: 37. In particular embodiments, a murine IRF8 mutant includes substitution of Lysine (K) at amino acid residue 310 with Arginine (R) (SEQ ID NO: 17). In particular embodiments, a murine IRF8 mutant including a substitution of K at amino acid residue 310 with R is encoded by a nucleotide sequence shown in SEQ ID NO: 39. Small ubiquitin-like modifiers (SUMO) bound to IRF8 primarily at K310 inhibit activation of IRF8 responsive genes. Sentrin-specific protease 1 (SENP1) targets SUMO 2/3. The activity of SENP1 "deSUMOylates" IRF8 (and other proteins) and causes IRF8 to go from a repressor of M1 macrophage differentiation to an activator (directly and through transactivation activities). Preventing SUMO binding to IRF8 by mutation of the K310 residue increases IRF8 specific gene transcription 2-5 fold (see Chang T-H et al. (2012) supra).

Particular embodiments of the present disclosure include engineered IRF transcription factors. In particular embodiments, engineered IRF transcription factors include IRFs that lack a functioning autoinhibitory domain and are therefore insensitive to feedback inactivation (Thompson et al. (2018) Front Immunol 9: 2622). For example, a human IRF5 with 2-3-fold increase in activity can be obtained by deleting aa 489-539 of the human IRF5 protein (Barnes et al. (2002) Mol Cell Biol 22: 5721-5740). In particular embodiments, an autoinhibitory domain of IRF4, a transcription factor that promotes an M2 phenotype, can be deleted or mutated to generate a more active IRF4 in the context of treating an autoimmune disease. In particular embodiments, an autoinhibitory domain of an IRF is found at the carboxy terminus of the IRF protein. In particular embodiments, engineered IRF transcription factors include IRFs that lack one or more functioning nuclear export signals (NES) to entrap IRFs in the nucleus and therefore enhance transcription. For example, nuclear accumulation of human IRF5 can be achieved by mutating the NES of human IRF5 by replacing two leucine residues with alanine (L157A/L159A) (Lin et al. (2000) Molecular and Cellular Biology 20: 6342-6353). In particular embodiments, engineered IRF transcription factors include fusions of one or more IRFs, fusions of fragments of one or more IRFs, and fusions of mutated IRFs.

NFκB is also a key transcription factor related to macrophage M1 activation. NFκB regulates the expression of a large number of inflammatory genes including TNFα, IL1B, cyclooxygenase 2 (COX-2), IL-6, and IL12p40. NFκB activity is modulated via the activation of the inhibitor of kappa B kinase (IKK) trimeric complex (two kinases, IKKα, IKKβ, and a regulatory protein, IKKγ). When upstream signals converge at the IKK complex, they first activate IKKβ kinase via phosphorylation, and activated IKKβ further phosphorylates the inhibitory molecule, inhibitor of kappa B (I-κB). This results in the proteosomal degradation of I-κB and the release of NFκB p65/p50 heterodimer from the NFκB/I-κB complex. The NFκB p65/p50 heterodimer is then translocated to the nucleus and binds to the promoters of inflammatory genes.

IKKβ is an activating kinase for NFκB as well as other transcription factors such as IRF5. IKKβ similarly phosphorylates several other signaling pathway components including FOXO3, NCOA3, BCL10, IRS1, NEMO/IKBKG, NFκB subunits RELA and NFKB1, as well as the IKK-related kinases TBK1 and IKBKE. In particular embodiments, isoforms of human IKKβ include isoform 1 (UniProt Accession O14920-1, SEQ ID NO: 18), isoform 2 (UniProt Accession O14920-2 SEQ ID NO: 19), isoform 3 (UniProt Accession O14920-3 SEQ ID NO: 20), and isoform 4 (UniProt Accession O14920-4 SEQ ID NO: 21). In particular embodiments, isoforms of human IKKβ include isoform 1 encoded by a nucleotide sequence shown in SEQ ID NO: 40, isoform 2 encoded by a nucleotide sequence shown in SEQ ID NO: 41, isoform 3 encoded by a nucleotide sequence shown in SEQ ID NO: 42, and isoform 4 encoded by a nucleotide sequence shown in SEQ ID NO: 43. In particular embodiments, murine IKKβ includes an amino acid sequence shown in SEQ ID NO: 22. In particular embodiments, murine IKKβ is encoded by a nucleotide sequence shown in SEQ ID NO: 44.

The present disclosure provides for the co-expression of IRF transcription factors with one or more molecules that can activate the IRFs to effect TAM reprogramming to an activated state for tumor killing. In particular embodiments, co-expression strategies include: co-expression of IRF5 and IKKβ; co-expression of IRF5 and TANK-binding kinase-1 (TBK-1), TNF receptor-associated factor 6 (TRAF6) adaptor, receptor interacting protein 2 (RIP2) kinase, and/or NFκB kinase-ε (IKKε) (Chang Foreman H-C et al. (2012) PLoS One 7(3): e33098); co-expression of IRF5 and protein kinase DNA-PK (Ryzhakov G et al. (2015) J of Interferon & Cytokine Res 35(2): 71-78); co-expression of IRF5 and protein kinase tyrosine kinase BCR-ABL (Massimo M et al. (2014) Carcinogenesis 35(5):1132-1143); and co-expression of IRF5 or IRF8 with one or more components of the COP9 signalosome (Korczeniewska J et al. (2013) Mol Cell Biol 33(6):1124-1138; Cohen H et al. (2000) J Biol Chem 275 (50):39081-39089).

In particular embodiments, the teachings of the current disclosure can be applied in the management of conditions triggered by hyper-immune activation (e.g., autoimmune diseases). Macrophages play key roles in autoimmune diseases such as systemic lupus erythematosus, multiple sclerosis, rheumatoid arthritis, and Sjögren's syndrome (Ushio et al. World J Immunol 2017; 7(1): 1-8). Thus, cellular pathways that support an immunosuppressive M2 phenotype are also described.

An activation regulator implicated in the induction of the M2 phenotype is Krüppel-like factor 4 (KLF-4). KLF-4 coordinates with STAT6 to induce M2 genes such as Arg-1, CD206 (Mrc1, mannose receptor), Fizz1 (resistin-like α) and peroxisome proliferator-activated receptor gamma (PPARγ), and to inhibit M1 genes such as TNFα, Cox-2, CCL5 and iNOS. The nuclear receptor, PPARγ, has been shown to regulate genes involved in oxidative metabolism and activation of the M2 phenotype (Odegaard J I et al. (2007) Nature 447: 1116-1120).

The cytokine IL-21 mediates M2 polarization by decreasing NOS2 expression and increasing STAT3 phosphorylation (Li S N et al. (2013) Mediators Inflamm 2013, 548073).

IRF4 negatively regulates TLR signaling in a MyD88 independent manner to drive the M2 phenotype (Satoh T et al. (2010) Nat Immunol 11, 936-944). In particular embodiments, human IRF4 is UniProt Accession Q15306. BMP-7 also induces M2 polarization in vitro via activation of the SMAD-PI3K-Akt-mTOR pathway (Rocher C et al. (2013) Plos One 8: e84009).

Transcription factor glucorticoid-induced leucine zipper (GILZ). GILZ is a dexamethasone-inducible gene that mediates glucocorticoid (GC) actions in a variety of cell types and it can induce the suppressive M2 macrophage phenotype. GILZ expression is rapidly and ubiquitously induced by GCs, and the protein product interacts with known transcription factors, such as NF-κB, Raf-1, TORC2, AP-1, Ras, and C/EBPs, inhibiting the expression of pro-inflammatory genes. Thus, GILZ could mimic the therapeutic anti-inflammatory effects of GCs while avoiding the detrimental ones (Ronchetti, S. et al. Front Endocrinol (Lausanne) 2015; 6: 170). In particular embodiments, GILZ is human GILZ of amino acid sequence shown in SEQ ID NO: 110. In particular embodiments, GILZ is human GILZ encoded by a nucleotide sequence shown in SEQ ID NO: 111.

As indicated, hypoxia also influences macrophage polarization through hypoxia inducible factors HIF-1α and HIF-2α. HIF-1α regulates NOS2 expression and supports emergence of an M1 phenotype while HIF-2α regulates Arg1 expression and supports emergence of an M2 phenotype (Takeda N et al. (2010) Genes Dev 24: 491-501).

TABLE 2

| Signaling molecules and genes involved in macrophage polarization. | | |
|---|---|---|
| | M1 | M2 |
| Signaling Molecules | STAT1alpha/beta IRF5 Btk P2Y(2)R SOCS3 Activin A HIF1-α | STAT6 KLF-4 NFκB p50 homodimers PPARγ HIF-2α IL-21 BMP-7 FABP4 LXRα |
| Genes | TNFα, Cox-2, CCL5, NOS2 | Arg-1, Mrc-1, Fizz1, PPARγ |

Adapted from Sica A and Mantovani A 2012 (supra) and Chávez-Galán L et al. (2015) Front Immunol 6, 253. Arg-1, arginase-1; Fizz1, resistin-like molecule-alpha (Retnl-alpha); STAT, signal transducers and activators of transcription; IRF, interferon regulatory factor; SOCS3, suppressor of cytokine signaling 3; Btk, Bruton's tyrosine kinase; HIF-1α, hypoxia inducible factor 1; KLF-4, Krüppel-like factor 4; TNFα, tumor necrosis factor-alpha; BMP-7, bone morphogenetic protein 7; P2Y(2)R, P2Y purinoceptor 2; PPARγ, peroxisome proliferator-activated receptor γ; NFκB, nuclear factor-kappa B; FABP4, fatty acid binding protein 4; LXRα; liver X receptor alpha.

(3) Nucleotides. Within the current disclosure, nucleotides encoding genes that regulate activation states are delivered to immune cells. "Gene" refers to a nucleotide sequence that encodes an activation regulator. This definition includes various sequence polymorphisms, mutations, and/or sequence variants wherein such alterations do not affect the function of the activation regulator. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleotide sequences encoding the activation regulator can be RNA that directs the expression of the activation regulator. These nucleotide sequences include RNA sequences that are translated, in particular embodiments, into protein. In particular embodiments, one of ordinary skill in the art can appreciate that DNA sequences including thymine (T) bases can be equivalent to mRNA sequences having the same sequence except that T bases are replaced by uracil (U) bases. The nucleotide sequences include both the full-length nucleotide sequences as well as non-full-length sequences derived from the full-length protein. The sequences can also include degenerate codons of the native sequence or sequences that may be introduced to provide codon preference in a specific immune cell. Gene sequences to encode activation regulators described herein are available in publicly available databases and publications. "Encoding" refers to a property of sequences of nucleotides, such as a plasmid, a gene, cDNA, mRNA, to serve as templates for synthesis of an activation regulator.

In particular embodiments, the nucleotides include synthetic mRNA. In particular embodiments, synthetic mRNA is engineered for increased intracellular stability using 5'-capping. Multiple distinct 5'-cap structures can be used to generate the 5'-cap of a synthetic mRNA molecule. For example, the Anti-Reverse Cap Analog (ARCA) cap contains a 5'-5'-triphosphate guanine-guanine linkage where one guanine contains an N7 methyl group as well as a 3'-O-methyl group. Synthetic mRNA molecules may also be capped post-transcriptionally using enzymes responsible for generating 5'-cap structures. For example, recombinant Vaccinia Virus Capping Enzyme and recombinant 2'-O-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure. This results in a cap with higher translational-competency and cellular stability and reduced activation of cellular pro-inflammatory cytokines.

In particular embodiments, other modifications of synthetic mRNA to reduce immunogenicity, promote mRNA stability, and/or promote translation of mRNA can include 5'- and 3'-terminal untranslated regions (UTRs), a Kozak translation initiation sequence in the 5' UTR, modified ribonucleosides, and/or a polyA tail. In particular embodiments, modified ribonucleosides can include pseudouridine (ψ), 5-methylcytidine (5 mC), N6-methyladenosine (m6A), 2-thiouridine (2sU), 5-methoxyuridine (5moU), and N-1-methylpseudouridine (m1ψ). In particular embodiments, UTRs can include alpha- and/or beta-globin UTRs. Particular embodiments of producing synthetic mRNA include generating a DNA template containing the coding DNA sequence of the desired protein with a 5' $T_{100-250}$ overhang by PCR amplification from a corresponding DNA plasmid. The DNA template can then be used to produce the mRNA by an in vitro transcription reaction. During in vitro transcription, a 5' cap structure (e.g., ARCA), modified ribonucleosides, and/or a 3' poly(A) tail can be incorporated. A number of in vitro transcription systems are commercially available including from, e.g., MEGAscript T7 transcription kit (ThermoFisher Scientific, Waltham, MA), Riboprobe™ System T7 (Promega, Madison, WI), AmpliScribe™ T7 high yield transcription kit (Epicentre, Madison, WI), and HiScribe™ T7 in vitro transcription kit (New England Biolabs, Ipswich, MA). In particular embodiments, synthetic mRNA can be synthesized by companies that synthesize nucleic acids (e.g., TriLink Biotechnologies, San Diego, CA).

Synthetic mRNA or other nucleotides may be made cyclic. Such nucleotides may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, or 3) ribozyme catalyzed. The newly formed 5'-/3'-linkage may be intramolecular or intermolecular.

In the first route, the 5'-end and the 3'-end of the nucleotide may contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a nucleotide molecule will undergo a nucleophilic attack on the 5'-NHS-ester moiety forming a new 5'-/3'-amide bond.

In the second route, T4 RNA ligase may be used to enzymatically link a 5'-phosphorylated nucleotide molecule to the 3'-hydroxyl group of a nucleic acid forming a new phosphorodiester linkage. In an example reaction, 1 μg of a nucleic acid molecule can be incubated at 37° C. for 1 hour with 1-10 units of T4 RNA ligase (New England Biolabs, Ipswich, MA) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of a cDNA template encodes a ligase ribozyme sequence such that during in vitro transcription, the resultant nucleotide molecule can contain an active ribozyme sequence capable of ligating the 5'-end of a nucleic acid molecule to the 3'-end of a nucleic acid molecule. The ligase ribozyme may be derived from the Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In particular embodiments, nucleotides include a plasmid, a cDNA, or an mRNA that can include, e.g., a sequence (e.g., a gene) for expressing an activation regulator. Suitable plasmids include standard plasmid vectors and minicircle plasmids that can be used to transfer a gene to a lymphocyte. The nucleotides (e.g., minicircle plasmids) can further include any additional sequence information to facilitate transient expression in a modified cell. For example, the nucleotides can include promoters, such as general promoters, tissue-specific promoters, cell-specific promoters, and/or promoters specific for the cytoplasm. As indicated, promoters and plasmids (e.g., minicircle plasmids) are generally well known in the art and can be prepared using conventional techniques.

In particular embodiments, a nucleotide encoding an IRF is used in combination with one or more additional nucleotides encoding other IRFs. In particular embodiments, a nucleotide encoding an IRF is used in combination with one or more additional nucleotides encoding other IRFs and with a nucleotide encoding a IKKβ. In particular embodiments, a nucleotide encoding an IRF is used in combination with a nucleotide encoding a IKKβ at a ratio of 0.5:1, 1:1, 2:1, 3:1, 4:1, or 5:1. In particular embodiments, a nucleotide encoding an IRF is used in combination with a nucleotide encoding a IKKβ at a ratio of 3:1.

Particular embodiments can deliver nucleotides within a gene editing system. Gene editing systems modify or affect particular sequences of a cell's endogenous genome. Gene editing systems are useful for targeted genome editing, for example gene disruption, gene editing by homologous recombination, and gene therapy to insert therapeutic genes at the appropriate chromosomal target sites with a human genome.

Particular embodiments utilize transcription activator-like effector nucleases (TALENs) as gene editing systems. TALENs refer to fusion proteins including a transcription activator-like effector (TALE) DNA binding protein and a DNA cleavage domain. TALENs are used to edit genes and genomes by inducing double strand breaks (DSBs) in the DNA, which induce repair mechanisms in cells. Generally, two TALENs must bind and flank each side of the target DNA site for the DNA cleavage domain to dimerize and induce a DSB. The DSB is repaired in the cell by non-homologous end-joining (NHEJ) or by homologous recombination (HR) with an exogenous double-stranded donor DNA fragment.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. The FokI domain functions as a dimer requiring two constructs with unique DNA binding domains for sites on the target sequence. The FokI cleavage domain cleaves within a five or six base pair spacer sequence separating the two inverted half-sites.

Particular embodiments utilize MegaTALs as gene editing systems. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Particular embodiments utilize zinc finger nucleases (ZFNs) as gene editing systems. ZFNs are a class of site-specific nucleases engineered to bind and cleave DNA at specific positions. ZFNs are used to introduce DSBs at a specific site in a DNA sequence which enables the ZFNs to target unique sequences within a genome in a variety of different cells. Moreover, subsequent to double-stranded breakage, homologous recombination or non-homologous end joining takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease.

Guide RNA can be used, for example, with gene-editing systems such as CRISPR-Cas systems. CRISPR-Cas systems include CRISPR repeats and a set of CRISPR-associated genes (Cas).

In general, any system capable of resulting in functional expression of delivered nucleotides can be used within the current disclosure. However, in particular embodiments, delivery utilizing viral vectors is excluded.

(4) Particles. Particles used within the systems and methods disclosed herein can function to condense and protect nucleotides from enzymatic degradation. Particularly useful materials to use within particles for this purpose include positively charged lipids and/or polymers, including poly(β-amino ester) (PbAE).

Examples of positively charged lipids include esters of phosphatidic acid with an aminoalcohol, such as an ester of dipalmitoyl phosphatidic acid or distearoyl phosphatidic acid with hydroxyethylenediamine. More particular examples of positively charged lipids include 3β-[N-(N',N'-dimethylaminoethyl)carbamoyl) cholesterol (DC-chol); N,N'-dimethyl-N,N'-dioctacyl ammonium bromide (DDAB); N,N'-dimethyl-N,N'-dioctacyl ammonium chloride (DDAC); 1,2-dioleoyloxypropyl-3-dimethyl-hydroxyethyl ammonium chloride (DORI); 1,2-dioleoyloxy-3-[trimethylammonio]-propane (DOTAP); N-(1-(2,3-dioleyloxy) propyl)-N,N,N-trimethylammonium chloride (DOTMA); dipalmitoylphosphatidylcholine (DPPC); 1,2-dioctadecyloxy-3-[trimethylammonio]-propane (DSTAP); and the cationic lipids described in e.g. Martin et al., Current Pharmaceutical Design 2005, 11, 375-394.

Examples of positively charged polymers that can be used within particles of the current disclosure include polyamines; polyorganic amines (e.g., polyethyleneimine (PEI), polyethyleneimine celluloses); poly(amidoamines) (PAMAM); polyamino acids (e.g., polylysine (PLL), polyarginine); polysaccharides (e.g, cellulose, dextran, DEAE dextran, starch); spermine, spermidine, poly(vinylbenzyl trialkyl ammonium), poly(4-vinyl-N-alkyl-pyridiumiun), poly(acryloyl-trialkyl ammonium), and Tat proteins.

Blends of lipids and polymers in any concentration and in any ratio can also be used. Blending different polymer types in different ratios using various grades can result in characteristics that borrow from each of the contributing polymers. Various terminal group chemistries can also be adopted.

Particular embodiments disclosed herein can also utilize porous particles constructed from any material capable of forming a porous network. Exemplary materials include metals, transition metals and metalloids. Exemplary metals, transition metals and metalloids include lithium, magnesium, zinc, aluminum and silica. In particular embodiments, the porous particles include silica. The exceptionally high surface area of mesoporous silica (exceeding 1,000 m2/g) enables nucleotide loading at levels exceeding conventional DNA carriers such as liposomes.

Particles can be formed in a variety of different shapes, including spheroidal, cuboidal, pyramidal, oblong, cylindrical, toroidal, and the like. The nucleotides can be included in the pores of the particles in a variety of ways. For example, the nucleotides can be encapsulated in the porous particles. In other aspects, the nucleotides can be associated (e.g., covalently and/or non-covalently) with the surface or close underlying vicinity of the surface of the porous particles. In particular embodiments, the nucleotides can be incorporated in the porous particles e.g., integrated in the material of the porous particles. For example, the nucleotides can be incorporated into a polymer matrix of polymer particles.

In particular embodiments, the particles disclosed herein include a coating. A coating can serve to shield the encapsulated nucleotides and/or reduce or prevent off-target binding. Off-target binding is reduced or prevented by reducing the surface charge of the particles to neutral or negative. As disclosed in more detail elsewhere herein, coatings can include neutral or negatively charged polymer- and/or liposome-based coatings. In particular embodiments, the coating is a dense surface coating of hydrophilic and/or neutrally charged hydrophilic polymer sufficient to prevent the encapsulated nucleotides from being exposed to the environment before release into an immune cell. In particular embodiments, the coating covers at least 80% or at least 90% of the surface of the particle. In particular embodiments, the coating includes polyglutamic acid (PGA). In particular embodiments, PGA can serve as a linker to attach a targeting ligand to a particle. In particular embodiments, PGA can serve as a linker to attach di-mannose to a particle. In particular embodiments, the coating includes hyaluronic acid.

Examples of neutrally charged polymers that can be used as coating within embodiments of the disclosure include polyethylene glycol (PEG); poly(propylene glycol); and polyalkylene oxide copolymers, (PLURONIC®, BASF Corp., Mount Olive, NJ).

Neutrally charged polymers also include zwitterionic polymers. Zwitterionic refers to the property of overall charge neutrality while having both a positive and a negative electrical charge. Zwitterionic polymers can behave like regions of cell membranes that resist cell and protein adhesion.

Zwitterionic polymers include zwitterionic constitutional units including pendant groups (i.e., groups pendant from the polymer backbone) with zwitterionic groups. Exemplary zwitterionic pendant groups include carboxybetaine groups (e.g., -Ra-N+(Rb)(Rc)-Rd-CO$_2$—, where Ra is a linker group that covalently couples the polymer backbone to the cationic nitrogen center of the carboxybetaine groups, Rb and Rc are nitrogen substituents, and Rd is a linker group that covalently couples the cationic nitrogen center to the carboxy group of the carboxybetaine group).

Examples of negatively charged polymers include alginic acids; carboxylic acid polysaccharides; carboxymethyl cellulose; carboxymethyl cellulose-cysteine; carrageenan (e.g., GELCARIN® 209, GELCARIN® 379, FMC Corporation, Philadelphia, PA); chondroitin sulfate; glycosaminoglycans; mucopolysaccharides; negatively charged polysaccharides (e.g., dextran sulfate); poly(acrylic acid); poly(D-aspartic acid); poly(L-aspartic acid); poly(L-aspartic acid) sodium salt; poly(D-glutamic acid); poly(L-glutamic acid); poly(L-glutamic acid) sodium salt; poly(methacrylic acid); sodium alginate (e.g., PROTANAL® LF 120M, PROTANAL® LF 200M, PROTANAL® LF 200D, FMC Biopolymer Corp., Drammen, Norway); sodium carboxymethyl cellulose (CMC); sulfated polysaccharides (heparins, agaropectins); pectin, gelatin and hyaluronic acid.

In particular embodiments, polymers disclosed herein can include "star shaped polymers," which refer to branched polymers in which two or more polymer branches extend from a core. The core is a group of atoms having two or more functional groups from which the branches can be extended by polymerization. In particular embodiments, nanoparticles of the present disclosure include star shaped polymers. In particular embodiments, nanoparticles of the present disclosure include star shaped polymers and a coating. In particular embodiments, nanoparticles of the present disclosure include star shaped polymers and a coating including PGA. In particular embodiments, nanoparticles of the present disclosure include star shaped polymers and a coating including hyaluronic acid.

In particular embodiments, the branches are zwitterionic or negatively-charged polymeric branches. For star polymers, the branch precursors can be converted to zwitterionic or negatively-charged polymers via hydrolysis, ultraviolet irradiation, or heat. The polymers also may be obtained by any polymerization method effective for polymerization of unsaturated monomers, including atom transfer radical polymerization (ATRP), reversible addition-fragmentation chain transfer polymerization (RAFT), photo-polymerization, ring-opening polymerization (ROP), condensation, Michael addition, branch generation/propagation reaction, or other reactions.

Liposomes are microscopic vesicles including at least one concentric lipid bilayer. Vesicle-forming lipids are selected to achieve a specified degree of fluidity or rigidity of the final complex. In particular embodiments, liposomes provide a lipid composition that is an outer layer surrounding a porous particle. In particular embodiments, nanoparticles of the present disclosure include liposomal nanoparticles.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, DDAB, dioctadecyl dimethyl ammonium chloride (DODAC), 1,2-dimyristoyl-3-trimethylammonium propane (DMTAP), DOTAP, DOTMA, DC—Chol, phosphatidic acid (PA), dipalmitoylphosphatidylglycerol (DPPG), dioleoylphosphatidylglycerol, DOPG, and dicetylphosphate. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

The size of particles can vary over a wide range and can be measured in different ways. In preferred embodiments, the particles are NPs<130 nm in size. However, NPs of the present disclosure can also have a minimum dimension of equal to or less than 500 nm, less than 150 nm, less than 140 nm, less than 120 nm, less than 110 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, the particles are NPs 90 to 130 nm in size.

In particular embodiments, the NPs can have a minimum dimension ranging between 5 nm and 500 nm, between 10 nm and 100 nm, between 20 nm and 90 nm, between 30 nm and 80 nm, between 40 nm and 70 nm, and between 40 nm and 60 nm. In particular embodiments, the dimension is the diameter of NPs or coated NPs. In particular embodiments, a population of particles of the present disclosure can have a mean minimum dimension of equal to or less than 500 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, a population of NPs in a composition of the present disclosure can have a mean diameter ranging between 5 nm and 500 nm, between 10 nm and 100 nm, between 20 nm and 90 nm, between 30 nm and 80 nm, between 40 nm and 70 nm, and between 40 nm and 60 nm, between 70 nm and 130 nm or between 75 nm and 125 nm. Dimensions of the particles can be determined using, e.g., conventional techniques, such as dynamic light scattering and/or electron microscopy. While not preferred, in particular embodiments, microparticles could also be used.

In particular embodiments, PbAE polymers are mixed with nucleotides (e.g., in vitro transcribed mRNA) in a ratio of 20:1, 30:1, 40:1, 50:1, 60:1, 70:1, 80:1, 90:1, 100:1, or more to generate PbAE-nucleotide polyplexes. In particular embodiments, PbAE polymers are mixed with nucleotides (e.g., in vitro transcribed mRNA) in a ratio of 60:1 to generate PbAE-nucleotide polyplexes. In particular embodiments, the PbAE-nucleotide polyplexes can be combined with PGA/Di-mannose to form the final NPs.

(5) Targeting Ligands. Targeting ligands can be used on the surface of particles and can lead to more selective binding of immune cells of interest within a heterogeneous cell population.

In particular embodiments, targeting ligands include binding domains derived from cell marker ligands, receptor ligands, antibodies, peptides, peptide aptamers, nucleic acids, nucleic acid aptamers, spiegelmers or combinations thereof. In particular embodiments, within the context of cell targeting ligands, binding domains include any substance that binds to another substance to form a complex capable of mediating endocytosis.

In particular embodiments, binding domains are derived from antibodies. Binding domains derived from antibodies can include whole antibodies or can include binding fragments of an antibody, e.g., Fv, Fab, Fab', F(ab')2, Fc, and single chain Fv fragments (scFvs) or any biologically effective fragments of an immunoglobulin that bind specifically to a targeted motif expressed by an immune cell. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind a motif expressed by an immune cell can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to an immune cell motif. For example, binding domains may be identified by screening a Fab phage library for Fab fragments that specifically bind to a target of interest (see Hoet et al., *Nat. Biotechnol.* 23:344, 2005). Phage display libraries of human antibodies are also available. Additionally, traditional strategies for hybridoma development using a target of interest as an immunogen in convenient systems (e.g., mice, HuMAb Mouse®, TC Mouse™, KM-Mouse®, llamas, chicken, rats, hamsters, rabbits, etc.) can be used to develop binding domains. In particular embodiments, antibodies specifically bind to motifs expressed by a selected immune cell and do not cross react with nonspecific components or unrelated targets. Once identified, the amino acid sequence or nucleotide sequence coding for the antibody can be isolated and/or determined.

An intact antibody can include at least two heavy (H) chains and two light (L) chains inter-connected by disulfide bonds. Each heavy chain is composed of a heavy chain variable region (abbreviated herein as VH or $V_H$) and a heavy chain constant region. The heavy chain constant region includes three domains, CH1, CH2 and CH3. Each light chain is composed of a light chain variable region (abbreviated herein as VL or $V_L$) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. In particular embodiments, an antibody includes antigen-binding portions of an intact antibody that retain capacity to bind. Examples of fragments that retain capacity to bind include: (i) an Fab fragment, a monovalent fragment including the VL, VH, CL and CH1 domains; (ii) a F(ab')$_2$ fragment, a bivalent fragment including two Fab fragments linked by a disulfide bridge at the hinge region; (iii) an Fd fragment including the VH and CH1 domains; (iv) an Fv fragment including the VL and VH domains of a single arm of an antibody, (v) a dAb fragment (Ward et al., Nature, 341:544-546 (1989)), including a VH domain; and (vi) an isolated complementarity determining region (CDR).

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, MD (Kabat numbering scheme); Al-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering. In particular embodiments, CDR regions are found within antibody regions as numbered by Kabat as follows: for the light chain: CDRL1 are amino acids 24-34; CDRL2 are amino acids 50-56; CDRL3 are amino acids 89-97 and for the heavy chain: CDRH1 are amino acids 31-35; CDRH2 are amino acids 50-65; and CDRH3 are amino acids 95-102.

Peptide aptamers include a peptide loop (which is specific for a target protein) attached at both ends to a protein scaffold. This double structural constraint greatly increases the binding affinity of the peptide aptamer to levels comparable to an antibody. The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor SpI). Peptide aptamer selection can be made using different systems, such as the yeast two-hybrid system (e.g., Gal4 yeast-two-hybrid system) or the LexA interaction trap system.

Nucleic acid aptamers are single-stranded nucleotide sequence (DNA or RNA) ligands that function by folding into a specific globular structure that dictates binding to target proteins or other molecules with high affinity and specificity, as described by Osborne et al., Curr. Opin. Chem. Biol. 1:5-9, 1997; and Cerchia et al., FEBS Letters 528:12-16, 2002. In particular embodiments, aptamers are small (15 KD; or between 15-80 nucleotides or between 20-50 nucleotides). Aptamers are generally isolated from libraries including $10^{14}$-$10^{15}$ random oligonucleotide sequences by a procedure termed SELEX (see, for example, Tuerk et al., Science, 249:505-510, 1990; Green et al., Methods Enzymology. 75-86, 1991; and Gold et al., Annu. Rev. Biochem., 64: 763-797, 1995). Further methods of generating aptamers are described in, for example, U.S. Pat. Nos. 6,344,318; 6,331,398; 6,110,900; 5,817,785; 5,756,291; 5,696,249; 5,670,637; 5,637,461; 5,595,877; 5,527,894; 5,496,938; 5,475,096; and 5,270,16. Spiegelmers are similar to nucleic acid aptamers except that at least one β-ribose unit is replaced by β-D-deoxyribose or a modified sugar unit selected from, for example, β-D-ribose, α-D-ribose, β-L-ribose.

In particular embodiments, targeted cells are TAMs. Targeted cells could also include regulatory T cells (TREG). TREG are a subpopulation of T cells, which modulate the immune system, maintain tolerance to self-antigens, and abrogate autoimmune disease. TREG express CD25, CTLA-4, GITR, GARP and LAP. Selected cell targeting ligands disclosed herein can bind CD25, CTLA-4, GITR, GARP and/or LAP to achieve selective delivery of nucleotides to naïve TREG. Other cell types that can be targeted include myeloid-derived suppressor cells (MDSC), regulatory dendritic cells (DCreg), neutrophils, T helper 17 cells (Th17), regulatory B cells (Breg), and/or mesenchymal stromal cells (MSC). One of ordinary skill in the art can identify appropriate cellular markers to target these cell types utilizing targeting ligands as disclosed herein.

M2 Binding Domains. In particular embodiments, Egr2 is targeted on M2 macrophages. Commercially available antibodies for Egr2 can be obtained from Thermo Fisher, Waltham, MA; Abcam, Cambridge, MA; Millipore Sigma, Burlington, MA; Miltenyi Biotec, Bergisch Gladbach, Germany; LifeSpan Biosciences, Inc., Seattle, WA; and Novus Biologicals, Littleton, CO Generation of anti-Egr2 antibodies are discussed, for example, in Murakami K et al. (1993) Oncogene 8(6): 1559-1566. Anti-Egr2 antibodies include: rabbit monoclonal anti-Egr2 antibody clone EPR4004; mouse monoclonal anti-Egr2 antibody clone 1G5; mouse monoclonal anti-Egr2 antibody clone OTI1B12: rabbit polyclonal anti-Egr2 antibody recognizing AA residues 200-300 of human Egr2; rabbit polyclonal anti-Egr2 antibody recognizing AA residues 340-420 of human Egr2; and rabbit polyclonal anti-Egr2 antibody recognizing AA residues 370-420 of human Egr2. Binding domains can be derived from these antibodies and other antibodies disclosed herein.

In particular embodiments, the targeting ligand includes a human or humanized binding domain (e.g., nanobody) including a variable heavy chain including a CDRH1 sequence including SGNIFSINAIG (SEQ ID NO: 45), a CDRH2 sequence including TITLSGSTN (SEQ ID NO: 46), and a CDRH3 sequence including NTYSDSDVYGY (SEQ ID NO: 47). These reflect CDR sequences that bind CD206.

In particular embodiments, the targeting ligand includes a human or humanized binding domain (e.g., nanobody) including a variable heavy chain including a CDRH1 sequence including PGFKLDYYAIA (SEQ ID NO: 48), a CDRH2 sequence including SINSSGGST (SEQ ID NO: 49), and a CDRH3 sequence including LRRYYGLNLDPGSYDY (SEQ ID NO: 50). These reflect CDR sequences that bind CD206.

In particular embodiments, the targeting ligand includes a human or humanized binding domain (e.g., nanobody) including a variable heavy chain including a CDRH1 sequence including GFPFNIYPMS (SEQ ID NO: 51), a CDRH2 sequence including YISHGGTTT (SEQ ID NO: 52), and a CDRH3 sequence including GYARLMTDSELV (SEQ ID NO: 53). These reflect CDR sequences that bind CD206.

A number of additional antibodies specific for CD206 are known to those of skill in the art and can be readily characterized for sequence, epitope binding, and affinity. See, for example, WO 2014/140376, WO 2013/174537, and U.S. Pat. No. 7,560,534. Commercially available antibodies for CD206 can be obtained from Thermo Fisher, Waltham, Mas.; Proteintech, Rosemont, IL; BioLegend, San Diego, CA; R & D Systems, Minneapolis, MN; LifeSpan Biosciences, Inc., Seattle, WA; Novus Biologicals, Littleton, CO; and Bio-Rad, Hercules, CA In particular embodiments, an anti-CD206 antibody includes a rat monoclonal anti-mouse CD206 monoclonal antibody clone C068C2 (Cat #141732, Biolegend, San Diego, CA).

In particular embodiments, the targeting ligand includes a human or humanized binding domain (e.g., scfv) including a variable light chain including a CDRL1 sequence including ASQSVSHDV (SEQ ID NO: 54), a CDRL2 sequence including YTS, and a CDRL3 sequence including QDYSSPRT (SEQ ID NO: 56). In particular embodiments, the targeting ligand includes a human or humanized binding domain (e.g., scfv) including a variable heavy chain including a CDRH1 sequence including GYSITSDY (SEQ ID NO: 57), a CDRH2 sequence including YSG, and a CDRH3 sequence including CVSGTYYFDYWG (SEQ ID NO: 59). These reflect CDR sequences of the Mac2-48 antibody that bind CD163.

In particular embodiments, the targeting ligand includes a human or humanized binding domain (e.g., scfv) including a variable light chain including a CDRL1 sequence including ASQSVSSDV (SEQ ID NO: 60), a CDRL2 sequence including YAS, and a CDRL3 sequence including QDYTSPRT (SEQ ID NO: 62). In particular embodiments, the targeting ligand includes a human or humanized binding domain (e.g., scfv) including a variable heavy chain including a CDRH1 sequence including GYSITSDY (SEQ ID NO: 63), a CDRH2 sequence including YSG, and a CDRH3 sequence including CVSGTYYFDYWG (SEQ ID NO: 65). These reflect CDR sequences of the Mac2-158 antibody that bind CD163.

A number of additional antibodies or binding domains specific for CD163 are known to those of skill in the art and can be readily characterized for sequence, epitope binding, and affinity. See, for example, WO 2011/039510, WO 2002/032941, WO 2002/076501, and US 2005/0214871. Commercially available antibodies for CD163 can be obtained from Thermo Fisher, Waltham, MA; Enzo Life Sciences, Inc., Farmingdale, NY; BioLegend, San Diego, CA; R & D Systems, Minneapolis, MN; LifeSpan Biosciences, Inc., Seattle, WA; and RDI Research Diagnostics, Flanders, NJ In particular embodiments, anti-CD163 antibodies can include: mouse monoclonal anti-CD163 antibody clone 3D4; mouse monoclonal anti-CD163 antibody clone Ber-Mac3; mouse monoclonal anti-CD163 antibody clone EDHu-1; and mouse monoclonal anti-CD163 antibody clone GHI/61.

In particular embodiments, the targeting ligand includes a human or humanized binding domain (e.g., scfv) including a variable light chain including a CDRL1 sequence including RSSKSLLYKDGKTYLN (SEQ ID NO: 66), a CDRL2 sequence including LMSTRAS (SEQ ID NO: 67), and a CDRL3 sequence including QQLVEYPFT (SEQ ID NO: 68). In particular embodiments, the targeting ligand includes a human or humanized binding domain (e.g., scfv) including a variable heavy chain including a CDRH1 sequence including GYWMS (SEQ ID NO: 69), a CDRH2 sequence including EIRLKSDNYATHYAESVKG (SEQ ID NO: 70), and a CDRH3 sequence including FID. These reflect CDR sequences that bind CD23.

A number of antibodies or binding domains specific for CD23 are known to those of skill in the art and can be readily characterized for sequence, epitope binding, and affinity. See, for example, U.S. Pat. Nos. 7,008,623, 6,011,138 A (antibodies including 5E8, 6G5, 2C8, B3B1 and 3G12), US 2009/0252725, Rector et al. (1985) J. Immunol. 55: 481-488; Flores-Rumeo et al. (1993) Science 241: 1038-1046; Sherr et al. (1989) J. Immunol. 142: 481-489; and Pene et al., (1988) PNAS 85: 6820-6824. Commercially available antibodies for CD23 can be obtained from Thermo Fisher, Waltham, MA; Abcam, Cambridge, MA; Bioss Antibodies, Inc., Woburn, MA; Bio-Rad, Hercules, CA; LifeSpan Biosciences, Inc., Seattle, WA; and Boster Biological Technology, Pleasanton, CA In particular embodiments, anti-CD23 antibodies can include: mouse monoclonal anti-CD23 antibody clone Tu 1; rabbit monoclonal anti-CD23 antibody clone SP23; rabbit monoclonal anti-CD23 antibody clone EPR3617; mouse monoclonal anti-CD23 antibody clone 5B5; mouse monoclonal anti-CD23 antibody clone 1B12; mouse monoclonal anti-CD23 antibody clone M-L23.4; and mouse monoclonal anti-CD23 antibody clone 3A2.

M1 Binding Domains. In particular embodiments, the targeting ligand includes a human or humanized binding domain (e.g., scfv) including a variable light chain including a CDRL1 sequence including SSNIGDNY (SEQ ID NO: 72), a CDRL2 sequence including RDS, and a CDRL3 sequence including QSYDSSLSGS (SEQ ID NO: 74). In particular embodiments, the targeting ligand includes a human or humanized binding domain (e.g., scfv) including a variable heavy chain including a CDRH1 sequence including GFTFDDYG (SEQ ID NO: 75), a CDRH2 sequence including ISWNGGKT (SEQ ID NO: 76), and a CDRH3 sequence including ARGSLFHDSSGFYFGH (SEQ ID NO: 77). These reflect CDR sequences of the Ab79 antibody that bind CD38.

In particular embodiments, the targeting ligand includes a human or humanized binding domain (e.g., scfv) including a variable light chain including a CDRL1 sequence including NSNIGSNT (SEQ ID NO: 78), a CDRL2 sequence including SDS, and a CDRL3 sequence including QSYDSSLSGSR (SEQ ID NO: 80). In particular embodiments, the targeting ligand includes a human or humanized binding domain (e.g., scfv) including a variable heavy chain including a CDRH1 sequence including GFTFNNYG (SEQ ID NO: 81), a CDRH2 sequence including ISYDGSDK (SEQ ID NO: 82), and a CDRH3 sequence including ARVYYYGFSGPSMDV (SEQ ID NO: 83). These reflect CDR sequences of the Ab19 antibody that bind CD38.

In particular embodiments, the targeting ligand includes a human or humanized binding domain (e.g., scfv) including a variable light chain including a CDRL1 sequence including RASQSVSSYLA (SEQ ID NO: 84), a CDRL2 sequence including DASNRAT (SEQ ID NO: 85), and a CDRL3 sequence including QQRSNWPPTF (SEQ ID NO: 86). In particular embodiments, the targeting ligand includes a human or humanized binding domain (e.g., scfv) including a variable heavy chain including a CDRH1 sequence including SFAMS (SEQ ID NO: 87), a CDRH2 sequence including AISGSGGGTYYADSVKG (SEQ ID NO: 88), and a CDRH3 sequence including DKILWFGEPVFDY (SEQ ID NO: 89). These reflect CDR sequences of the daratumumab antibody that bind CD38 described in U.S. Pat. No. 7,829, 693.

A number of antibodies specific for CD38 are known to those of skill in the art and can be readily characterized for sequence, epitope binding, and affinity. See, for example, WO 2005/103083, WO 2006/125640, WO 2007/042309, WO 2008/047242, WO 2012/092612, WO 2006/099875, WO 2011/154453, WO 2015/130728, U.S. Pat. Nos. 7,829, 693, and US 2016/0200828. Commercially available antibodies for CD38 can be obtained from Thermo Fisher, Waltham, MA; Abcam, Cambridge, MA; and Millipore Sigma, Burlington, MA In particular embodiments, anti-CD23 antibodies can include: rabbit monoclonal anti-CD38 antibody clone GAD-3; mouse monoclonal anti-CD38 antibody clone HIT2; mouse monoclonal anti-CD38 antibody clone AT1; mouse monoclonal anti-CD38 antibody clone AT13/5; rat monoclonal anti-CD38 antibody clone NIMR-5; and rat monoclonal IgG2a, K anti-CD38 antibody clone 90/CD38 (Cat #BD Biosciences, San Jose, CA).

In particular embodiments, G-protein coupled receptor 18 (Gpr18) is targeted on M1 macrophages. Commercially available antibodies for Gpr18 can be obtained from Assay Biotechnology Company Inc., Sunnyvale, CA; Thermo Fisher, Waltham, MA; Abcam, Cambridge, MA; GeneTex, Inc., Irvine, CA; and Novus Biologicals, Littleton, CO In particular embodiments, anti-Gpr18 antibodies include: rabbit polyclonal anti-Gpr18 antibody recognizing a portion of amino acids 1-50 of human Gpr18; rabbit polyclonal anti-Gpr18 antibody recognizing a region including amino acids 160-240 of human Gpr18; rabbit polyclonal anti-Gpr18 antibody recognizing a region including amino acids 100-180 of human Gpr18; rabbit monoclonal anti-Gpr18 antibody clone EPR12359; and rabbit polyclonal anti-Gpr18 antibody recognizing a region including amino acids 140-190 of human Gpr18.

In particular embodiments, formyl peptide receptor 2 (Fpr2) is targeted on M1 macrophages. Commercially available antibodies for Fpr2 can be obtained from Atlas Antibodies, Bromma, Sweden; Biorbyt, LLC, San Francisco, CA; Cloud-Clone Corp., Katy, TX; US Biological Life Sciences, Salem, MA; and Novus Biologicals, Littleton, CO In particular embodiments, anti-fpr2 antibodies include: mouse monoclonal anti-fpr2 antibody clone GM1D6; mouse monoclonal anti-fpr2 antibody clone 304405; recombinant anti-fpr2 antibody clone REA663; and rabbit polyclonal anti-fpr2 antibody recognizing a region including amino acids 300-350 of fpr2.

In particular embodiments, the targeting ligand includes a human or humanized binding domain (e.g., scfv) including a variable light chain including a CDRL1 sequence including RASQSVSSYLA (SEQ ID NO: 90), a CDRL2 sequence including DASSRAT (SEQ ID NO: 91), and a CDRL3 sequence including QLRSNWPPYT (SEQ ID NO: 92). In particular embodiments, the targeting ligand includes a human or humanized binding domain (e.g., scfv) including a variable heavy chain including a CDRH1 sequence including GYGMH (SEQ ID NO: 93), a CDRH2 sequence including VIWYDGSNKYYADSVKG (SEQ ID NO: 94), and a CDRH3 sequence including DTGDRFFDY (SEQ ID NO: 95). These reflect CDR sequences that bind CD64.

A number of antibodies specific for CD64 are known to those of skill in the art and can be readily characterized for sequence, epitope binding, and affinity. See, for example, U.S. Pat. No. 7,378,504, WO 2006/131953, and WO 2008/074867. Commercially available antibodies for CD64 can be obtained from Ancell, Bayport, MN; Thermo Fisher, Waltham, MA; Abcam, Cambridge, MA; LifeSpan Biosciences, Inc., Seattle, WA; and Novus Biologicals, Littleton, CO In particular embodiments, anti-CD64 antibodies include: mouse monoclonal anti-CD64 antibody clone 32-2; mouse monoclonal anti-CD64 antibody clone UMAB74; rat monoclonal anti-CD64 antibody clone 290322; mouse monoclonal anti-CD64 antibody clone 10.1; and mouse monoclonal anti-CD64 antibody clone 1D3.

In particular embodiments, CD86 is targeted on M1 macrophages. A number of antibodies specific for CD86 are known to those of skill in the art and can be readily characterized for sequence, epitope binding, and affinity. See, for example, WO 2004/076488, U.S. Pat. No. 8,378,082 (mAb 2D4) and U.S. Pat. No. 6,346,248 (IG10H6D10). Commercially available antibodies for CD86 can be obtained from Thermo Fisher, Waltham, MA; Miltenyi Biotec, Bergisch Gladbach, Germany; LifeSpan Biosciences, Inc., Seattle, WA; Bio-Rad, Hercules, CA; and Novus Biologicals, Littleton, CO In particular embodiments, anti-CD86 antibodies include: mouse monoclonal anti-CD86 antibody clone BU63; polyclonal goat anti-CD86 antibody recognizing a region including Ala23 to His244 of human CD86; mouse monoclonal anti-CD86 antibody clone IT2.2; rabbit monoclonal anti-CD86 antibody clone BFF-3; and mouse monoclonal anti-CD86 antibody clone C86/1146.

Other agents that can facilitate internalization by and/or transfection of lymphocytes, such as poly(ethyleneimine)/DNA (PEI/DNA) complexes can also be used.

(6) Compositions. The particles disclosed herein can be provided as part of compositions formulated for administration to subjects. Compositions include a particle disclosed herein and a pharmaceutically acceptable carrier.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol, sulfur-containing reducing agents, amino acids, low molecular weight polypeptides, proteins, immunoglobulins, hydrophilic polymers or polysaccharides.

In particular embodiments, compositions are formulated for intraperitoneal, intravenous, or intracranial injection. The compositions disclosed herein can further be formulated for intraarterial, intranodal, intralymphatic, intratumoral, intramuscular, oral, and/or subcutaneous administration and more particularly by intraarterial, intranodal, intralymphatic, intratumoral, intramuscular, and/or subcutaneous injection. The compositions disclosed herein can be formulated for administration by infusion, perfusion, or ingestion.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing particles. Various sustained-release materials have been established and are well known by those of ordinary skill in the art. Sustained-release systems may, depending on their chemical nature, release particles following administration for a few weeks up to over 100 days.

For oral administration, the compositions can be formulated as tablets, pills, dragees, capsules, liquids, gels, syrups, slurries, suspensions and the like.

When formulated to treat cancer, the disclosed compositions can also include nucleotides carrying one or more anticancer genes selected from p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, TNFα and/or HSV-tk.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

In particular embodiments, the particles are provided as part of a composition that can include, for example, at least 0.1% w/v or w/w particles; at least 1% w/v or w/w particles; at least 10% w/v or w/w particles; at least 20% w/v or w/w particles; at least 30% w/v or w/w particles; at least 40% w/v or w/w particles; at least 50% w/v or w/w particles; at least 60% w/v or w/w particles; at least 70% w/v or w/w particles; at least 80% w/v or w/w particles; at least 90% w/v or w/w particles; at least 95% w/v or w/w particles; or at least 99% w/v or w/w particles.

Methods of use. Methods disclosed herein include altering the activation state of macrophages from an inactivated state to an activated state by introducing into macrophages nanoparticles including nucleotides encoding one or more IRFs and IKKβ. In particular embodiments, the altering results in reducing the percentage of macrophages in an inactivated state (e.g., M2 macrophages) in a population of macrophages treated with nanoparticles including nucleotides encoding one or more IRFs and IKKβ by 5-fold, 10-fold, 15-fold, 20-fold, or more compared to the percentage of macrophages in an inactivated state that have not been treated with the nanoparticles including nucleotides encoding one or more IRFs and IKKβ. In particular embodiments, the altering results in reducing the number of macrophages in an inactivated state (e.g., M2 macrophages) in a population of macrophages treated with the nanoparticles including nucleotides encoding one or more IRFs and IKKβ by 5-fold, 10-fold, 20-fold, 30-fold, 40-fold, 50-fold, 60-fold, 70-fold, 80-fold, 90-fold, 100-fold, or more compared to the number of macrophages in an inactivated state that have not been treated with the nanoparticles including nucleotides encoding one or more IRFs and IKKβ. In particular embodiments, the altering results in increasing the percentage of macrophages in an activated state (e.g., M1 macrophages) in a population of macrophages treated with the nanoparticles including nucleotides encoding one or more IRFs and IKKβ by 5-fold, 10-fold, 15-fold, 20-fold, or more compared to the percentage of macrophages in an activated state that have not been treated with the nanoparticles including nucleotides encoding one or more IRFs and IKKβ. In particular embodiments, the altering results in increasing the number of macrophages in an activated state in a population of macrophages treated with the nanoparticles including nucleotides encoding one or more IRFs and IKKβ by 5-fold, 10-fold, 20-fold, 30-fold, 40-fold, 50-fold, 60-fold, 70-fold, 80-fold, 90-fold, 100-fold, or more compared to the number of macrophages in an activated state that have not been treated with the nanoparticles including nucleotides encoding one or more IRFs and IKKβ.

In particular embodiments, altering the activation state of macrophages from an inactivated state to an activated state by introducing into macrophages nanoparticles including nucleotides encoding one or more IRFs and IKKβ results in: restoring lymphocyte migration and infiltration into solid tumors; increasing release of pro-inflammatory (anti-tumor) cytokines including IL-1β, IL-12, IFNγ, and/or TNFα by 1.5-fold, 2-fold, 2.5-fold, 3-fold, 3.5-fold, 4-fold, 5-fold, 6-fold, 7-fold, 8-fold, 9-fold, 10-fold, 15-fold, 20-fold, or more; reducing release of cytokines associated with M2 macrophage phenotype including IL-6 by 1.5-fold, 2-fold, 2.5-fold, 3-fold, 3.5-fold, 4-fold, 5-fold, 6-fold, 7-fold, 8-fold, 9-fold, 10-fold, 15-fold, 20-fold, or more.

In particular embodiments, altering the activation state of macrophages from an inactivated state to an activated state includes introducing into macrophages nanoparticles including nucleotides encoding IRF5 and IRF8. In particular embodiments, altering the activation of macrophages from an inactivated state to an activated state includes introducing into macrophages nanoparticles including nucleotides encoding mutant IRFs that are constitutively active or more active than their wild type counterpart IRFs.

Methods disclosed herein include treating subjects (humans, veterinary animals, livestock and research animals) with compositions disclosed herein. Treating subjects includes delivering a therapeutically effective amount. Therapeutically effective amounts can provide effective amounts, prophylactic treatments and/or therapeutic treatments.

An "effective amount" is the amount of a compound necessary to result in a desired physiological change in a subject. Effective amounts are often administered for research purposes. Effective amounts disclosed herein immunomodulate cells in a subject. In particular embodiments, the cells to be immunomodulated are immunosuppressed cells. In particular embodiments, the cells to be immunomodulated are macrophages. In particular embodiments, immunomodulation of macrophages includes switching immunosuppressed macrophages into activated macrophages. In particular embodiments, immunomodulation of macrophages includes switching M2 macrophages to M1 macrophages. In particular embodiments, cells to be immunomodulated include immunosuppressed cells including MDSC, Treg, DCreg, neutrophils, Th17, Breg, and/or MSC. In particular embodiments, immunomodulation of immunosuppressed cells includes phenotypic and/or functional switch of the immunosuppressed cells from being protumor to being antitumor.

A "prophylactic treatment" includes a treatment administered to a subject who does not display signs or symptoms of a disease or condition or displays only early signs or symptoms of the disease or condition such that treatment is administered for the purpose of diminishing, preventing, or decreasing the risk of developing the disease or condition further. Thus, a prophylactic treatment functions as a preventative treatment against a disease or disorder. In particular embodiments, a prophylactic treatment includes administration of the compositions disclosed herein to a subject who had cancer but is in remission such that treatment is administered for the purpose of reducing or delaying the occurrence of relapse.

A "therapeutic treatment" includes a treatment administered to a subject who displays symptoms or signs of a disease or condition and is administered to the subject for the purpose of diminishing or eliminating those signs or symptoms of the disease or condition. In particular embodiments, a therapeutic treatment includes administration of the compositions disclosed herein to a subject who has cancer to diminish or eliminate tumors and/or metastasis.

In particular embodiments, therapeutically effective amounts provide an anti-cancer effect in a subject. Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential.

In particular embodiments, therapeutically effective amounts provide an anti-tumor effect in a subject. A "tumor" is a swelling or lesion formed by an abnormal growth of cells (called neoplastic cells or tumor cells). A "tumor cell" is an abnormal cell that divides by a rapid, uncontrolled cellular proliferation and continues to divide after the stimuli that initiated the new division cease. Tumors show partial or complete lack of structural organization and functional coordination with the normal tissue, and usually form a distinct mass of tissue, which may be either benign, pre-malignant or malignant.

An anti-tumor effect refers to a biological effect, which can be manifested by a decrease in the number of tumor cells, a decrease in the number of metastases, a decrease in tumor volume, an increase life expectancy, induced apoptosis of cancer cells, induced cancer cell death, induced chemo- or radiosensitivity in cancer cells, inhibited angiogenesis near cancer cells, inhibited cancer cell proliferation, inhibited tumor growth, prevented metastasis, prolonged life for a subject, reduced cancer-associated pain, reduced number of metastases, and/or reduced relapse or re-occurrence of the cancer following treatment. Accordingly, the compositions disclosed herein can be used to treat a variety of cancers, can prevent or significantly delay metastasis, and/or can prevent or significantly delay relapse. In particular embodiments, overall survival of a subject with cancer treated with a nanoparticle composition disclosed herein is improved by 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, or more as compared to a control subject with the same cancer not treated with the nanoparticle composition. In particular embodiments, the number of metastases in a subject with cancer treated with a nanoparticle composition disclosed herein is decreased by 1.5-fold, 2-fold, 3-fold, 4-fold, 5-fold, 6-fold, 7-fold, 8-fold, 9-fold, 10-fold, or more as compared to a control subject with the same cancer not treated with the nanoparticle composition.

In particular embodiments, a therapeutic treatment includes administration of the compositions disclosed herein in combination with another therapy to a subject who has cancer to diminish or eliminate tumors. In particular embodiments, the therapy to use in combination with the compositions disclosed herein include cancer vaccines, CAR immunotherapy (e.g., CAR-T immunotherapy), chemotherapy, radiotherapy, hormone therapy, signal transduction inhibitors, gene expression modulators, apoptosis inducers, angiogenesis inhibitors, and monoclonal antibodies that deliver toxic molecules. In particular embodiments, administration of a nanoparticle composition disclosed herein in combination with radiotherapy to a subject who has cancer improves overall survival by 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, or more as compared to a control subject with the same cancer not administered the nanoparticle composition in combination with radiotherapy.

Cancers that can be treated with systems and methods disclosed herein include ovarian cancer, breast cancer, brain cancer, melanomas, lung metastases, seminomas, teratomas, neuroblastomas, gliomas, rectal cancer, endometrial cancer, kidney cancer, adrenal cancer, thyroid cancer, skin cancer, cervical cancer, intestinal cancer, liver cancer, colon cancer, stomach cancer, head and neck cancer, gastrointestinal cancer, lymph node cancer, esophagus cancer, colorectal cancer, pancreatic cancer, ear, nose and throat (ENT) cancer, prostate cancer, cancer of the uterus, lung cancer, and metastases thereof.

As indicated, the teachings of the current disclosure can also be used in methods of modulating the activation state of immune cells to inactivate the immune system in conditions such as autoimmune diseases. In particular embodiments, altering the activation state of macrophages from an activated state to an inactivated state in autoimmune diseases includes introducing into macrophages nanoparticles including nucleotides encoding IRFs that induce M2 phenotypes. Particular embodiments of IRFs that induce M2 phenotypes include IRF3 and/or IRF4. In particular embodiments, altering the activation state of macrophages from an activated state to an inactivated state in autoimmune diseases includes introducing into macrophages nanoparticles including nucleotides encoding GILZ (Glucocorticoid-induced leucine zipper) transcription factor which mediates glucocorticoid anti-inflammatory effects and can induce M2 phenotypes. In particular embodiments, altering the activation state of macrophages from an activated state to an inactivated state in autoimmune diseases includes introducing into macrophages nanoparticles including nucleotides encoding GILZ and IRF4. Exemplary autoimmune diseases include acute necrotizing hemorrhagic encephalopathy, allergic asthma, alopecia areata, anemia, aphthous ulcer, arthritis (including rheumatoid arthritis, juvenile rheumatoid arthritis, osteoarthritis, psoriatic arthritis), asthma, autoimmune thyroiditis, conjunctivitis, Crohn's disease, cutaneous lupus erythematosus, dermatitis (including atopic dermatitis and eczematous dermatitis), diabetes, diabetes mellitus, erythema nodosum leprosum, keratoconjunctivitis, multiple sclerosis, myasthenia gravis, psoriasis, scleroderma, Sjogren's syndrome, including keratoconjunctivitis sicca secondary to Sjogren's syndrome, Stevens-Johnson syndrome, systemic lupus erythematosus, ulcerative colitis, vaginitis and Wegener's granulomatosis.

For administration, therapeutically effective amounts (also referred to herein as doses) can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of disease, previous or concurrent therapeutic interventions, idiopathy of the subject and route of administration.

Useful doses often range from 0.1 to 5 µg/kg or from 0.5 to 1 µg/kg. In particular embodiments, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In particular embodiments, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly. In particular embodiments, therapeutically effective amounts can be achieved by administering repeated doses during the course of a treatment regimen.

The nanoparticle compositions described herein can be administered by injection, inhalation, infusion, perfusion, lavage or ingestion. Routes of administration can include intravenous, intradermal, intraarterial, intraparenteral, intranasal, intranodal, intralymphatic, intraperitoneal, intracranial, intralesional, intraprostatic, intravaginal, intrarectal, topical, intrathecal, intratumoral, intramuscular, intravesicular, oral, subcutaneous, and/or sublingual administration and more particularly by intravenous, intratumoral, intraperitoneal, and/or intracranial injection. Local administration includes administration of a therapeutically effective amount of a composition disclosed herein to a particular region, organ, or cavity of the body. For example, intraperitoneal injection can be used to deliver a therapeutic to treat ovarian cancer or intracranial injection can be used to deliver a therapeutic to treat a glioma. Administration of a therapeutic at a tumor site can include ligand mediated targeting of a therapeutic (e.g., nanoparticle compositions) to tumor cells and/or tumor supporting cells and not to healthy tissue using targeting ligands as described above. Administration of a therapeutic at a tumor site can include passive targeting of a therapeutic (e.g., nanoparticle compositions) to tumor cells and/or tumor supporting cells and not to healthy tissue. Particular embodiments of passive targeting can include enhanced permeability and retention (EPR) phenomenon based on size range of nanoparticles and the leaky vasculature and impaired lymphatic drainage of tumor tissues. Systemic administration, by contrast, is body-wide, and is typically achieved by intravenous injection of a composition or therapeutic into the circulation. Systemic administration of a therapeutic can be useful for less localized forms of cancer, such as cancers that have metastasized.

FIG. 5 provides exemplary sequences (SEQ ID NO: 1-44, 110, and 111) supporting the disclosure. CDR sequences are also described herein. The current disclosure includes variants of these sequences. Variants of protein sequences can include those having one or more conservative amino acid substitutions or one or more non-conservative substitutions that do not adversely affect the function of the protein. A "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gin); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

A fragment of a protein consists of less than the complete amino acid sequence of the corresponding protein, but retains the function of the full length protein.

Variants of nucleotide sequences can include one or more of degenerate codons, sequence polymorphisms, and mutations wherein such alterations do not affect the function of the encoded activation regulator or do not substantially affect the function of the encoded activation regulator.

In particular embodiments, variants of sequences include sequences with at least 70% sequence identity, at least 80%, at least 85%, at least 90%, at least 95%, at least 96%, at least 97%, at least 98%, or at least 99% sequence identity to the sequences described or disclosed herein.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine % sequence identity are designed to give the best match between the sequences tested. Methods to determine % sequence identity and similarity are codified in publicly available computer programs. Sequence alignments and % sequence identity calculations may be performed using the Megalign program of the LASERGENE bioinformatics computing suite (DNASTAR, Inc., Madison, WI). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, WI); BLASTP, BLASTN, BLASTX (Altschul, et al., J. Mol. Biol. 215:403-410 (1990); DNASTAR (DNASTAR, Inc., Madison, WI); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, NY Within the context of this disclosure it will be understood that where sequence analysis software is used for analysis, the results of the analysis are based on the "default values" of the program referenced. "Default values" will mean any set of values or parameters, which originally load with the software when first initialized.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of altering an activation state of immune cells in vivo including: administering nanoparticles including nucleotides encoding one or more interferon regulatory factors (IRFs) thereby altering the activation state of immune cells in vivo.

2. A method of embodiment 1 wherein the immune cell is a macrophage, a regulatory T cell (TREG), a myeloid-derived suppressor cell (MDSC), a regulatory dendritic cell (DCreg), a neutrophil, a T helper 17 cell (Th17), a regulatory B cell (Breg), and/or a mesenchymal stromal cell (MSC).

3. A method of embodiment 1 or 2 wherein the nanoparticles include a positively-charged core, a poly($\beta$)-amino ester core, star-shaped polymers, a polyglutamic acid coating, a hyaluronic acid coating, a neutrally-charged coating, and/or liposomal nanoparticles.

4. A method of any one of embodiments 1-3 wherein the nanoparticles are <130 nm.

5. A method of any one of embodiments 1-4 wherein the nucleotides include in vitro transcribed mRNA.

6. A method of any one of embodiments 1-5 wherein the nucleotides are encapsulated within a core.

7. A method of any one of embodiments 1-6 wherein the encoded one or more IRFs lack a functional autoinhibitory domain.

8. A method of any one of embodiments 1-7 wherein the encoded one or more IRFs lack a functional nuclear export signal (NES).

9. A method of any one of embodiments 1-8 wherein the administering is locally administering.

10. A method of embodiment 9 wherein the locally administering is intraperitoneal or intracranial.

11. A method of any one of embodiments 1-9 wherein the administering is systemic administering.

12. A method of any one of embodiments 1-11 wherein the nanoparticles further include a targeting ligand.

13. A method of embodiment 12 wherein the targeting ligand is linked to a coating.

14. A method of any one of embodiments 1-13 wherein the activation state is altered from an inactivated state to an activated state.

15. A method of any one of embodiments 1-14 wherein the immune cells include macrophages.

16. A method of embodiment 15 wherein the macrophages are within a tumor.

17. A method of embodiment 16 wherein the tumor is an ovarian cancer tumor, a glioblastoma tumor, or a metastatic lung cancer tumor.

18. A method of any one of embodiments 1-17 wherein the encoded one or more IRFs is selected from IRF1, IRF3, IRF5, IRF7, IRF8, and/or a fusion of IRF7 and IRF3.

19. A method of any one of embodiments 1-18 wherein the encoded one or more IRFs is selected from a sequence having >90%, >95%, or greater than 98% identity to SEQ ID NOs: 1-17.

20. A method of any one of embodiments 1-19 wherein the encoded one or more IRFs is IRF5 selected from SEQ ID NOs: 1-7.

21. A method of embodiment 20 wherein IRF5 is SEQ ID NO: 1.

22. A method of embodiment 20 or 21 wherein IRF5 is SEQ ID NO: 1 or SEQ ID NO: 3 with one or more mutations selected from S156D, S158D and T160D.

23. A method of any one of embodiments 20-22 wherein IRF5 is SEQ ID NO: 2 with one or more mutations selected from T10D, S158D, S309D, S317D, S451D, and S462D.

24. A method of any one of embodiments 20-23 wherein IRF5 is SEQ ID NO: 4 with one or more mutations selected from S425D, S427D, S430D, and S436D.

25. A method of any one of embodiments 1-24 wherein the encoded one or more IRFs is IRF1 selected from SEQ ID NOs: 8 and 12.

26. A method of any one of embodiments 1-24 wherein the encoded one or more IRFs is IRF8 selected from SEQ ID NOs: 11,16, and 17.

27. A method of embodiment 26 wherein IRF8 is SEQ ID NO: 11 with a K310R mutation.

28. A method of any one of embodiments 1-27 wherein the encoded one or more IRFs includes an IRF7/IRF3 fusion protein including an N-terminal IRF7 DNA binding domain (DBD) and constitutively active domain (CAD) and C-terminal IRF3 NES (Nuclear Export Signal) and association domains.

29. A method of embodiment 28 wherein the IRF7/IRF3 fusion protein further includes mutations mimicking phosphorylation in the IRF3 association domain.

30. A method of embodiment 28 or 29 wherein the IRF7/IRF3 fusion protein is set forth in SEQ ID NO: 15.

31. A method of any one of embodiments 1-30 wherein the nanoparticles further include nucleotides encoding IKKβ.

32. A method of embodiment 31 wherein the encoded IKKβ is selected from a sequence having >90%, >95%, or greater than 98% identity to SEQ ID NOs: 18-22.

33. A method of embodiment 31 or 32 wherein the encoded IKKβ is selected from SEQ ID NOs: 18-22.

34. A method of any one of embodiments 1-33 wherein the nucleotides include a sequence selected from SEQ ID NOs: 23-44.

35. A method of any one of embodiments 12-34 wherein the targeting ligand binds CD206, CD163, or CD23.

36. A method of any one of embodiments 12-35 wherein the targeting ligand is di-mannose.

37. A method of any one of embodiments 31-36 wherein the nucleotides encoding one or more IRFs and IKKβ are encapsulated in the same nanoparticle.

38. A method of any one of embodiments 31-37 wherein the nucleotides encoding one or more IRFs and IKKβ are encapsulated in different nanoparticles.

39. A method of any one of embodiments 1-38 wherein altering the activation state of immune cells includes reducing the percentage of immune cells in the inactivated state in a population of immune cells by 5-fold, 10-fold, 15-fold, 20-fold, or more.

40. A method of any one of embodiments 1-39 wherein altering the activation state of immune cells includes reducing the number of immune cells in the inactivated state in a population of immune cells by 5-fold, 10-fold, 20-fold, 30-fold, 40-fold, 50-fold, 60-fold, 70-fold, 80-fold, 90-fold, 100-fold, or more.

41. A method of any one of embodiments 1-40 wherein altering the activation state of immune cells includes increasing the percentage of immune cells in the activated state in a population of immune cells by 5-fold, 10-fold, 15-fold, 20-fold, or more.

42. A method of any one of embodiments 1-41 wherein altering the activation state of immune cells includes increasing the number of immune cells in the activated state in a population of immune cells by 5-fold, 10-fold, 20-fold, 30-fold, 40-fold, 50-fold, 60-fold, 70-fold, 80-fold, 90-fold, 100-fold, or more.

43. A method of any one of embodiments 1-13 wherein the activation state is altered from an activated state to an inactivated state.

44. A method of any one of embodiments 1-13, and 43 wherein the immune cells include macrophages.

45. A method of any one of embodiments 1-13, 43, and 44 wherein the encoded one or more IRFs is IRF4.

46. A method of any one of embodiments 1-13, and 43-45 wherein the nanoparticles further include nucleotides encoding glucocorticoid-induced leuzine zipper (GILZ).

47. A method of any one of embodiments 12, and 43-46 wherein the targeting ligand binds CD38, G-protein coupled receptor 18 (Gpr18), formyl peptide receptor 2 (Fpr2), CD64, or CD68.

48. A method of any one of embodiments 1-13, and 43-47 wherein altering the activation state of immune cells includes reducing the percentage of immune cells in the activated state in a population of immune cells by 5-fold, 10-fold, 15-fold, 20-fold, or more.

49. A method of any one of embodiments 1-13, and 43-48 wherein altering the activation state of immune cells includes reducing the number of immune cells in the activated state in a population of immune cells by 5-fold, 10-fold, 20-fold, 30-fold, 40-fold, 50-fold, 60-fold, 70-fold, 80-fold, 90-fold, 100-fold, or more.

50. A method of any one of embodiments 1-13, and 43-49 wherein altering the activation state of immune cells includes increasing the percentage of immune cells in the inactivated state in a population of immune cells by 5-fold, 10-fold, 15-fold, 20-fold, or more.

51. A method of any one of embodiments 1-13, and 43-50 wherein altering the activation state of immune cells includes increasing the number of immune cells in the inactivated state in a population of immune cells by 5-fold, 10-fold, 20-fold, 30-fold, 40-fold, 50-fold, 60-fold, 70-fold, 80-fold, 90-fold, 100-fold, or more.

52. A method of treating cancer in a subject in need thereof including altering the activation state of tumor-associated macrophages in a tumor within the subject from inactivated to activated thereby treating cancer in the subject in need thereof.

53. A method of embodiment 52 wherein the tumor is an ovarian cancer tumor, a glioblastoma tumor, or a metastatic lung cancer tumor.

54. A method of embodiment 52 or 53 wherein the altering follows administration of a therapeutically effective amount of nanoparticles including nucleotides that encode one or more transcription factors that alter the activation state of tumor-associated macrophages from inactivated to activated.

55. A method of embodiment 54 wherein the nanoparticles include a positively-charged core, a poly(β)-amino ester core, star-shaped polymers, a polyglutamic acid coating, a hyaluronic acid coating, a neutrally-charged coating, and/or liposomal nanoparticles.

56. A method of embodiment 54 or 55 wherein the nanoparticles are <130 nm.

57. A method of any one of embodiments 54-56 wherein the nucleotides include in vitro transcribed mRNA.

58. A method of any one of embodiments 54-57 wherein the nucleotides are encapsulated within a core.

59. A method of any one of embodiments 54-58 wherein the administration is local administration.

60. A method of embodiment 59 wherein the local administration is intraperitoneal or intracranial.

61. A method of any one of embodiments 54-59 wherein the administration is systemic administration.

62. A method of any one of embodiments 54-61 wherein the encoded one or more transcription factors include one or more interferon regulatory factors (IRFs).

63. A method of embodiment 62 wherein the encoded one or more IRFs lack a functional autoinhibitory domain.

64. A method of embodiment 62 or 63 wherein the encoded one or more IRFs lack a functional nuclear export signal (NES).

65. A method of any one of embodiments 62-64 wherein the encoded one or more IRFs is selected from IRF1, IRF3, IRF5, IRF7, IRF8, and/or a fusion of IRF7 and IRF3.

66. A method of any one of embodiments 62-65 wherein the encoded one or more IRFs is selected from a sequence having >90%, >95%, or greater than 98% identity to SEQ ID NOs: 1-17.

67. A method of any one of embodiments 62-66 wherein the encoded one or more IRFs is IRF5 selected from SEQ ID NOs: 1-7.

68. A method of embodiment 67 wherein IRF5 is SEQ ID NO: 1.

69. A method of embodiment 67 or 68 wherein IRF5 is SEQ ID NO: 1 or SEQ ID NO: 3 with one or more mutations selected from S156D, S158D and T160D.

70. A method of any one of embodiments 67-69 wherein IRF5 is SEQ ID NO: 2 with one or more mutations selected from T10D, S158D, S309D, S317D, S451D, and S462D.

71. A method of any one of embodiments 67-70 wherein IRF5 is SEQ ID NO: 4 with one or more mutations selected from S425D, S427D, S430D, and S436D.

72. A method of any one of embodiments 62-71 wherein the encoded one or more IRFs is IRF1 selected from SEQ ID NOs: 8 and 12.

73. A method of any one of embodiments 62-72 wherein the encoded one or more IRFs is IRF8 selected from SEQ ID NOs: 11,16, and 17.

74. A method of embodiment 73 wherein IRF8 is SEQ ID NO: 11 with a K310R mutation.

75. A method of any one of embodiments 62-74 wherein the encoded one or more IRFs includes an IRF7/IRF3 fusion protein including an N-terminal IRF7 DNA binding domain (DBD) and constitutively active domain (CAD) and C-terminal IRF3 NES (Nuclear Export Signal) and association domains.

76. A method of embodiment 75 wherein the IRF7/IRF3 fusion protein further includes mutations mimicking phosphorylation in the IRF3 association domain.

77. A method of embodiment 75 or 76 wherein the IRF7/IRF3 fusion protein is set forth in SEQ ID NO: 15.

78. A method of any one of embodiments 54-77 wherein the nanoparticles further include nucleotides encoding IKKβ.

79. A method of embodiment 78 wherein the encoded IKKβ is selected from a sequence having >90%, >95%, or greater than 98% identity to SEQ ID NOs: 18-22.

80. A method of embodiment 78 or 79 wherein the encoded IKKβ is selected from SEQ ID NOs: 18-22.

81. A method of any one of embodiments 54-79 wherein the nucleotides include a sequence selected from SEQ ID NOs: 23-44.

82. A method of any one of embodiments 54-81 wherein the nanoparticles further include a targeting ligand.

83. A method of embodiment 82 wherein the targeting ligand is linked to a coating.

84. A method of embodiment 82 or 83 wherein the targeting ligand binds CD206, CD163, or CD23.

85. A method of any one of embodiments 82-84 wherein the targeting ligand is di-mannose.

86. A method of any one of embodiments 54-85 wherein the nucleotides encoding one or more IRFs and IKKβ are encapsulated in the same nanoparticle.

87. A method of any one of embodiments 54-86 wherein the nucleotides encoding one or more IRFs and IKKβ are encapsulated in different nanoparticles.

88. A method of any one of embodiments 54-87 wherein altering the activation state of macrophages includes reducing the percentage of macrophages in the inactivated state in a population of macrophages within the tumor by 5-fold, 10-fold, 15-fold, 20-fold, or more.

89. A method of any one of embodiments 54-88 wherein altering the activation state of macrophages includes reducing the number of macrophages in the inactivated state in a population of macrophages within the tumor by 5-fold, 10-fold, 20-fold, 30-fold, 40-fold, 50-fold, 60-fold, 70-fold, 80-fold, 90-fold, 100-fold, or more.

90. A method of any one of embodiments 54-89 wherein altering the activation state of macrophages includes increasing the percentage of macrophages in the activated state in a population of macrophages within the tumor by 5-fold, 10-fold, 15-fold, 20-fold, or more.

91. A method of any one of embodiments 54-90 wherein altering the activation state of macrophages includes increasing the number of macrophages in the activated state in a population of macrophages within the tumor by 5-fold, 10-fold, 20-fold, 30-fold, 40-fold, 50-fold, 60-fold, 70-fold, 80-fold, 90-fold, 100-fold, or more.

92. A method of any one of embodiments 54-91 further including administering in combination with the therapeutically effective amount of nanoparticles a therapy selected from cancer vaccines, chimeric antigen receptor (CAR) immunotherapy, chemotherapy, radiotherapy, hormone therapy, signal transduction inhibitors, gene expression modulators, apoptosis inducers, angiogenesis inhibitors, and monoclonal antibodies that deliver toxic molecules.

93. A method of treating an autoimmune disease in a subject in need thereof including altering the activation state of macrophages within the subject from activated to inactivated thereby treating an autoimmune disease in the subject in need thereof.

94. A method of embodiment 93 wherein the autoimmune disease includes acute necrotizing hemorrhagic encephalopathy, allergic asthma, alopecia areata, anemia, aphthous ulcer, arthritis (including rheumatoid arthritis, juvenile rheumatoid arthritis, osteoarthritis, psoriatic arthritis), asthma, autoimmune thyroiditis, conjunctivitis, Crohn's disease, cutaneous lupus erythematosus, dermatitis (including atopic dermatitis and eczematous dermatitis), diabetes, diabetes mellitus, erythema nodosum leprosum, keratoconjunctivitis, multiple sclerosis, myasthenia gravis, psoriasis, scleroderma, Sjogren's syndrome, including keratoconjunctivitis sicca secondary to Sjogren's syndrome, Stevens-Johnson syndrome, systemic lupus erythematosus, ulcerative colitis, vaginitis and Wegener's granulomatosis.

95. A method of embodiment 93 or 94 wherein the altering follows administration of a therapeutically effective amount of nanoparticles including nucleotides encoding one or more transcription factors that alter the activation state of macrophages from activated to inactivated.

96. A method of embodiment 94 wherein the nanoparticles include a positively-charged core, a poly(β)-amino ester core, star-shaped polymers, a polyglutamic acid coating, a hyaluronic acid coating, a neutrally-charged coating, and/or liposomal nanoparticles.

97. A method of embodiment 94 or 95 wherein the nanoparticles are <130 nm.

98. A method of any one of embodiments 95-97 wherein the nucleotides include in vitro transcribed mRNA.

99. A method of any one of embodiments 95-98 wherein the nucleotides are encapsulated within a core.

100. A method of any one of embodiments 95-99 wherein the administration is local administration.

101. A method of embodiment 100 wherein the local administration is intraperitoneal or intracranial.

102. A method of any one of embodiments 92-99 wherein the administration is systemic administration.

103. A method of any one of embodiments 95-102 wherein the encoded one or more transcription factors include one or more interferon regulatory factors (IRFs).

104. A method of embodiment 103 wherein the encoded one or more IRFs lack a functional autoinhibitory domain.

105. A method of embodiment 103 or 104 wherein the encoded one or more IRFs lack a functional nuclear export signal (NES).

106. A method of any one of embodiments 103-105 wherein the encoded one or more IRFs is IRF4.

107. A method of any one of embodiments 95-106 wherein the nanoparticles further include nucleotides encoding glucocorticoid-induced leuzine zipper (GILZ).

108. A method of any one of embodiments 85-107 wherein the nanoparticles further include a targeting ligand.

109. A method of embodiment 108 wherein the targeting ligand is linked to a coating.

110. A method of embodiment 108 or 109 wherein the targeting ligand binds CD38, G-protein coupled receptor 18 (Gpr18), formyl peptide receptor 2 (Fpr2), CD64, or CD68.

111. A method of any one of embodiments 93-110 wherein altering the activation state of macrophages includes reducing the percentage of macrophages in the activated state in a population of macrophages by 5-fold, 10-fold, 15-fold, 20-fold, or more.

112. A method of any one of embodiments 93-111 wherein altering the activation state of macrophages includes reducing the number of macrophages in the activated state in a population of macrophages by 5-fold, 10-fold, 20-fold, 30-fold, 40-fold, 50-fold, 60-fold, 70-fold, 80-fold, 90-fold, 100-fold, or more.

113. A method of any one of embodiments 95-112 wherein altering the activation state of macrophages includes increasing the percentage of macrophages in the inactivated state in a population of macrophages by 5-fold, 10-fold, 15-fold, 20-fold, or more.

114. A method of any one of embodiments 95-113 wherein altering the activation state of macrophages includes increasing the number of macrophages in the inactivated state in a population of macrophages by 5-fold, 10-fold, 20-fold, 30-fold, 40-fold, 50-fold, 60-fold, 70-fold, 80-fold, 90-fold, 100-fold, or more.

115. A composition including nanoparticles including nucleotides encoding one or more interferon regulatory factors (IRFs).

116. A composition of embodiment 115 further including a pharmaceutically acceptable carrier.

117. A composition of embodiment 115 or 116 wherein the nanoparticles include a positively-charged core, a poly(R)-amino ester core, star-shaped polymers, a polyglutamic acid coating, a hyaluronic acid coating, a neutrally-charged coating, and/or liposomal nanoparticles.

118. A composition of any one of embodiments 115-117 wherein the nanoparticles are <130 nm.

119. A composition of any one of embodiments 115-118 wherein the nucleotides include in vitro transcribed mRNA.

120. A composition of any one of embodiments 115-119 wherein the nucleotides are encapsulated within a core.

121. A composition of any one of embodiments 115-120 wherein the encoded one or more IRFs lack a functional autoinhibitory domain.

122. A composition of any one of embodiments 115-121 wherein the encoded one or more IRFs lack a functional nuclear export signal (NES).

123. A composition of any one of embodiments 115-122 wherein the encoded one or more IRFs is selected from IRF1, IRF3, IRF5, IRF7, IRF8, and/or a fusion of IRF7 and IRF3.

124. A composition of any one of embodiments 115-123 wherein the encoded one or more IRFs is selected from a sequence having >90%, >95%, or greater than 98% identity to SEQ ID NOs: 1-17.

125. A composition of any one of embodiments 115-124 wherein the encoded one or more IRFs is IRF5 selected from SEQ ID NOs: 1-7.

126. A composition of embodiment 125 wherein IRF5 is SEQ ID NO: 1.

127. A composition of embodiment 125 or 126 wherein IRF5 is SEQ ID NO: 1 or SEQ ID NO: 3 with one or more mutations selected from S156D, S158D and T160D.

128. A composition of any one of embodiments 125-127 wherein IRF5 is SEQ ID NO: 2 with one or more mutations selected from T10D, S158D, S309D, S317D, S451D, and S462D.

129. A composition of any one of embodiments 125-128 wherein IRF5 is SEQ ID NO: 4 with one or more mutations selected from S425D, S427D, 5430D, and S436D.

130. A composition of any one of embodiments 115-129 wherein the encoded one or more IRFs is IRF1 selected from SEQ ID NOs: 8 and 12.

131. A composition of any one of embodiments 115-130 wherein the encoded one or more IRFs is IRF8 selected from SEQ ID NOs: 11,16, and 17.

132. A composition of embodiment 131 wherein IRF8 is SEQ ID NO: 11 with a K310R mutation.

133. A composition of any one of embodiments 115-132 wherein the encoded one or more IRFs includes an IRF7/IRF3 fusion protein including an N-terminal IRF7 DNA binding domain (DBD) and constitutively active domain (CAD) and C-terminal IRF3 NES (Nuclear Export Signal) and association domains.

134. A composition of embodiment 133 wherein the IRF7/IRF3 fusion protein further includes mutations mimicking phosphorylation in the IRF3 association domain.

135. A composition of embodiment 133 or 134 wherein the IRF7/IRF3 fusion protein is set forth in SEQ ID NO: 15.

136. A composition of any one of embodiments 115-135 wherein the nanoparticles further include nucleotides encoding IKKβ.

137. A composition of embodiment 136 wherein the encoded IKKβ is selected from a sequence having >90%, >95%, or greater than 98% identity to SEQ ID NOs: 18-22.

138. A composition of embodiment 136 or 137 wherein the encoded IKKβ is selected from SEQ ID NOs: 18-22.

139. A composition of any one of embodiments 115-138 wherein the nucleotides include a sequence selected from SEQ ID NOs: 23-44.

140. A composition of any one of embodiments 115-139 wherein the nanoparticles further include nucleotides carrying one or more anticancer genes selected from p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, TNFα and/or HSV-tk.

141. A composition of any one of embodiments 115-122 wherein the encoded one or more IRFs is IRF4.

142. A composition of any one of embodiments 115-122, and 141 wherein the nanoparticles further include nucleotides encoding glucocorticoid-induced leuzine zipper (GILZ).

143. A composition of any one of embodiments 115-142 wherein the nanoparticles further include a targeting ligand.

144. A composition of embodiment 143 wherein the targeting ligand is linked to a coating.

145. A composition of embodiment 143 or 144 wherein the targeting ligand binds CD206, CD163, or CD23.

146. A composition of embodiment 145 wherein the targeting ligand is di-mannose.

147. A composition of embodiment 143 or 144 wherein the targeting ligand binds CD38, G-protein coupled receptor 18 (Gpr18), formyl peptide receptor 2 (Fpr2), CD64, or CD68.

148. A composition of any one of embodiments 115-147 wherein the nucleotides encoding one or more IRFs, IKKβ, and/or GILZ are encapsulated in the same nanoparticle.

149. A composition of any one of embodiments 115-148 wherein the nucleotides encoding one or more IRFs, IKKβ, and/or GILZ are encapsulated in different nanoparticles.

Example 1

Materials and Methods. PbAE synthesis. The methods used to synthesize the polymer were described previously (Mangraviti A et al. (2015) ACS Nano 9: 1236-1249). 1,4-butanediol diacrylate was combined with 4-amino-1-butanol in a 1:1 molar ratio of diacrylate to amine monomers. Acrylate-terminated poly(4-amino-1-butanol-co-1,4-butanediol diacrylate) was formed by heating the mixture to 90° C. with stirring for 24 hours. 2.3 g of this polymer was dissolved in 2 mL tetrahydrofuran (THF). To form the piperazine-capped 447 polymer, 786 mg of 1-(3-aminopropyl)-4-methylpiperazine in 13 mL THF was added to the polymer/THF solution and stirred at room temperature (RT) for 2 hours. The capped polymer was precipitated with 5 volumes of diethyl ether, washed with 2 volumes of fresh ether, and dried under vacuum for 1 day. Neat polymer was dissolved in dimethyl sulfoxide (DMSO) to a concentration of 100 mg/mL and stored at −20° C.

PGA conjugation to Di-mannose. α-D-mannopyranosyl-(1→2)-α-D-mannopyranose (Di-mannose, Omicron Biochemicals Inc.) was modified into glycosylamine before being conjugated to polyglutamic acid (PGA). First, the Di-mannose (157 mg) was dissolved in 10.5 mL of saturated aqueous ammonium carbonate, then stirred at RT for 24 hours. On the second day, more solid ammonium carbonate was added until the Di-mannose precipitated from the reaction solution. The mixture was stirred until completion, as measured by TLC, followed by lyophilization to remove the excess ammonium carbonate. Complete removal of volatile salt was accomplished by re-dissolving the solid in methanol. These procedures created an amine on the anomeric carbon for future conjugation with PGA.

To conjugate aminated Di-mannose to PGA, the substrate was dissolved in water to 30 mg m/L, then sonicated for 10 minutes. Ethyl-N'-(3-dimethylaminopropyl) carbodiimide•HCl in water (4 mg/mL, 30 equiv.) was added with mixing at RT for 4 min. N-hydroxysulfosuccinimide in water (30 mg/mL, 35 equiv.) was incubated with the PGA/EDC solution for 1 minute. Aminated Dimannose in phosphate-buffered saline (PBS) was combined with the resulting activated PGA in a 44:1 molar ratio and mixed at RT for 6 h. Excess reagents were removed by dialysis against water for 24 hours.

mRNA synthesis. Codon-optimized mRNA for eGFP, IRF5, and IKK (TriLink Biotechnologies) were capped with the Anti-Reverse Cap Analog 3'-O-Me-m7G(5')ppp(5')G (ARCA), and fully substituted with the modified ribonucleotides pseudouridine ($\psi$) and 5-methylcytidine (m5C).

Nanoparticle preparation. IRF5 and IKKβ mRNAs were combined at a 3:1 (w:w) ratio and diluted to 100 μg/mL in 25 mM sodium acetate (NaOAc) buffer (pH=5.2). Poly(β-amino esters)-447 (PbAE-447) polymer in DMSO (prepared as described above) was diluted from 100 μg/μL to 6 μg/μL, also in NaOAc buffer. To form the nanoparticles, PbAE-447 polymers were added to the mRNA at a ratio of 60:1 (w:w) and vortexed immediately for 15 seconds at a medium speed, then the mixture was incubated at RT for 5 min to allow the formation of PbAE-mRNA polyplexes. In the next step, 100 μg/mL PGA/Di-mannose in NaOAc buffer was added to the polyplexes solution, vortexed for 15 seconds at medium speed, and incubated for 5 min at room temperature. In this process, PGA/Di-mannose coated the surfaces of PbAE-mRNA polyplexes to form the final NPs. For long-term storage, D-sucrose (60 mg/mL) was added to the NP solutions as a cryoprotectant. The nanoparticles were snap-frozen in dry ice, then lyophilized. The dried NPs were stored at −20° C. or −80° C. until use. For in vivo experiments, lyophilized NPs were re-suspended in water at a 1:20 (w:v) ratio.

Characterization of nanoparticle size distribution and ζ-potential. The physiochemical properties of NPs (including hydrodynamic radius, polydispersity, ζ-potential, and stability) were characterized using a Zetapals instrument (Brookhaven Instrument Corporation) at 25° C. To measure the hydrodynamic radius and polydispersity based on dynamic light scattering, NPs were diluted 5-fold into 25 mM NaOAc (pH=5.2). To measure the ζ-potential, NPs were diluted 10-fold in 10 mM PBS (pH=7.0). To assess the stability of NPs, freshly prepared particles were diluted in 10 mM PBS buffer (pH=7.4). The hydrodynamic radius and polydispersity of NPs were measured every 10 minutes for 5 hours, and their sizes and particle concentrations were derived from Particle Tracking Analysis using a Nanosite 300 instrument (Malvern). To characterize the NPs using transmission electron microscopy, previously described protocols were followed (Smith T T et al. (2017) Nat Nanotechnol 12: 813-820). Freshly made NPs (25 μL containing 0.83 μg of mRNA) were deposited on glow discharge-treated 200 mesh carbon/Formvar-coated copper grids. After 30 seconds, the grids were treated sequentially with 50% Karnovsky's fixative, 0.1 M cacodylate buffer, dH2O, then 1% (w/v) uranyl acetate. Samples were imaged with a JEOL JEM-1400 transmission electron microscope operating at 120 kV (JEOL USA).

Bone marrow derived macrophages (BMDMs) and other cell lines. To prepare BMDMs, bone marrow progenitor cells were harvested from mouse femurs following established protocols (Zhang X et al. (2008) Curr Protoc Immunol Chapter 14: Unit 14 11). These cells were cultured in complete medium [DMEM supplemented with 4.5 g/L D-glucose, L-glutamine, 10% heat-inactivated fetal bovine serum (FBS), 100 U/mL penicillin and 100 μg/mL, Gluta-max 50 mL/500 mL, supplemented with 20 ng/mL M-CSF (Peprotech, cat #315-02)] at a seeding density of 0.5-1.0 e6/ml. Cells were allowed to differentiate into BMDMs ex vivo for 7 days under 5% CO2 at 37° C. Next, they were conditioned with macrophage-conditioned medium [macrophage complete medium supplemented with 20 ng/mL MPLA (Sigma, cat #L6895) or 20 ng/mL IL4 (eBioscience, cat #34-8041)]. BMDMs were used between 7-21 days ex vivo. The murine ovarian cancer cell line ID8, a gift from Dr. Katherine Roby (University of Kansas Medical Center, Kansas City, KS), was cultured in DMEM supplemented with 10% FBS, 100 U/mL penicillin, 5 μg/mL insulin, 5 μg/mL transferrin, and 5 ng/mL sodium selenite (all Sigma-Aldrich). To generate the more aggressive vascular endothelial growth factor (VEGF)-expressing ID8 strain, ID8 tumor cells were transfected with the pUNO1 plasmid (Invivogen) encoding murine VEGF along with the blasticidin-resistance gene. To obtain stable transfectants, tumor cells were cultured in complete medium containing 10 μg/mL blasticidin (Invivogen) for 3 weeks. The B16F10 melanoma cell line (American Type Culture Collection) was cultured in complete RPMI 1640 medium with 10% FBS, 100 U/mL penicillin, 2 mM/L-glutamine, 1.5 g/L sodium bicarbonate, 4.5 g/L glucose, 10 mM HEPES, 1.0 mM sodium pyruvate, and 0.05 mM 2-mercaptoethanol. For in vivo bioluminescent imaging, both ID8-VEGF and B16F10 cell lines were retrovirally transduced with firefly luciferase. The DF-1 cell line carrying RACS-PDGFβ or RCAS-cre retrovirus was cultured in complete medium supplemented with 10% FBS and 100 U/mL penicillin under 5% CO2 at 39° C.

mRNA transfection of BMDMs. One day prior to transfection, BMDMs were reseeded on 24-well plates in macrophage complete medium at a concentration of 250,000/well. Before transfection, the complete medium was replaced with 300 μL unsupplemented DMEM. To transfect these cells, NPs containing 2 μg mRNA were added into the base medium and co-cultured with the BMDMs at 37° C. After 1 hour, medium containing NPs was removed, and the cells were cultured an additional 24 hours before evaluation of transfection efficiency and cell viability.

Transfection of BMDMs for macrophage signature gene analysis. BMDMs were reseeded on 24-well plates in conditioned medium 24 hours prior to transfection, allowing transformation of the cells into their phenotypes. M2-like macrophages were then exposed to either IRF5/IKKβ NPs carrying 25% eGFP mRNA as a reporter, or eGFP NPs (control) containing 2 μg mRNA, following the transfection protocol described above. After 24 hours, the top 10% percent of highly transfected BMDMs (as measured by eGFP expression) were sorted at 24 hours after transfection and were re-challenged in low-dose (10 ng/mL) 1L4 medium for another 48 hours before RNA isolation. RNAs extracted from these cells were compared to those from standard M1- or M2-like macrophages so that signature genes associated with IRF5-NP treatment could be identified.

RNA isolation and preparation. To harvest RNAs, BMDMs were lysed in Trizol reagent (Ambion), and total RNAs were extracted and purified using RNeasy® Plus Universal Mini-Kits (QIAGEN) following the manufacturer's instructions. Sample RNA was quantified using a Nano-Drop Microvolume Spectrophotometer (Thermo Fisher) and then subjected to quality control performed by the FHCRC Genomics Shared Resource with an Agilent 4200 TapeStation analyzer (Agi lent).

Macrophage signature gene analysis by NanoString Technology. Gene expression values from stimulated BMDM cultures were measured using the nCounter® Myeloid Innate Immunity Panel (NanoString Technologies, Seattle, WA), which analyzes 770 genes occurring in 19 different pathways and processes them across 7 different myeloid cell types. The samples were tested using an nCounter Analysis System (NanoString Technologies, Seattle, WA). Raw data were processed and checked for quality using the R/Bioconductor NanoStringQCPro software package (Nickles D, Sandmann T, Ziman R and Bourgon R (2018) NanoStringQCPro: Quality metrics and data processing methods for NanoString mRNA gene expression data. R package version 1.10.0.). Expression values were normalized to the geometric mean of housekeeping genes and log2-transformed using nSolver 4.0 software (NanoString Technologies, Seattle, WA). False Discovery Rates for ratio data were calculated from the p-values returned by the t-tests using the Benjamini-Yekutieli method.

Flow Cytometry and cell sorting. Cells obtained from spleen, blood, peritoneal lavage, and bronchoalveolar lavage were analyzed by flow cytometry with myeloid and lymphoid immunophenotyping panels using the anti-mouse antibody probes listed in FIG. 9. Data were collected using a BD LSRFortessa analyzer running FACSDIVA software (Beckton Dickinson). CD11b+ and F4/80+ peritoneal macrophages were sorted using BD FACS ARIA II. All collected data were analyzed using FlowJo 10.0 software.

Cytokine analysis. Cytokine levels were evaluated using a Luminex 200 system (Luminex) at the FHCRC Immune Monitoring Shared Resource center. For ex vivo studies, cell culture supernatant was collected for the measurement of IL-6, IL-12p70, INFγ, and TNFα concentrations. For in vivo studies, plasma concentration of GM-CSF, INFγ, IL-12p70, IL-2, IL-6, and TNFα were measured.

qRT-PCR analysis. Gene expression levels were determined by qRT-PCR. To measure selected macrophage signature genes (SerpinB2, Retnla, Ccl5, Ccl11, codon-optimized IRF5, endogenous IRF5, and housekeeping GAPD genes), total RNA was isolated with RNeasy mini-columns (Qiagen) according to the manufacturer's instructions. cDNA was synthesized using a qScript cDNA Synthesis Kit (Quanta). For each sample, qRT-PCR was performed in triplicate via PerfeCTa qPCR SuperMix Low ROX (Quanta) using gene-specific probes from the Roche's Universal Probe Library (UPL) and PCR primers optimized by ProbeFinder (Roche): SerpinB2, UPL-049, F-ACTGGGGCAGTTATGACAGG (SEQ ID NO: 96), R-GATGATCGGCCACAAACTG (SEQ ID NO: 97); Retnla, UPL-078, F-TTGTTCCCTTCTCATCTGCAT (SEQ ID NO: 98), R-CCTTGACCTTATTCTCCACGA (SEQ ID NO: 99); Ccl5, UPL-105, F-CCTACTCCCACTCGGTCCT (SEQ ID NO: 100), R-CTGATTTCTTGGGTTTGCTGT (SEQ ID NO: 101); Ccl11, UPL-018, F-AGAGCTCCACAGCGCTTC (SEQ ID NO: 102), R-CAGCACCTGGGAGGTGAA (SEQ ID NO: 103); codon-optimized IRF5, UPL-022, F-TCTTAAAGACCACATGGTAGAACAGT (SEQ ID NO: 104), R-AGCTGCTGTTGGGATTGC (SEQ ID NO: 105); endogenous IRF5, UPL-011, F-GCTGTGCCCTTAACAAAAGC (SEQ ID NO: 106), R-GGCTGAGGTGGCATGTCT (SEQ ID NO: 107). Signature gene mRNA levels were normalized based on amplification of GAPD, UPL-060, F-AGCCACATCGCTCAGACAC (SEQ ID NO: 108) and R-GCCCAATACGACCAAATCC (SEQ ID NO: 109). All qRT-PCR reactions were performed using Quant Studio5 RT-PCR machines running QuantStudio6 software (Applied Biosystems). In cases when the amplification plot did not cross the threshold and no Ct value was obtained ("undetermined"), a Ct value equal to the highest cycle number of in the assay (40 cycles) was used for comparisons of relative expression.

Mice and in vivo tumor models. Except for the brain tumor model-related experiments, the mice used in these experiments were obtained from Jackson Laboratory; the others were bred and housed in the FHCRC animal facility. All of the mice were used in the context of a protocol approved by the center's Institutional Animal Care and Use Committee. To model ovarian tumors, 5×106 vascular epithelial growth factor (VEGFP)-expressing 1D8 cells were injected intraperitoneally (i.p.) into 4-to 6-week-old female albino B6 (C57BL/6J-Tyr<c-2J>) mice and allowed to establish for 2 weeks. For survival studies, the animals were treated i.p. with IRF5 NPs/eGFP NPs carrying 50 μg mRNA (two doses per week for 9 weeks, or until health conditions reached euthanizing requirements). For mechanism studies, the treatments for either 1, 2, or 3 weeks, were used followed by euthanization at 48 hours following the last dose. Peritoneal lavage was performed to collect the peritoneal cells. To compare the efficacy of IRF5/IKKβ NPs with status quo macrophage targeting therapies, one group of mice received treatment with IRF5/IKKβ NPs carrying 50 μg mRNA for 3 weeks with 2 doses per week; the second received oral gavage of 15 mg/kg PI3Kγ inhibitor IPI-594 (MedKoo Biosciences Inc) formulated in vehicle (5% 1-methyl-2-pyrrolidinone in polyethylene glycol 400) daily for 3 weeks; the third group received i.p. injection of 30 mg/kg CSF1R inhibitor Pexidartinib (PLX3397, MedKoo Biosciences Inc) formulated in the same vehicle daily for 3 weeks.

To model metastatic lung cancer, 2.5×104 16F10 cells transduced with F-luc and suspended in 200 μL RPMI medium were injected into 4- to 6-week-old female albino B6 (C57BL/6J-Tyr<c-2J>) mice (Jackson Laboratories) and allowed to establish for 1 week. For survival studies, mice were treated retro-orbitally with (or without) IRF5/IKKβ or eGFP NPs carrying 30 μg mRNA suspended in PBS. Mice were treated with 3 doses/wk for 3 weeks or until health conditions reached euthanizing requirements. For mechanism studies, the mice received the same treatments for 2 weeks. Bronchoalveolar lavage was performed to collect alveolar cells for analysis.

Mice bearing glioma were generated following published protocols (Uhrbom L et al. (2004) Nat Med 10: 1257-1260). Avian DF-1 cells producing RCAS-PDGFβ and RCAS-cre retroviruses were injected intracranially into both brain hemispheres (coordinates: 1 mm caudal from bregma, 2 mm lateral, depth of 2 mm from the dural surface) of Nestin-tv-a/Ink4a-arf-/–; Pten-/– mice (C57BL/6) between 4-6 weeks of age. Tumors were allowed to establish for 2 weeks. At day 15, mice received 10Gy radiation to one hemisphere, while the unirradiated hemisphere was shielded with lead. The next day, mice received retro-orbital injections of IRF5/IKKβ NPs carrying 30 μg mRNA (3 doses/wk for 3 weeks), or were assigned to the PBS control group.

In vivo bioluminescence imaging. D-Luciferin (Xenogen) in PBS (15 mg/mL) was used as a substrate for firefly luciferase imaging. Bioluminescence images were collected with a Xenogen IVIS Spectrum Imaging System (Xenogen). Mice were anesthetized with 2% isoflurane (Forane, Baxter Healthcare) before and during imaging. For ID8-VEGF ovarian tumors, each mouse was injected i.p. with 300 μg of D-Luciferin, and images were collected 10 minutes later. For B16F10 lung metastatic tumors, mice were injected i.p. with 3 mg of D-Luciferin, and images were collected 15 minutes afterwards. For brain tumor models, the mice received retro-orbital injection of 75 mg/kg body weight D-Luciferin, and images were collected 4 minutes later. Acquisition times ranged from 10 s to 5 min.

Biodistribution analysis. To determine the biodistribution of IRF5 NPs in the ID8-VEGF ovarian tumor model, mice in 7-8 groups received an i.p. or retro-orbital dose of NPs carrying 50 μg mRNA. Twenty-four hours after injection, whole blood was collected, and mice were euthanized with $CO_2$ to retrieve organs (liver, spleen, lung, kidney, heart, intestine, pancreases, and diaphragm). All tissues were stabilized with RNAlater, then frozen on dry ice. The codon-optimized IRF5 mRNA levels in each organ were measured using RT-qPCR.

Toxicity analysis. To measure potential in vivo toxicities of repeatedly infusing macrophage-targeting NPs, we injected mice (5/group) intravenously with 6 sequential doses of IRF5/IKKβ or eGFP NPs carrying 50 μg mRNA over the course of 3 weeks. Controls received no treatment. Twenty-four hours after the final infusion, mice were anesthetized and blood was collected by retro-orbital bleed to determine the complete blood counts. Blood was also collected for serum chemistry and cytokine profile analyses (performed by Phoenix Central Laboratories, Mukilteo, WA). Animals were then euthanized with $CO_2$ to retrieve organs, which were washed with deionized water before fixation in 4% paraformaldehyde. The tissues were processed routinely, and sections were stained with hematoxylin and eosin. The specimens were interpreted by Dr. Smitha Pillai MVSc, PhD, DACVP, a board-certified staff pathologist, in a blinded fashion.

Cytokine assays. Cytokine levels were evaluated using a Luminex 200 system (Luminex) at the FHCRC Immune Monitoring Shared Resources. For ex vivo studies, cell culture supernatant was collected for the measurement of IL-6, IL12p70, INFγ, and TNFα concentrations. For in vivo studies, we measured plasma concentrations of GM-CSF, INFγ, IL-12p70, IL-2, IL-6, and TNFα.

Statistical analysis. The statistical significance of observed differences were analyzed using the unpaired, two-tailed one-way ANOVA test. The P values for each measurement are listed in the figure or figure legends. Survival data was characterized using the Log-rank test. All statistical analyses were performed either using GraphPad Prism software version 6.0 or R software.

Figure 2A:
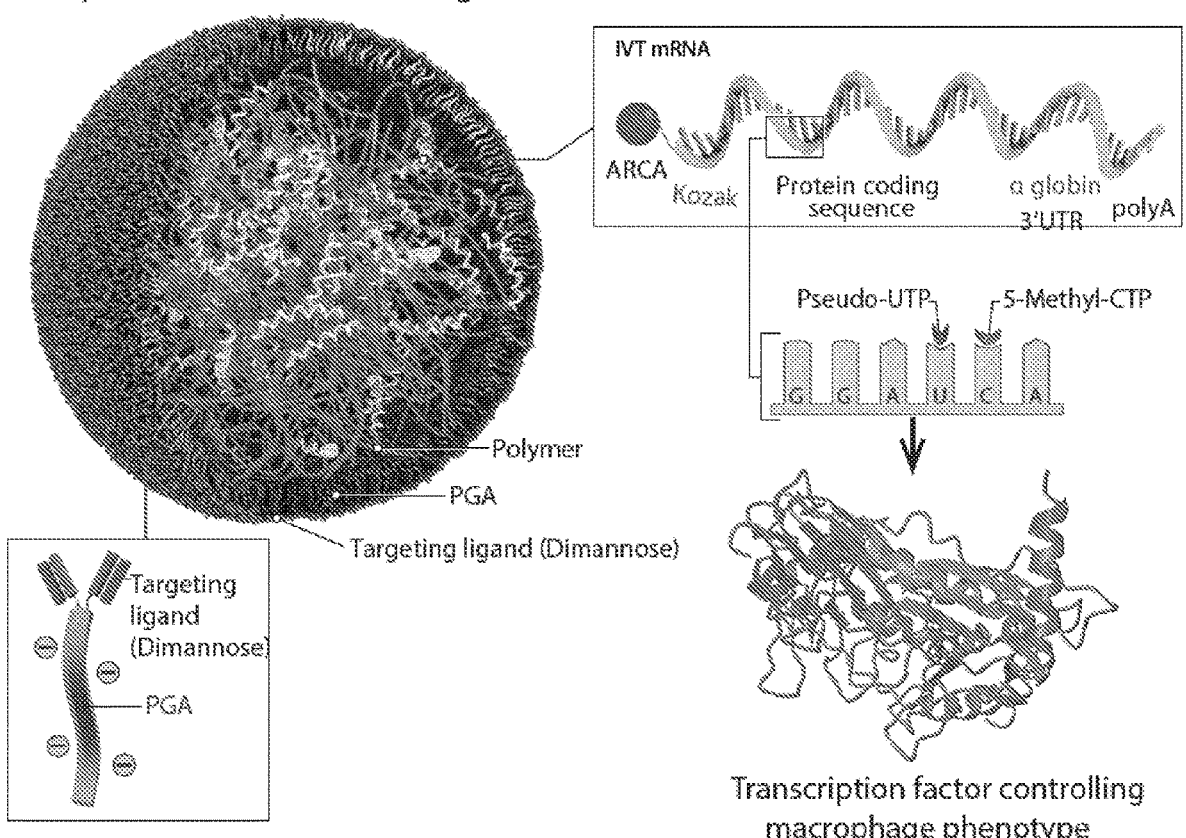
FIGS. 2A-2K. Nanoparticles carrying mRNA encoding IRF5 and IKKβ can imprint a pro-inflammatory M1-like phenotype.
Figure 2B:
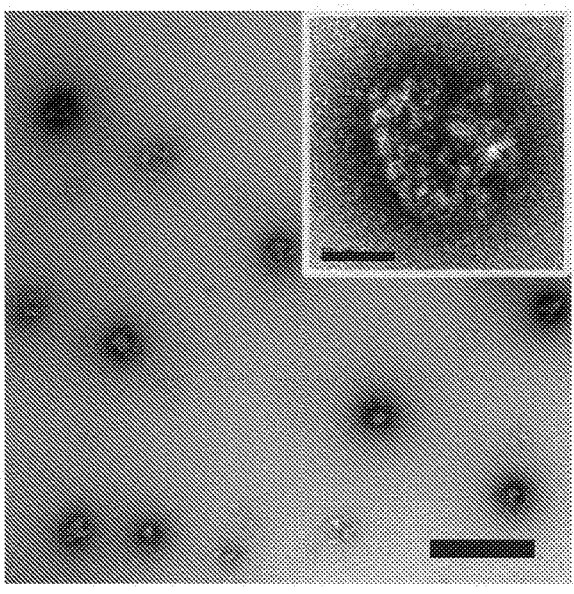
Figure 2C:
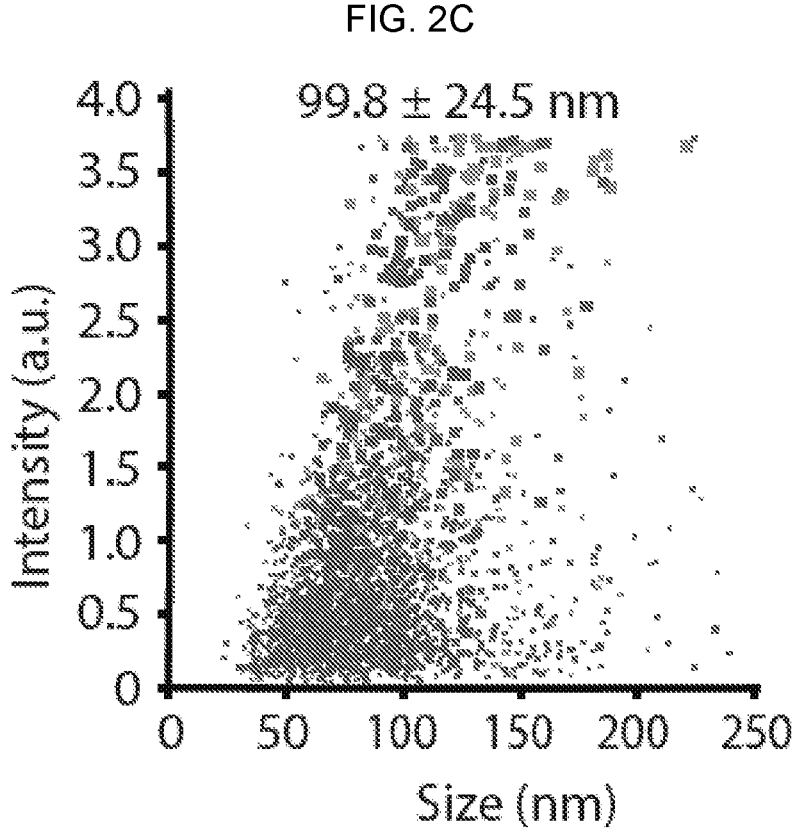
Figure 2D:
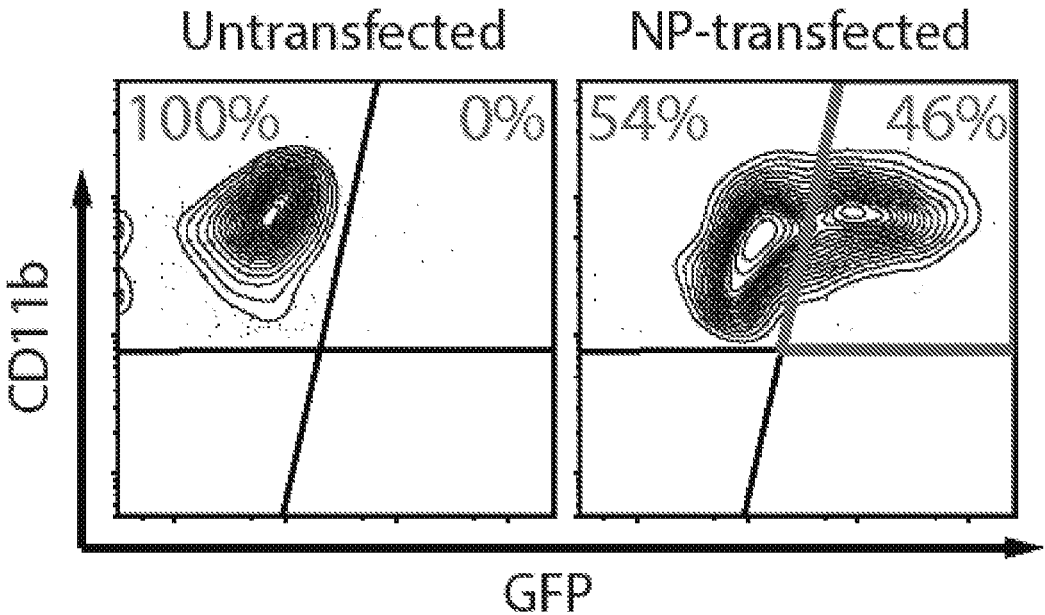
Figure 2E:
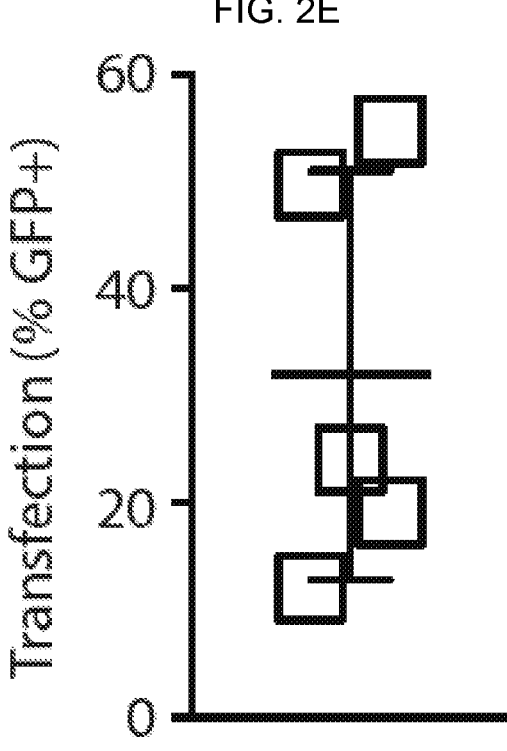
Figure 2F:
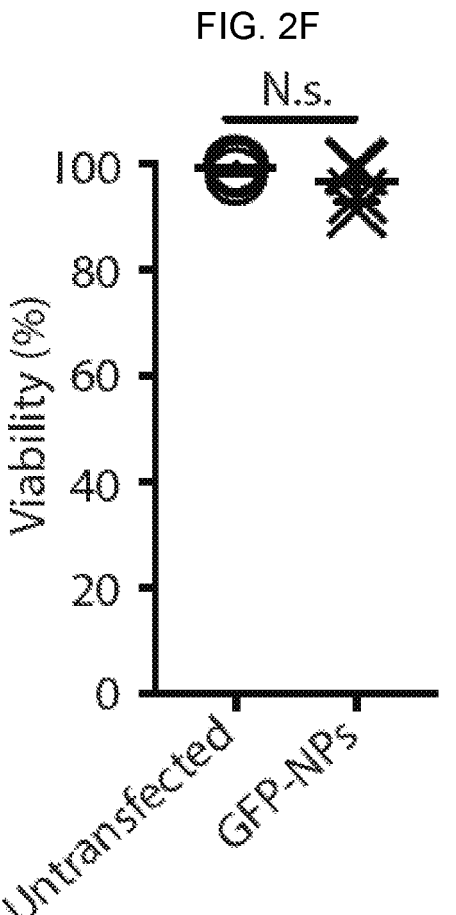
Figure 2G:
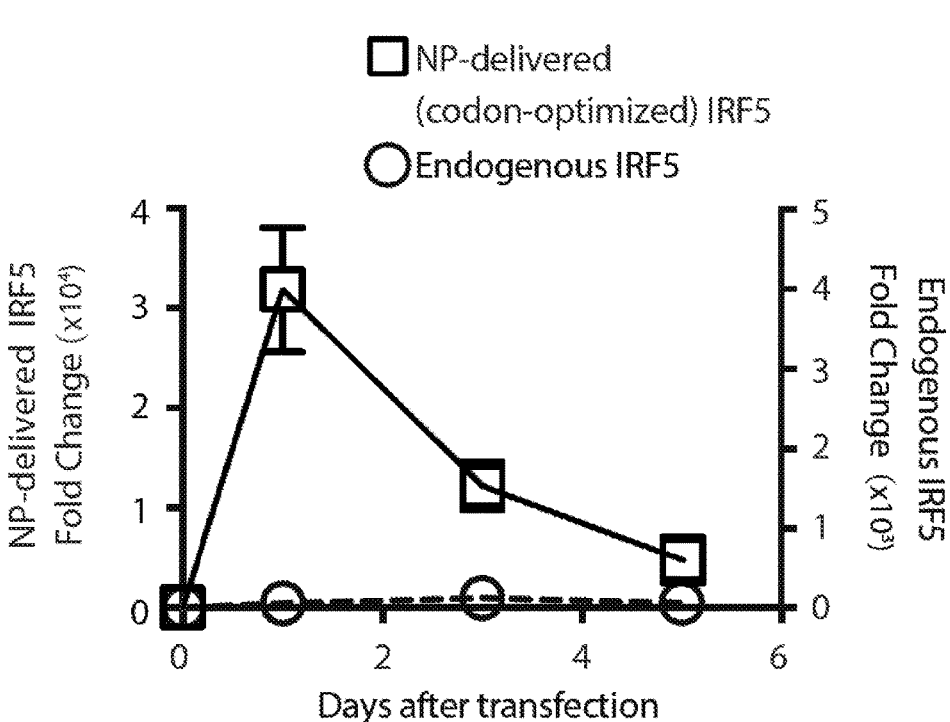

Results. Designing NPs to choreograph IVT mRNA transfection of TAMs. A targeted mRNA delivery system was developed that can introduce robust gene expression in the targeted cells by taking advantage of electrostatic interactions between cationic poly(β-amino ester) (PbAE) polymers and anionic mRNA (FIG. 2A). To improve the stability and translation of the mRNA encapsulated in the resulting nanocarriers, synthetic versions of the message were used that incorporate the modified ribonucleotides pseudouridine (ψ) (Kariko K et al. (2008) Mol Ther 16: 1833-1840) and 5-methylcytidine (m5C), and that are capped with ARCA (Anti-Reverse Cap Analog) (Quabius E S et al. (2015) N Biotechnol 32: 229-235). The mRNA is released from the mRNA-PbAE complex intracellularly by hydrolytic cleavage of ester bonds in the PbAE backbone. Efficient in vivo T cell transfection was previously demonstrated using this system (Smith T T et al. (2017) Nat Nanotechnol). To target the nanoparticles to TAMs as well as further stabilize the mRNA-PbAE complexes they contain, Di-mannose moieties were engineered onto their surfaces using polyglutamic acid (PGA) as a linker (FIG. 2A). The NPs were manufactured utilizing a simple two-step, charge driven self-assembly process. First, the synthetic mRNA was complexed with a positively charged PBAE polymer, which condenses the mRNA into nano-sized complexes. This step was followed by the addition of PGA functionalized with Di-mannose, which shields the positive charge of the PBAE-mRNA particles and confers macrophage-targeting. The resulting mRNA nanocarriers had a size of 99.8±24.5 nm, a polydispersity of 0.183, and a neutral surface charge (3.40±2.15 mV ζ-potential, FIG. 2B-2C). The transfection efficiency was first tested in murine bone marrow-derived macrophages (BMDMs) using NPs formulated with green fluorescent protein-encoding mRNA (GFP-NPs). Briefly, 50,000 BMDMs were exposed to NPs containing 1 μg mRNA for 1 hour, followed by flow cytometry measurements of GFP expression the next day. Following a single NP application, we routinely transfected 31.9% (±8.5%) of these primary macrophages without reducing their viability (FIG. 2E-2F). Surface modification of particles with Di-mannose was relevant, as transfection rates with untargeted (but PGA-coated) nanocarriers dropped to an average of 25% (±2.1%) in this inherently phagocytic cell type. The NPs selectively targeted the CD11b+, F4/80+ macrophage population, with 46% of macrophages transfected and expressing high levels of eGFP (FIG. 2D). This high transfection efficiency demonstrates the potency of the disclosed systems and methods in targeted delivery of mRNA to TAMs. Based on the results of an in vitro screen for transcription factor candidates that induce macrophage polarization, two mRNAs were selected for inclusion in the NP: the first encodes IRF5, a key member of the IRF family that favors the polarization of macrophages toward the M1 phenotype, and the second encodes IKKβ, a kinase that phosphorylates and activates IRF5.

Programming immunosuppressive macrophages into proinflammatory phenotypes. To induce macrophage polarization, two mRNAs were selected for inclusion into the NPs: the first encodes IRF5, a key member of the interferon regulatory factor family that favors the polarization of macrophages toward the M1 phenotype (Krausgruber T et al. (2011) Nat Immunol 12: 231-238); the second encodes IKKβ, a kinase that phosphorylates and activates IRF5 (Ren J et al. (2014) Proc Natl Acad Sci USA 111: 17438-17443). A ratio of 3 IRF5 mRNAs to 1 IKKβ mRNA was used. Using real-time quantitative PCR specific for the NP-delivered (and codon-optimized) IRF5 mRNA, it was found that mRNA expression in macrophages was maximal at day 1, resulting in a 1,500-fold increase in IRF5 relative to endogenous factor levels (FIG. 2A). As expected, gene expression was transient but IRF5 levels remained strongly upregulated through day 3 (581-fold increased) and day 5 (87-fold increased) before returning to baseline.

Figure 2H:
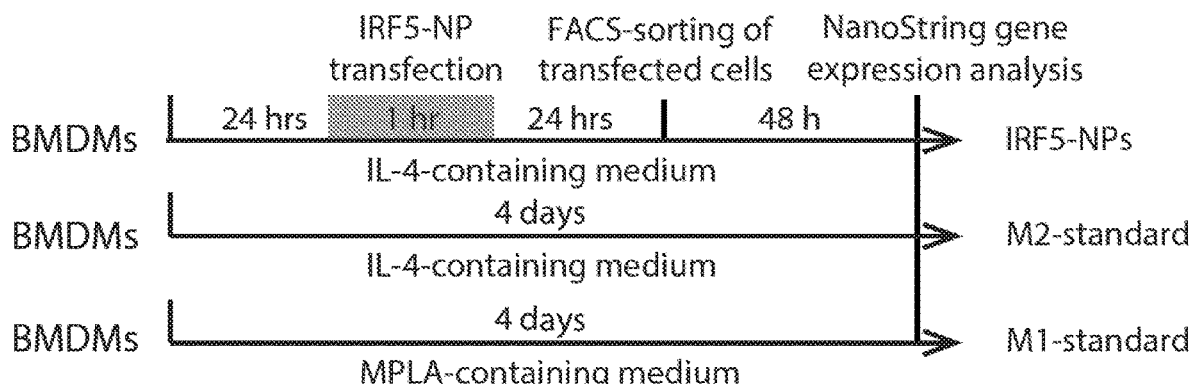
Figure 2I:
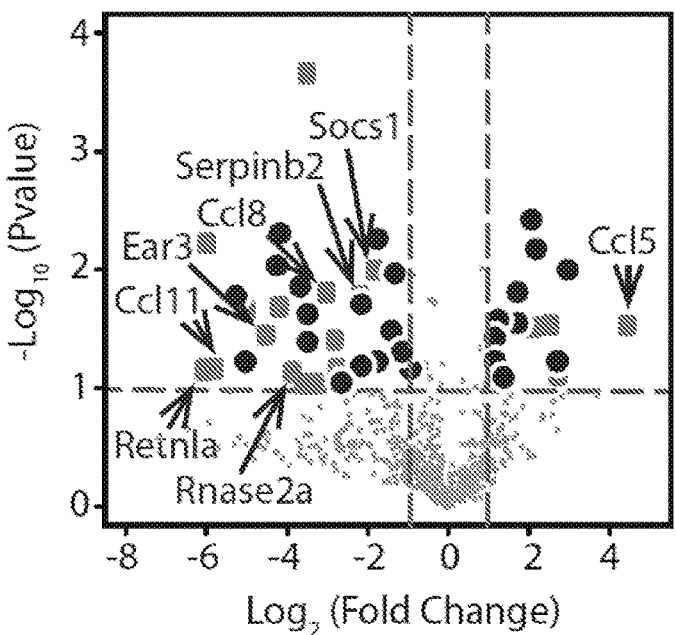
Figure 2J:
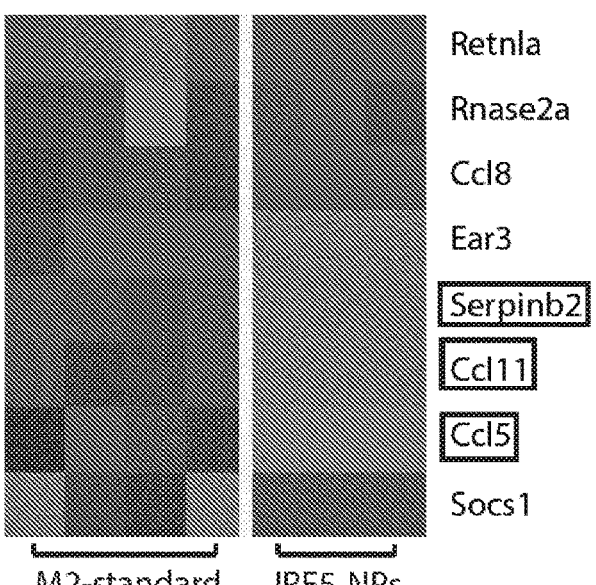
Figure 2K:
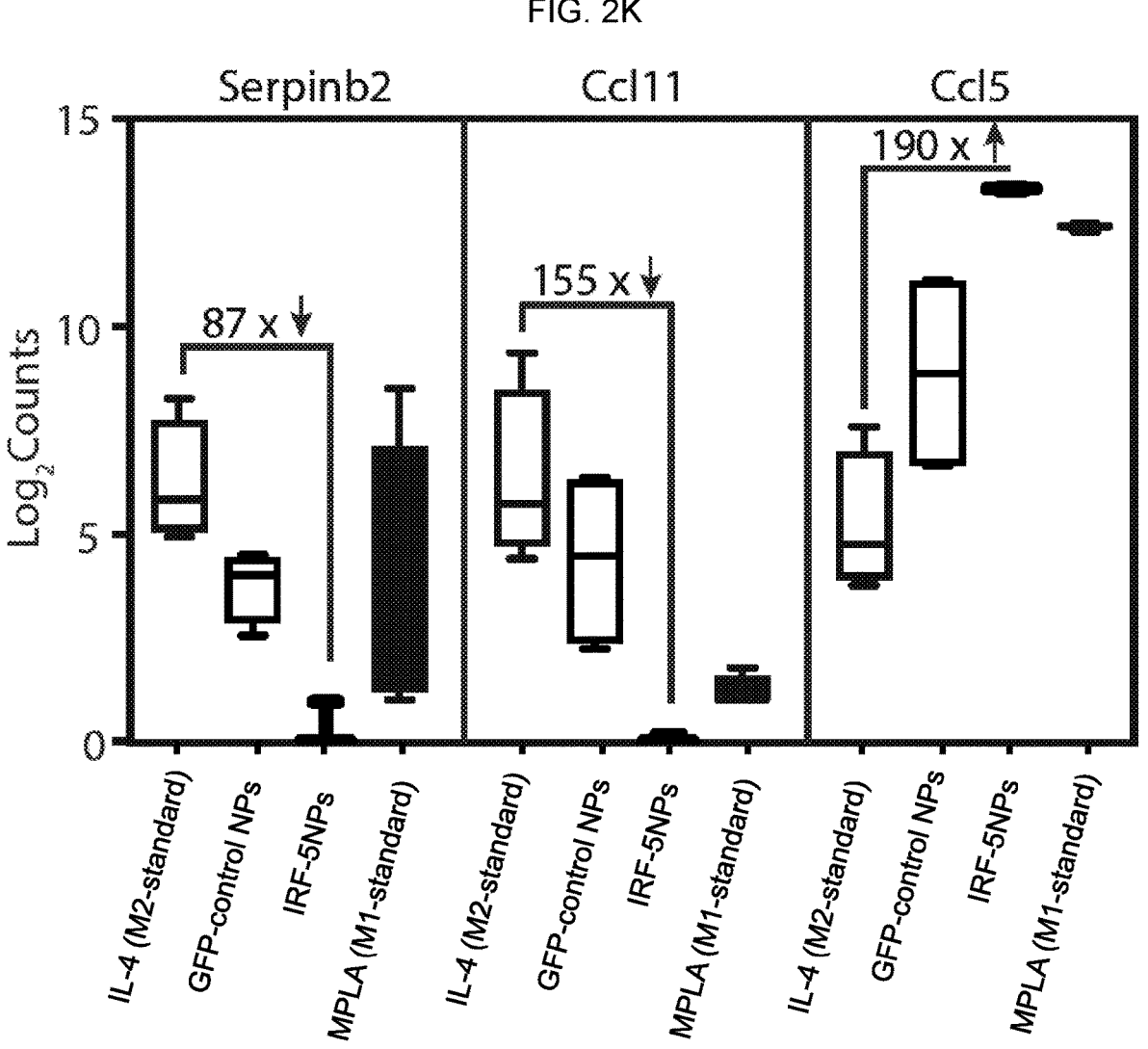
Figure 3:
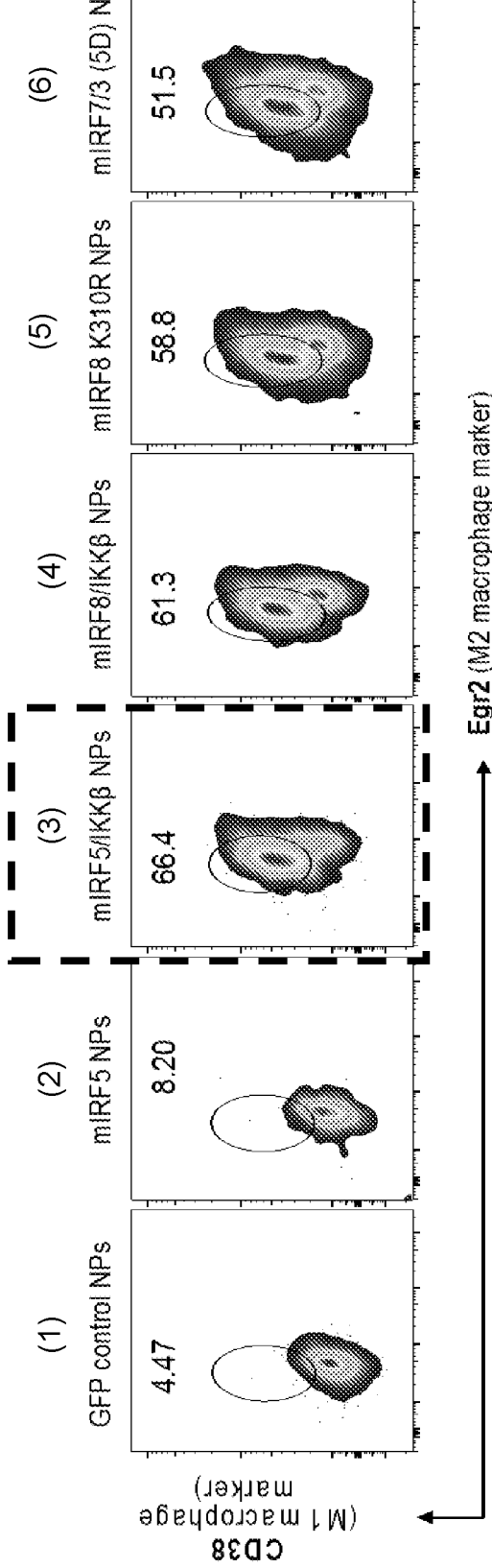
FIG. 3. In vitro screening of the effect of different members of the interferon-regulatory factor (IRF) family (delivered in combination with or without their activating kinase) on the phenotype of mouse macrophages. BMDMs from C57BL/6 mice were incubated in M-CSF conditioning media and transfected with mRNA-PBAE NPs carrying synthetic mRNA encoding (1) control GFP, (2) murine IRF5, (3) murine IRF5 and the IKKβ kinase, which phosphorylates IRF5, (4) murine IRF8 and the IKKβ kinase, (5) murine IRF8 K310R, which is a mutant of IRF8, with a Lys-310 to Arg (K310R) conversion (White et al., J Biol Chem. 2016 Jun. 24), or (6) murine IRF7/3 (5D). This fusion protein includes the DNA binding domain (DBD) and constitutively active domain (CAD) of IRF-7 and the nuclear export signal (NES) and IRF association domain of IRF3 (Lin et al., Molecular and Cellular Biology. 18.5, 1998). Two days after NP transfection, cells were harvested for flow cytometric analysis for the TAM-associated macrophage marker Egr2 and the activated macrophage marker CD38. Based on this in vitro screen, NPs co-delivering mRNA encoding mIRF5 and IKKβ kinase were chosen for the remainder of in vitro and therapeutic in vivo experiments described herein.

To determine if IRF5/IKKβ-encoding NPs can reprogram M2 macrophages into the therapeutically desirable anti-cancer M1 phenotype, NanoString gene expression analysis was used. BMDMs were first cultured in the presence of interleukin-4 (IL-4) to induce a suppressive M2 phenotype (FIG. 2H). Following transfection with either control GFP-mRNA nanoparticles or IRF5/IKKβ mRNA-containing NPs, gene expression profiles were analyzed and compared with inflammatory macrophages, which were generated separately by exposing BMDMs to the TLR4 agonist Mono-phosphoryl Lipid A. Despite being cultured in suppressive IL-4-containing medium, macrophages transfected with IRF5/IKKβ mRNA NPs display gene expression profiles similar to inflammatory macrophages (FIG. 2I). Signature M2 macrophage genes, such as Serpinb2 and Ccl2 (Jablonski K et al. (2015) Plos One 10: e0145342; Varga T et al. (2016) J Immunol 196: 4771-4782), were strongly downregulated while key M1 differentiation genes, such as Ccl5 (Sica A et al. (2012) J Clin Invest 122: 787-795), were upregulated (FIG. 2J, 2K). These data establish that NP-mediated expression of IRF5 and its kinase skews suppressive macrophages toward a proinflammatory phenotype.

Example 2

Figure 4A:
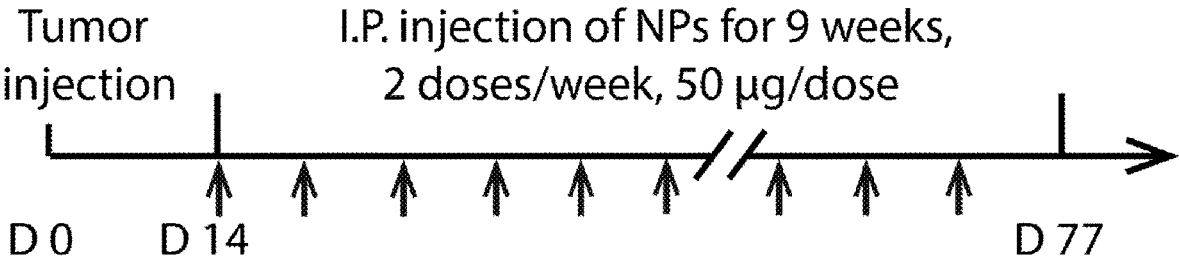
FIGS. 4A-4J. Repeated intraperitoneal injections of mRNA nanocarriers delivering IRF5 and IKKβ genes into macrophages more than doubles mean survival of mice with disseminated ovarian cancer.
Figure 4B:
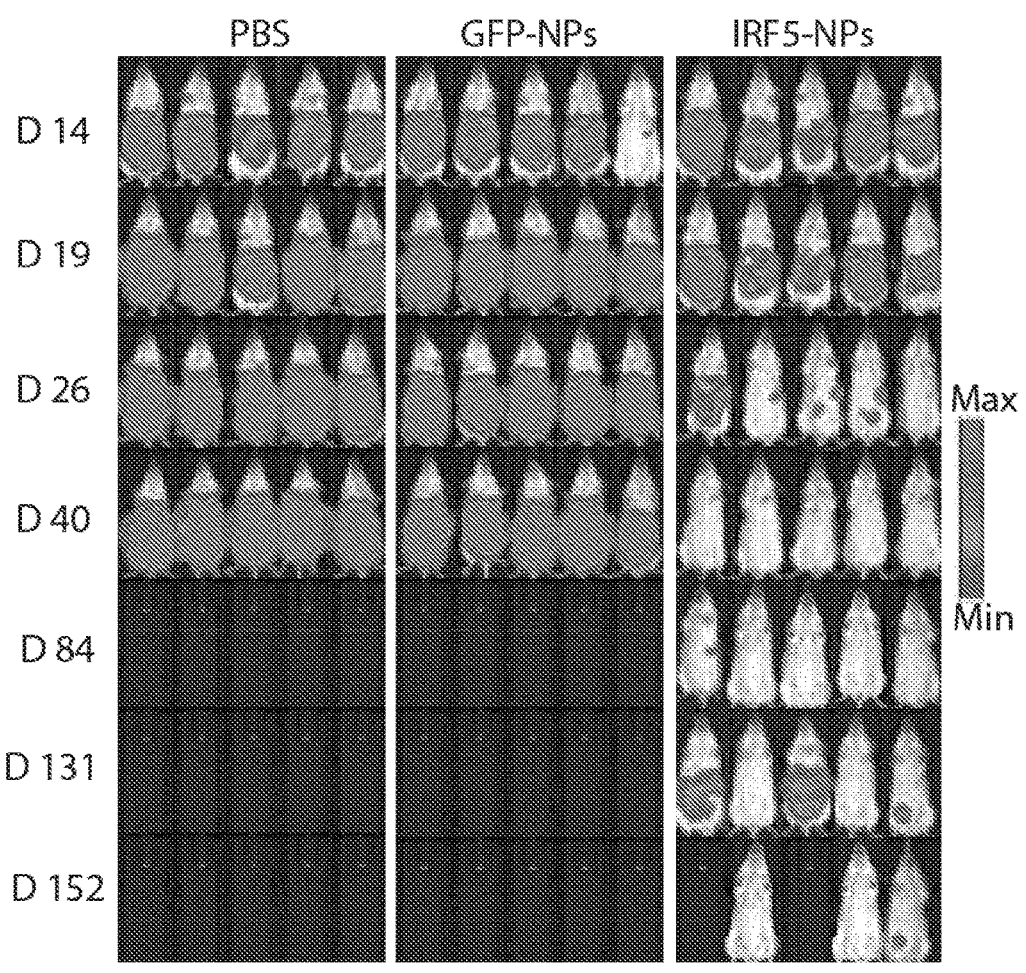
Figure 4C:
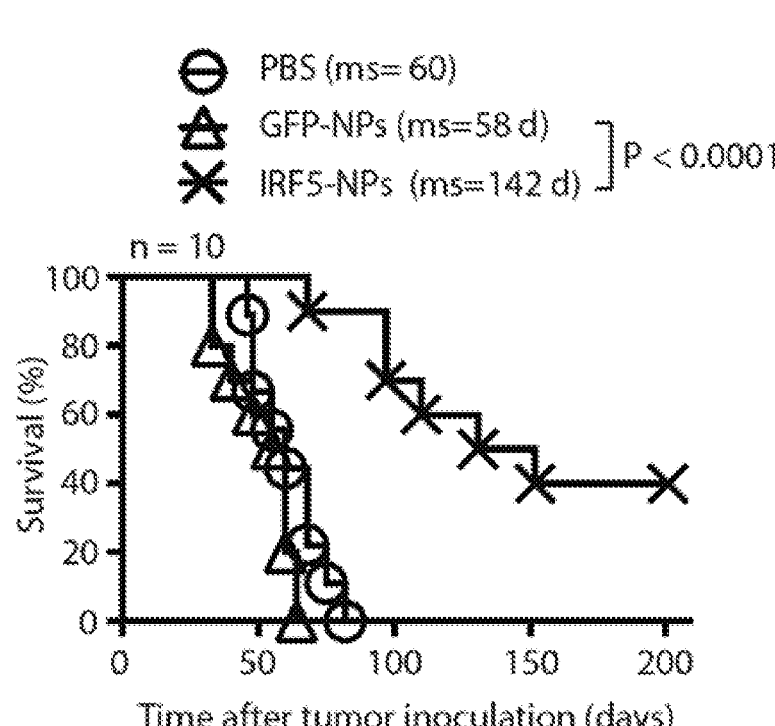
Figure 4D:
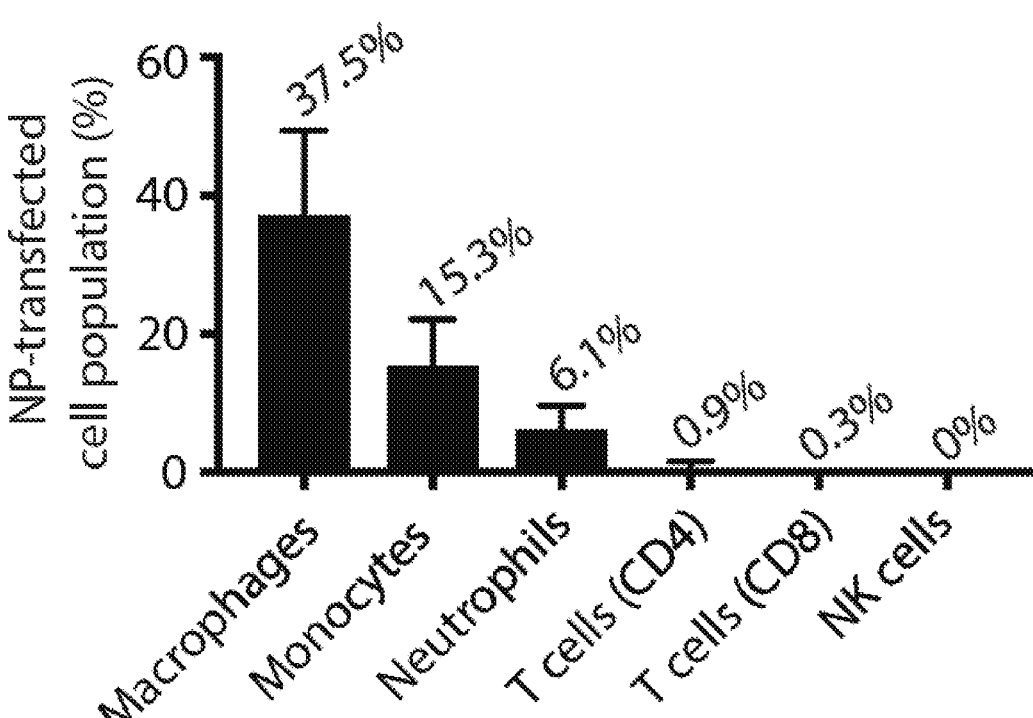
Figure 4E:
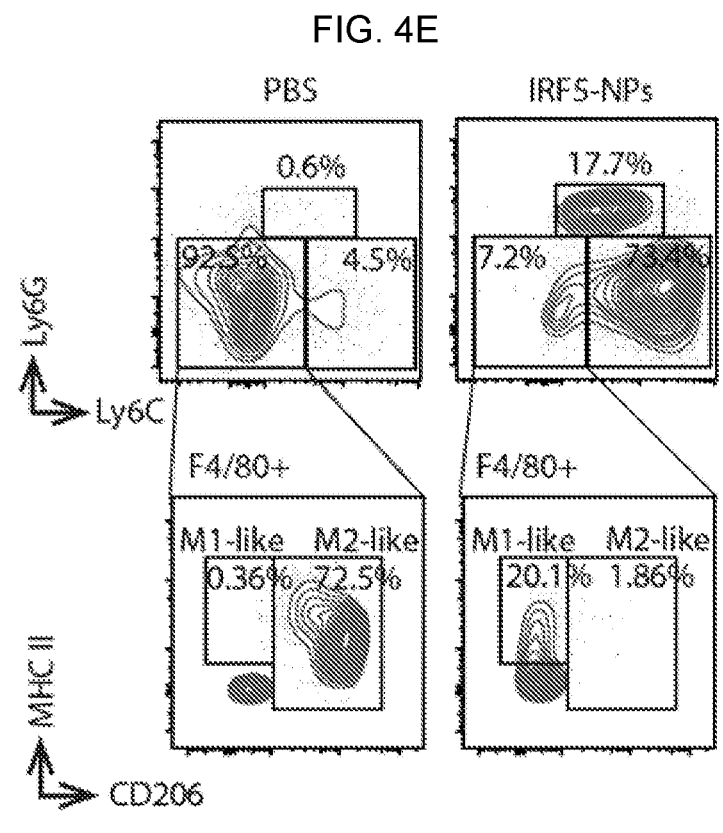
Figure 4F:
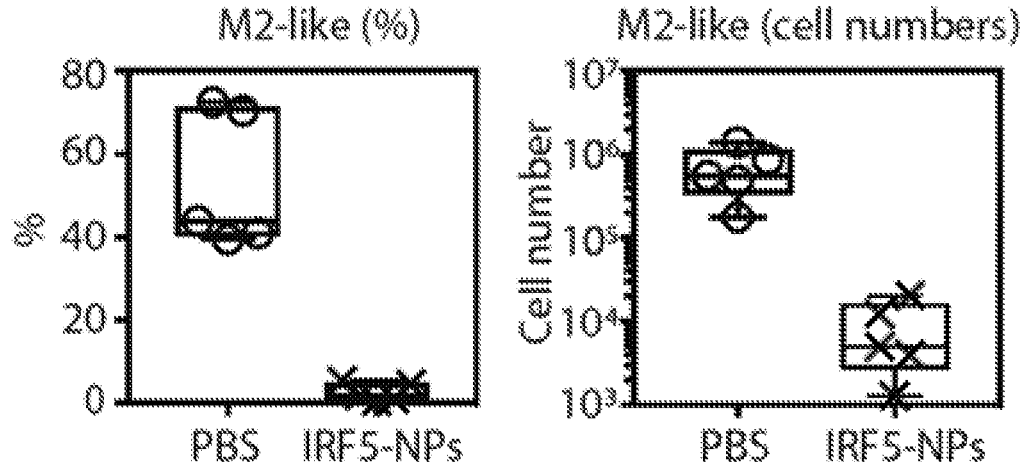
Figure 4G:
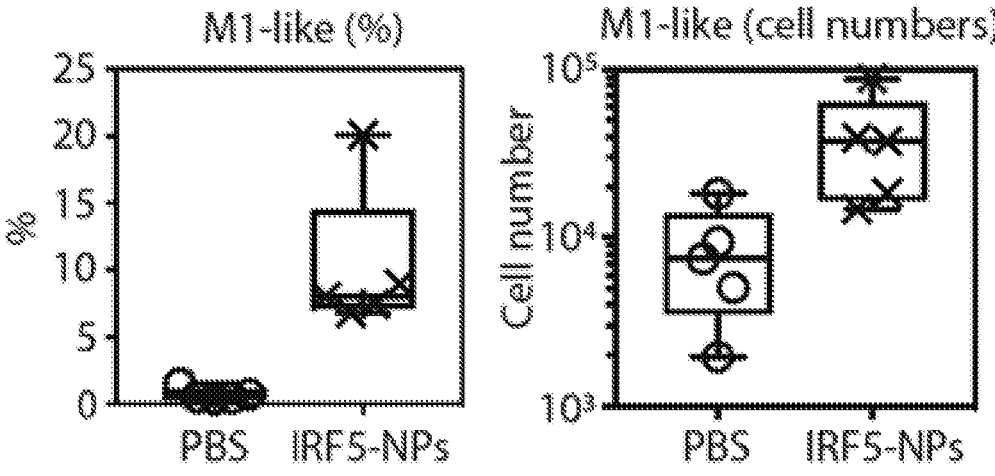
Figure 4H:
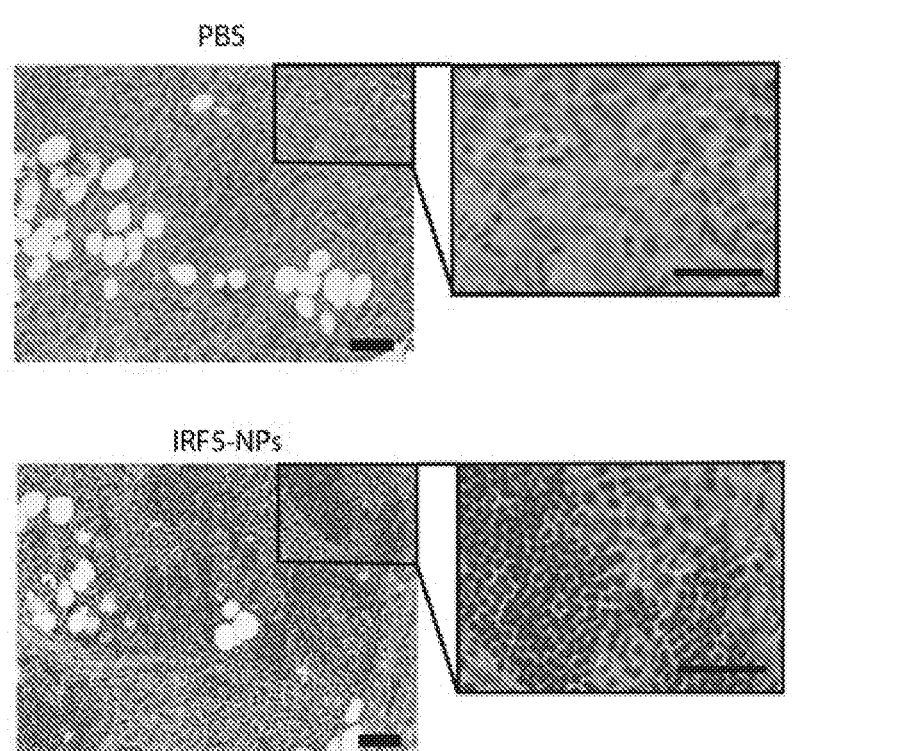

Therapeutic effects of NP-delivered pro-M1 genes for disseminated ovarian cancer. To evaluate this treatment approach in a clinically-relevant in vivo test system, a model that recapitulates late-stage, unresectable ovarian tumors in C57BL/6 mice was used; these animals are injected with ID8 ovarian cancer cells which were tagged with luciferase to enable serial bioluminescent imaging of tumor growth (Liao J B et al. (2015) J Immunother Cancer 3: 16; Stephan S B et al. (2015) Nat Biotechnol 33: 97-101). The tumors were allowed to establish for two weeks. By this stage, the mice have developed nodules throughout the peritoneal wall and in the intestinal mesentery. The animals were divided into 3 groups that received PBS (control), GFPNPs (sham), or IRF5/IKKβ NP treatment at an i.p. dose of 100 μg mRNA/mouse/week for 9 weeks (FIG. 4A). It was observed that in the IRF5/IKKβ NP treated group, the disease regressed and was eventually cleared in 40% of animals (overall 142 d median survival versus 60 d in controls; FIG. 4B-4C). To understand the underlying mechanisms of IRF5/IKKβ NP-mediated anti-tumor effects, how exclusively mannose receptor-targeting confined NP interaction to phagocytes was first examined. Flow cytometry of peritoneal lavage fluid collected 24 h after the first dose of NPs targeted with Di-mannose revealed preferential gene transfer into macrophages and monocytes (average 37.1% and 15.3%, respectively, FIG. 4D), while transfection into off-target cells was low or undetectable. A detailed phenotypic and functional analysis of macrophage/monocyte populations in the peritoneum of mice with established ovarian cancer following treatment with IRF5/IKKβ nanoparticles or PBS over a 3-week period (two weekly injections) was conducted next. Flow cytometric analysis revealed that IRF5/IKKβ NPs reduced the population of immune-suppressive macrophages (Ly6C−, F4/80+, CD206+) to an average 2.6%±2.1% versus 43%±15.6% in controls (FIG. 4E-4F). Conversely, the fraction of M1-like macrophages increased from 0.5%±0.2% to 10.2%±4.1% (FIG. 4E, 4G). IRF5 gene therapy also affected the population of other immune cells. In particular, inflammatory monocytes (CD11b+, Ly6C+, Ly6G−) were more abundant (73.4%±3.6% compared to 4.5%±1.9% in untreated mice). One interesting finding in all IRF5 NP-treated animals were multifocal dense clusters of lymphocytes present within or surrounding the neoplasms (FIG. 4H), indicating that genetic programming of immune stimulatory macrophages may restore lymphocyte migration and infiltration into solid tumors.

Figure 4I:
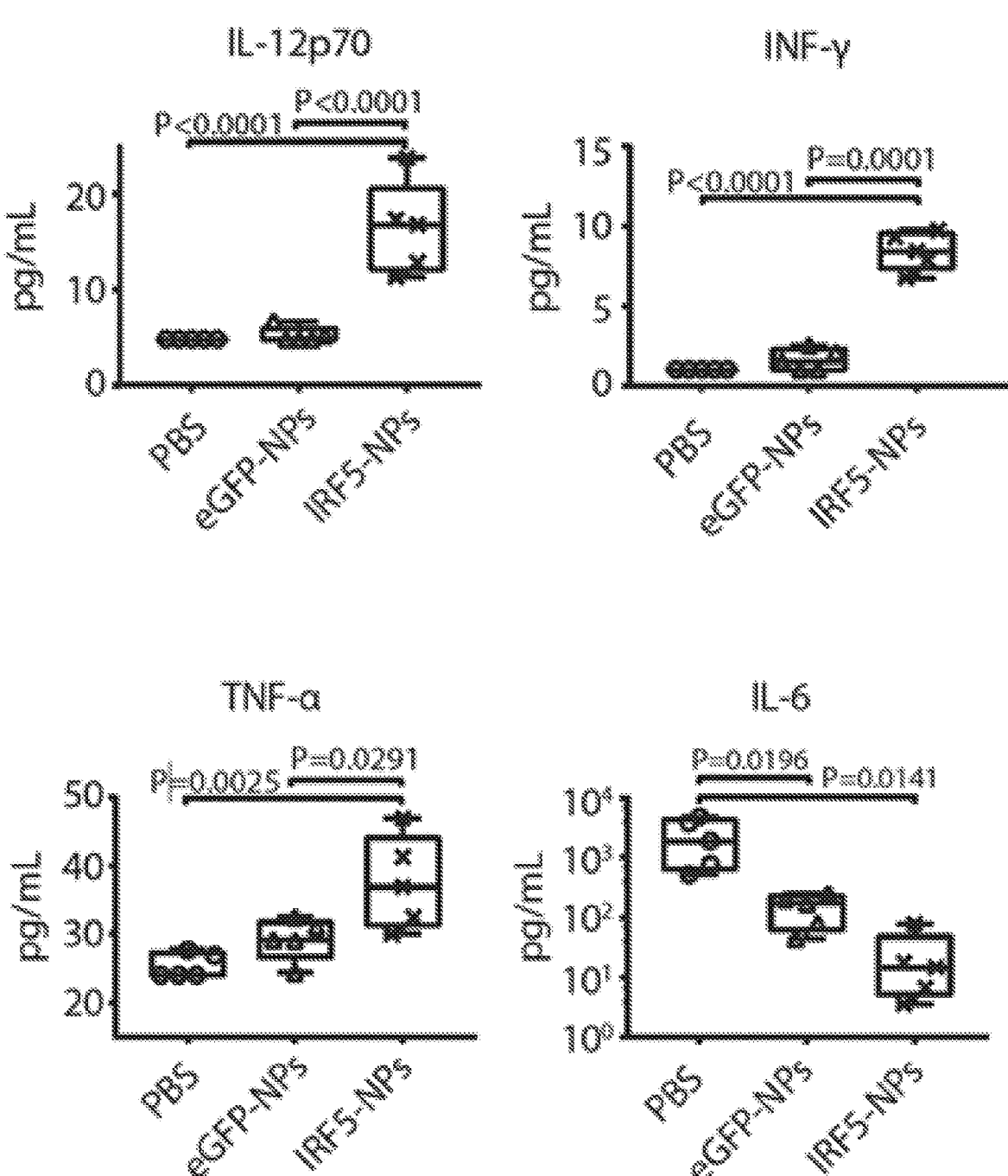
Figure 4J:
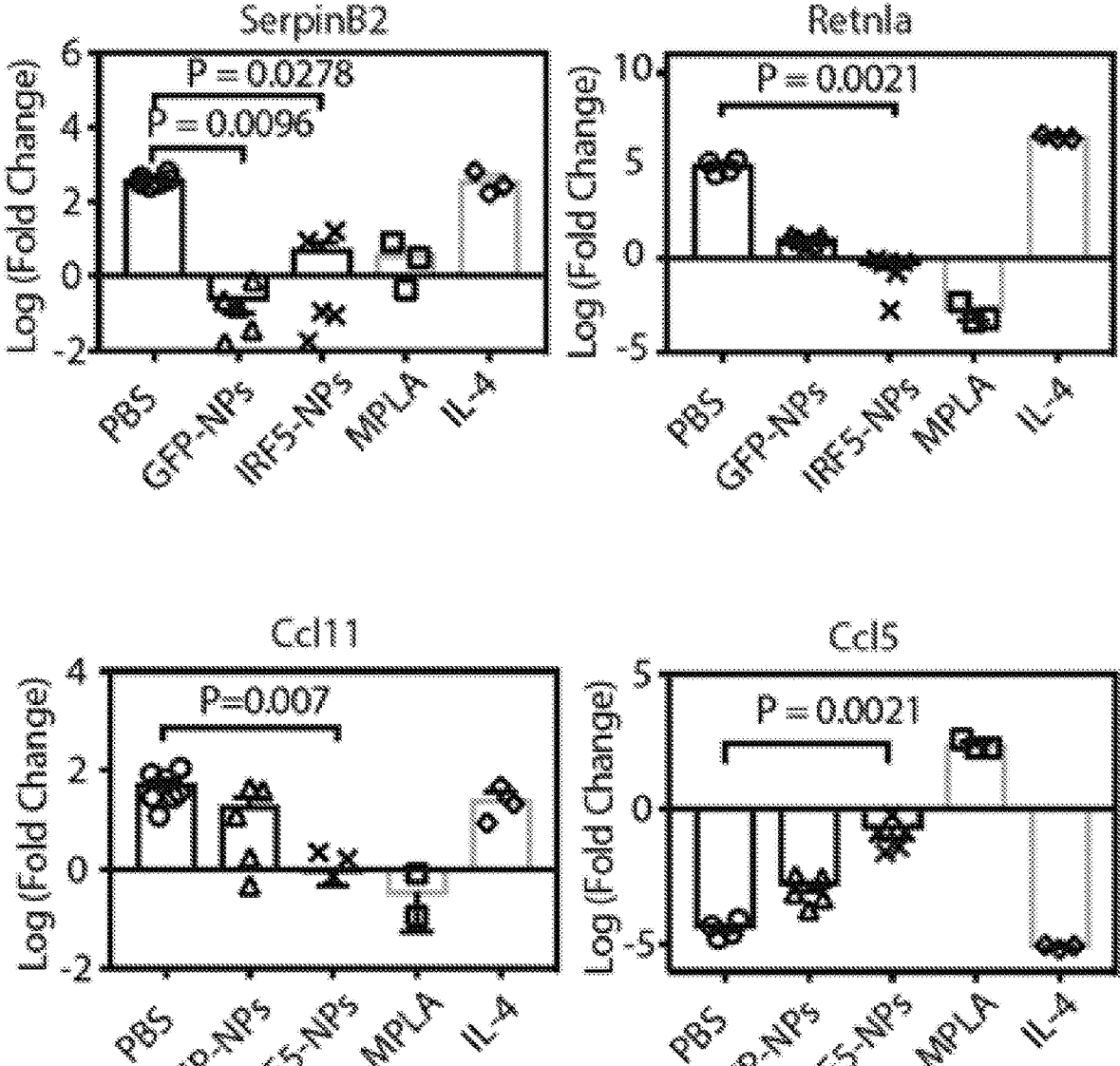

Peritoneal macrophages were isolated by fluorescence-activated cell sorting to analyze their cytokine secretion, and detected a robust increase in the release of pro-inflammatory (anti-tumor) cytokines IL-12 (3.4-fold higher), IFN-g (8.4-fold higher), and TNF-α (1.5-fold higher), whereas the levels of IL-6, a regulatory cytokine associated with differentiation toward alternatively activated (M2-like) macrophages, were reduced by 97-fold; FIG. 4I). Genome expression profiling confirmed differentiation toward an M1-like macrophage phenotype in IRF5/IKKβ nanoparticle-treated mice. Gene expression levels of macrophages cultured ex vivo in MPLA or IL-4 were included to provide reference values for classic M1-like or M2-like macrophages, respectively (FIG. 4J).

Figure 5A:
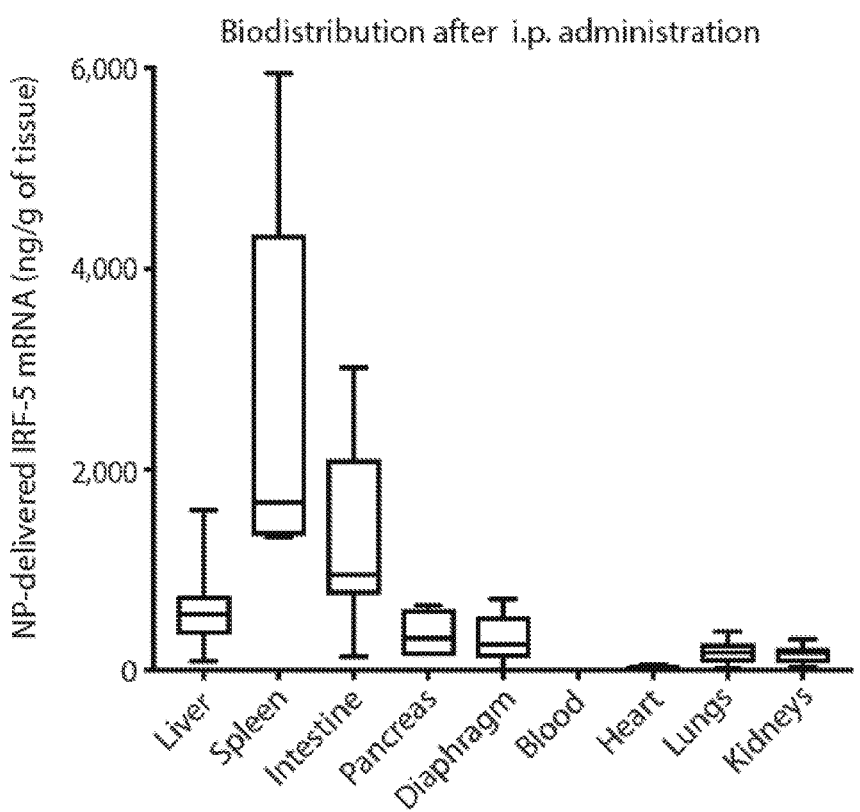
Figure 5B:
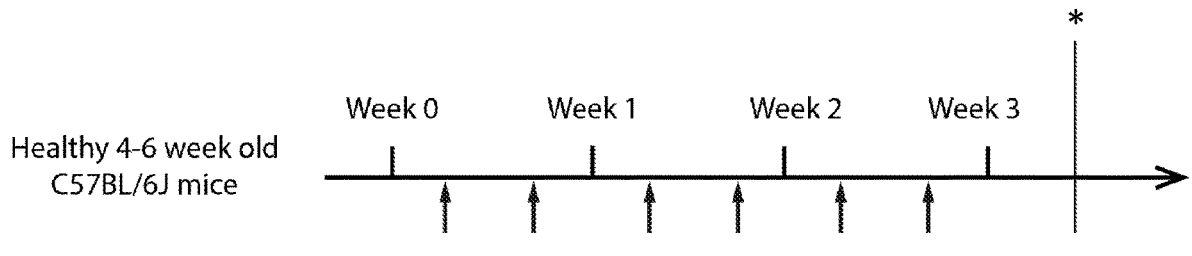
Figure 5C:
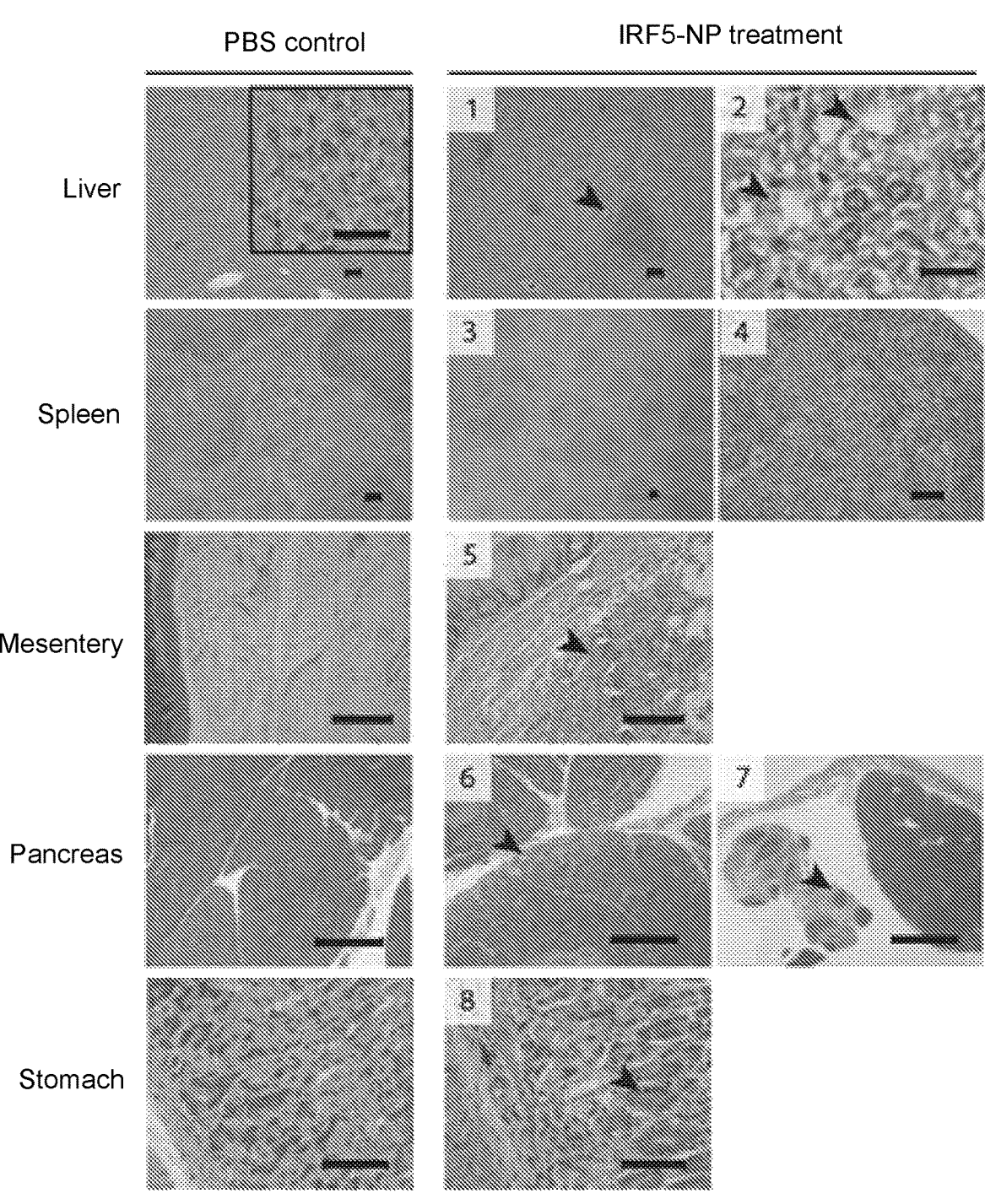
Figure 5E:
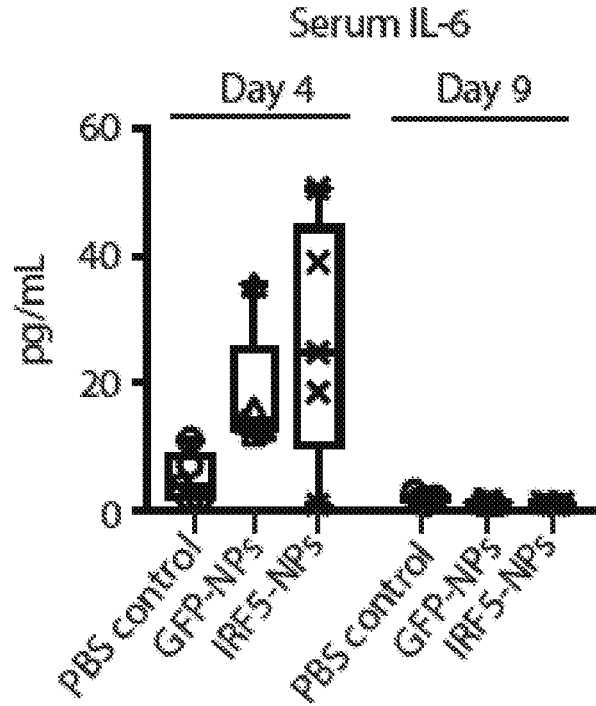
Figure 5F:
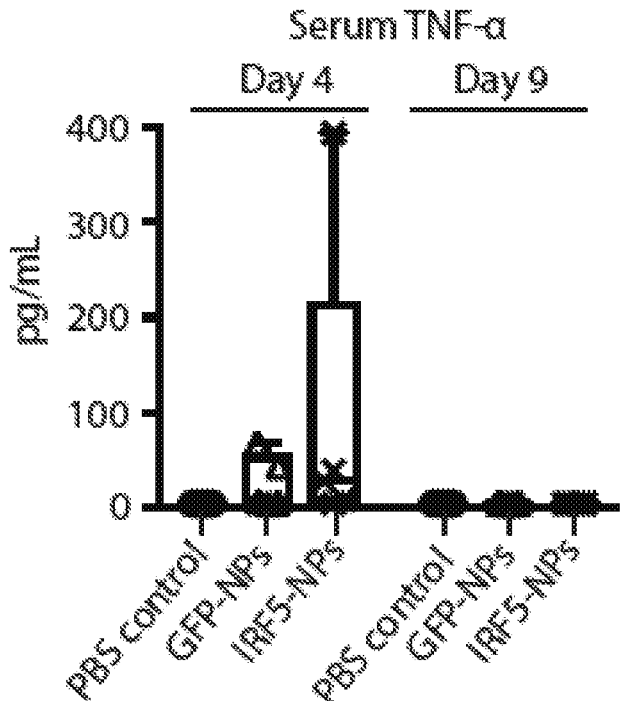

Biodistribution and safety. The distribution of nanoparticles in various organs 24 h after intraperitoneal injection using RT-qPCR assays designed to detect only nanoparticle-delivered (codon optimized) IRF5 was next quantified. The highest concentrations of IVT mRNA were found in organs located in the peritoneum, including liver, spleen, intestine, pancreas, and diaphragm (FIG. 5A). Small amounts of particle-delivered mRNA in organs that lie outside of the peritoneum (heart, lungs, kidneys) were detected, suggesting that a fraction of i.p. injected nanocarriers entered the systemic circulation. Guided by the distribution data, we next assessed whether these nanoreagents are biocompatible and safe for repeated dosing. Mice were injected with a total of 8 doses of IRF5/IKKβ NPs (two 50 μg mRNA doses/week for 4 weeks, FIG. 5B). They were euthanized 24 h after the final dose, body weight was recorded, blood was collected by retroorbital bleed for serum chemistry, and a complete gross necropsy was performed. There was no difference in body weights between groups. The following tissues were evaluated by a board certified staff pathologist: liver, spleen, mesentery, pancreas, stomach, kidney, heart, and lungs. Histopathological evaluation revealed in all cases multifocal dense clusters of lymphocytes within or surrounding tumor lesions, but no evidence of inflammation or frank necrosis was observed in tissues where neoplastic cells were not present (FIG. 5C). Also, serum chemistry of IRF5/IKKβ NP-treated mice was comparable to that of PBS controls, indicating that systemic toxicities did not occur (FIG. 5D). Because small amounts of IRF5-mRNA were detected systemically in biodistribution studies, parallel experiments were designed to quantitate inflammatory cytokines in the peripheral blood. Following a single i.p. injection of IRF5/IKKβ NPs, moderate and transient increase was measured in serum levels of interleukin-6 (IL-6) to an average of 26.8 pg/mL (FIG. 5E), and tumor necrosis factor-a (TNF-a) to an average 94.7 pg/mL (FIG. 5F). Based on previous reports, these levels are 500-fold lower than those associated with pathological findings and thus can be considered safe Tarrant J. M. (2010) Toxicol Sci 117: 4-16; Copeland S et al. (2005) Clin Diagn Lab Immunol 12: 60-67).

Figure 6A:
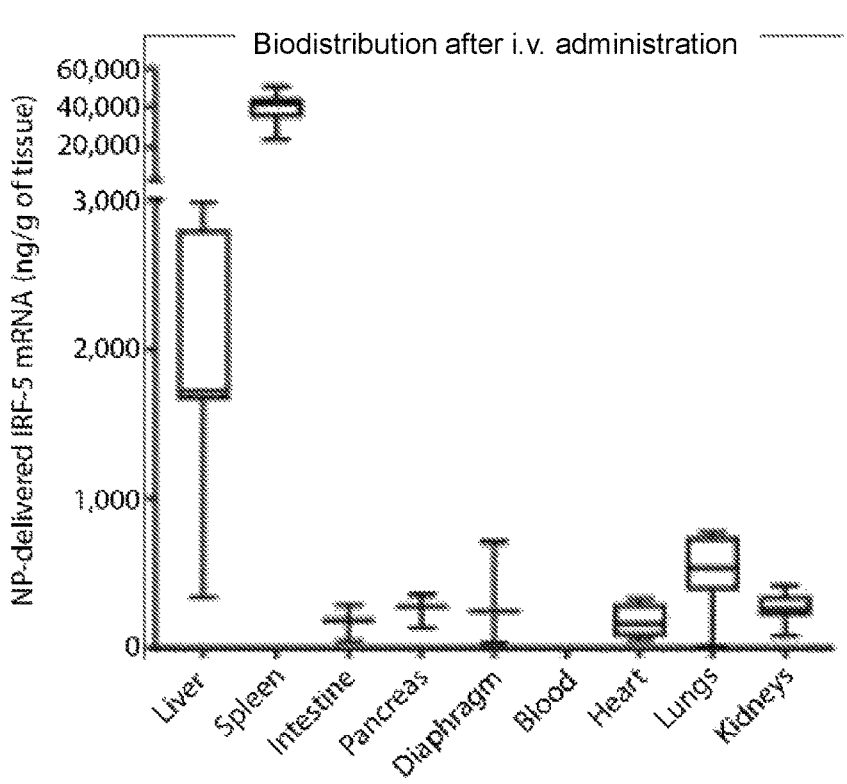
Figure 6B:
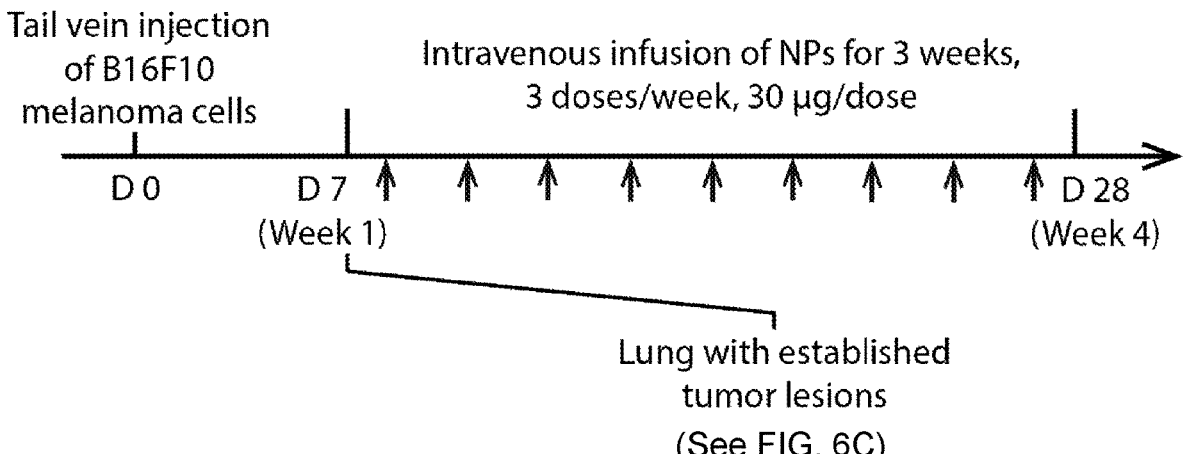
Figure 6C:
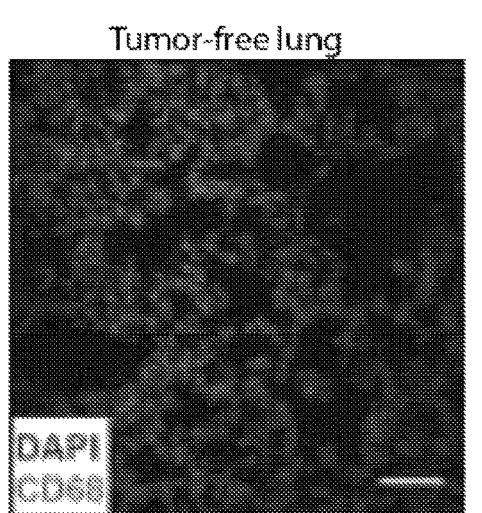
Figure 6C:
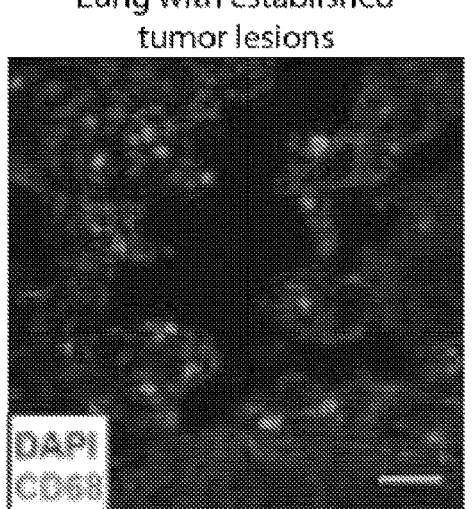
Figure 6D:
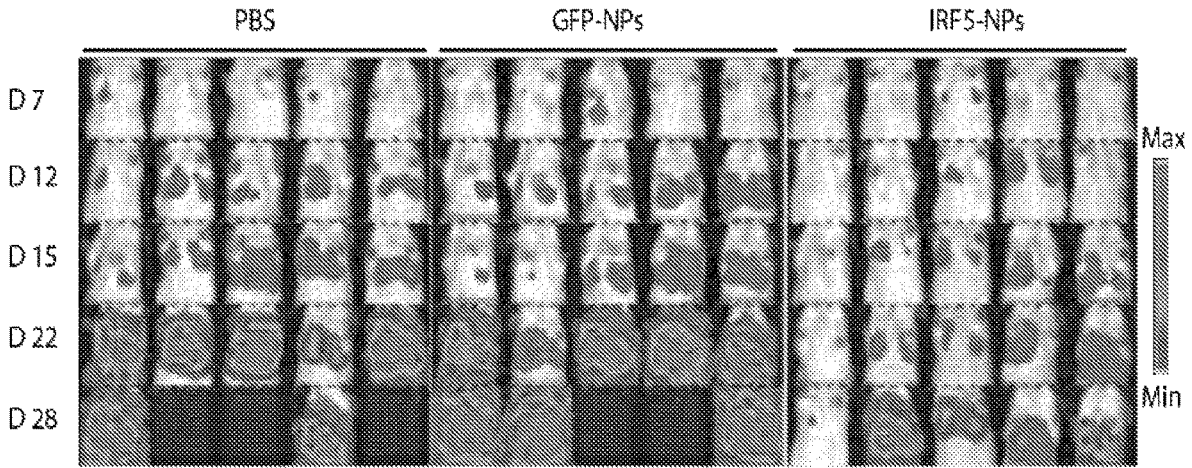
Figure 6E:
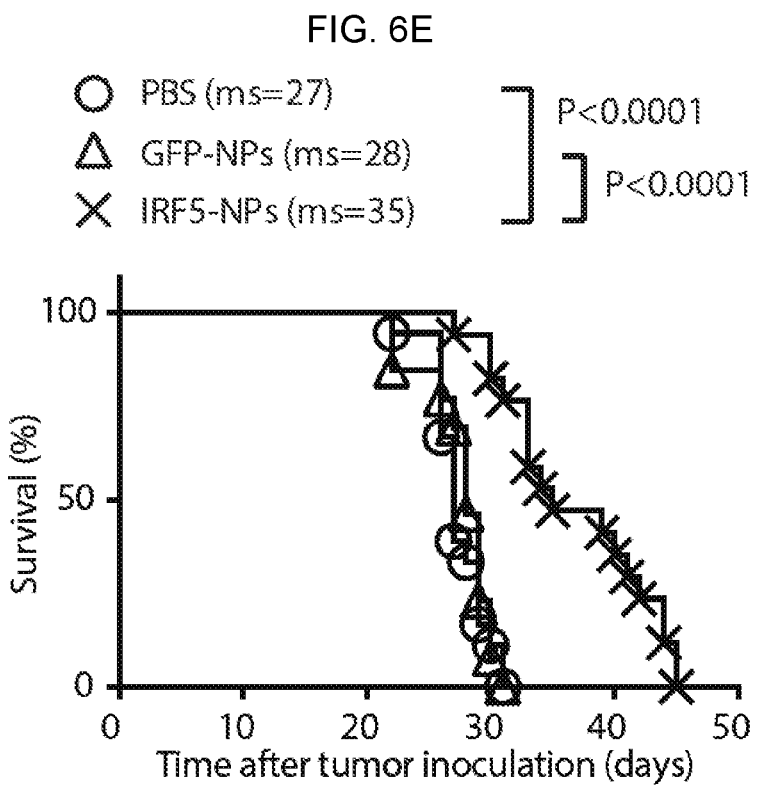
Figure 6F:
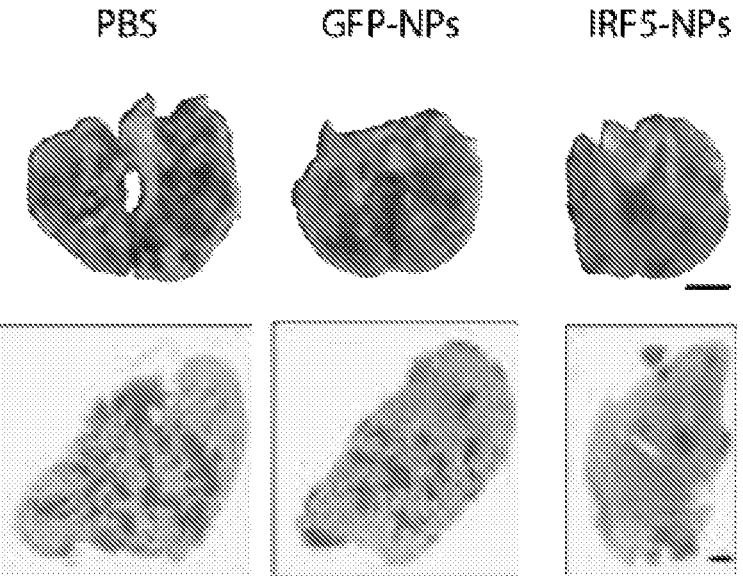
Figure 6G:
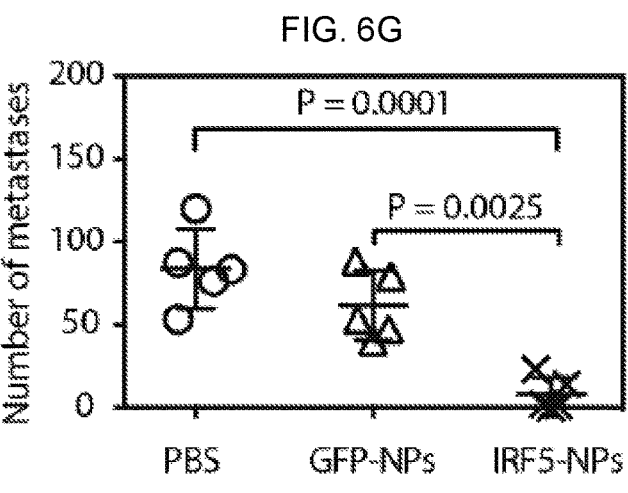
Figure 6H:
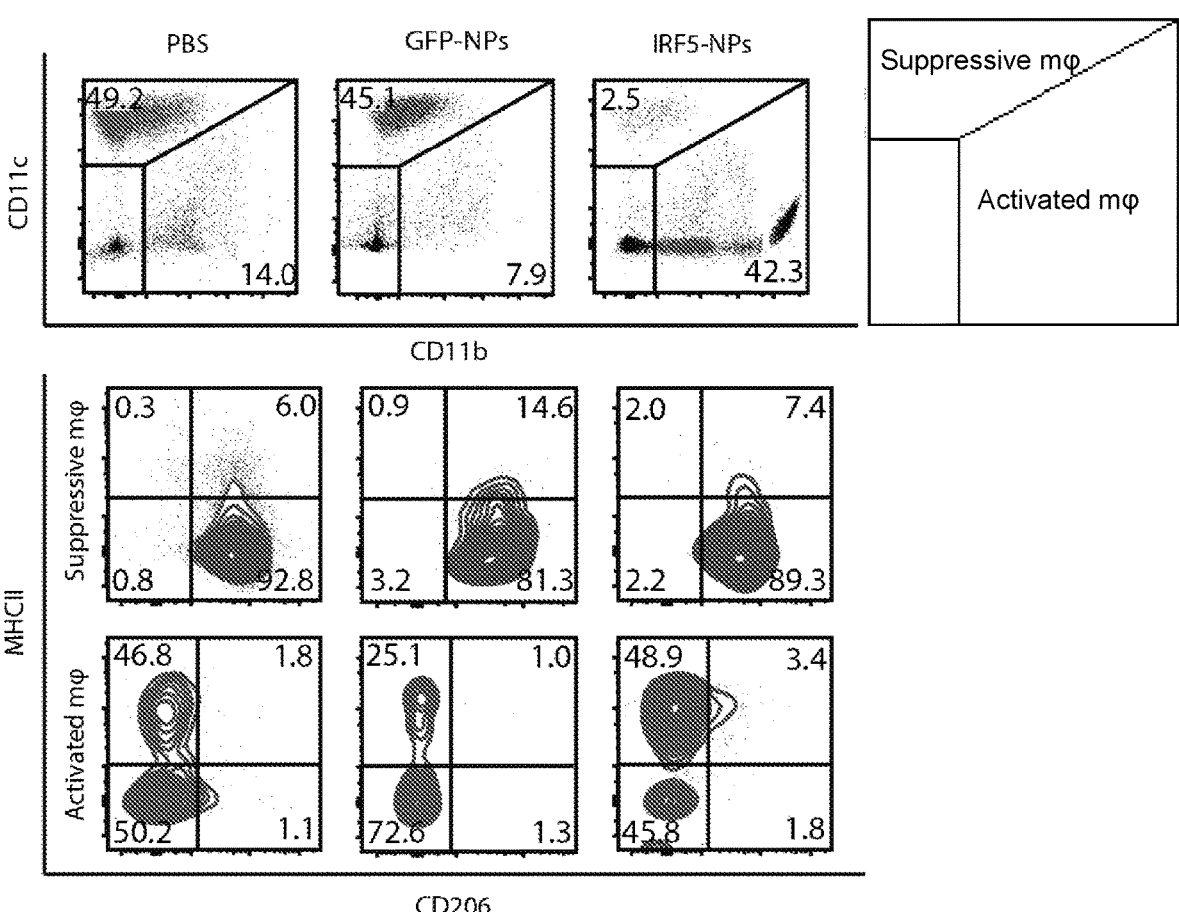
Figure 6I:
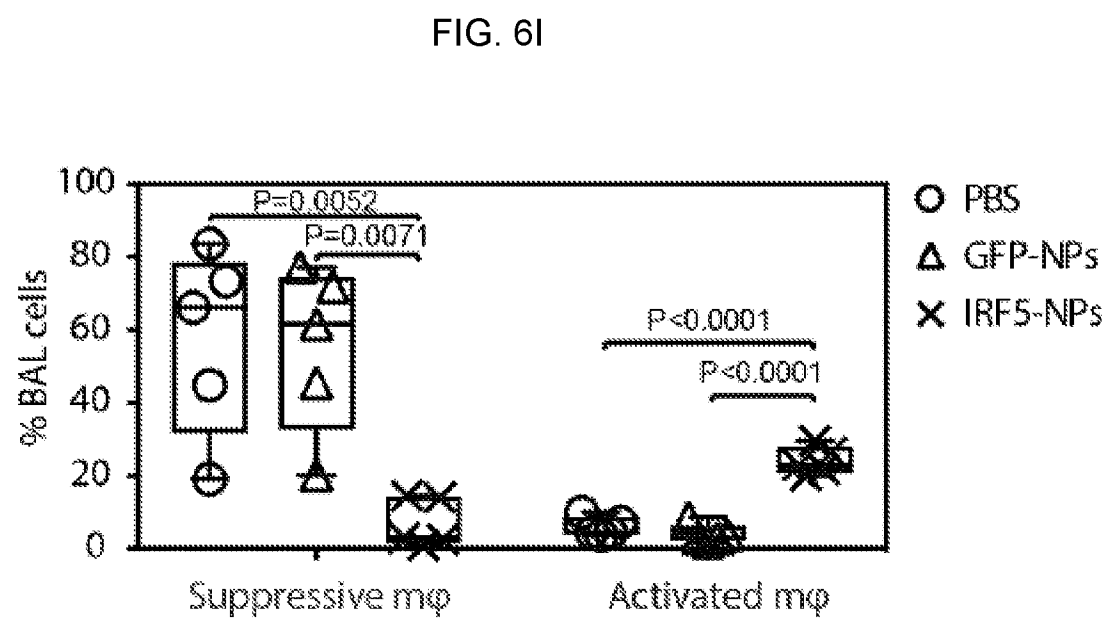

Controlling systemic tumor metastases with intravenous infusions of IRF5/IKKβ nanoparticles. Based on the therapeutic responses achieved with IRF5/IKKβ NPs administered directly into the peritoneal cavity to treat tumor lesions spread throughout the peritoneum, the next question asked was whether intravenously infused mRNA nanocarriers could program macrophages systemically to control disseminated disease. RT-qPCR biodistribution studies revealed that i.v.-infused nanocarriers preferentially deliver their mRNA cargo to organs with high levels of resident macrophages/phagocytes, mostly the spleen, liver, and lungs (FIG. 6A). To measure anti-tumor responses in a clinically relevant in vivo test system, particles containing IRF5/IKKβ mRNA were administered into mice with disseminated pulmonary melanoma metastases (FIG. 6B). Recent work describes the foundational role of monocytes and macrophages in establishing metastases caused by this disease (Butler K L et al. (2017) Sci Rep 7: 45593; Nielsen S R et al. (2017) Mediators Inflamm 2017: 9624760), and it was confirmed by confocal microscopy that tumor engraftment was coordinate with phagocyte accumulation in the lungs (FIG. 6C). Tumor burdens were determined by bioluminescent imaging, and mice with detectable cancers were sorted into groups that had matching levels. Groups were then randomly assigned to treatment conditions, receiving no therapy (PBS), or intravenous injections of GFP- or IRF5/IKKβ-encapsulating nanoparticles. Only IRF/IKKβ nanoparticle therapy substantially reduced tumor burdens in the lungs; in fact, they improved overall survival by a mean 1.3-fold (FIG. 6D-6E). In parallel experiments, mice were sacrificed 22 days after tumor inoculation to validate bioluminescence tumor signals with counts of pulmonary metastases and to assess macrophage polarization by flow cytometry. The total number of metastases in the lungs of IRF5/IKK NP-treated animals was 8.7-fold reduced (average 40±16 metastases) compared to PBS controls (average 419±139 metastases; FIG. 6F-6G). Flow cytometry of bronchoalveolar lavage fluid cells revealed a strong shift from immune-suppressive (CD206+, MHCII–, CD11c+, CD11blow) macrophages toward activated (CD206–, MHCII+, CD11c–, CD11b+) phagocytes (FIG. 6H-6I).

Figures 7A, 7B:
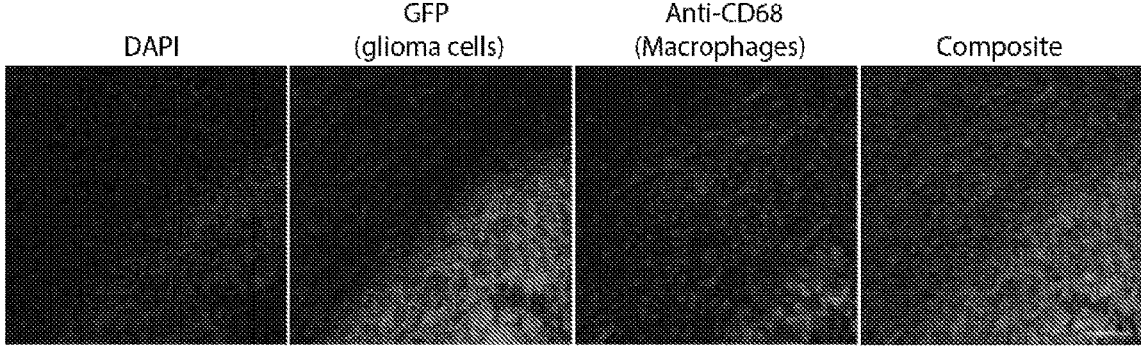
FIGS. 7A-7F. Macrophage reprogramming improves the outcome of radiotherapy in glioma.
Figure 7C:
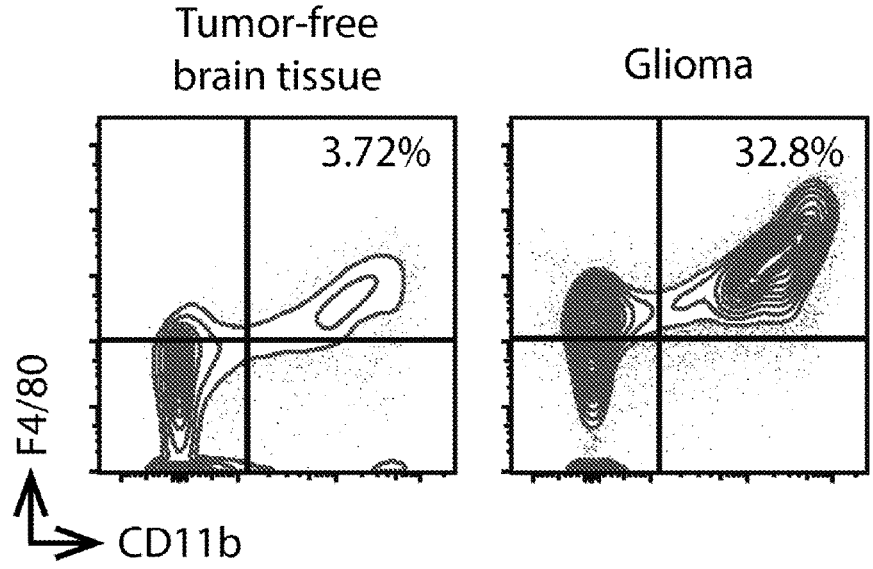
Figure 7D:
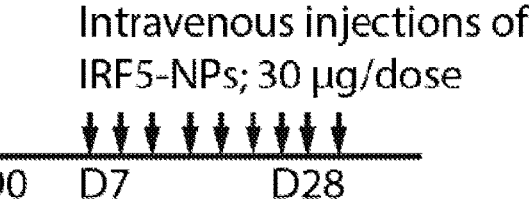
Figure 7D:
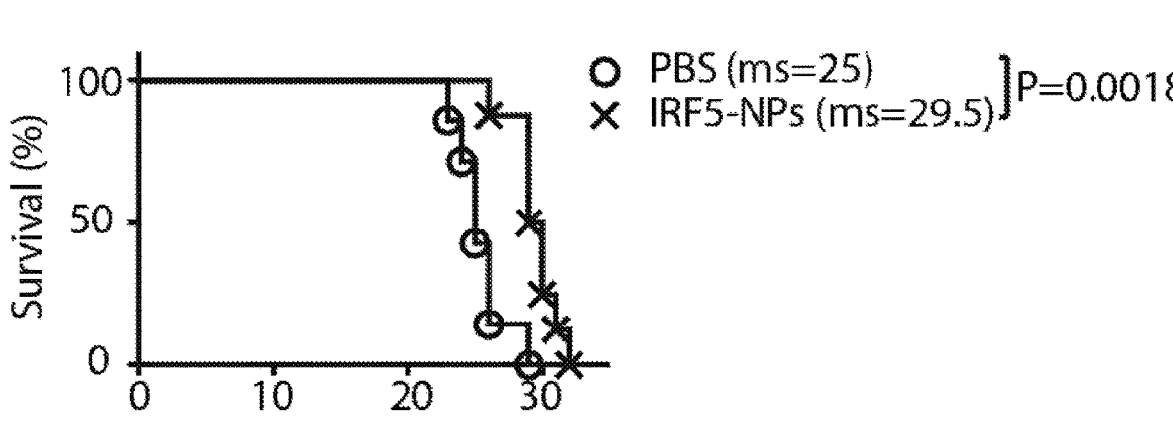
Figure 7E:
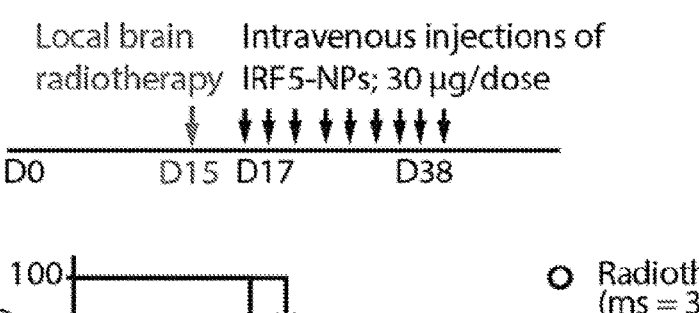
Figure 7E:
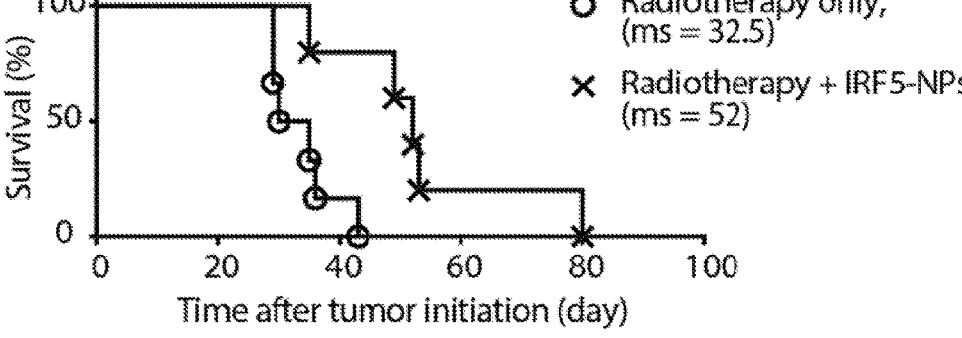
Figure 7F:
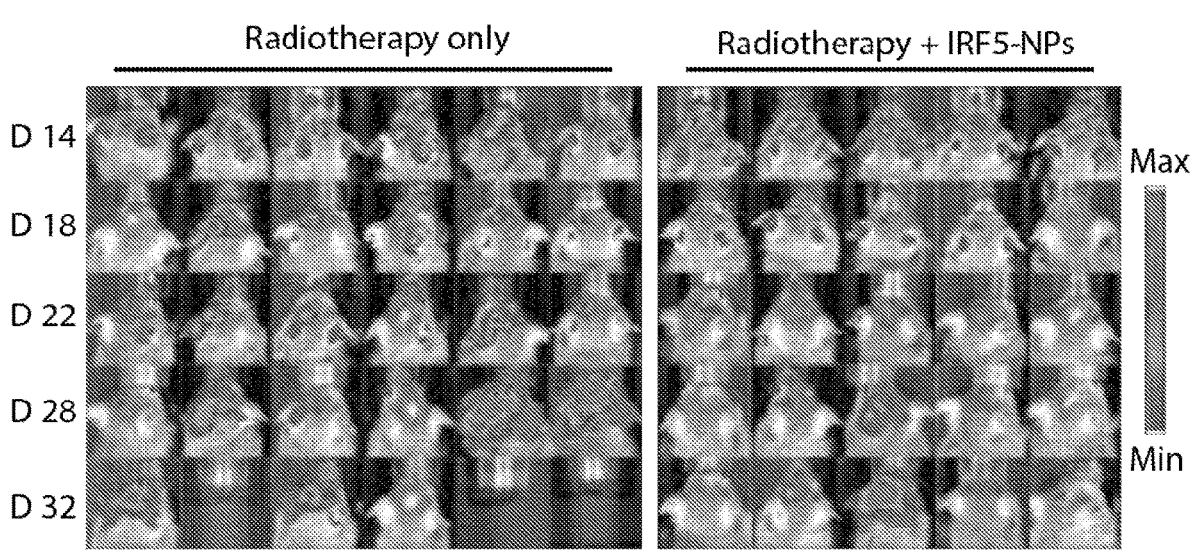

Programming tumor-suppressing phagocytes to treat glioma. For a third in vivo test system glioma was examined, which is a difficult to manage cancer type where M2-like macrophages represent the majority of non-neoplastic cells and promote tumor growth and invasion (Hambardzumyan D et al. (2016) Nat Neurosci 19: 20-27). Currently, the standard of care for this disease is radiotherapy, which unfortunately offers only a temporary stabilization or reduction of symptoms and extends median survival by 3 months (Mann J et al. (2017) Front Neurol 8: 748). To recapitulate the genetic events and subsequent molecular evolution of the disease, the RCAS-PDGF-B/Nestin-Tv-a; Ink4a/Arf–/–; Pten–/– transgenic mouse model of PDGFβ-driven glioma (PDG mice (Hambardzumyan D et al. (2009) Transl Oncol 2: 89-95; Quail D F et al. (2016) Science 352: aad3018)) was used. Brain tissue was stereotactically injected with a mixture of DF-1 cells transfected with either RCAS-PDGFβ or RCAS-cre retrovirus (1:1 mixture, 2 μL). Overexpression of the PDGFβ oncogene and the absence of the tumor suppressor genes Ink4a-arf and Pten in glioma progenitors led to the formation of 4-5 mm diameter tumors (FIG. 7A) with a nearly complete penetrance within 21 days (as established previously (Hambardzumyan D et al. (2009) Transl Oncol 2: 89-95)). Using immunofluorescence, the presence of tumor-infiltrating (CD68+) macrophages (FIG. 7B, indicated in third panel from the left) were confirmed in established gliomas (shown in second panel from the left). Flow cytometry revealed that the F4/80+, CD11b+ macrophage population accounted for 32.8% of total cells in the tumor, which is 9-fold higher than seen in age-matched healthy control mice (3.7%) (FIG. 7C). The PDG mice in the experiments express the firefly luciferase gene linked to a key cancer gene promoter. Bioluminescence from this reporter has been demonstrated to be positively correlated with tumor grade (Uhrbom L et al. (2004) Nat Med 10: 1257-1260), so it was used to monitor tumor development every four days after the onset of treatment. IRF/IKKβ NPs as a monotherapy was first tested: PDG mice received intravenous infusions of 9 doses of NPs loaded with IRF5/IKKβ mRNA, or PBS in the control group (3 doses/week for 3 weeks). IRF/IKKβ NP treatments only modestly suppressed tumor progression (producing on average only a 5-day survival advantage compared to untreated controls; FIG. 7D). However, combining radiotherapy as the standard-of-care with IRF5/IKKβ NP injections substantially reduced tumor growth and more than doubled the survival of treated mice compared to the PBS control group (52 d versus 25 days, respectively; FIG. 7E-7F).

In conclusion, in vivo results from three preclinical solid tumor models demonstrate that nanoparticles, administered either locally or systemically, can deliver genes encoding master regulators of macrophage polarization to re-program immunosuppressive macrophages into tumor-clearing phenotypes.

Figure 8A:
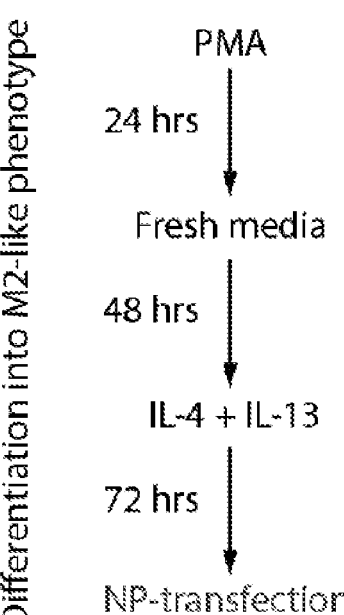
FIGS. 8A-8E. IVT mRNA-carrying nanoparticles encoding human IRF5/IKKβ efficiently reprogram human macrophages.
Figure 8B:
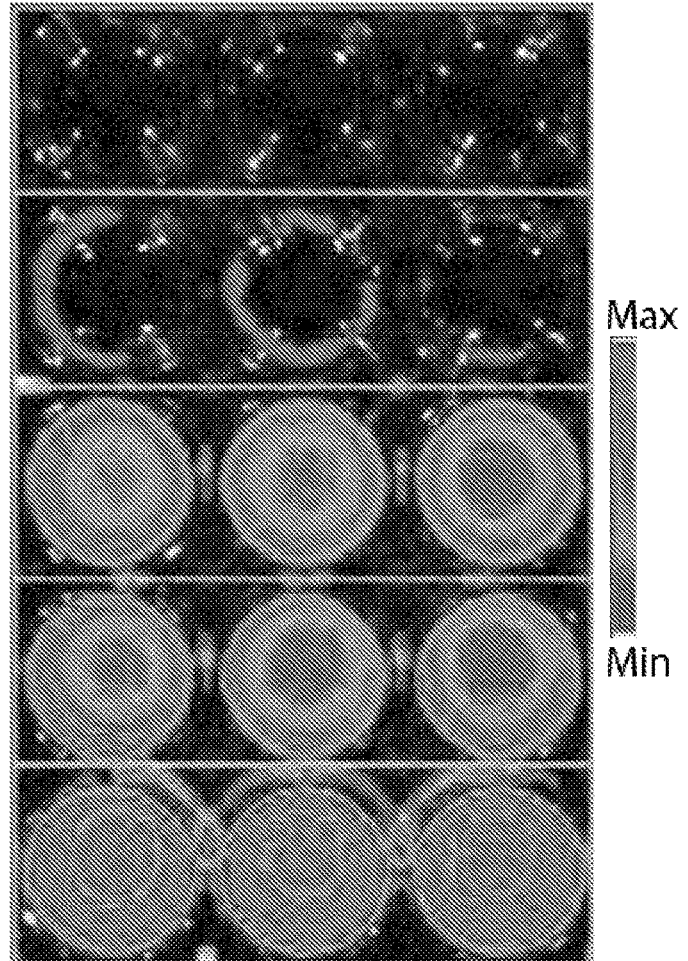
Figure 8C:
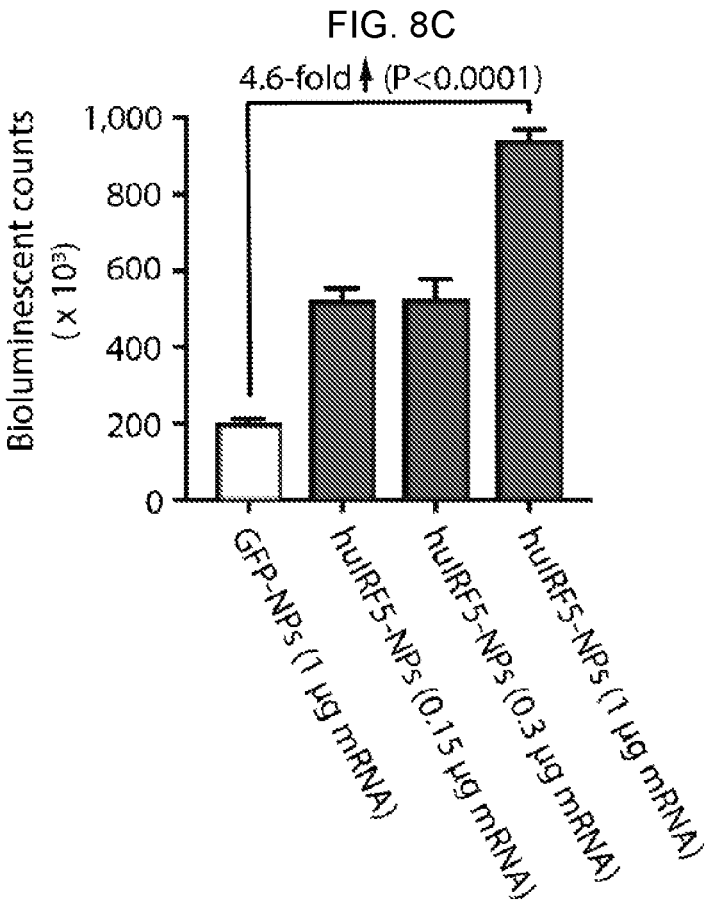
Figure 8D:
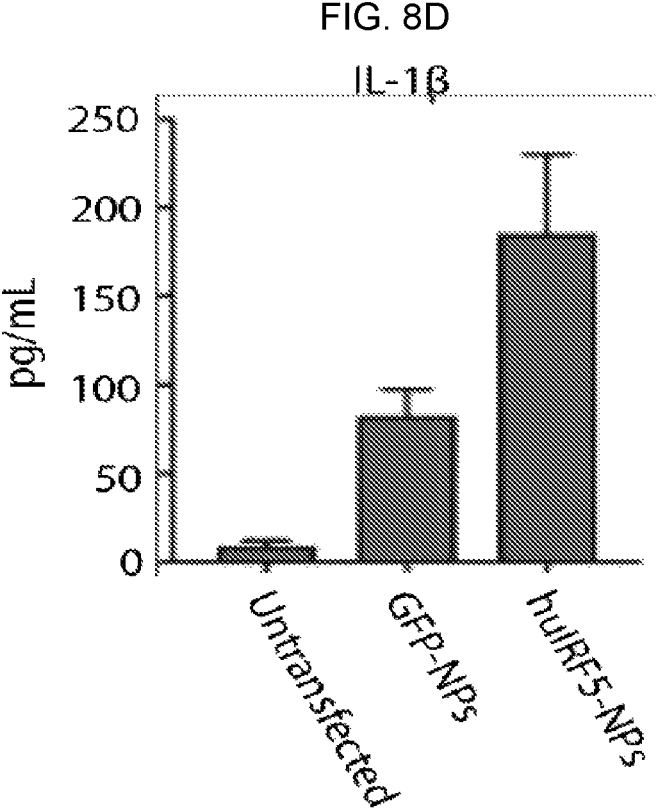
Figure 8E:
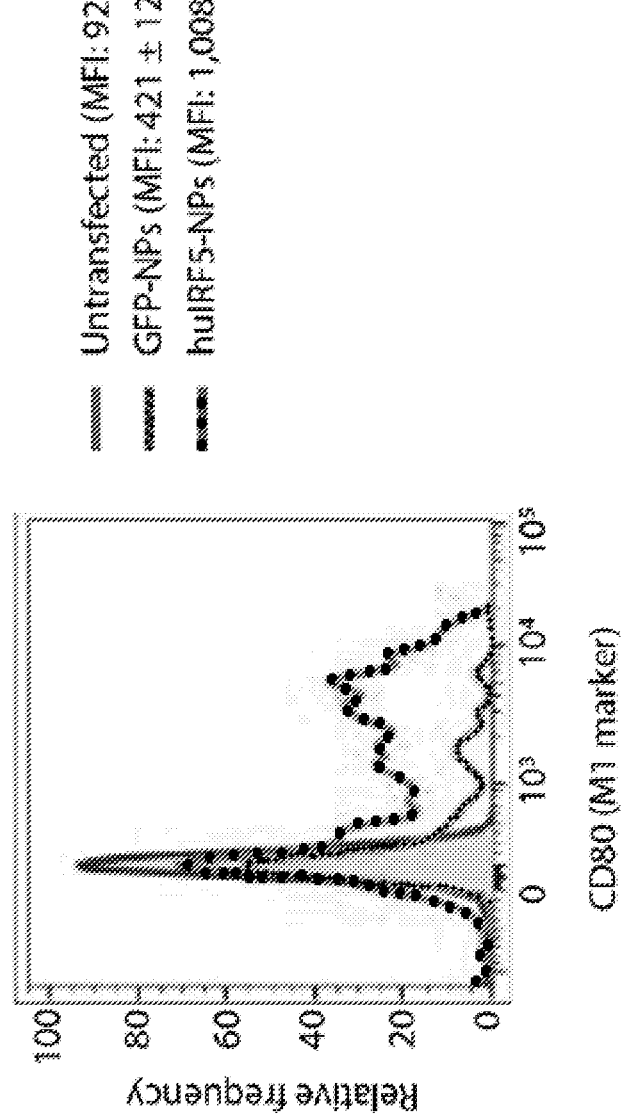

Translation from murine to human macrophages. To confirm that the data acquired in mice has relevance to treat human disease, NPs delivering IVT mRNA encoding human IRF5 and IKKβ (huIRF5 NPs) were fabricated. The human monocytic cell line THP-1 was used as a well-established M1 and M2 macrophage polarization model to test these nanocarriers (Li C et al. (2016) Sci Rep 6: 21044; Surdziel E et al. (2017) Plos One 12: e0183679). M2-type macrophages were generated by treating THP-1 cells with PMA and polarizing them with IL-4 and IL-13 (FIG. 8A). To confirm that huIRF5 NPs are functional and activate the IRF pathway, THP1-Lucia™ ISG cells were transfected with nanoparticles loaded with huIRF5/IKKβ or GFP control mRNAs. THP1-Lucia™ ISG cells secrete the fluorescent Lucia reporter under the control of an IRF-inducible promoter. This composite promoter is includes five IFN-stimulated response elements (ISRE) fused to an ISG54 minimal promoter, which is unresponsive to activators of the NF-κB or AP-1 pathways. As a result, THP1-Lucia™ ISG cells allow the monitoring of the IRF pathway by determining the activity of the Lucia luciferase. It was found that huIRF5 NPs strongly upregulated luciferase expression in M2-polarized THP-1 cells, indicating that the mRNA constructs are functional in human cells (FIG. 8B-8C). To determine whether IRF5 pathway activation can reprogram M2-polarized THP-1 cells toward an M1-like phenotype, secretion of the pro-inflammatory cytokine IL-1β following NP transfection was measured. Production of IL-1β was significantly increased in THP-1 cells transfected with huIRF5 NPs versus untransfected controls (mean 21-fold; P<0.0001, FIG. 8D), which correlated with a robust upregulation (10.9-fold increased MFI, P<0.0001) of the M1 macrophage cell surface marker CD80 (FIG. 8E).

SEQ ID NO: Key

The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate. SEQ ID NOs: 55, 58, 61, 64, 71, 73 and 79 are not used in this sequence listing. The accompanying Sequence Listing shows the following sequences:

| SEQ ID NO: | Description |
|---|---|
| SEQ ID NO: 1 | Human IRF5 Isoform 1 (UniProt Accession Q13568-1) |
| SEQ ID NO: 2 | Human IRF5 Isoform 2 (UniProt Accession Q13568-2) |
| SEQ ID NO: 3 | Human IRF5 Isoform 3 (UniProt Accession Q13568-3) |
| SEQ ID NO: 4 | Human IRF5 Isoform 4 (UniProt Accession Q13568-4) |
| SEQ ID NO: 5 | Human IRF5 Isoform 5 (UniProt Accession Q13568-5) |

-continued

| SEQ ID NO: | Description |
|---|---|
| SEQ ID NO: 6 | Human IRF5 Isoform 6 (UniProt Accession Q13568-6) |
| SEQ ID NO: 7 | Murine IRF5 protein (UniProt Accession P56477) |
| SEQ ID NO: 8 | Human IRF1 (UniProt Accession P10914) |
| SEQ ID NO: 9 | Human IRF3 isoform 1 (UniProt Accession Q14653-1) |
| SEQ ID NO: 10 | Human IRF7 isoform A (UniProt Accession Q92985-1) |
| SEQ ID NO: 11 | Human IRF8 (UniProt Accession Q02556) |
| SEQ ID NO: 12 | Murine IRF1 (UniProt Accession P15314) |
| SEQ ID NO: 13 | Murine IRF3 (UniProt Accession P70671) |
| SEQ ID NO: 14 | Murine IRF7 (UniProt Accession P70434) |
| SEQ ID NO: 15 | Murine IRF7/IRF3 5(D) protein |
| SEQ ID NO: 16 | Murine IRF8 (UniProt Accession P23611) |
| SEQ ID NO: 17 | Murine IRF8 (K310R) protein |
| SEQ ID NO: 18 | Human IKKβ isoform 1 (UniProt Accession O14920-1) |
| SEQ ID NO: 19 | Human IKKβ isoform 2 (UniProt Accession O14920-2) |
| SEQ ID NO: 20 | Human IKKβ isoform 3 (UniProt Accession O14920-3) |
| SEQ ID NO: 21 | Human IKKβ isoform 4 (UniProt Accession O14920-4) |
| SEQ ID NO: 22 | Murine IKK β protein (GenBank Accession no. NP_034676.1) |
| SEQ ID NO: 23 | Human IRF5 isoform 1 cds |
| SEQ ID NO: 24 | Human IRF5 isoform 2 cds |
| SEQ ID NO: 25 | Human IRF5 isoform 3 cds (GenBank Accession U51127) |
| SEQ ID NO: 26 | Human IRF5 isoform 4 cds (GenBank Accession nos. AY504946 or AY504947) |
| SEQ ID NO: 27 | Human IRF5 isoform 5 cds |
| SEQ ID NO: 28 | Human IRF5 isoform 6 cds |
| SEQ ID NO: 29 | Murine IRF5 cds |
| SEQ ID NO: 30 | Human IRF1 cds |
| SEQ ID NO: 31 | Human IRF3 isoform 1 cds (NM_001571.5) |
| SEQ ID NO: 32 | Human IRF7 isoform A cds (NM_001572.3) |
| SEQ ID NO: 33 | Human IRF8 cds |
| SEQ ID NO: 34 | Murine IRF1 cds (NM_001159396.1) |
| SEQ ID NO: 35 | Murine IRF3 cds (NM_016849.4) |
| SEQ ID NO: 36 | Murine IRF7 cds (NM_016850.3) |
| SEQ ID NO: 37 | Murine IRF-7/IRF-3 5(D) cds |
| SEQ ID NO: 38 | Murine IRF8 cds |
| SEQ ID NO: 39 | Murine IRF8 K310R cds |
| SEQ ID NO: 40 | Human IKKβ isoform 1 cds |
| SEQ ID NO: 41 | Human IKKβ isoform 2 cds |
| SEQ ID NO: 42 | Human IKKβ isoform cds |
| SEQ ID NO: 43 | Human IKKβ isoform 4 cds |
| SEQ ID NO: 44 | Murine IKKβ cds |
| SEQ ID NO: 45 | CDRH1 that binds CD206 |
| SEQ ID NO: 46 | CDRH2 that binds CD206 |
| SEQ ID NO: 47 | CDRH3 that binds CD206 |
| SEQ ID NO: 48 | CDRH1 that binds CD206 |
| SEQ ID NO: 49 | CDRH2 that binds CD206 |
| SEQ ID NO: 50 | CDRH3 that binds CD206 |
| SEQ ID NO: 51 | CDRH1 that binds CD206 |
| SEQ ID NO: 52 | CDRH2 that binds CD206 |
| SEQ ID NO: 53 | CDRH3 that binds CD206 |
| SEQ ID NO: 54 | CDRL1 that binds CD163 |
| SEQ ID NO: 56 | CDRL3 that binds CD163 |
| SEQ ID NO: 57 | CDRH1 that binds CD163 |
| SEQ ID NO: 59 | CDRH3 that binds CD163 |
| SEQ ID NO: 60 | CDRL1 that binds CD163 |
| SEQ ID NO: 62 | CDRL3 that binds CD163 |
| SEQ ID NO: 63 | CDRH1 that binds CD163 |
| SEQ ID NO: 65 | CDRH3 that binds CD163 |
| SEQ ID NO: 66 | CDRL1 that bind CD23 |
| SEQ ID NO: 67 | CDRL2 that bind CD23 |
| SEQ ID NO: 68 | CDRL3 that bind CD23 |
| SEQ ID NO: 69 | CDRH1 that bind CD23 |
| SEQ ID NO: 70 | CDRH2 that bind CD23 |
| SEQ ID NO: 72 | CDRL1 that bind CD38 |
| SEQ ID NO: 74 | CDRL3 that bind CD38 |
| SEQ ID NO: 75 | CDRH1 that bind CD38 |
| SEQ ID NO: 76 | CDRH2 that binds CD38 |
| SEQ ID NO: 77 | CDRH3 that binds CD38 |

-continued

| SEQ ID NO: | Description |
|---|---|
| SEQ ID NO: 78 | CDRL1 that binds CD38 |
| SEQ ID NO: 80 | CDRL3 that binds CD38 |
| SEQ ID NO: 81 | CDRH1 that binds CD38 |
| SEQ ID NO: 82 | CDRH2 that binds CD38 |
| SEQ ID NO: 83 | CDRH3 that binds CD38 |
| SEQ ID NO: 84 | CDRL1 that binds CD38 |
| SEQ ID NO: 85 | CDRL2 that binds CD38 |
| SEQ ID NO: 86 | CDRL3 that binds CD38 |
| SEQ ID NO: 87 | CDRH1 that binds CD38 |
| SEQ ID NO: 88 | CDRH2 that binds CD38 |
| SEQ ID NO: 89 | CDRH3 that binds CD38 |
| SEQ ID NO: 90 | CDRL1 that binds CD64 |
| SEQ ID NO: 91 | CDRL2 that binds CD64 |
| SEQ ID NO: 92 | CDRL3 that binds CD64 |
| SEQ ID NO: 93 | CDRH1 that binds CD64 |
| SEQ ID NO: 94 | CDRH2 that binds CD64 |
| SEQ ID NO: 95 | CDRH3 that binds CD64 |
| SEQ ID NO: 96 | Forward primer SerpinB2 |
| SEQ ID NO: 97 | Reverse primer SerpinB2 |
| SEQ ID NO: 98 | Forward primer Retnla |
| SEQ ID NO: 99 | Reverse primer Retnla |
| SEQ ID NO: 100 | Forward primer Ccl5 |
| SEQ ID NO: 101 | Reverse primer Ccl5 |
| SEQ ID NO: 102 | Forward primer Ccl11 |
| SEQ ID NO: 103 | Reverse primer Cdl11 |
| SEQ ID NO: 104 | Forward primer codon optimized IRF5 |
| SEQ ID NO: 105 | Reverse primer codon optimized IRF5 |
| SEQ ID NO: 106 | Forward primer endogenous IRF5 |
| SEQ ID NO: 107 | Reverse primer endogenous IRF5 |
| SEQ ID NO: 108 | Forward primer GAPD |
| SEQ ID NO: 109 | Reverse primer GAPD |
| SEQ ID NO: 110 | Human glucocorticoid-induced leuzine zipper (GILZ) isoform 1 (UniProt Accession Q99576-1) |
| SEQ ID NO: 111 | Human glucocorticoid-induced leuzine zipper (GILZ) cds (GenBank Accession no. NM_004089.3 |

As will be understood by one of ordinary skill in the art, each embodiment disclosed herein can comprise, consist essentially of or consist of its particular stated element, step, ingredient or component. Thus, "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the ability to treat the mouse model of ovarian cancer as described in Example 2.

Unless otherwise indicated, all numbers expressing quantities of ingredients, properties such as molecular weight, reaction conditions, and so forth used in the specification and claims are to be understood as being modified in all instances by "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"A", "an", "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to Pat., printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A therapeutic composition comprising nanoparticles comprising mRNA encoding interferon regulatory factor 5 (IRF5) and mRNA encoding IKKβ.

2. The therapeutic composition of claim 1, further comprising a pharmaceutically acceptable carrier.

3. The therapeutic composition of claim 1, wherein the nanoparticles further comprise mRNA encoding an anticancer gene comprising p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, TNFα, HSV-tk, or a combination thereof.

4. The therapeutic composition of claim 1, wherein the nanoparticles further comprise mRNA encoding glucocorticoid-induced leucine zipper (GILZ).

5. The therapeutic composition of claim 1, wherein the nanoparticles further comprise a targeting ligand linked to a surface of the nanoparticles.

6. The therapeutic composition of claim 5, wherein the targeting ligand binds CD206, CD163, CD23, CD38, G-protein coupled receptor 18 (Gpr18), formyl peptide receptor 2 (Fpr2), CD64, or CD68.

7. The therapeutic composition of claim 5, wherein the targeting ligand comprises di-mannose.

8. The therapeutic composition of claim 1, wherein the nanoparticles comprise a positively-charged poly(β)-amino ester core, a star-shaped polymer, a polyglutamic acid coating, a hyaluronic acid coating, a liposome, or a combination thereof.

9. The therapeutic composition of claim 1, wherein the nanoparticles comprise a mean diameter of <130 nm.

10. The therapeutic composition of claim 1, wherein the nanoparticles comprise a ratio of the mRNA encoding IRF5 to the mRNA encoding Iκκβ of 0.5:1, 1:1, 2:1, 3:1, 4:1, or 5:1.

11. The therapeutic composition of claim 1, wherein the nanoparticles comprise a ratio of the mRNA encoding IRF5 to the mRNA encoding Iκκβ of 3:1.

12. The therapeutic composition of claim 5, wherein the targeting ligand binds selectively to an immune cell.

13. The therapeutic composition of claim 12, wherein the immune cell is a tumor-associated macrophage.

14. The therapeutic composition of claim 5, wherein the targeting ligand is an antibody or an antigen-binding fragment thereof.

* * * * *

SEQUENCE LISTING

```
<160> NUMBER OF SEQ ID NOS: 111

<210> SEQ ID NO 1
<211> LENGTH: 498
<212> TYPE: PRT
<213> ORGANISM: Homo sapiens

<400> SEQUENCE: 1

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
```

-continued

```
              20                25                30
Leu Gln Trp Val Asn Gly Glu Lys Lys Leu Phe Cys Ile Pro Trp Arg
         35                40                45
His Ala Thr Arg His Gly Pro Ser Gln Asp Gly Asp Asn Thr Ile Phe
      50                55                60
Lys Ala Trp Ala Lys Glu Thr Gly Lys Tyr Thr Glu Gly Val Asp Glu
65                70                75                80
Ala Asp Pro Ala Lys Trp Lys Ala Asn Leu Arg Cys Ala Leu Asn Lys
              85                90                95
Ser Arg Asp Phe Arg Leu Ile Tyr Asp Gly Pro Arg Asp Met Pro Pro
             100               105               110
Gln Pro Tyr Lys Ile Tyr Glu Val Cys Ser Asn Gly Pro Ala Pro Thr
             115               120               125
Asp Ser Gln Pro Pro Glu Asp Tyr Ser Phe Gly Ala Gly Glu Glu Glu
         130               135               140
Glu Glu Glu Glu Glu Leu Gln Arg Met Leu Pro Ser Leu Ser Leu Thr
145               150               155               160
Glu Asp Val Lys Trp Pro Pro Thr Leu Gln Pro Pro Thr Leu Arg Pro
             165               170               175
Pro Thr Leu Gln Pro Pro Thr Leu Gln Pro Pro Val Val Leu Gly Pro
             180               185               190
Pro Ala Pro Asp Pro Ser Pro Leu Ala Pro Pro Pro Gly Asn Pro Ala
             195               200               205
Gly Phe Arg Glu Leu Leu Ser Glu Val Leu Glu Pro Gly Pro Leu Pro
         210               215               220
Ala Ser Leu Pro Pro Ala Gly Glu Gln Leu Leu Pro Asp Leu Leu Ile
225               230               235               240
Ser Pro His Met Leu Pro Leu Thr Asp Leu Glu Ile Lys Phe Gln Tyr
             245               250               255
Arg Gly Arg Pro Pro Arg Ala Leu Thr Ile Ser Asn Pro His Gly Cys
             260               265               270
Arg Leu Phe Tyr Ser Gln Leu Glu Ala Thr Gln Glu Gln Val Glu Leu
         275               280               285
Phe Gly Pro Ile Ser Leu Glu Gln Val Arg Phe Pro Ser Pro Glu Asp
         290               295               300
Ile Pro Ser Asp Lys Gln Arg Phe Tyr Thr Asn Gln Leu Leu Asp Val
305               310               315               320
Leu Asp Arg Gly Leu Ile Leu Gln Leu Gln Gly Gln Asp Leu Tyr Ala
             325               330               335
Ile Arg Leu Cys Gln Cys Lys Val Phe Trp Ser Gly Pro Cys Ala Ser
             340               345               350
Ala His Asp Ser Cys Pro Asn Pro Ile Gln Arg Glu Val Lys Thr Lys
             355               360               365
Leu Phe Ser Leu Glu His Phe Leu Asn Glu Leu Ile Leu Phe Gln Lys
         370               375               380
Gly Gln Thr Asn Thr Pro Pro Phe Glu Ile Phe Phe Cys Phe Gly
385               390               395               400
Glu Glu Trp Pro Asp Arg Lys Pro Arg Glu Lys Lys Leu Ile Thr Val
             405               410               415
Gln Val Val Pro Val Ala Ala Arg Leu Leu Leu Glu Met Phe Ser Gly
             420               425               430
Glu Leu Ser Trp Ser Ala Asp Ser Ile Arg Leu Gln Ile Ser Asn Pro
         435               440               445
```

-continued

```
Asp Leu Lys Asp Arg Met Val Glu Gln Phe Lys Glu Leu His His Ile
    450             455             460

Trp Gln Ser Gln Gln Arg Leu Gln Pro Val Ala Gln Ala Pro Pro Gly
465             470             475             480

Ala Gly Leu Gly Val Gly Gln Gly Pro Trp Pro Met His Pro Ala Gly
            485             490             495

Met Gln

<210> SEQ ID NO 2
<211> LENGTH: 514
<212> TYPE: PRT
<213> ORGANISM: Homo sapiens

<400> SEQUENCE: 2

Met Asn Gln Ser Ile Pro Val Ala Pro Thr Pro Pro Arg Arg Val Arg
1               5               10              15

Leu Lys Pro Trp Leu Val Ala Gln Val Asn Ser Cys Gln Tyr Pro Gly
            20              25              30

Leu Gln Trp Val Asn Gly Glu Lys Lys Leu Phe Cys Ile Pro Trp Arg
        35              40              45

His Ala Thr Arg His Gly Pro Ser Gln Asp Gly Asp Asn Thr Ile Phe
    50              55              60

Lys Ala Trp Ala Lys Glu Thr Gly Lys Tyr Thr Glu Gly Val Asp Glu
65              70              75              80

Ala Asp Pro Ala Lys Trp Lys Ala Asn Leu Arg Cys Ala Leu Asn Lys
            85              90              95

Ser Arg Asp Phe Arg Leu Ile Tyr Asp Gly Pro Arg Asp Met Pro Pro
            100             105             110

Gln Pro Tyr Lys Ile Tyr Glu Val Cys Ser Asn Gly Pro Ala Pro Thr
        115             120             125

Asp Ser Gln Pro Pro Glu Asp Tyr Ser Phe Gly Ala Gly Glu Glu Glu
    130             135             140

Glu Glu Glu Glu Glu Leu Gln Arg Met Leu Pro Ser Leu Ser Leu Thr
145             150             155             160

Asp Ala Val Gln Ser Gly Pro His Met Thr Pro Tyr Ser Leu Leu Lys
            165             170             175

Glu Asp Val Lys Trp Pro Pro Thr Leu Gln Pro Pro Thr Leu Arg Pro
            180             185             190

Pro Thr Leu Gln Pro Pro Thr Leu Gln Pro Pro Val Val Leu Gly Pro
        195             200             205

Pro Ala Pro Asp Pro Ser Pro Leu Ala Pro Pro Gly Asn Pro Ala
    210             215             220

Gly Phe Arg Glu Leu Leu Ser Glu Val Leu Glu Pro Gly Pro Leu Pro
225             230             235             240

Ala Ser Leu Pro Pro Ala Gly Glu Gln Leu Leu Pro Asp Leu Leu Ile
            245             250             255

Ser Pro His Met Leu Pro Leu Thr Asp Leu Glu Ile Lys Phe Gln Tyr
            260             265             270

Arg Gly Arg Pro Pro Arg Ala Leu Thr Ile Ser Asn Pro His Gly Cys
        275             280             285

Arg Leu Phe Tyr Ser Gln Leu Glu Ala Thr Gln Glu Gln Val Glu Leu
    290             295             300

Phe Gly Pro Ile Ser Leu Glu Gln Val Arg Phe Pro Ser Pro Glu Asp
305             310             315             320
```

```
Ile Pro Ser Asp Lys Gln Arg Phe Tyr Thr Asn Gln Leu Leu Asp Val
            325                 330                 335

Leu Asp Arg Gly Leu Ile Leu Gln Leu Gln Gly Gln Asp Leu Tyr Ala
            340                 345                 350

Ile Arg Leu Cys Gln Cys Lys Val Phe Trp Ser Gly Pro Cys Ala Ser
            355                 360                 365

Ala His Asp Ser Cys Pro Asn Pro Ile Gln Arg Glu Val Lys Thr Lys
            370                 375                 380

Leu Phe Ser Leu Glu His Phe Leu Asn Glu Leu Ile Leu Phe Gln Lys
385                 390                 395                 400

Gly Gln Thr Asn Thr Pro Pro Pro Phe Glu Ile Phe Phe Cys Phe Gly
            405                 410                 415

Glu Glu Trp Pro Asp Arg Lys Pro Arg Glu Lys Lys Leu Ile Thr Val
            420                 425                 430

Gln Val Val Pro Val Ala Ala Arg Leu Leu Leu Glu Met Phe Ser Gly
            435                 440                 445

Glu Leu Ser Trp Ser Ala Asp Ser Ile Arg Leu Gln Ile Ser Asn Pro
            450                 455                 460

Asp Leu Lys Asp Arg Met Val Glu Gln Phe Lys Glu Leu His His Ile
465                 470                 475                 480

Trp Gln Ser Gln Gln Arg Leu Gln Pro Val Ala Gln Ala Pro Pro Gly
            485                 490                 495

Ala Gly Leu Gly Val Gly Gln Gly Pro Trp Pro Met His Pro Ala Gly
            500                 505                 510

Met Gln

<210> SEQ ID NO 3
<211> LENGTH: 504
<212> TYPE: PRT
<213> ORGANISM: Homo sapiens

<400> SEQUENCE: 3

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Cys Ile Pro Trp Arg
            35                  40                  45

His Ala Thr Arg His Gly Pro Ser Gln Asp Gly Asp Asn Thr Ile Phe
            50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
            85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
            130                 135                 140

Glu Glu Glu Glu Glu Leu Gln Arg Met Leu Pro Ser Leu Ser Leu Thr
145                 150                 155                 160

Asp Ala Val Gln Ser Gly Pro His Met Thr Pro Tyr Ser Leu Leu Lys
            165                 170                 175
```

-continued

```
Glu Asp Val Lys Trp Pro Pro Thr Leu Gln Pro Pro Thr Leu Gln Pro
            180             185             190

Pro Val Val Leu Gly Pro Pro Ala Pro Asp Pro Ser Pro Leu Ala Pro
            195             200             205

Pro Pro Gly Asn Pro Ala Gly Phe Arg Glu Leu Leu Ser Glu Val Leu
    210             215             220

Glu Pro Gly Pro Leu Pro Ala Ser Leu Pro Pro Ala Gly Glu Gln Leu
225             230             235             240

Leu Pro Asp Leu Leu Ile Ser Pro His Met Leu Pro Leu Thr Asp Leu
            245             250             255

Glu Ile Lys Phe Gln Tyr Arg Gly Arg Pro Pro Arg Ala Leu Thr Ile
            260             265             270

Ser Asn Pro His Gly Cys Arg Leu Phe Tyr Ser Gln Leu Glu Ala Thr
            275             280             285

Gln Glu Gln Val Glu Leu Phe Gly Pro Ile Ser Leu Glu Gln Val Arg
    290             295             300

Phe Pro Ser Pro Glu Asp Ile Pro Ser Asp Lys Gln Arg Phe Tyr Thr
305             310             315             320

Asn Gln Leu Leu Asp Val Leu Asp Arg Gly Leu Ile Leu Gln Leu Gln
            325             330             335

Gly Gln Asp Leu Tyr Ala Ile Arg Leu Cys Gln Cys Lys Val Phe Trp
            340             345             350

Ser Gly Pro Cys Ala Ser Ala His Asp Ser Cys Pro Asn Pro Ile Gln
            355             360             365

Arg Glu Val Lys Thr Lys Leu Phe Ser Leu Glu His Phe Leu Asn Glu
    370             375             380

Leu Ile Leu Phe Gln Lys Gly Gln Thr Asn Thr Pro Pro Pro Phe Glu
385             390             395             400

Ile Phe Phe Cys Phe Gly Glu Glu Trp Pro Asp Arg Lys Pro Arg Glu
            405             410             415

Lys Lys Leu Ile Thr Val Gln Val Val Pro Val Ala Ala Arg Leu Leu
            420             425             430

Leu Glu Met Phe Ser Gly Glu Leu Ser Trp Ser Ala Asp Ser Ile Arg
            435             440             445

Leu Gln Ile Ser Asn Pro Asp Leu Lys Asp Arg Met Val Glu Gln Phe
    450             455             460

Lys Glu Leu His His Ile Trp Gln Ser Gln Gln Arg Leu Gln Pro Val
465             470             475             480

Ala Gln Ala Pro Pro Gly Ala Gly Leu Gly Val Gly Gln Gly Pro Trp
            485             490             495

Pro Met His Pro Ala Gly Met Gln
            500
```

```
<210> SEQ ID NO 4
<211> LENGTH: 488
<212> TYPE: PRT
<213> ORGANISM: Homo sapiens

<400> SEQUENCE: 4

Met Asn Gln Ser Ile Pro Val Ala Pro Thr Pro Pro Arg Arg Val Arg
1               5               10              15

Leu Lys Pro Trp Leu Val Ala Gln Val Asn Ser Cys Gln Tyr Pro Gly
            20              25              30

Leu Gln Trp Val Asn Gly Glu Lys Lys Leu Phe Cys Ile Pro Trp Arg
```

-continued

```
                35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
    130                 135                 140

Glu Glu Glu Glu Glu Leu Gln Arg Met Leu Pro Ser Leu Ser Leu Thr
145                 150                 155                 160

Glu Asp Val Lys Trp Pro Pro Thr Leu Gln Pro Pro Thr Leu Gln Pro
            165                 170                 175

Pro Val Val Leu Gly Pro Pro Ala Pro Asp Pro Ser Pro Leu Ala Pro
            180                 185                 190

Pro Pro Gly Asn Pro Ala Gly Phe Arg Glu Leu Leu Ser Glu Val Leu
            195                 200                 205

Glu Pro Gly Pro Leu Pro Ala Ser Leu Pro Pro Ala Gly Glu Gln Leu
    210                 215                 220

Leu Pro Asp Leu Leu Ile Ser Pro His Met Leu Pro Leu Thr Asp Leu
225                 230                 235                 240

Glu Ile Lys Phe Gln Tyr Arg Gly Arg Pro Pro Arg Ala Leu Thr Ile
            245                 250                 255

Ser Asn Pro His Gly Cys Arg Leu Phe Tyr Ser Gln Leu Glu Ala Thr
            260                 265                 270

Gln Glu Gln Val Glu Leu Phe Gly Pro Ile Ser Leu Glu Gln Val Arg
            275                 280                 285

Phe Pro Ser Pro Glu Asp Ile Pro Ser Asp Lys Gln Arg Phe Tyr Thr
    290                 295                 300

Asn Gln Leu Leu Asp Val Leu Asp Arg Gly Leu Ile Leu Gln Leu Gln
305                 310                 315                 320

Gly Gln Asp Leu Tyr Ala Ile Arg Leu Cys Gln Cys Lys Val Phe Trp
            325                 330                 335

Ser Gly Pro Cys Ala Ser Ala His Asp Ser Cys Pro Asn Pro Ile Gln
            340                 345                 350

Arg Glu Val Lys Thr Lys Leu Phe Ser Leu Glu His Phe Leu Asn Glu
            355                 360                 365

Leu Ile Leu Phe Gln Lys Gly Gln Thr Asn Thr Pro Pro Phe Glu
    370                 375                 380

Ile Phe Phe Cys Phe Gly Glu Glu Trp Pro Asp Arg Lys Pro Arg Glu
385                 390                 395                 400

Lys Lys Leu Ile Thr Val Gln Val Val Pro Val Ala Ala Arg Leu Leu
            405                 410                 415

Leu Glu Met Phe Ser Gly Glu Leu Ser Trp Ser Ala Asp Ser Ile Arg
            420                 425                 430

Leu Gln Ile Ser Asn Pro Asp Leu Lys Asp Arg Met Val Glu Gln Phe
            435                 440                 445

Lys Glu Leu His His Ile Trp Gln Ser Gln Gln Arg Leu Gln Pro Val
    450                 455                 460
```

```
Ala Gln Ala Pro Pro Gly Ala Gly Leu Gly Val Gly Gln Gly Pro Trp
465                 470                 475                 480

Pro Met His Pro Ala Gly Met Gln
                485

<210> SEQ ID NO 5
<211> LENGTH: 412
<212> TYPE: PRT
<213> ORGANISM: Homo sapiens

<400> SEQUENCE: 5

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Cys Ile Pro Trp Arg
        35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
                100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
            130                 135                 140

Glu Glu Glu Glu Glu Leu Gln Arg Met Leu Pro Ser Leu Ser Leu Thr
145                 150                 155                 160

Val Thr Asp Leu Glu Ile Lys Phe Gln Tyr Arg Gly Arg Pro Pro Arg
                165                 170                 175

Ala Leu Thr Ile Ser Asn Pro His Gly Cys Arg Leu Phe Tyr Ser Gln
                180                 185                 190

Leu Glu Ala Thr Gln Glu Gln Val Glu Leu Phe Gly Pro Ile Ser Leu
            195                 200                 205

Glu Gln Val Arg Phe Pro Ser Pro Glu Asp Ile Pro Ser Asp Lys Gln
            210                 215                 220

Arg Phe Tyr Thr Asn Gln Leu Leu Asp Val Leu Asp Arg Gly Leu Ile
225                 230                 235                 240

Leu Gln Leu Gln Gly Gln Asp Leu Tyr Ala Ile Arg Leu Cys Gln Cys
                245                 250                 255

Lys Val Phe Trp Ser Gly Pro Cys Ala Ser Ala His Asp Ser Cys Pro
                260                 265                 270

Asn Pro Ile Gln Arg Glu Val Lys Thr Lys Leu Phe Ser Leu Glu His
            275                 280                 285

Phe Leu Asn Glu Leu Ile Leu Phe Gln Lys Gly Gln Thr Asn Thr Pro
        290                 295                 300

Pro Pro Phe Glu Ile Phe Phe Cys Phe Gly Glu Glu Trp Pro Asp Arg
305                 310                 315                 320

Lys Pro Arg Glu Lys Lys Leu Ile Thr Val Gln Val Val Pro Val Ala
                325                 330                 335

Ala Arg Leu Leu Leu Glu Met Phe Ser Gly Glu Leu Ser Trp Ser Ala
```

-continued

```
                340             345             350

Asp Ser Ile Arg Leu Gln Ile Ser Asn Pro Asp Leu Lys Asp Arg Met
        355             360             365

Val Glu Gln Phe Lys Glu Leu His His Ile Trp Gln Ser Gln Gln Arg
    370             375             380

Leu Gln Pro Val Ala Gln Ala Pro Pro Gly Ala Gly Leu Gly Val Gly
385             390             395             400

Gln Gly Pro Trp Pro Met His Pro Ala Gly Met Gln
            405             410

<210> SEQ ID NO 6
<211> LENGTH: 147
<212> TYPE: PRT
<213> ORGANISM: Homo sapiens

<400> SEQUENCE: 6

Met Asn Gln Ser Ile Pro Val Ala Pro Thr Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Cys Ile Pro Trp Arg
        35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
            100                 105                 110

Gln Pro Tyr Lys Ile Tyr Glu Thr Pro Ser Pro Leu Arg Ile Thr Leu
        115                 120                 125

Leu Val Gln Glu Arg Arg Arg Lys Lys Arg Lys Ser Cys Arg Gly Cys
    130                 135                 140

Cys Gln Ala
145

<210> SEQ ID NO 7
<211> LENGTH: 497
<212> TYPE: PRT
<213> ORGANISM: Mus musculus

<400> SEQUENCE: 7

Met Asn His Ser Ala Pro Gly Ile Pro Pro Pro Pro Arg Arg Val Arg
1               5                   10                  15

Leu Lys Pro Trp Leu Val Ala Gln Val Asn Ser Cys Gln Tyr Pro Gly
            20                  25                  30

Leu Gln Trp Val Asn Gly Glu Lys Lys Leu Phe Tyr Ile Pro Trp Arg
        35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Gln Leu Phe Tyr Asp Gly Pro Arg Asp Met Pro Pro
```

-continued

```
                100                 105                 110

Gln Pro Tyr Lys Ile Tyr Glu Val Cys Ser Asn Gly Pro Ala Pro Thr
            115                 120                 125

Glu Ser Gln Pro Thr Asp Asp Tyr Val Leu Gly Glu Glu Glu Glu
            130                 135                 140

Glu Glu Glu Glu Leu Gln Arg Met Leu Pro Gly Leu Ser Ile Thr Glu
145                 150                 155                 160

Pro Ala Leu Pro Gly Pro Pro Asn Ala Pro Tyr Ser Leu Pro Lys Glu
                165                 170                 175

Asp Thr Lys Trp Pro Pro Ala Leu Gln Pro Pro Val Gly Leu Gly Pro
                180                 185                 190

Pro Val Pro Asp Pro Asn Leu Leu Ala Pro Pro Ser Gly Asn Pro Ala
                195                 200                 205

Gly Phe Arg Gln Leu Leu Pro Glu Val Leu Glu Pro Gly Pro Leu Ala
            210                 215                 220

Ser Ser Gln Pro Pro Thr Glu Pro Leu Leu Pro Asp Leu Leu Ile Ser
225                 230                 235                 240

Pro His Met Leu Pro Leu Thr Asp Leu Glu Ile Lys Phe Gln Tyr Arg
                245                 250                 255

Gly Arg Ala Pro Arg Thr Leu Thr Ile Ser Asn Pro Gln Gly Cys Arg
                260                 265                 270

Leu Phe Tyr Ser Gln Leu Glu Ala Thr Gln Glu Gln Val Glu Leu Phe
            275                 280                 285

Gly Pro Val Thr Leu Glu Gln Val Arg Phe Pro Ser Pro Glu Asp Ile
            290                 295                 300

Pro Ser Asp Lys Gln Arg Phe Tyr Thr Asn Gln Leu Leu Asp Val Leu
305                 310                 315                 320

Asp Arg Gly Leu Ile Leu Gln Leu Gln Gly Gln Asp Leu Tyr Ala Ile
                325                 330                 335

Arg Leu Cys Gln Cys Lys Val Phe Trp Ser Gly Pro Cys Ala Leu Ala
                340                 345                 350

His Gly Ser Cys Pro Asn Pro Ile Gln Arg Glu Val Lys Thr Lys Leu
            355                 360                 365

Phe Ser Leu Glu Gln Phe Leu Asn Glu Leu Ile Leu Phe Gln Lys Gly
            370                 375                 380

Gln Thr Asn Thr Pro Pro Pro Phe Glu Ile Phe Phe Cys Phe Gly Glu
385                 390                 395                 400

Glu Trp Pro Asp Val Lys Pro Arg Glu Lys Lys Leu Ile Thr Val Gln
                405                 410                 415

Val Val Pro Val Ala Ala Arg Leu Leu Leu Glu Met Phe Ser Gly Glu
                420                 425                 430

Leu Ser Trp Ser Ala Asp Ser Ile Arg Leu Gln Ile Ser Asn Pro Asp
            435                 440                 445

Leu Lys Asp His Met Val Glu Gln Phe Lys Glu Leu His His Leu Trp
            450                 455                 460

Gln Ser Gln Gln Gln Leu Gln Pro Met Val Gln Ala Pro Pro Val Ala
465                 470                 475                 480

Gly Leu Asp Ala Ser Gln Gly Pro Trp Pro Met His Pro Val Gly Met
                485                 490                 495

Gln
```

<210> SEQ ID NO 8
<211> LENGTH: 325

```
<212> TYPE: PRT
<213> ORGANISM: Homo sapiens

<400> SEQUENCE: 8

Met Pro Ile Thr Arg Met Arg Met Arg Pro Trp Leu Glu Met Gln Ile
1               5                   10                  15

Asn Ser Asn Gln Ile Pro Gly Leu Ile Trp Ile Asn Lys Glu Glu Met
            20                  25                  30

Ile Phe Gln Ile Pro Trp Lys His Ala Ala Lys His Gly Trp Asp Ile
        35                  40                  45

Asn Lys Asp Ala Cys Leu Phe Arg Ser Trp Ala Ile His Thr Gly Arg
    50                  55                  60

Tyr Lys Ala Gly Glu Lys Glu Pro Asp Pro Lys Thr Trp Lys Ala Asn
65                  70                  75                  80

Phe Arg Cys Ala Met Asn Ser Leu Pro Asp Ile Glu Glu Val Lys Asp
                85                  90                  95

Gln Ser Arg Asn Lys Gly Ser Ser Ala Val Arg Val Tyr Arg Met Leu
                100                 105                 110

Pro Pro Leu Thr Lys Asn Gln Arg Lys Glu Arg Lys Ser Lys Ser Ser
            115                 120                 125

Arg Asp Ala Lys Ser Lys Ala Lys Arg Lys Ser Cys Gly Asp Ser Ser
            130                 135                 140

Pro Asp Thr Phe Ser Asp Gly Leu Ser Ser Ser Thr Leu Pro Asp Asp
145                 150                 155                 160

His Ser Ser Tyr Thr Val Pro Gly Tyr Met Gln Asp Leu Glu Val Glu
                165                 170                 175

Gln Ala Leu Thr Pro Ala Leu Ser Pro Cys Ala Val Ser Ser Thr Leu
                180                 185                 190

Pro Asp Trp His Ile Pro Val Glu Val Val Pro Asp Ser Thr Ser Asp
                195                 200                 205

Leu Tyr Asn Phe Gln Val Ser Pro Met Pro Ser Thr Ser Glu Ala Thr
            210                 215                 220

Thr Asp Glu Asp Glu Glu Gly Lys Leu Pro Glu Asp Ile Met Lys Leu
225                 230                 235                 240

Leu Glu Gln Ser Glu Trp Gln Pro Thr Asn Val Asp Gly Lys Gly Tyr
                245                 250                 255

Leu Leu Asn Glu Pro Gly Val Gln Pro Thr Ser Val Tyr Gly Asp Phe
                260                 265                 270

Ser Cys Lys Glu Glu Pro Glu Ile Asp Ser Pro Gly Gly Asp Ile Gly
                275                 280                 285

Leu Ser Leu Gln Arg Val Phe Thr Asp Leu Lys Asn Met Asp Ala Thr
            290                 295                 300

Trp Leu Asp Ser Leu Leu Thr Pro Val Arg Leu Pro Ser Ile Gln Ala
305                 310                 315                 320

Ile Pro Cys Ala Pro
                325

<210> SEQ ID NO 9
<211> LENGTH: 427
<212> TYPE: PRT
<213> ORGANISM: Homo sapiens

<400> SEQUENCE: 9

Met Gly Thr Pro Lys Pro Arg Ile Leu Pro Trp Leu Val Ser Gln Leu
1               5                   10                  15
```

```
Asp Leu Gly Gln Leu Glu Gly Val Ala Trp Val Asn Lys Ser Arg Thr
            20              25              30

Arg Phe Arg Ile Pro Trp Lys His Gly Leu Arg Gln Asp Ala Gln Gln
        35              40              45

Glu Asp Phe Gly Ile Phe Gln Ala Trp Ala Glu Ala Thr Gly Ala Tyr
    50              55              60

Val Pro Gly Arg Asp Lys Pro Asp Leu Pro Thr Trp Lys Arg Asn Phe
65              70              75              80

Arg Ser Ala Leu Asn Arg Lys Glu Gly Leu Arg Leu Ala Glu Asp Arg
                85              90              95

Ser Lys Asp Pro His Asp Pro His Lys Ile Tyr Glu Phe Val Asn Ser
            100             105             110

Gly Val Gly Asp Phe Ser Gln Pro Asp Thr Ser Pro Asp Thr Asn Gly
            115             120             125

Gly Gly Ser Thr Ser Asp Thr Gln Glu Asp Ile Leu Asp Glu Leu Leu
            130             135             140

Gly Asn Met Val Leu Ala Pro Leu Pro Asp Pro Gly Pro Pro Ser Leu
145             150             155             160

Ala Val Ala Pro Glu Pro Cys Pro Gln Pro Leu Arg Ser Pro Ser Leu
            165             170             175

Asp Asn Pro Thr Pro Phe Pro Asn Leu Gly Pro Ser Glu Asn Pro Leu
            180             185             190

Lys Arg Leu Leu Val Pro Gly Glu Glu Trp Glu Phe Glu Val Thr Ala
            195             200             205

Phe Tyr Arg Gly Arg Gln Val Phe Gln Gln Thr Ile Ser Cys Pro Glu
    210             215             220

Gly Leu Arg Leu Val Gly Ser Glu Val Gly Asp Arg Thr Leu Pro Gly
225             230             235             240

Trp Pro Val Thr Leu Pro Asp Pro Gly Met Ser Leu Thr Asp Arg Gly
            245             250             255

Val Met Ser Tyr Val Arg His Val Leu Ser Cys Leu Gly Gly Gly Leu
            260             265             270

Ala Leu Trp Arg Ala Gly Gln Trp Leu Trp Ala Gln Arg Leu Gly His
            275             280             285

Cys His Thr Tyr Trp Ala Val Ser Glu Glu Leu Leu Pro Asn Ser Gly
    290             295             300

His Gly Pro Asp Gly Glu Val Pro Lys Asp Lys Glu Gly Gly Val Phe
305             310             315             320

Asp Leu Gly Pro Phe Ile Val Asp Leu Ile Thr Phe Thr Glu Gly Ser
            325             330             335

Gly Arg Ser Pro Arg Tyr Ala Leu Trp Phe Cys Val Gly Glu Ser Trp
            340             345             350

Pro Gln Asp Gln Pro Trp Thr Lys Arg Leu Val Met Val Lys Val Val
            355             360             365

Pro Thr Cys Leu Arg Ala Leu Val Glu Met Ala Arg Val Gly Gly Ala
    370             375             380

Ser Ser Leu Glu Asn Thr Val Asp Leu His Ile Ser Asn Ser His Pro
385             390             395             400

Leu Ser Leu Thr Ser Asp Gln Tyr Lys Ala Tyr Leu Gln Asp Leu Val
            405             410             415

Glu Gly Met Asp Phe Gln Gly Pro Gly Glu Ser
            420             425
```

```
<210> SEQ ID NO 10
<211> LENGTH: 503
<212> TYPE: PRT
<213> ORGANISM: Homo sapiens

<400> SEQUENCE: 10

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
                20                  25                  30

Leu Asp Glu Ala Arg Thr Cys Phe Arg Val Pro Trp Lys His Phe Ala
            35                  40                  45

Arg Lys Asp Leu Ser Glu Ala Asp Ala Arg Ile Phe Lys Ala Trp Ala
        50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
            165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
    275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
            325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380
```

-continued

```
Gly Ser Ala Ser Pro Ser Thr Pro Ala Cys Leu Leu Pro Arg Asn Cys
385             390             395             400

Asp Thr Pro Ile Phe Asp Phe Arg Val Phe Phe Gln Glu Leu Val Glu
            405             410             415

Phe Arg Ala Arg Gln Arg Arg Gly Ser Pro Arg Tyr Thr Ile Tyr Leu
            420             425             430

Gly Phe Gly Gln Asp Leu Ser Ala Gly Arg Pro Lys Glu Lys Ser Leu
            435             440             445

Val Leu Val Lys Leu Glu Pro Trp Leu Cys Arg Val His Leu Glu Gly
    450             455             460

Thr Gln Arg Glu Gly Val Ser Ser Leu Asp Ser Ser Ser Leu Ser Leu
465             470             475             480

Cys Leu Ser Ser Ala Asn Ser Leu Tyr Asp Asp Ile Glu Cys Phe Leu
            485             490             495

Met Glu Leu Glu Gln Pro Ala
            500

<210> SEQ ID NO 11
<211> LENGTH: 426
<212> TYPE: PRT
<213> ORGANISM: Homo sapiens

<400> SEQUENCE: 11

Met Cys Asp Arg Asn Gly Gly Arg Arg Leu Arg Gln Trp Leu Ile Glu
1               5               10              15

Gln Ile Asp Ser Ser Met Tyr Pro Gly Leu Ile Trp Glu Asn Glu Glu
            20              25              30

Lys Ser Met Phe Arg Ile Pro Trp Lys His Ala Gly Lys Gln Asp Tyr
            35              40              45

Asn Gln Glu Val Asp Ala Ser Ile Phe Lys Ala Trp Ala Val Phe Lys
    50              55              60

Gly Lys Phe Lys Glu Gly Asp Lys Ala Glu Pro Ala Thr Trp Lys Thr
65              70              75              80

Arg Leu Arg Cys Ala Leu Asn Lys Ser Pro Asp Phe Glu Glu Val Thr
            85              90              95

Asp Arg Ser Gln Leu Asp Ile Ser Glu Pro Tyr Lys Val Tyr Arg Ile
            100             105             110

Val Pro Glu Glu Glu Gln Lys Cys Lys Leu Gly Val Ala Thr Ala Gly
            115             120             125

Cys Val Asn Glu Val Thr Glu Met Glu Cys Gly Arg Ser Glu Ile Asp
    130             135             140

Glu Leu Ile Lys Glu Pro Ser Val Asp Asp Tyr Met Gly Met Ile Lys
145             150             155             160

Arg Ser Pro Ser Pro Pro Glu Ala Cys Arg Ser Gln Leu Leu Pro Asp
            165             170             175

Trp Trp Ala Gln Gln Pro Ser Thr Gly Val Pro Leu Val Thr Gly Tyr
            180             185             190

Thr Thr Tyr Asp Ala His His Ser Ala Phe Ser Gln Met Val Ile Ser
            195             200             205

Phe Tyr Tyr Gly Gly Lys Leu Val Gly Gln Ala Thr Thr Thr Cys Pro
    210             215             220

Glu Gly Cys Arg Leu Ser Leu Ser Gln Pro Gly Leu Pro Gly Thr Lys
225             230             235             240

Leu Tyr Gly Pro Glu Gly Leu Glu Leu Val Arg Phe Pro Pro Ala Asp
            245             250             255
```

-continued

```
Ala Ile Pro Ser Glu Arg Gln Arg Gln Val Thr Arg Lys Leu Phe Gly
            260                 265                 270

His Leu Glu Arg Gly Val Leu Leu His Ser Ser Arg Gln Gly Val Phe
            275                 280                 285

Val Lys Arg Leu Cys Gln Gly Arg Val Phe Cys Ser Gly Asn Ala Val
    290                 295                 300

Val Cys Lys Gly Arg Pro Asn Lys Leu Glu Arg Asp Glu Val Val Gln
305                 310                 315                 320

Val Phe Asp Thr Ser Gln Phe Phe Arg Glu Leu Gln Gln Phe Tyr Asn
                325                 330                 335

Ser Gln Gly Arg Leu Pro Asp Gly Arg Val Val Leu Cys Phe Gly Glu
            340                 345                 350

Glu Phe Pro Asp Met Ala Pro Leu Arg Ser Lys Leu Ile Leu Val Gln
            355                 360                 365

Ile Glu Gln Leu Tyr Val Arg Gln Leu Ala Glu Glu Ala Gly Lys Ser
    370                 375                 380

Cys Gly Ala Gly Ser Val Met Gln Ala Pro Glu Glu Pro Pro Asp
385                 390                 395                 400

Gln Val Phe Arg Met Phe Pro Asp Ile Cys Ala Ser His Gln Arg Ser
                405                 410                 415

Phe Phe Arg Glu Asn Gln Gln Ile Thr Val
            420                 425
```

<210> SEQ ID NO 12
<211> LENGTH: 329
<212> TYPE: PRT
<213> ORGANISM: Mus musculus

<400> SEQUENCE: 12

```
Met Pro Ile Thr Arg Met Arg Met Arg Pro Trp Leu Glu Met Gln Ile
1               5                   10                  15

Asn Ser Asn Gln Ile Pro Gly Leu Ile Trp Ile Asn Lys Glu Glu Met
            20                  25                  30

Ile Phe Gln Ile Pro Trp Lys His Ala Ala Lys His Gly Trp Asp Ile
        35                  40                  45

Asn Lys Asp Ala Cys Leu Phe Arg Ser Trp Ala Ile His Thr Gly Arg
    50                  55                  60

Tyr Lys Ala Gly Glu Lys Glu Pro Asp Pro Lys Thr Trp Lys Ala Asn
65                  70                  75                  80

Phe Arg Cys Ala Met Asn Ser Leu Pro Asp Ile Glu Glu Val Lys Asp
                85                  90                  95

Gln Ser Arg Asn Lys Gly Ser Ser Ala Val Arg Val Tyr Arg Met Leu
            100                 105                 110

Pro Pro Leu Thr Arg Asn Gln Arg Lys Glu Arg Lys Ser Lys Ser Ser
            115                 120                 125

Arg Asp Thr Lys Ser Lys Thr Lys Arg Lys Leu Cys Gly Asp Val Ser
        130                 135                 140

Pro Asp Thr Phe Ser Asp Gly Leu Ser Ser Ser Thr Leu Pro Asp Asp
145                 150                 155                 160

His Ser Ser Tyr Thr Thr Gln Gly Tyr Leu Gly Gln Asp Leu Asp Met
                165                 170                 175

Glu Arg Asp Ile Thr Pro Ala Leu Ser Pro Cys Val Val Ser Ser Ser
            180                 185                 190

Leu Ser Glu Trp His Met Gln Met Asp Ile Ile Pro Asp Ser Thr Thr
```

-continued

```
            195                 200                 205

Asp Leu Tyr Asn Leu Gln Val Ser Pro Met Pro Ser Thr Ser Glu Ala
    210                 215                 220

Ala Thr Asp Glu Asp Glu Glu Gly Lys Ile Ala Glu Asp Leu Met Lys
225                 230                 235                 240

Leu Phe Glu Gln Ser Glu Trp Gln Pro Thr His Ile Asp Gly Lys Gly
                245                 250                 255

Tyr Leu Leu Asn Glu Pro Gly Thr Gln Leu Ser Ser Val Tyr Gly Asp
                260                 265                 270

Phe Ser Cys Lys Glu Glu Pro Glu Ile Asp Ser Pro Arg Gly Asp Ile
                275                 280                 285

Gly Ile Gly Ile Gln His Val Phe Thr Glu Met Lys Asn Met Asp Ser
    290                 295                 300

Ile Met Trp Met Asp Ser Leu Leu Gly Asn Ser Val Arg Leu Pro Pro
305                 310                 315                 320

Ser Ile Gln Ala Ile Pro Cys Ala Pro
                325

<210> SEQ ID NO 13
<211> LENGTH: 419
<212> TYPE: PRT
<213> ORGANISM: Mus musculus

<400> SEQUENCE: 13

Met Glu Thr Pro Lys Pro Arg Ile Leu Pro Trp Leu Val Ser Gln Leu
1               5                   10                  15

Asp Leu Gly Gln Leu Glu Gly Val Ala Trp Leu Asp Glu Ser Arg Thr
                20                  25                  30

Arg Phe Arg Ile Pro Trp Lys His Gly Leu Arg Gln Asp Ala Gln Met
            35                  40                  45

Ala Asp Phe Gly Ile Phe Gln Ala Trp Ala Glu Ala Ser Gly Ala Tyr
        50                  55                  60

Thr Pro Gly Lys Asp Lys Pro Asp Val Ser Thr Trp Lys Arg Asn Phe
65                  70                  75                  80

Arg Ser Ala Leu Asn Arg Lys Glu Val Leu Arg Leu Ala Ala Asp Asn
                85                  90                  95

Ser Lys Asp Pro Tyr Asp Pro His Lys Val Tyr Glu Phe Val Thr Pro
                100                 105                 110

Gly Ala Arg Asp Phe Val His Leu Gly Ala Ser Pro Asp Thr Asn Gly
            115                 120                 125

Lys Ser Ser Leu Pro His Ser Gln Glu Asn Leu Pro Lys Leu Phe Asp
    130                 135                 140

Gly Leu Ile Leu Gly Pro Leu Lys Asp Glu Gly Ser Ser Asp Leu Ala
145                 150                 155                 160

Ile Val Ser Asp Pro Ser Gln Gln Leu Pro Ser Pro Asn Val Asn Asn
                165                 170                 175

Phe Leu Asn Pro Ala Pro Gln Glu Asn Pro Leu Lys Gln Leu Leu Ala
                180                 185                 190

Glu Glu Gln Trp Glu Phe Glu Val Thr Ala Phe Tyr Arg Gly Arg Gln
            195                 200                 205

Val Phe Gln Gln Thr Leu Phe Cys Pro Gly Gly Leu Arg Leu Val Gly
    210                 215                 220

Ser Thr Ala Asp Met Thr Leu Pro Trp Gln Pro Val Thr Leu Pro Asp
225                 230                 235                 240
```

```
Pro Glu Gly Phe Leu Thr Asp Lys Leu Val Lys Glu Tyr Val Gly Gln
                245             250             255

Val Leu Lys Gly Leu Gly Asn Gly Leu Ala Leu Trp Gln Ala Gly Gln
            260             265             270

Cys Leu Trp Ala Gln Arg Leu Gly His Ser His Ala Phe Trp Ala Leu
            275             280             285

Gly Glu Glu Leu Leu Pro Asp Ser Gly Arg Gly Pro Asp Gly Glu Val
        290             295             300

His Lys Asp Lys Asp Gly Ala Val Phe Asp Leu Arg Pro Phe Val Ala
305             310             315             320

Asp Leu Ile Ala Phe Met Glu Gly Ser Gly His Ser Pro Arg Tyr Thr
                325             330             335

Leu Trp Phe Cys Met Gly Glu Met Trp Pro Gln Asp Gln Pro Trp Val
                340             345             350

Lys Arg Leu Val Met Val Lys Val Val Pro Thr Cys Leu Lys Glu Leu
            355             360             365

Leu Glu Met Ala Arg Glu Gly Gly Ala Ser Ser Leu Lys Thr Val Asp
        370             375             380

Leu His Ile Ser Asn Ser Gln Pro Ile Ser Leu Thr Ser Asp Gln Tyr
385             390             395             400

Lys Ala Tyr Leu Gln Asp Leu Val Glu Asp Met Asp Phe Gln Ala Thr
                405             410             415

Gly Asn Ile

<210> SEQ ID NO 14
<211> LENGTH: 457
<212> TYPE: PRT
<213> ORGANISM: Mus musculus

<400> SEQUENCE: 14

Met Ala Glu Val Arg Gly Val Gln Arg Val Leu Phe Gly Asp Trp Leu
1               5               10              15

Leu Gly Glu Val Ser Ser Gly Gln Tyr Glu Gly Leu Gln Trp Leu Asn
            20              25              30

Glu Ala Arg Thr Val Phe Arg Val Pro Trp Lys His Phe Gly Arg Arg
            35              40              45

Asp Leu Asp Glu Glu Asp Ala Gln Ile Phe Lys Ala Trp Ala Val Ala
        50              55              60

Arg Gly Arg Trp Pro Pro Ser Gly Val Asn Leu Pro Pro Pro Glu Ala
65              70              75              80

Glu Ala Ala Glu Arg Arg Glu Arg Arg Gly Trp Lys Thr Asn Phe Arg
                85              90              95

Cys Ala Leu His Ser Thr Gly Arg Phe Ile Leu Arg Gln Asp Asn Ser
            100             105             110

Gly Asp Pro Val Asp Pro His Lys Val Tyr Glu Leu Ser Arg Glu Leu
        115             120             125

Gly Ser Thr Val Gly Pro Ala Thr Glu Asn Arg Glu Glu Val Ser Leu
        130             135             140

Ser Asn Ala Leu Pro Thr Gln Gly Val Ser Pro Gly Ser Phe Leu Ala
145             150             155             160

Arg Glu Asn Ala Gly Leu Gln Thr Pro Ser Pro Leu Leu Ser Ser Asp
                165             170             175

Ala Gly Asp Leu Leu Leu Gln Val Leu Gln Tyr Ser His Ile Leu Glu
            180             185             190
```

-continued

```
Ser Glu Ser Gly Ala Asp Pro Val Pro Pro Gln Ala Pro Gly Gln Glu
        195                 200             205

Gln Asp Arg Val Tyr Glu Glu Pro Tyr Ala Ala Trp Gln Val Glu Ala
        210                 215             220

Val Pro Ser Pro Arg Pro Gln Gln Pro Ala Leu Thr Glu Arg Ser Leu
225                     230             235                 240

Gly Phe Leu Asp Val Thr Ile Met Tyr Lys Gly Arg Thr Val Leu Gln
                245                 250             255

Ala Val Val Gly His Pro Arg Cys Val Phe Leu Tyr Ser Pro Met Ala
                260                 265             270

Pro Ala Val Arg Thr Ser Glu Pro Gln Pro Val Ile Phe Pro Ser Pro
        275                 280             285

Ala Glu Leu Pro Asp Gln Lys Gln Leu His Tyr Thr Glu Thr Leu Leu
        290                 295             300

Gln His Val Ser Pro Gly Leu Gln Leu Glu Leu Arg Gly Pro Ser Leu
305                     310             315                 320

Trp Ala Leu Arg Met Gly Lys Cys Lys Val Tyr Trp Glu Val Gly Ser
                325                 330             335

Pro Met Gly Thr Thr Gly Pro Ser Thr Pro Pro Gln Leu Leu Glu Arg
                340                 345             350

Asn Arg His Thr Pro Ile Phe Asp Phe Ser Thr Phe Phe Arg Glu Leu
        355                 360             365

Glu Glu Phe Arg Ala Arg Arg Arg Gln Gly Ser Pro His Tyr Thr Ile
        370                 375             380

Tyr Leu Gly Phe Gly Gln Asp Leu Ser Ala Gly Arg Pro Lys Glu Lys
385                     390             395                 400

Thr Leu Ile Leu Val Lys Leu Glu Pro Trp Val Cys Lys Ala Tyr Leu
                405                 410             415

Glu Gly Val Gln Arg Glu Gly Val Ser Ser Leu Asp Ser Ser Ser Leu
                420                 425             430

Gly Leu Cys Leu Ser Ser Thr Asn Ser Leu Tyr Glu Asp Ile Glu His
        435                 440             445

Phe Leu Met Asp Leu Gly Gln Trp Pro
    450                 455
```

```
<210> SEQ ID NO 15
<211> LENGTH: 525
<212> TYPE: PRT
<213> ORGANISM: Mus musculus

<400> SEQUENCE: 15

Met Ala Glu Val Arg Gly Val Gln Arg Val Leu Phe Gly Asp Trp Leu
1               5                   10                  15

Leu Gly Glu Val Ser Ser Gly Gln Tyr Glu Gly Leu Gln Trp Leu Asn
                20                  25                  30

Glu Ala Arg Thr Val Phe Arg Val Pro Trp Lys His Phe Gly Arg Arg
        35                  40                  45

Asp Leu Asp Glu Glu Asp Ala Gln Ile Phe Lys Ala Trp Ala Val Ala
        50                  55                  60

Arg Gly Arg Trp Pro Pro Ser Gly Val Asn Leu Pro Pro Pro Glu Ala
65                  70                  75                  80

Glu Ala Ala Glu Arg Arg Glu Arg Arg Gly Trp Lys Thr Asn Phe Arg
                85                  90                  95

Cys Ala Leu His Ser Thr Gly Arg Phe Ile Leu Arg Gln Asp Asn Ser
        100                 105                 110
```

```
Gly Asp Pro Val Asp Pro His Lys Val Tyr Glu Leu Ser Arg Glu Leu
        115             120             125

Gly Ser Thr Val Gly Pro Ala Thr Glu Asn Arg Glu Glu Val Ser Leu
        130             135             140

Ser Asn Ala Leu Pro Thr Gln Gly Val Ser Pro Gly Ser Phe Leu Ala
145             150             155             160

Arg Glu Asn Ala Gly Leu Gln Thr Pro Ser Pro Leu Leu Ser Ser Asp
        165             170             175

Ala Gly Asp Leu Leu Leu Gln Val Leu Gln Tyr Ser His Ile Leu Glu
        180             185             190

Ser Glu Ser Gly Ala Asp Pro Val Pro Pro Gln Ala Pro Gly Gln Glu
        195             200             205

Gln Asp Arg Val Tyr Glu Glu Pro Tyr Ala Ala Trp Gln Val Glu Ala
        210             215             220

Val Pro Ser Pro Arg Pro Gln Gln Pro Ala Leu Thr Glu Arg Ser Leu
225             230             235             240

Gly Phe Leu Asp Val Thr Lys Leu Phe Asp Gly Leu Ile Leu Gly Pro
        245             250             255

Leu Lys Asp Glu Gly Ser Ser Asp Leu Ala Ile Val Ser Asp Pro Ser
        260             265             270

Gln Gln Leu Pro Ser Pro Asn Val Asn Asn Phe Leu Asn Pro Ala Pro
        275             280             285

Gln Glu Asn Pro Leu Lys Gln Leu Leu Ala Glu Glu Gln Trp Glu Phe
        290             295             300

Glu Val Thr Ala Phe Tyr Arg Gly Arg Gln Val Phe Gln Gln Thr Leu
305             310             315             320

Phe Cys Pro Gly Gly Leu Arg Leu Val Gly Ser Thr Ala Asp Met Thr
        325             330             335

Leu Pro Trp Gln Pro Val Thr Leu Pro Asp Pro Glu Gly Phe Leu Thr
        340             345             350

Asp Lys Leu Val Lys Glu Tyr Val Gly Gln Val Leu Lys Gly Leu Gly
        355             360             365

Asn Gly Leu Ala Leu Trp Gln Ala Gly Gln Cys Leu Trp Ala Gln Arg
        370             375             380

Leu Gly His Ser His Ala Phe Trp Ala Leu Gly Glu Glu Leu Leu Pro
385             390             395             400

Asp Ser Gly Arg Gly Pro Asp Gly Glu Val His Lys Asp Lys Asp Gly
        405             410             415

Ala Val Phe Asp Leu Arg Pro Phe Val Ala Asp Leu Ile Ala Phe Met
        420             425             430

Glu Gly Ser Gly His Ser Pro Arg Tyr Thr Leu Trp Phe Cys Met Gly
        435             440             445

Glu Met Trp Pro Gln Asp Gln Pro Trp Val Lys Arg Leu Val Met Val
        450             455             460

Lys Val Val Pro Thr Cys Leu Lys Glu Leu Leu Glu Met Ala Arg Glu
465             470             475             480

Gly Gly Ala Ser Ser Leu Lys Thr Val Asp Leu His Ile Asp Asn Asp
        485             490             495

Gln Pro Ile Asp Leu Asp Asp Asp Gln Tyr Lys Ala Tyr Leu Gln Asp
        500             505             510

Leu Val Glu Asp Met Asp Phe Gln Ala Thr Gly Asn Ile
        515             520             525
```

-continued

```
<210> SEQ ID NO 16
<211> LENGTH: 424
<212> TYPE: PRT
<213> ORGANISM: Mus musculus

<400> SEQUENCE: 16

Met Cys Asp Arg Asn Gly Gly Arg Arg Leu Arg Gln Trp Leu Ile Glu
1               5                   10                  15

Gln Ile Asp Ser Ser Met Tyr Pro Gly Leu Ile Trp Glu Asn Asp Glu
            20                  25                  30

Lys Thr Met Phe Arg Ile Pro Trp Lys His Ala Gly Lys Gln Asp Tyr
        35                  40                  45

Asn Gln Glu Val Asp Ala Ser Ile Phe Lys Ala Trp Ala Val Phe Lys
    50                  55                  60

Gly Lys Phe Lys Glu Gly Asp Lys Ala Glu Pro Ala Thr Trp Lys Thr
65                  70                  75                  80

Arg Leu Arg Cys Ala Leu Asn Lys Ser Pro Asp Phe Glu Glu Val Thr
            85                  90                  95

Asp Arg Ser Gln Leu Asp Ile Ser Glu Pro Tyr Lys Val Tyr Arg Ile
            100                 105                 110

Val Pro Glu Glu Glu Gln Lys Cys Lys Leu Gly Val Ala Pro Ala Gly
        115                 120                 125

Cys Met Ser Glu Val Pro Glu Met Glu Cys Gly Arg Ser Glu Ile Glu
    130                 135                 140

Glu Leu Ile Lys Glu Pro Ser Val Asp Glu Tyr Met Gly Met Thr Lys
145                 150                 155                 160

Arg Ser Pro Ser Pro Pro Glu Ala Cys Arg Ser Gln Ile Leu Pro Asp
            165                 170                 175

Trp Trp Val Gln Gln Pro Ser Ala Gly Leu Pro Leu Val Thr Gly Tyr
        180                 185                 190

Ala Ala Tyr Asp Thr His His Ser Ala Phe Ser Gln Met Val Ile Ser
        195                 200                 205

Phe Tyr Tyr Gly Gly Lys Leu Val Gly Gln Ala Thr Thr Thr Cys Leu
    210                 215                 220

Glu Gly Cys Arg Leu Ser Leu Ser Gln Pro Gly Leu Pro Lys Leu Tyr
225                 230                 235                 240

Gly Pro Asp Gly Leu Glu Pro Val Cys Phe Pro Thr Ala Asp Thr Ile
            245                 250                 255

Pro Ser Glu Arg Gln Arg Gln Val Thr Arg Lys Leu Phe Gly His Leu
            260                 265                 270

Glu Arg Gly Val Leu Leu His Ser Asn Arg Lys Gly Val Phe Val Lys
        275                 280                 285

Arg Leu Cys Gln Gly Arg Val Phe Cys Ser Gly Asn Ala Val Val Cys
    290                 295                 300

Lys Gly Arg Pro Asn Lys Leu Glu Arg Asp Glu Val Val Gln Val Phe
305                 310                 315                 320

Asp Thr Asn Gln Phe Ile Arg Glu Leu Gln Gln Phe Tyr Ala Thr Gln
            325                 330                 335

Ser Arg Leu Pro Asp Ser Arg Val Val Leu Cys Phe Gly Glu Glu Phe
            340                 345                 350

Pro Asp Thr Val Pro Leu Arg Ser Lys Leu Ile Leu Val Gln Val Glu
        355                 360                 365

Gln Leu Tyr Ala Arg Gln Leu Val Glu Glu Ala Gly Lys Ser Cys Gly
    370                 375                 380
```

Ala Gly Ser Leu Met Pro Ala Leu Glu Glu Pro Gln Pro Asp Gln Ala
385                 390                 395                 400

Phe Arg Met Phe Pro Asp Ile Cys Thr Ser His Gln Arg Pro Phe Phe
                405                 410                 415

Arg Glu Asn Gln Gln Ile Thr Val
            420

<210> SEQ ID NO 17
<211> LENGTH: 424
<212> TYPE: PRT
<213> ORGANISM: Mus musculus

<400> SEQUENCE: 17

Met Cys Asp Arg Asn Gly Gly Arg Arg Leu Arg Gln Trp Leu Ile Glu
1               5                   10                  15

Gln Ile Asp Ser Ser Met Tyr Pro Gly Leu Ile Trp Glu Asn Asp Glu
                20                  25                  30

Lys Thr Met Phe Arg Ile Pro Trp Lys His Ala Gly Lys Gln Asp Tyr
            35                  40                  45

Asn Gln Glu Val Asp Ala Ser Ile Phe Lys Ala Trp Ala Val Phe Lys
        50                  55                  60

Gly Lys Phe Lys Glu Gly Asp Lys Ala Glu Pro Ala Thr Trp Lys Thr
65                  70                  75                  80

Arg Leu Arg Cys Ala Leu Asn Lys Ser Pro Asp Phe Glu Glu Val Thr
                85                  90                  95

Asp Arg Ser Gln Leu Asp Ile Ser Glu Pro Tyr Lys Val Tyr Arg Ile
            100                 105                 110

Val Pro Glu Glu Glu Gln Lys Cys Lys Leu Gly Val Ala Pro Ala Gly
            115                 120                 125

Cys Met Ser Glu Val Pro Glu Met Glu Cys Gly Arg Ser Glu Ile Glu
        130                 135                 140

Glu Leu Ile Lys Glu Pro Ser Val Asp Glu Tyr Met Gly Met Thr Lys
145                 150                 155                 160

Arg Ser Pro Ser Pro Pro Glu Ala Cys Arg Ser Gln Ile Leu Pro Asp
                165                 170                 175

Trp Trp Val Gln Gln Pro Ser Ala Gly Leu Pro Leu Val Thr Gly Tyr
            180                 185                 190

Ala Ala Tyr Asp Thr His His Ser Ala Phe Ser Gln Met Val Ile Ser
            195                 200                 205

Phe Tyr Tyr Gly Gly Lys Leu Val Gly Gln Ala Thr Thr Thr Cys Leu
        210                 215                 220

Glu Gly Cys Arg Leu Ser Leu Ser Gln Pro Gly Leu Pro Lys Leu Tyr
225                 230                 235                 240

Gly Pro Asp Gly Leu Glu Pro Val Cys Phe Pro Thr Ala Asp Thr Ile
                245                 250                 255

Pro Ser Glu Arg Gln Arg Gln Val Thr Arg Lys Leu Phe Gly His Leu
            260                 265                 270

Glu Arg Gly Val Leu Leu His Ser Asn Arg Lys Gly Val Phe Val Lys
            275                 280                 285

Arg Leu Cys Gln Gly Arg Val Phe Cys Ser Gly Asn Ala Val Val Cys
        290                 295                 300

Lys Gly Arg Pro Asn Arg Leu Glu Arg Asp Glu Val Val Gln Val Phe
305                 310                 315                 320

Asp Thr Asn Gln Phe Ile Arg Glu Leu Gln Gln Phe Tyr Ala Thr Gln

-continued

```
                    325              330              335

Ser Arg Leu Pro Asp Ser Arg Val Val Leu Cys Phe Gly Glu Glu Phe
        340              345              350

Pro Asp Thr Val Pro Leu Arg Ser Lys Leu Ile Leu Val Gln Val Glu
        355              360              365

Gln Leu Tyr Ala Arg Gln Leu Val Glu Glu Ala Gly Lys Ser Cys Gly
        370              375              380

Ala Gly Ser Leu Met Pro Ala Leu Glu Glu Pro Gln Pro Asp Gln Ala
385              390              395              400

Phe Arg Met Phe Pro Asp Ile Cys Thr Ser His Gln Arg Pro Phe Phe
                405              410              415

Arg Glu Asn Gln Gln Ile Thr Val
                420

<210> SEQ ID NO 18
<211> LENGTH: 756
<212> TYPE: PRT
<213> ORGANISM: Homo sapiens

<400> SEQUENCE: 18

Met Ser Trp Ser Pro Ser Leu Thr Thr Gln Thr Cys Gly Ala Trp Glu
1               5               10              15

Met Lys Glu Arg Leu Gly Thr Gly Gly Phe Gly Asn Val Ile Arg Trp
                20              25              30

His Asn Gln Glu Thr Gly Glu Gln Ile Ala Ile Lys Gln Cys Arg Gln
        35              40              45

Glu Leu Ser Pro Arg Asn Arg Glu Arg Trp Cys Leu Glu Ile Gln Ile
        50              55              60

Met Arg Arg Leu Thr His Pro Asn Val Val Ala Ala Arg Asp Val Pro
65              70              75              80

Glu Gly Met Gln Asn Leu Ala Pro Asn Asp Leu Pro Leu Leu Ala Met
                85              90              95

Glu Tyr Cys Gln Gly Gly Asp Leu Arg Lys Tyr Leu Asn Gln Phe Glu
                100             105             110

Asn Cys Cys Gly Leu Arg Glu Gly Ala Ile Leu Thr Leu Leu Ser Asp
        115             120             125

Ile Ala Ser Ala Leu Arg Tyr Leu His Glu Asn Arg Ile Ile His Arg
        130             135             140

Asp Leu Lys Pro Glu Asn Ile Val Leu Gln Gln Gly Glu Gln Arg Leu
145             150             155             160

Ile His Lys Ile Ile Asp Leu Gly Tyr Ala Lys Glu Leu Asp Gln Gly
                165             170             175

Ser Leu Cys Thr Ser Phe Val Gly Thr Leu Gln Tyr Leu Ala Pro Glu
                180             185             190

Leu Leu Glu Gln Gln Lys Tyr Thr Val Thr Val Asp Tyr Trp Ser Phe
                195             200             205

Gly Thr Leu Ala Phe Glu Cys Ile Thr Gly Phe Arg Pro Phe Leu Pro
        210             215             220

Asn Trp Gln Pro Val Gln Trp His Ser Lys Val Arg Gln Lys Ser Glu
225             230             235             240

Val Asp Ile Val Val Ser Glu Asp Leu Asn Gly Thr Val Lys Phe Ser
                245             250             255

Ser Ser Leu Pro Tyr Pro Asn Asn Leu Asn Ser Val Leu Ala Glu Arg
        260             265             270
```

```
Leu Glu Lys Trp Leu Gln Leu Met Leu Met Trp His Pro Arg Gln Arg
        275             280             285

Gly Thr Asp Pro Thr Tyr Gly Pro Asn Gly Cys Phe Lys Ala Leu Asp
    290             295             300

Asp Ile Leu Asn Leu Lys Leu Val His Ile Leu Asn Met Val Thr Gly
305             310             315             320

Thr Ile His Thr Tyr Pro Val Thr Glu Asp Glu Ser Leu Gln Ser Leu
            325             330             335

Lys Ala Arg Ile Gln Gln Asp Thr Gly Ile Pro Glu Glu Asp Gln Glu
            340             345             350

Leu Leu Gln Glu Ala Gly Leu Ala Leu Ile Pro Asp Lys Pro Ala Thr
        355             360             365

Gln Cys Ile Ser Asp Gly Lys Leu Asn Glu Gly His Thr Leu Asp Met
    370             375             380

Asp Leu Val Phe Leu Phe Asp Asn Ser Lys Ile Thr Tyr Glu Thr Gln
385             390             395             400

Ile Ser Pro Arg Pro Gln Pro Glu Ser Val Ser Cys Ile Leu Gln Glu
            405             410             415

Pro Lys Arg Asn Leu Ala Phe Phe Gln Leu Arg Lys Val Trp Gly Gln
            420             425             430

Val Trp His Ser Ile Gln Thr Leu Lys Glu Asp Cys Asn Arg Leu Gln
        435             440             445

Gln Gly Gln Arg Ala Ala Met Met Asn Leu Leu Arg Asn Asn Ser Cys
    450             455             460

Leu Ser Lys Met Lys Asn Ser Met Ala Ser Met Ser Gln Gln Leu Lys
465             470             475             480

Ala Lys Leu Asp Phe Phe Lys Thr Ser Ile Gln Ile Asp Leu Glu Lys
            485             490             495

Tyr Ser Glu Gln Thr Glu Phe Gly Ile Thr Ser Asp Lys Leu Leu Leu
            500             505             510

Ala Trp Arg Glu Met Glu Gln Ala Val Glu Leu Cys Gly Arg Glu Asn
        515             520             525

Glu Val Lys Leu Leu Val Glu Arg Met Met Ala Leu Gln Thr Asp Ile
    530             535             540

Val Asp Leu Gln Arg Ser Pro Met Gly Arg Lys Gln Gly Gly Thr Leu
545             550             555             560

Asp Asp Leu Glu Glu Gln Ala Arg Glu Leu Tyr Arg Arg Leu Arg Glu
            565             570             575

Lys Pro Arg Asp Gln Arg Thr Glu Gly Asp Ser Gln Glu Met Val Arg
            580             585             590

Leu Leu Leu Gln Ala Ile Gln Ser Phe Glu Lys Lys Val Arg Val Ile
        595             600             605

Tyr Thr Gln Leu Ser Lys Thr Val Val Cys Lys Gln Lys Ala Leu Glu
    610             615             620

Leu Leu Pro Lys Val Glu Glu Val Val Ser Leu Met Asn Glu Asp Glu
625             630             635             640

Lys Thr Val Val Arg Leu Gln Glu Lys Arg Gln Lys Glu Leu Trp Asn
            645             650             655

Leu Leu Lys Ile Ala Cys Ser Lys Val Arg Gly Pro Val Ser Gly Ser
            660             665             670

Pro Asp Ser Met Asn Ala Ser Arg Leu Ser Gln Pro Gly Gln Leu Met
        675             680             685

Ser Gln Pro Ser Thr Ala Ser Asn Ser Leu Pro Glu Pro Ala Lys Lys
```

-continued

```
          690              695              700

Ser Glu Glu Leu Val Ala Glu Ala His Asn Leu Cys Thr Leu Leu Glu
705                  710                  715                  720

Asn Ala Ile Gln Asp Thr Val Arg Glu Gln Asp Gln Ser Phe Thr Ala
                 725                  730                  735

Leu Asp Trp Ser Trp Leu Gln Thr Glu Glu Glu His Ser Cys Leu
                 740                  745                  750

Glu Gln Ala Ser
        755

<210> SEQ ID NO 19
<211> LENGTH: 754
<212> TYPE: PRT
<213> ORGANISM: Homo sapiens

<400> SEQUENCE: 19

Met Phe Ser Gly Gly Cys His Ser Pro Gly Phe Gly Arg Pro Ser Pro
1               5                  10                  15

Ala Phe Pro Ala Pro Gly Ser Pro Pro Pro Ala Pro Arg Pro Cys Arg
                 20                  25                  30

Gln Glu Thr Gly Glu Gln Ile Ala Ile Lys Gln Cys Arg Gln Glu Leu
             35                  40                  45

Ser Pro Arg Asn Arg Glu Arg Trp Cys Leu Glu Ile Gln Ile Met Arg
         50                  55                  60

Arg Leu Thr His Pro Asn Val Val Ala Ala Arg Asp Val Pro Glu Gly
65                  70                  75                  80

Met Gln Asn Leu Ala Pro Asn Asp Leu Pro Leu Leu Ala Met Glu Tyr
                 85                  90                  95

Cys Gln Gly Gly Asp Leu Arg Lys Tyr Leu Asn Gln Phe Glu Asn Cys
                 100                 105                 110

Cys Gly Leu Arg Glu Gly Ala Ile Leu Thr Leu Leu Ser Asp Ile Ala
             115                 120                 125

Ser Ala Leu Arg Tyr Leu His Glu Asn Arg Ile Ile His Arg Asp Leu
         130                 135                 140

Lys Pro Glu Asn Ile Val Leu Gln Gln Gly Glu Gln Arg Leu Ile His
145                 150                 155                 160

Lys Ile Ile Asp Leu Gly Tyr Ala Lys Glu Leu Asp Gln Gly Ser Leu
                 165                 170                 175

Cys Thr Ser Phe Val Gly Thr Leu Gln Tyr Leu Ala Pro Glu Leu Leu
                 180                 185                 190

Glu Gln Gln Lys Tyr Thr Val Thr Val Asp Tyr Trp Ser Phe Gly Thr
             195                 200                 205

Leu Ala Phe Glu Cys Ile Thr Gly Phe Arg Pro Phe Leu Pro Asn Trp
         210                 215                 220

Gln Pro Val Gln Trp His Ser Lys Val Arg Gln Lys Ser Glu Val Asp
225                 230                 235                 240

Ile Val Val Ser Glu Asp Leu Asn Gly Thr Val Lys Phe Ser Ser Ser
                 245                 250                 255

Leu Pro Tyr Pro Asn Asn Leu Asn Ser Val Leu Ala Glu Arg Leu Glu
                 260                 265                 270

Lys Trp Leu Gln Leu Met Leu Met Trp His Pro Arg Gln Arg Gly Thr
             275                 280                 285

Asp Pro Thr Tyr Gly Pro Asn Gly Cys Phe Lys Ala Leu Asp Asp Ile
         290                 295                 300
```

-continued

```
Leu Asn Leu Lys Leu Val His Ile Leu Asn Met Val Thr Gly Thr Ile
305                 310                 315                 320

His Thr Tyr Pro Val Thr Glu Asp Glu Ser Leu Gln Ser Leu Lys Ala
                325                 330                 335

Arg Ile Gln Gln Asp Thr Gly Ile Pro Glu Glu Asp Gln Glu Leu Leu
            340                 345                 350

Gln Glu Ala Gly Leu Ala Leu Ile Pro Asp Lys Pro Ala Thr Gln Cys
            355                 360                 365

Ile Ser Asp Gly Lys Leu Asn Glu Gly His Thr Leu Asp Met Asp Leu
            370                 375                 380

Val Phe Leu Phe Asp Asn Ser Lys Ile Thr Tyr Glu Thr Gln Ile Ser
385                 390                 395                 400

Pro Arg Pro Gln Pro Glu Ser Val Ser Cys Ile Leu Gln Glu Pro Lys
                405                 410                 415

Arg Asn Leu Ala Phe Phe Gln Leu Arg Lys Val Trp Gly Gln Val Trp
            420                 425                 430

His Ser Ile Gln Thr Leu Lys Glu Asp Cys Asn Arg Leu Gln Gln Gly
            435                 440                 445

Gln Arg Ala Ala Met Met Asn Leu Leu Arg Asn Asn Ser Cys Leu Ser
    450                 455                 460

Lys Met Lys Asn Ser Met Ala Ser Met Ser Gln Gln Leu Lys Ala Lys
465                 470                 475                 480

Leu Asp Phe Phe Lys Thr Ser Ile Gln Ile Asp Leu Glu Lys Tyr Ser
                485                 490                 495

Glu Gln Thr Glu Phe Gly Ile Thr Ser Asp Lys Leu Leu Leu Ala Trp
            500                 505                 510

Arg Glu Met Glu Gln Ala Val Glu Leu Cys Gly Arg Glu Asn Glu Val
            515                 520                 525

Lys Leu Leu Val Glu Arg Met Met Ala Leu Gln Thr Asp Ile Val Asp
    530                 535                 540

Leu Gln Arg Ser Pro Met Gly Arg Lys Gln Gly Gly Thr Leu Asp Asp
545                 550                 555                 560

Leu Glu Glu Gln Ala Arg Glu Leu Tyr Arg Arg Leu Arg Glu Lys Pro
                565                 570                 575

Arg Asp Gln Arg Thr Glu Gly Asp Ser Gln Glu Met Val Arg Leu Leu
            580                 585                 590

Leu Gln Ala Ile Gln Ser Phe Glu Lys Lys Val Arg Val Ile Tyr Thr
            595                 600                 605

Gln Leu Ser Lys Thr Val Val Cys Lys Gln Lys Ala Leu Glu Leu Leu
    610                 615                 620

Pro Lys Val Glu Glu Val Val Ser Leu Met Asn Glu Asp Glu Lys Thr
625                 630                 635                 640

Val Val Arg Leu Gln Glu Lys Arg Gln Lys Glu Leu Trp Asn Leu Leu
                645                 650                 655

Lys Ile Ala Cys Ser Lys Val Arg Gly Pro Val Ser Gly Ser Pro Asp
            660                 665                 670

Ser Met Asn Ala Ser Arg Leu Ser Gln Pro Gly Gln Leu Met Ser Gln
            675                 680                 685

Pro Ser Thr Ala Ser Asn Ser Leu Pro Glu Pro Ala Lys Lys Ser Glu
    690                 695                 700

Glu Leu Val Ala Glu Ala His Asn Leu Cys Thr Leu Leu Glu Asn Ala
705                 710                 715                 720

Ile Gln Asp Thr Val Arg Glu Gln Asp Gln Ser Phe Thr Ala Leu Asp
```

```
                 725                 730                 735
Trp Ser Trp Leu Gln Thr Glu Glu Glu His Ser Cys Leu Glu Gln
            740                 745                 750

Ala Ser

<210> SEQ ID NO 20
<211> LENGTH: 256
<212> TYPE: PRT
<213> ORGANISM: Homo sapiens

<400> SEQUENCE: 20

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
            115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
            195                 200                 205

Gly Thr Leu Ala Phe Glu Cys Ile Thr Gly Phe Arg Pro Phe Leu Pro
    210                 215                 220

Asn Trp Gln Pro Val Gln Cys Val Arg Met Trp Pro Gly Thr Val Ala
225                 230                 235                 240

His Ser Cys Asn Pro Ser Thr Leu Gly Gly Arg Gly Arg Trp Ile Ser
                245                 250                 255

<210> SEQ ID NO 21
<211> LENGTH: 697
<212> TYPE: PRT
<213> ORGANISM: Homo sapiens

<400> SEQUENCE: 21

Met Ser Ser Asp Gly Thr Ile Arg Leu Thr His Pro Asn Val Val Ala
1               5                   10                  15

Ala Arg Asp Val Pro Glu Gly Met Gln Asn Leu Ala Pro Asn Asp Leu
            20                  25                  30

Pro Leu Leu Ala Met Glu Tyr Cys Gln Gly Gly Asp Leu Arg Lys Tyr
        35                  40                  45
```

```
Leu Asn Gln Phe Glu Asn Cys Cys Gly Leu Arg Glu Gly Ala Ile Leu
    50              55              60

Thr Leu Leu Ser Asp Ile Ala Ser Ala Leu Arg Tyr Leu His Glu Asn
65              70              75              80

Arg Ile Ile His Arg Asp Leu Lys Pro Glu Asn Ile Val Leu Gln Gln
                85              90              95

Gly Glu Gln Arg Leu Ile His Lys Ile Ile Asp Leu Gly Tyr Ala Lys
            100             105             110

Glu Leu Asp Gln Gly Ser Leu Cys Thr Ser Phe Val Gly Thr Leu Gln
        115             120             125

Tyr Leu Ala Pro Glu Leu Leu Glu Gln Gln Lys Tyr Thr Val Thr Val
    130             135             140

Asp Tyr Trp Ser Phe Gly Thr Leu Ala Phe Glu Cys Ile Thr Gly Phe
145             150             155             160

Arg Pro Phe Leu Pro Asn Trp Gln Pro Val Gln Trp His Ser Lys Val
            165             170             175

Arg Gln Lys Ser Glu Val Asp Ile Val Val Ser Glu Asp Leu Asn Gly
            180             185             190

Thr Val Lys Phe Ser Ser Ser Leu Pro Tyr Pro Asn Asn Leu Asn Ser
            195             200             205

Val Leu Ala Glu Arg Leu Glu Lys Trp Leu Gln Leu Met Leu Met Trp
    210             215             220

His Pro Arg Gln Arg Gly Thr Asp Pro Thr Tyr Gly Pro Asn Gly Cys
225             230             235             240

Phe Lys Ala Leu Asp Asp Ile Leu Asn Leu Lys Leu Val His Ile Leu
            245             250             255

Asn Met Val Thr Gly Thr Ile His Thr Tyr Pro Val Thr Glu Asp Glu
            260             265             270

Ser Leu Gln Ser Leu Lys Ala Arg Ile Gln Gln Asp Thr Gly Ile Pro
            275             280             285

Glu Glu Asp Gln Glu Leu Leu Gln Glu Ala Gly Leu Ala Leu Ile Pro
    290             295             300

Asp Lys Pro Ala Thr Gln Cys Ile Ser Asp Gly Lys Leu Asn Glu Gly
305             310             315             320

His Thr Leu Asp Met Asp Leu Val Phe Leu Phe Asp Asn Ser Lys Ile
            325             330             335

Thr Tyr Glu Thr Gln Ile Ser Pro Arg Pro Gln Pro Glu Ser Val Ser
            340             345             350

Cys Ile Leu Gln Glu Pro Lys Arg Asn Leu Ala Phe Phe Gln Leu Arg
            355             360             365

Lys Val Trp Gly Gln Val Trp His Ser Ile Gln Thr Leu Lys Glu Asp
    370             375             380

Cys Asn Arg Leu Gln Gln Gly Gln Arg Ala Ala Met Met Asn Leu Leu
385             390             395             400

Arg Asn Asn Ser Cys Leu Ser Lys Met Lys Asn Ser Met Ala Ser Met
            405             410             415

Ser Gln Gln Leu Lys Ala Lys Leu Asp Phe Phe Lys Thr Ser Ile Gln
            420             425             430

Ile Asp Leu Glu Lys Tyr Ser Glu Gln Thr Glu Phe Gly Ile Thr Ser
            435             440             445

Asp Lys Leu Leu Leu Ala Trp Arg Glu Met Glu Gln Ala Val Glu Leu
    450             455             460
```

-continued

```
Cys Gly Arg Glu Asn Glu Val Lys Leu Leu Val Glu Arg Met Met Ala
465                 470                 475                 480

Leu Gln Thr Asp Ile Val Asp Leu Gln Arg Ser Pro Met Gly Arg Lys
                485                 490                 495

Gln Gly Gly Thr Leu Asp Asp Leu Glu Glu Gln Ala Arg Glu Leu Tyr
                500                 505                 510

Arg Arg Leu Arg Glu Lys Pro Arg Asp Gln Arg Thr Glu Gly Asp Ser
            515                 520                 525

Gln Glu Met Val Arg Leu Leu Leu Gln Ala Ile Gln Ser Phe Glu Lys
        530                 535                 540

Lys Val Arg Val Ile Tyr Thr Gln Leu Ser Lys Thr Val Val Cys Lys
545                 550                 555                 560

Gln Lys Ala Leu Glu Leu Leu Pro Lys Val Glu Glu Val Val Ser Leu
                565                 570                 575

Met Asn Glu Asp Glu Lys Thr Val Val Arg Leu Gln Glu Lys Arg Gln
                580                 585                 590

Lys Glu Leu Trp Asn Leu Leu Lys Ile Ala Cys Ser Lys Val Arg Gly
            595                 600                 605

Pro Val Ser Gly Ser Pro Asp Ser Met Asn Ala Ser Arg Leu Ser Gln
        610                 615                 620

Pro Gly Gln Leu Met Ser Gln Pro Ser Thr Ala Ser Asn Ser Leu Pro
625                 630                 635                 640

Glu Pro Ala Lys Lys Ser Glu Glu Leu Val Ala Glu Ala His Asn Leu
                645                 650                 655

Cys Thr Leu Leu Glu Asn Ala Ile Gln Asp Thr Val Arg Glu Gln Asp
                660                 665                 670

Gln Ser Phe Thr Ala Leu Asp Trp Ser Trp Leu Gln Thr Glu Glu Glu
            675                 680                 685

Glu His Ser Cys Leu Glu Gln Ala Ser
        690                 695

<210> SEQ ID NO 22
<211> LENGTH: 738
<212> TYPE: PRT
<213> ORGANISM: Mus musculus

<400> SEQUENCE: 22

Met Ser Trp Ser Pro Ser Leu Pro Thr Gln Thr Cys Gly Ala Trp Glu
1               5                   10                  15

Met Lys Glu Arg Leu Gly Thr Gly Gly Phe Gly Asn Val Ile Arg Trp
                20                  25                  30

His Asn Gln Ala Thr Gly Glu Gln Ile Ala Ile Lys Gln Cys Arg Gln
        35                  40                  45

Glu Leu Ser Pro Lys Asn Arg Asp Arg Trp Cys Leu Glu Ile Gln Ile
        50                  55                  60

Met Arg Arg Leu Asn His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Arg Tyr Leu Asn Gln Phe Glu
                100                 105                 110

Asn Cys Cys Gly Leu Arg Glu Gly Ala Val Leu Thr Leu Leu Ser Asp
        115                 120                 125

Ile Ala Ser Ala Leu Arg Tyr Leu His Glu Asn Arg Ile Ile His Arg
        130                 135                 140
```

-continued

```
Asp Leu Lys Pro Glu Asn Ile Val Leu Gln Gln Gly Glu Lys Arg Leu
145                 150             155             160

Ile His Lys Ile Ile Asp Leu Gly Tyr Ala Lys Glu Leu Asp Gln Gly
                165             170             175

Ser Leu Cys Thr Ser Phe Val Gly Thr Leu Gln Tyr Leu Ala Pro Glu
        180             185             190

Leu Leu Glu Gln Gln Lys Tyr Thr Val Thr Val Asp Tyr Trp Ser Phe
        195             200             205

Gly Thr Leu Ala Phe Glu Cys Ile Thr Gly Phe Arg Pro Phe Leu Pro
    210             215             220

Asn Trp Gln Pro Val Gln Trp His Ser Lys Val Arg Gln Lys Ser Glu
225                 230             235             240

Val Asp Ile Val Val Ser Glu Asp Leu Asn Gly Ala Val Lys Phe Ser
            245             250             255

Ser Ser Leu Pro Phe Pro Asn Asn Leu Asn Ser Val Leu Ala Glu Arg
        260             265             270

Leu Glu Lys Trp Leu Gln Leu Met Leu Met Trp His Pro Arg Gln Arg
        275             280             285

Gly Thr Asp Pro Gln Tyr Gly Pro Asn Gly Cys Phe Arg Ala Leu Asp
    290             295             300

Asp Ile Leu Asn Leu Lys Leu Val His Val Leu Asn Met Val Thr Gly
305                 310             315             320

Thr Val His Thr Tyr Pro Val Thr Glu Asp Glu Ser Leu Gln Ser Leu
            325             330             335

Lys Thr Arg Ile Gln Glu Asp Thr Gly Ile Leu Glu Thr Asp Gln Glu
            340             345             350

Leu Leu Gln Glu Ala Gly Leu Val Leu Leu Pro Asp Lys Pro Ala Thr
        355             360             365

Gln Cys Ile Ser Asp Ser Lys Thr Asn Glu Gly Leu Thr Leu Asp Met
    370             375             380

Asp Leu Val Phe Leu Phe Asp Asn Ser Lys Ile Asn Tyr Glu Thr Gln
385                 390             395             400

Ile Thr Pro Arg Pro Gln Pro Glu Ser Val Ser Cys Ile Leu Gln Glu
            405             410             415

Pro Lys Arg Asn Leu Ser Phe Phe Gln Leu Arg Lys Val Trp Gly Gln
            420             425             430

Val Trp His Ser Ile Gln Thr Leu Lys Glu Asp Cys Asn Arg Leu Gln
        435             440             445

Gln Gly Gln Arg Ala Ala Met Met Ser Leu Leu Arg Asn Asn Ser Cys
    450             455             460

Leu Ser Lys Met Lys Asn Ala Met Ala Ser Thr Ala Gln Gln Leu Lys
465                 470             475             480

Ala Lys Leu Asp Phe Phe Lys Thr Ser Ile Gln Ile Asp Leu Glu Lys
            485             490             495

Tyr Lys Glu Gln Thr Glu Phe Gly Ile Thr Ser Asp Lys Leu Leu Leu
            500             505             510

Ala Trp Arg Glu Met Glu Gln Ala Val Glu Gln Cys Gly Arg Glu Asn
        515             520             525

Asp Val Lys His Leu Val Glu Arg Met Met Ala Leu Gln Thr Asp Ile
    530             535             540

Val Asp Leu Gln Arg Ser Pro Met Gly Arg Lys Gln Gly Gly Thr Leu
545                 550             555             560
```

-continued

```
Asp Asp Leu Glu Glu Gln Ala Arg Glu Leu Tyr Arg Arg Leu Arg Glu
            565                 570                 575

Lys Pro Arg Asp Gln Arg Thr Glu Gly Asp Ser Gln Glu Met Val Arg
        580                 585                 590

Leu Leu Leu Gln Ala Ile Gln Ser Phe Glu Lys Lys Val Arg Val Ile
            595                 600                 605

Tyr Thr Gln Leu Ser Lys Thr Val Val Cys Lys Gln Lys Ala Leu Glu
        610                 615                 620

Leu Leu Pro Lys Val Glu Glu Val Val Ser Leu Met Asn Glu Asp Glu
625                 630                 635                 640

Arg Thr Val Val Arg Leu Gln Glu Lys Arg Gln Lys Glu Leu Trp Asn
            645                 650                 655

Leu Leu Lys Ile Ala Cys Ser Lys Val Arg Gly Pro Val Ser Gly Ser
            660                 665                 670

Pro Asp Ser Met Asn Val Ser Arg Leu Ser His Pro Gly Gln Leu Met
        675                 680                 685

Ser Gln Pro Ser Ser Ala Cys Asp Ser Leu Pro Glu Ser Asp Lys Lys
        690                 695                 700

Ser Glu Glu Leu Val Ala Glu Ala His Ala Leu Cys Ser Arg Leu Glu
705                 710                 715                 720

Ser Ala Leu Gln Asp Thr Val Lys Glu Gln Asp Arg Ser Phe Thr Val
            725                 730                 735

Thr Ala
```

```
<210> SEQ ID NO 23
<211> LENGTH: 1497
<212> TYPE: DNA
<213> ORGANISM: Homo sapiens

<400> SEQUENCE: 23
atgaaccagt ccatcccagt ggctcccacc ccacccccgcc gcgtgcggct gaagccctgg      60
ctggtggccc aggtgaacag ctgccagtac ccagggcttc aatgggtcaa cggggaaaag     120
aaattattct gcatcccctg gaggcatgcc acaaggcatg gtcccagcca ggacggagat     180
aacaccatct tcaaggcctg ggccaaggag acagggaaat acaccgaagg cgtggatgaa     240
gccgatccgg ccaagtggaa ggccaacctg cgctgtgccc ttaacaagag ccgggacttc     300
cgcctcatct acgacgggcc ccgggacatg ccacctcagc cctacaagat ctacgaggtc     360
tgctccaatg ccctgctcc cacagactcc cagcccctg aggattactc ttttggtgca     420
ggagaggagg aggaagaaga ggaagagctg cagaggatgt gccaagcct gagcctcaca     480 gaggatgtca agtggccgcc cactctgcag ccgcccactc tgcggccgcc tactctgcag     540
ccgcccactc tgcagccgcc cgtggtgctg gtccccctg ctccagaccc cagcccctg     600 gctcctcccc ctggcaaccc tgctggcttc agggagcttc tctctgaggt cctggagcct     660
gggcccctgc ctgccagcct gcccctgca ggcgaacagc tcctgccaga cctgctgatc     720
agcccccaca tgctgcctct gaccgacctg gagatcaagt ttcagtaccg ggggcggcca     780
ccccgggccc tcaccatcag caaccccat ggctgccggc tcttctacag ccagctggag     840
gccacccagg agcaggtgga actcttcggc cccataagcc tggagcaagt gcgcttcccc     900
agccctgagg acatccccag tgacaagcag cgcttctaca cgaaccagct gctggatgtc     960
ctggaccgcg ggctcatcct ccagctacag ggccaggacc tttatgccat ccgcctgtgt    1020
cagtgcaagg tgttctggag cgggccttgt gcctcagccc atgactcatg ccccaacccc    1080
```

-continued

```
atccagcggg aggtcaagac caagcttttc agcctggagc attttctcaa tgagctcatc   1140
ctgttccaaa agggccagac caacacccca ccacccttcg agatcttctt ctgctttggg   1200
gaagaatggc ctgaccgcaa accccgagag aagaagctca ttactgtaca ggtggtgcct   1260
gtagcagctc gactgctgct ggagatgttc tcaggggagc tatcttggtc agctgatagt   1320
atccggctac agatctcaaa cccagacctc aaagaccgca tggtggagca attcaaggag   1380
ctccatcaca tctggcagtc ccagcagcgg ttgcagcctg tggcccaggc ccctcctgga   1440
gcaggccttg gtgttggcca ggggccctgg cctatgcacc cagctggcat gcaataa       1497
```

<210> SEQ ID NO 24
<211> LENGTH: 1545
<212> TYPE: DNA
<213> ORGANISM: Homo sapiens

<400> SEQUENCE: 24

```
atgaaccagt ccatcccagt ggctcccacc ccaccccgcc gcgtgcggct gaagccctgg     60
ctggtggccc aggtgaacag ctgccagtac ccagggcttc aatgggtcaa cggggaaaag    120
aaattattct gcatcccctg gaggcatgcc acaaggcatg gtcccagcca ggacggagat    180
aacaccatct tcaaggcctg ggccaaggag acagggaaat acaccgaagg cgtggatgaa    240
gccgatccgg ccaagtggaa ggccaacctg cgctgtgccc ttaacaagag ccgggacttc    300
cgcctcatct acgacgggcc ccgggacatg ccacctcagc cctacaagat ctacgaggtc    360
tgctccaatg ccctgctcc cacagactcc cagcccctg aggattactc ttttggtgca     420
ggagaggagg aggaagaaga ggaagagctg cagaggatgt tgccaagcct gagcctcaca    480
gatgcagtgc agtctggccc ccacatgaca ccctattctt tactcaaaga ggatgtcaag    540
tggccgccca ctctgcagcc gcccactctg cggccgccta ctctgcagcc gcccactctg    600
cagccgcccg tggtgctggg tccccctgct ccagacccca gcccctggc tcctcccct     660 ggcaaccctg ctggcttcag ggagcttctc tctgaggtcc tggagcctgg gccctgcct     720 gccagcctgc ccctgcagg cgaacagctc ctgccagacc tgctgatcag cccccacatg    780
ctgcctctga ccgacctgga gatcaagttt cagtaccggg ggcggccacc ccgggccctc    840
accatcagca accccatgg ctgccggctc ttctacagcc agctggaggc cacccaggag    900
caggtggaac tcttcggccc cataagcctg gagcaagtgc gcttccccag ccctgaggac    960
atccccagtg acaagcagcg cttctacacg aaccagctgc tggatgtcct ggaccgcggg   1020
ctcatcctcc agctacaggg ccaggacctt tatgccatcc gcctgtgtca gtgcaaggtg   1080
ttctggagcg ggccttgtgc ctcagcccat gactcatgcc ccaaccccat ccagcgggag   1140
gtcaagacca agcttttcag cctggagcat tttctcaatg agctcatcct gttccaaaag   1200
ggccagacca acaccccacc acccttcgag atcttcttct gctttgggga agaatggcct   1260
gaccgcaaac cccgagagaa gaagctcatt actgtacagg tggtgcctgt agcagctcga   1320
ctgctgctgg agatgttctc aggggagcta tcttggtcag ctgatagtat ccggctacag   1380
atctcaaacc cagacctcaa agaccgcatg gtggagcaat caaggagct ccatcacatc    1440 tggcagtccc agcagcggtt gcagcctgtg cccaggccc ctcctggagc aggccttggt    1500
gttggccagg ggccctggcc tatgcaccca gctggcatgc aataa                     1545
```

<210> SEQ ID NO 25
<211> LENGTH: 1514
<212> TYPE: DNA
<213> ORGANISM: Homo sapiens

<400> SEQUENCE: 25

```
atgaaccagt ccatcccagt ggctcccacc ccaccccgcc gcgtgcggct gaagccctgg     60
ctggtggccc aggtgaacag ctgccagtac ccagggcttc aatgggtcaa cggggaaaag    120
aaattattct gcatcccctg gaggcatgcc acaaggcatg gtcccagcca ggacggagat    180
aacaccatct tcaaggcctg ggccaaggag acagggaaat acaccgaagg cgtggatgaa    240
gccgatccgg ccaagggaag gccaacctgc gctgtgccct aacaagagc cgggacttcc    300 gcctcatcta cgacgggccc cgggacatgc cacctcagcc ctacaagatc tacgaggtct    360
gctccaatgg ccctgctccc acagactccc agcccctga ggattactct tttggtgcag    420
gagaggagga ggaagaagag gaagagctgc agaggatgtt gccaagcctg agcctcacag    480
atgcagtgca gtctggcccc acatgacac cctattcttt actcaaagag gatgtcaagt    540
ggccgcccac tctgcagccg cccactctgc agccgcccgt ggtgctgggt cccctgctc    600 cagaccccag cccctggct cctccccctg gcaaccctgc tggcttcagg gagcttctct    660
ctgaggtcct ggagcctggg cccctgcctg ccagcctgcc ccctgcaggc gaacagctcc    720
tgccagacct gctgatcagc ccccacatgc tgcctctgac cgacctggag atcaagtttc    780
agtaccgggg gcggccaccc cgggccctca ccatcagcaa cccccatggc tgccggctct    840
tctacagcca gctggaggcc acccaggagc aggtggaact cttcggcccc ataagcctgg    900
agcaagtgcg cttccccagc cctgaggaca tccccagtga caagcagcgc ttctacacga    960
accagctgct ggatgtcctg gaccgcgggc tcatcctcca gctacagggc caggacctttt   1020 atgccatccg cctgtgtcag tgcaaggtgt tctggagcgg gccttgtgcc tcagcccatg   1080
actcatgccc caaccccatc cagcgggagg tcaagaccaa gcttttcagc ctggagcatt   1140
ttctcaatga gctcatcctg ttccaaaagg gccagaccaa cacccccacca cccttcgaga   1200 tcttcttctg ctttgggga gaatggcctg accgcaaacc ccgagagaag aagctcatta   1260
ctgtacaggt ggtgcctgta gcagctcgac tgctgctgga gatgttctca ggggagctat   1320
cttggtcagc tgatagtatc cggctacaga tctcaaaccc agacctcaaa gaccgcatgg   1380
tggagcaatt caaggagctc catcacatct ggcagtccca gcagcggttg cagcctgtgg   1440
cccaggcccc tcctggagca ggccttggtg ttggccaggg gccctggcct atgcacccag   1500
ctggcatgca ataa                                                     1514
```

<210> SEQ ID NO 26
<211> LENGTH: 1467
<212> TYPE: DNA
<213> ORGANISM: Homo sapiens

<400> SEQUENCE: 26

```
atgaaccagt ccatcccagt ggctcccacc ccaccccgcc gcgtgcggct gaagccctgg     60
ctggtggccc aggtgaacag ctgccagtac ccagggcttc aatgggtcaa cggggaaaag    120
aaattattct gcatcccctg gaggcatgcc acaaggcatg gtcccagcca ggacggagat    180
aacaccatct tcaaggcctg ggccaaggag acagggaaat acaccgaagg cgtggatgaa    240
gccgatccgg ccaagtggaa ggccaacctg cgctgtgccc ttaacaagag ccgggacttc    300
cgcctcatct acgacgggcc ccgggacatg ccacctcagc cctacaagat ctacgaggtc    360
tgctccaatg gccctgctcc cacagactcc cagcccctg aggattactc ttttggtgca    420
ggagaggagg aggaagaaga ggaagagctg cagaggatgt tgccaagcct gagcctcaca    480
```

-continued

```
gaggatgtca agtggccgcc cactctgcag ccgcccactc tgcagccgcc cgtggtgctg      540 ggtcccctg ctccagaccc cagccccctg gctcctcccc ctggcaaccc tgctggcttc       600
agggagcttc tctctgaggt cctggagcct gggcccctgc ctgccagcct gccccctgca      660
ggcgaacagc tcctgccaga cctgctgatc agccccaca tgctgcctct gaccgacctg       720
gagatcaagt ttcagtaccg ggggcggcca ccccgggccc tcaccatcag caacccccat      780
ggctgccggc tcttctacag ccagctggag gccacccagg agcaggtgga actcttcggc      840
cccataagcc tggagcaagt gcgcttcccc agccctgagg acatccccag tgacaagcag      900
cgcttctaca cgaaccagct gctggatgtc ctggaccgcg ggctcatcct ccagctacag      960
ggccaggacc tttatgccat ccgcctgtgt cagtgcaagg tgttctggag cgggccttgt     1020
gcctcagccc atgactcatg ccccaacccc atccagcggg aggtcaagac caagcttttc     1080
agcctggagc attttctcaa tgagctcatc ctgttccaaa agggccagac caacacccca     1140
ccacccttcg agatcttctt ctgctttggg aagaatggc ctgaccgcaa accccgagag      1200
aagaagctca ttactgtaca ggtggtgcct gtagcagctc gactgctgct ggagatgttc     1260
tcaggggagc tatcttggtc agctgatagt atccggctac agatctcaaa cccagacctc     1320
aaagaccgca tggtggagca attcaaggag ctccatcaca tctggcagtc ccagcagcgg     1380
ttgcagcctg tggcccaggc ccctcctgga gcaggccttg gtgttggcca ggggccctgg     1440
cctatgcacc cagctggcat gcaataa                                         1467
```

```
<210> SEQ ID NO 27
<211> LENGTH: 1239
<212> TYPE: DNA
<213> ORGANISM: Homo sapiens

<400> SEQUENCE: 27
```

```
atgaaccagt ccatcccagt ggctcccacc ccaccccgcc gcgtgcggct gaagccctgg       60
ctggtggccc aggtgaacag ctgccagtac ccagggcttc aatgggtcaa cggggaaaag      120
aaattattct gcatcccctg gaggcatgcc acaaggcatg gtcccagcca ggacggagat      180
aacaccatct tcaaggcctg ggccaaggag acagggaaat acaccgaagg cgtggatgaa      240
gccgatccgg ccaagtggaa ggccaacctg cgctgtgccc ttaacaagag ccgggacttc      300
cgcctcatct acgacgggcc ccgggacatg ccacctcagc cctacaagat ctacgaggtc      360
tgctccaatg ccctgctcc cacagactcc cagcccctg aggattactc ttttggtgca        420
ggagaggagg aggaagaaga ggaagagctg cagaggatgt tgccaagcct gagcctcaca      480
gtgaccgacc tggagatcaa gtttcagtac cggggggcggc caccccgggc cctcaccatc      540 agcaacccc atggctgccg gctcttctac agccagctgg aggccaccca ggagcaggtg      600
gaactcttcg cccccataag cctggagcaa gtgcgcttcc ccagccctga ggacatcccc      660
agtgacaagc agcgcttcta cacgaaccag ctgctggatg tcctggaccg cgggctcatc      720
ctccagctac agggccagga cctttatgcc atccgcctgt gtcagtgcaa ggtgttctgg      780
agcgggcctt gtgcctcagc ccatgactca tgccccaacc ccatccagcg ggaggtcaag      840
accaagcttt tcagcctgga gcattttctc aatgagctca tcctgttcca aaagggccag      900
accaacaccc caccacccctt cgagatcttc ttctgctttg gggaagaatg gcctgaccgc      960
aaaccccgag agaagaagct cattactgta caggtggtgc ctgtagcagc tcgactgctg     1020
ctggagatgt tctcaggggga gctatcttgg tcagctgata gtatccggct acagatctca     1080
aacccagacc tcaaagaccg catggtggag caattcaagg agctccatca catctggcag     1140
```

-continued

```
tcccagcagc ggttgcagcc tgtggcccag gcccctcctg gagcaggcct tggtgttggc       1200
caggggccct ggcctatgca cccagctggc atgcaataa                             1239

<210> SEQ ID NO 28
<211> LENGTH: 444
<212> TYPE: DNA
<213> ORGANISM: Homo sapiens

<400> SEQUENCE: 28
atgaaccagt ccatcccagt ggctcccacc ccaccccgcc gcgtgcggct gaagccctgg        60
ctggtggccc aggtgaacag ctgccagtac ccagggcttc aatgggtcaa cggggaaaag       120
aaattattct gcatccctg gaggcatgcc acaaggcatg gtcccagcca ggacggagat        180
aacaccatct tcaaggcctg ggccaaggag acagggaaat acaccgaagg cgtggatgaa       240
gccgatccgg ccaagtggaa ggccaacctg cgctgtgccc ttaacaagag ccgggacttc       300
cgcctcatct acgacgggcc ccgggacatg ccacctcagc cctacaagat ctacgagact       360
cccagccccc tgaggattac tcttttggtg caggagagga ggaggaagaa gaggaagagc       420
tgcagaggat gttgccaagc ctga                                            444

<210> SEQ ID NO 29
<211> LENGTH: 1494
<212> TYPE: DNA
<213> ORGANISM: Mus musculus

<400> SEQUENCE: 29
atgaatcata gtgcacccgg gatccctcct cctccaagac gagtacgcct caagccctgg        60
ttggtagctc aagtcaactc atgccaatac cctgggcttc agtgggtgaa cggtgagaag       120
aaattgtttt atatcccatg gcgacacgca acaagacatg gcccatcaca ggatggagat       180
aacaccatat ttaaggcatg ggcaaaggaa acaggaaagt acactgaggg cgttgatgag       240
gccgatcctg caaaatggaa agcaaatttg cgatgcgctc tcaataaatc acgagatttc       300
caactctttt acgacggccc aagggacatg ccaccacaac cttataaaat ctacgaggta       360
tgttccaacg gtccagcccc aactgaatcc cagcctactg acgactatgt ccttggagaa       420
gaggaggaag aagaagagga ggaacttcag cggatgttgc ctgggttgtc cataactgag       480
cctgccttgc caggacccc taatgcacca tactcccttc ccaaagaaga tacaaaatgg       540 cccccccgcat tgcaacccccc cgttggtttg ggaccacctg tgcccgaccc aaatctcttg       600
gccccaccaa gcggtaaccc agccggattt cgacaacttc tgcccgaagt ccttgagcca       660
ggtcccttgg cctcttctca gcccctaca gaacctctgc tccccgatct cttgatatct       720
ccccacatgc ttcccttgac tgatttggag ataaaatttc agtatcgcgg ccgagctccc       780
agaacactga ctatatcaaa tccccaaggt tgccgcctgt tttacagtca gttggaggca       840
actcaggagc aagtagagct ctttgggcca gttactctgg agcaggtgag attccctagt       900
ccagaggaca taccaagcga taagcaaaga ttttacacaa atcaacttct ggatgtactt       960
gatcgaggtt tgatccttca gttgcagggc caagatttgt atgccattcg actctgtcaa      1020
tgcaaggtat tttggagcgg cccatgtgcc cttgctcatg gcagctgccc taatcccatc      1080
caaagagaag taaagactaa acttttcagc ctggaacaat ttctcaacga actcattctg      1140
tttcaaaaag gtcagaccaa cacacccct cctttcgaga ttttcttctg cttcggcgaa      1200
gagtggcctg atgtgaagcc ccgcgaaaaa aagcttatca ccgttcaagt ggtacccgtc      1260
```

-continued

```
gcagccaggc tccttcttga aatgtttagc ggtgaactct catggtccgc tgacagtatc    1320
cggctccaaa tatcaaaccc tgatcttaaa gaccacatgg tagaacagtt taaagaactc    1380
caccacctgt ggcaatccca acagcagctc cagccaatgg ttcaagctcc tccagtcgct    1440
gggctggacg cctcacaagg accctggccc atgcaccccg tcgggatgca gtaa          1494

<210> SEQ ID NO 30
<211> LENGTH: 978
<212> TYPE: DNA
<213> ORGANISM: Homo sapiens

<400> SEQUENCE: 30
atgcccatca ctcggatgcg catgagaccc tggctagaga tgcagattaa ttccaaccaa     60
atcccggggc tcatctggat taataaagag gagatgatct tccagatccc atggaagcat    120
gctgccaagc atggctggga catcaacaag gatgcctgtt tgttccggag ctgggccatt    180
cacacaggcc gatacaaagc agggggaaag gagccagatc ccaagacgtg gaaggccaac    240
tttcgctgtg ccatgaactc cctgccagat atcgaggagg tgaaagacca gagcaggaac    300
aagggcagct cagctgtgcg agtgtaccgg atgcttccac ctctcaccaa gaaccagaga    360
aaagaaagaa agtcgaagtc cagccgagat gctaagagca aggccaagag gaagtcatgt    420
ggggattcca gccctgatac cttctctgat ggactcagca gctccactct gcctgatgac    480
cacagcagct acacagttcc aggctacatg caggacttgg aggtggagca ggccctgact    540
ccagcactgt cgccatgtgc tgtcagcagc actctccccg actggcacat cccagtggaa    600
gttgtgccgg acagcaccag tgatctgtac aacttccagg tgtcacccat gccctccacc    660
tctgaagcta aacagatga ggatgaggaa gggaaattac ctgaggacat catgaagctc    720
ttggagcagt cggagtggca gccaacaaac gtggatggga aggggtacct actcaatgaa    780
cctggagtcc agcccacctc tgtctatgga gactttagct gtaaggagga gccagaaatt    840
gacagcccag gggggatat tgggctgagt ctacagcgtg tcttcacaga tctgaagaac    900
atggatgcca cctggctgga cagcctgctg accccagtcc ggttgccctc catccaggcc    960
attccctgtg caccgtag                                                  978

<210> SEQ ID NO 31
<211> LENGTH: 1284
<212> TYPE: DNA
<213> ORGANISM: Homo sapiens

<400> SEQUENCE: 31
atgggaaccc caaagccacg gatcctgccc tggctggtgt cgcagctgga cctggggcaa     60
ctggagggcg tggcctgggt gaacaagagc cgcacgcgct tccgcatccc ttggaagcac    120
ggcctacggc aggatgcaca gcaggaggat ttcggaatct tccaggcctg ggccgaggcc    180
actggtgcat atgttcccgg gagggataag ccagacctgc caacctggaa gaggaatttc    240
cgctctgccc tcaaccgcaa agaagggttg cgtttagcag aggaccggag caaggaccct    300
cacgacccac ataaaatcta cgagtttgtg aactcaggag ttggggactt ttcccagcca    360
gacacctctc cggacaccaa tggtggaggc agtacttctg atacccagga agacattctg    420
gatgagttac tgggtaacat ggtgttggcc ccactcccag atccgggacc cccaagcctg    480
gctgtagccc ctgagccctg ccctcagccc ctgcggagcc ccagcttgga caatcccact    540
cccttcccaa acctggggcc ctctgagaac ccactgaagc ggctgttggt gccggggggaa    600 gagtgggagt cgaggtgac agccttctac cggggccgcc aagtcttcca gcagaccatc    660
```

-continued

```
tcctgcccgg agggcctgcg gctggtgggg tccgaagtgg gagacaggac gctgcctgga          720
tggccagtca cactgccaga ccctggcatg tccctgacag acaggggagt gatgagctac          780
gtgaggcatg tgctgagctg cctgggtggg ggactggctc tctggcgggc cgggcagtgg          840
ctctgggccc agcggctggg gcactgccac acatactggg cagtgagcga ggagctgctc          900
cccaacagcg ggcatgggcc tgatggcgag gtccccaagg acaaggaagg aggcgtgttt          960
gacctggggc ccttcattgt agatctgatt accttcacgg aaggaagcgg acgctcacca         1020
cgctatgccc tctggttctg tgtgggggag tcatggcccc aggaccagcc gtggaccaag         1080
aggctcgtga tggtcaaggt tgtgcccacg tgcctcaggg ccttggtaga aatggcccgg         1140
gtagggggtg cctcctccct ggagaatact gtggacctgc acatttccaa cagccaccca         1200
ctctccctca cctccgacca gtacaaggcc tacctgcagg acttggtgga gggcatggat         1260
ttccagggcc ctggggagag ctga                                                 1284
```

```
<210> SEQ ID NO 32
<211> LENGTH: 1512
<212> TYPE: DNA
<213> ORGANISM: Homo sapiens

<400> SEQUENCE: 32
```

```
atggccttgg ctcctgagag ggcagcccca cgcgtgctgt tcggagagtg gctccttgga           60
gagatcagca gcggctgcta tgaggggctg cagtggctgg acgaggcccg cacctgtttc          120
cgcgtgccct ggaagcactt cgcgcgcaag gacctgagcg aggccgacgc gcgcatcttc          180
aaggcctggg ctgtggcccg cggcaggtgg ccgcctagca gcaggggagg tggcccgccc          240
cccgaggctg agactgcgga gcgcgccggc tggaaaacca acttccgctg cgcactgcgc          300
agcacgcgtc gcttcgtgat gctgcgggat aactcggggg acccggccga cccgcacaag          360
gtgtacgcgc tcagccggga gctgtgctgg cgagaaggcc caggcacgga ccagactgag          420
gcagaggccc ccgcagctgt cccaccacca cagggtgggc ccccagggcc attcctggca          480
cacacacatg ctggactcca agccccaggc ccctccctg cccagctgg tgacaagggg           540 gacctcctgc tccaggcagt gcaacagagc tgcctggcag accatctgct gacagcgtca          600
tggggggcag atccagtccc aaccaaggct cctggagagg acaagaagg gcttcccctg           660 actggggcct gtgctggagg cccagggctc cctgctgggg agctgtacgg gtgggcagta          720
gagacgaccc ccagccccgg gccccagccc gcggcactaa cgacaggcga ggccgcggcc          780
ccagagtccc cgcaccaggc agagccgtac ctgtcaccct ccccaagcgc ctgcaccgcg          840
gtgcaagagc ccagcccagg ggcgctggac gtgaccatca tgtacaaggg ccgcacggtg          900
ctgcagaagg tggtgggaca cccgagctgc acgttcctat acggccccc agacccagct          960 gtccgggcca cagaccccca gcaggtagca ttccccagcc ctgccgagct cccggaccag         1020
aagcagctgc gctacacgga ggaactgctg cggcacgtgg cccctgggtt gcacctggag         1080
cttcgggggc cacagctgtg ggcccggcgc atgggcaagt gcaaggtgta ctgggaggtg         1140
ggcggacccc caggctccgc cagcccctcc accccagcct gcctgctgcc tcggaactgt         1200 gacacccca tcttcgactt cagagtcttc ttccaagagc tggtggaatt ccgggcacgg         1260
cagcgccgtg gctccccacg ctataccatc tacctgggct tcgggcagga cctgtcagct         1320
gggaggccca aggagaagag cctggtcctg gtgaagctgg aaccctggct gtgccgagtg         1380
cacctagagg gcacgcagcg tgagggtgtg tcttccctgg atagcagcag cctcagcctc         1440
```

-continued

```
tgcctgtcca gcgccaacag cctctatgac gacatcgagt gcttccttat ggagctggag    1500
cagcccgcct ag                                                        1512

<210> SEQ ID NO 33
<211> LENGTH: 1281
<212> TYPE: DNA
<213> ORGANISM: Homo sapiens

<400> SEQUENCE: 33
atgtgtgacc ggaatggtgg tcggcggctt cgacagtggc tgatcgagca gattgacagt      60
agcatgtatc caggactgat ttgggagaat gaggagaaga gcatgttccg gatcccttgg     120
aaacacgctg gcaagcaaga ttataatcag gaagtggatg cctccatttt taaggcctgg     180
gcagttttta aagggaagtt taaagaaggg gacaaagctg aaccagccac ttggaagacg     240
aggttacgct gtgctttgaa taagagccca gattttgagg aagtgacgga ccggtcccaa     300
ctggacattt ccgagccata caaagtttac cgaattgttc ctgaggaaga gcaaaaatgc     360
aaactaggcg tggcaactgc tggctgcgtg aatgaagtta cagagatgga gtgcggtcgc     420
tctgaaatcg acgagctgat caaggagcct tctgtggacg attacatggg gatgatcaaa     480 aggagcccctt ccccgccgga ggcctgtcgg agtcagctcc ttccagactg gtgggcgcag     540
cagcccagca caggcgtgcc gctggtgacg gggtacacca cctacgacgc gcaccattca     600
gcattctccc agatggtgat cagcttctac tatggggggca agctggtggg ccaggccacc     660
accacctgcc ccgagggctg ccgcctgtcc ctgagccagc ctgggctgcc cggcaccaag     720
ctgtatgggc ccgagggcct ggagctggtg cgcttcccgc cggccgacgc catccccagc     780
gagcgacaga ggcaggtgac gcggaagctg ttcgggcacc tggagcgcgg ggtgctgctg     840
cacagcagcc ggcaggcgt gttcgtcaag cggctgtgcc agggccgcgt gttctgcagc     900
ggcaacgccg tggtgtgcaa aggcaggccc aacaagctgg agcgtgatga ggtggtccag     960
gtcttcgaca ccagccagtt cttccgagag ctgcagcagt ctataacag ccagggccgg    1020 cttcctgacg gcagggtggt gctgtgcttt ggggaagagt ttccggatat ggcccccttg    1080
cgctccaaac tcattctcgt gcagattgag cagctgtatg tccggcaact ggcagaagag    1140
gctgggaaga gctgtggagc cggctctgtg atgcaggccc ccgaggagcc gccgccagac    1200
caggtcttcc ggatgtttcc agatatttgt gcctcacacc agagatcatt tttcagagaa    1260
aaccaacaga tcaccgtcta a                                             1281

<210> SEQ ID NO 34
<211> LENGTH: 990
<212> TYPE: DNA
<213> ORGANISM: Mus musculus

<400> SEQUENCE: 34
atgccaatca ctcgaatgcg gatgagaccc tggctagaga tgcagattaa ttccaaccaa      60
atcccagggc tgatctggat caataaagaa gagatgatct tccagattcc atggaagcac     120
gctgctaagc acggctggga catcaacaag gatgcctgtc tgttccggag ctgggccatt     180
cacacaggcc gatacaaagc aggagaaaaa gagccagatc ccaagacatg gaaggcaaac     240
ttccgttgtg ccatgaactc cctgccagac atcgaggaag tgaaggatca gagtaggaac     300
aagggcagct ctgctgtgcg ggtgtaccgg atgctgccac ccctcaccag gaaccagagg     360
aaagagagaa agtccaagtc cagccgagac actaagagca aaaccaagag gaagctgtgt     420
ggagatgtta gcccggacac tttctctgat ggactcagca gctctaccct acctgatgac     480
```

-continued

```
cacagcagtt acaccactca gggctacctg ggtcaggact tggatatgga aagggacata      540
actccagcac tgtcaccgtg tgtcgtcagc agcagtctct ctgagtggca tatgcagatg      600
gacattatac cagatagcac cactgatctg tataacctac aggtgtcacc catgccttcc      660
acctccgaag ccgcaacaga cgaggatgag gaagggaaga tagccgaaga ccttatgaag      720
ctctttgaac agtctgagtg gcagccgaca cacatcgatg gcaagggata cttgctcaat      780
gagccaggga cccagctctc ttctgtctat ggagacttca gctgcaaaga ggaaccagag      840
attgacagcc ctcgagggga cattgggata ggcatacaac atgtcttcac ggagatgaag      900
aatatggact ccatcatgtg gatggacagc ctgctgggca actctgtgag gctgccgccc      960
tctattcagg ccattccttg tgcaccatag                                       990
```

```
<210> SEQ ID NO 35
<211> LENGTH: 1260
<212> TYPE: DNA
<213> ORGANISM: Mus musculus

<400> SEQUENCE: 35
```

```
atggaaaccc cgaaaccgcg gatttttgccc tggctggtgt cacagctgga cctggggcag       60
ctggaaggcg tggcctggct ggacgagagc cgaacgaggt tcaggatccc gtggaagcat      120
ggcctacggc aggacgcaca gatggctgac tttggcatct tccaggcctg ggcagaagcc      180
agtggtgcct acaccccggg gaaggataag ccggacgtgt caacctggaa gaggaatttc      240
cggtcagccc tgaaccggaa agaagtgttg cggttagctg ctgacaatag caaggaccct      300
tatgaccctc ataaagtgta tgagtttgtg actccagggg cgcgggactt cgtacatctg      360
ggtgcctctc ctgacaccaa tggcaaaagc agcctgcctc actcccagga aaacctaccg      420
aagttatttg atggcctgat cttggggccc ctcaaagatg aggggtcctc agatctggct      480
attgtttctg atccttctca caactgcca agccccaatg tgaacaactt cctaaaccct      540
gcaccccaag aaaatccact gaagcagctg ctagctgagg aacaatggga gttcgaggtg      600
accgccttct accgaggccg ccaggtcttc agcagacac tcttttgccc ggggggcctg      660
cggctggtgg gcagcacagc tgacatgaca ctgccctggc agccagtcac cctgcccgat      720
cctgaggggt ttctgacgga caagcttgtg aaggagtacg tggggcaggt gctcaaaggg      780
ctgggcaatg ggctggcact gtggcaggct gggcagtgcc tctgggccca gcgcctaggc      840
cactcccacg ccttctgggc tctgggggag gagctgcttc cagacagtgg gcgagggcct      900
gatggagagg tccacaagga caaggacgga gccgtgttcg acctcaggcc cttcgtggca      960
gatctgattg ccttcatgga aggaagtgga cactccccac gctacactct gtggttctgc     1020
atgggggaaa tgtggcccca ggaccagcca tgggtcaaga ggcttgtgat ggtcaaggtt     1080
gttcctacat gtcttaagga gctgttagag atggcccggg aagggggagc ctcttcactg     1140
aaaaccgtgg acttgcacat tccaacagc agcctatct cccttacctc tgaccagtac       1200
aaggcctacc tccaggactt ggtggaggac atggacttcc aggccactgg aaatatctga     1260
```

```
<210> SEQ ID NO 36
<211> LENGTH: 1374
<212> TYPE: DNA
<213> ORGANISM: Mus musculus

<400> SEQUENCE: 36
```

```
atggctgaag tgaggggggt ccagcgagtg ctgtttggag actggctatt ggggggaggtc       60
```

```
agcagcggcc agtacgaggg gctgcagtgg ctgaacgagg ctcgcacagt cttccgcgta      120
ccctggaagc atttcggtcg tagggatctg gatgaagaag atgcacagat cttcaaggcc      180
tgggctgtgg cccgagggag gtggccacct agtggagtta acctgccacc cccagaggct      240
gaggctgctg agcgaagaga gcgaagaggc tggaagacca acttccgctg tgcactccac      300
agcacagggc gttttatctt gcgccaagac aattcagggg atccagttga tccgcataag      360
gtgtacgaac ttagccggga gcttggatct actgtgggcc cagccacgga aaatagggaa      420
gaagtgagcc tcagcaatgc tctgcccaca cagggtgtgt ccccaggatc atttctggca      480
agagaaaatg ctgggctcca aaccccaagc cctctgcttt ctagtgatgc cggggacctc      540
ttgcttcagg ttctgcagta cagccacata ctggaatccg agtctggggc agaccccgtc      600
ccaccacagg ctcctggcca ggagcaagac cgtgtttacg aggaacccta tgcagcatgg      660
caggtggaag ctgtccccag tcccaggcct caacagccag ctctcaccga gcgcagcctt      720
gggttcctgg atgtgaccat catgtacaag ggccgcacag tgctacaggc agtggtgggg      780 cacccccagat gcgtgttcct gtacagcccc atggcccccag cagtaagaac ttcagagccc      840
cagccggtga tctttcccag tcctgctgag ctcccagatc agaagcagct gcactacaca      900
gagacgcttc tccagcatgt gtctcccggc cttcagctgg agcttcgagg accgtcactg      960
tgggccctgc gtatgggcaa gtgcaaggtg tactgggagg taggcagccc tatgggcact     1020
accggcccct ccacccacc ccagctgctg gagcgcaacc gccacacccc catcttcgac     1080
ttcagcactt tcttccgaga actggaggag tttcgggctc ggaggcggca agggtcacca     1140
cactacacca tctacctggg ttttgggcaa gacttgtcag cagggaggcc caaggagaag     1200
accctgatcc tggtgaagct ggagccatgg gtatgcaagg catacctgga gggcgtgcag     1260
cgtgagggtg tgtcctccct ggacagcagc agtctcggct tgtgcttgtc tagcaccaac     1320
agtctctacg aagacatcga acacttcctc atggacctgg gtcagtggcc ttga          1374
```

```
<210> SEQ ID NO 37
<211> LENGTH: 1578
<212> TYPE: DNA
<213> ORGANISM: Mus musculus

<400> SEQUENCE: 37
atggccgaag ttcgaggagt acagcgcgtg ctgtttgggg actggttgct tggtgaagtc       60
tcttctggtc agtatgaagg cctgcaatgg cttaatgagg cacgcacagt ttttcgagtg      120
ccatggaaac acttcggtag gcgcgatctc gacgaagagg atgcccagat tttcaaggca      180
tgggcagtcg cacgggggcag gtggccccct tcaggcgtaa atttgccccc cccagaggct      240
gaagctgctg aacgcagaga acgccgggga tggaagacta actttcgatg tgcccttcac      300
agtacaggca ggttcatctt gcggcaggat aatagtggcg accctgtaga cccacacaag      360
gtttatgagc tgagccggga gcttggctca acagtcggtc ctgcaaccga gaacagagaa      420
gaggtgtcct tgtctaacgc cctcccaact cagggtgtgt ctcccggtag cttcctggca      480
cgcgaaaacg ctggactcca aaccccctcc ccactgttgt ccagtgatgc cggtgatctt      540
ctccttcagt tgctccaata ctcccatata ctggagagcg agtcagggc tgatcccgtg      600 cccccctcaag ctcctggaca ggaacaagat cgcgtctacg aggagccata tgctgcctgg      660
caggtcgagg ctgtgccatc acctcggcct caacagcccg ctctcaccga gcgctcactt      720
gggtttttgg atgtcactaa actttttcgac ggcctgatac ttggcccatt gaaggacgag      780
ggatcatccg atcttgccat agtaagtgac ccatcacagc agttgccctc accaaacgtc      840
```

-continued

```
aacaacttcc tcaatccagc tccccaggag aaccccctca aacagcttct cgcagaagag      900
caatgggagt ttgaggtgac tgctttctat agaggtaggc aggtgttcca acaaactctg      960
ttttgccccg gaggtctgcg ccttgtaggt agcaccgcag acatgacact tccctggcaa     1020
cctgtgacac ttcccgatcc tgagggattt ctcacagata aactcgttaa ggaatatgtg     1080
gggcaagtac tcaaaggtct gggcaatggg ttggcccttt ggcaagctgg tcaatgtctc     1140
tgggctcaac gactcgggca ctcacatgct ttttgggctc ttggcgagga gctgctcccc     1200
gacagcgggc gcggacctga cggggaggtt cataaggaca aagacggcgc cgtatttgat     1260
cttagaccct tcgtggcaga tctgatcgct ttcatggaag gatcaggtca tagccccagg     1320
tacacacttt ggttttgcat gggtgaaatg tggcctcagg accaaccttg ggtcaagcgc     1380
ttggtcatgg ttaaggtggt tcccacttgc ctcaaagagt tgttggagat ggctagggaa     1440
ggtggggctt cctcactgaa aaccgtagat ctccacattg ataatgatca gcctatagat     1500
ttggacgacg accaatacaa agcttatctc caggacctgg ttgaagatat ggactttcag     1560
gctacaggta acatctaa                                                  1578

<210> SEQ ID NO 38
<211> LENGTH: 1275
<212> TYPE: DNA
<213> ORGANISM: Mus musculus

<400> SEQUENCE: 38
atgtgtgaca ggaacggcgg tagaagactg agacagtggc tgatcgagca aattgacagc       60
tcaatgtacc ctgggttgat atgggaaaac gatgaaaaga caatgttcag aataccctgg      120
aagcacgctg gaaagcagga ttacaaccag gaagtggacg ccagtatttt taaggcttgg      180
gctgtcttca aagggaagtt taaagagggc gacaaagcag agccagcaac ctggaaaacc      240
cgcttgaggt gtgcactcaa taagtcaccc gacttcgagg aagtcactga ccgcagtcaa      300
ttggacatat cagaaccata caaagtctac aggatagtcc ccgaagaaga gcagaaatgc      360
aaactcggtg tagcacctgc tggctgtatg agtgaagtgc ctgaaatgga atgcggcaga      420
tcagaaatcg aagaactcat aaaagaacca agtgtagatg agtatatggg aatgaccaaa      480
agatccccat cccccccaga agcctgtcgg agccaaatct tgcctgactg gtgggtacag      540
caaccctccg ccggacttcc ccttgtgaca ggctatgccg cttacgatac tcatcacagc      600
gcttttagcc agatggttat ttccttctat tatggaggaa aactggtcgg ccaagccaca      660
accacctgcc tcgaggggtg tcgcttgagt ttgagtcaac ccggtcttcc caaactctat      720
ggccccgatg ggcttgaacc tgtctgcttt cccactgctg atactattcc ctcagagaga      780
caacgacaag tcacccgaaa attgtttggc cacctcgaga ggggagtact cttgcactct      840
aacaggaagg gtgtctttgt gaaacgcctc tgtcaaggta gggtattctg ttctggaaat      900
gcagttgttt gcaaaggcag gcctaacaaa ctggaacggg atgaagtcgt acaagtgttc      960
gataccaatc agtttattcg ggagttgcag cagttttacg ctacacaaag tcgcctccct     1020
gacagtcggg ttgtgttgtg cttcgggggag gagtttcccg cacctgtacc cctccgaagc     1080
aaactcatac tggtacaggt agaacaactt tatgccaggc aactggtgga agaggccggt     1140
aagtcctgtg gcgcaggatc cctgatgcca gccctggaag agccccagcc tgaccaagca     1200
tttaggatgt ttcccgacat ttgtacctca caccagaggc cttttttccg cgaaaaccag     1260
cagataaccg tgtaa                                                     1275
```

-continued

```
<210> SEQ ID NO 39
<211> LENGTH: 1275
<212> TYPE: DNA
<213> ORGANISM: Mus musculus

<400> SEQUENCE: 39
atgtgtgaca ggaacggcgg tagaagactg agacagtggc tgatcgagca aattgacagc        60
tcaatgtacc ctgggttgat atgggaaaac gatgaaaaga caatgttcag aataccctgg       120
aagcacgctg gaaagcagga ttacaaccag gaagtggacg ccagtatttt taaggcttgg       180
gctgtcttca aagggaagtt taaagagggc gacaaagcag agccagcaac ctggaaaacc       240
cgcttgaggt gtgcactcaa taagtcaccc gacttcgagg aagtcactga ccgcagtcaa       300
ttggacatat cagaaccata caaagtctac aggatagtcc ccgaagaaga gcagaaatgc       360
aaactcggtg tagcacctgc tggctgtatg agtgaagtgc ctgaaatgga atgcggcaga       420
tcagaaatcg aagaactcat aaaagaacca agtgtagatg agtatatggg aatgaccaaa       480
agatccccat cccccccaga agcctgtcgg agccaaatct tgcctgactg gtgggtacag       540
caaccctccg ccggacttcc ccttgtgaca ggctatgccg cttacgatac tcatcacagc       600
gcttttagcc agatggttat ttccttctat tatggaggaa aactggtcgg ccaagccaca       660
accacctgcc tcgaggggtg tcgcttgagt ttgagtcaac ccggtcttcc caaactctat       720
ggccccgatg ggcttgaacc tgtctgcttt cccactgctg atactattcc ctcagagaga       780
caacgacaag tcacccgaaa attgtttggc cacctcgaga ggggagtact cttgcactct       840
aacaggaagg gtgtctttgt gaaacgcctc tgtcaaggta gggtattctg ttctggaaat       900
gcagttgttt gcaaaggcag gcctaacaga ctggaacggg atgaagtcgt acaagtgttc       960
gataccaatc agtttattcg ggagttgcag cagtttttacg ctacacaaag tcgcctccct      1020
gacagtcggg ttgtgttgtg cttcggggag gagtttcccg cacactgtacc cctccgaagc      1080 aaactcatac tggtacaggt agaacaactt tatgccaggc aactggtgga agaggccggt      1140
aagtcctgtg gcgcaggatc cctgatgcca gccctggaag agccccagcc tgaccaagca      1200
tttaggatgt ttcccgacat ttgtacctca caccagaggc cttttttccg cgaaaaccag      1260
cagataaccg tgtaa                                                       1275

<210> SEQ ID NO 40
<211> LENGTH: 2271
<212> TYPE: DNA
<213> ORGANISM: Homo sapiens

<400> SEQUENCE: 40
atgagctggt caccttccct gacaacgcag acatgtgggg cctgggaaat gaaagagcgc        60
cttgggacag ggggatttgg aaatgtcatc cgatggcaca tcaggaaac aggtgagcag       120 attgccatca gcagtgccg gcaggagctc agccccgga accgagagcg gtggtgcctg        180
gagatccaga tcatgagaag gctgacccac cccaatgtgg tggctgcccg agatgtccct       240
gaggggatgc agaacttggc gcccaatgac ctgcccctgc tggccatgga gtactgccaa       300
ggaggagatc tccggaagta cctgaaccag tttgagaact gctgtggtct gcgggaaggt       360
gccatcctca ccttgctgag tgacattgcc tctgcgctta gataccttca tgaaaacaga       420
atcatccatc gggatctaaa gccagaaaac atcgtcctgc agcaaggaga acagaggtta       480
atacacaaaa ttattgacct aggatatgcc aaggagctgg atcagggcag tctttgcaca       540
tcattcgtgg ggacccctgca gtacctggcc ccagagctac tggagcagca gaagtacaca       600
```

-continued

```
gtgaccgtcg actactggag cttcggcacc ctggcctttg agtgcatcac gggcttccgg      660
cccttcctcc ccaactggca gcccgtgcag tggcattcaa aagtgcggca gaagagtgag      720
gtggacattg ttgttagcga agacttgaat ggaacggtga agttttcaag ctctttaccc      780
taccccaata atcttaacag tgtcctggct gagcgactgg agaagtggct gcaactgatg      840
ctgatgtggc accccgaca gaggggcacg gatcccacgt atgggcccaa tggctgcttc      900
aaggccctgg atgacatctt aaacttaaag ctggttcata tcttgaacat ggtcacgggc      960
accatccaca cctaccctgt gacagaggat gagagtctgc agagcttgaa ggccagaatc     1020
caacaggaca cgggcatccc agaggaggac caggagctgc tgcaggaagc gggcctggcg     1080
ttgatccccg ataagcctgc cactcagtgt atttcagacg gcaagttaaa tgagggccac     1140
acattggaca tggatcttgt ttttctcttt gacaacagta aaatcaccta tgagactcag     1200
atctccccac ggccccaacc tgaaagtgtc agctgtatcc ttcaagagcc caagaggaat     1260
ctcgccttct tccagctgag gaaggtgtgg ggccaggtct ggcacagcat ccagaccctg     1320
aaggaagatt gcaaccggct gcagcaggga cagcgagccg ccatgatgaa tctcctccga     1380
aacaacagct gcctctccaa aatgaagaat tccatggctt ccatgtctca gcagctcaag     1440
gccaagttgg atttcttcaa aaccagcatc cagattgacc tggagaagta cagcgagcaa     1500
accgagtttg ggatcacatc agataaactg ctgctggcct ggagggaaat gggagcaggct     1560 gtggagctct gtgggcggga aacgaagtg aaactcctgg tagaacggat gatggctctg     1620
cagaccgaca ttgtggactt acagaggagc cccatgggcc ggaagcaggg gggaacgctg     1680
gacgacctag aggagcaagc aagggagctg tacaggagac taagggaaaa acctcgagac     1740
cagcgaactg agggtgacag tcaggaaatg gtacggctgc tgcttcaggc aattcagagc     1800
ttcgagaaga aagtgcgagt gatctatacg cagctcagta aaactgtggt ttgcaagcag     1860
aaggcgctgg aactgttgcc caaggtggaa gaggtggtga gcttaatgaa tgaggatgag     1920
aagactgttg tccggctgca ggagaagcgg cagaaggagc tctggaatct cctgaagatt     1980
gcttgtagca aggtccgtgg tcctgtcagt ggaagcccgg atagcatgaa tgcctctcga     2040
cttagccagc ctgggcagct gatgtctcag ccctccacgg cctccaacag cttacctgag     2100
ccagccaaga gagtgaaga actggtggct gaagcacata acctctgcac cctgctagaa     2160
aatgccatac aggacactgt gagggaacaa gaccagagtt tcacggccct agactggagc     2220
tggttacaga cggaagaaga agagcacagc tgcctggagc aggcctcatg a              2271
```

```
<210> SEQ ID NO 41
<211> LENGTH: 2265
<212> TYPE: DNA
<213> ORGANISM: Homo sapiens

<400> SEQUENCE: 41
```

```
atgtttttcag gggggtgtca tagccccggg tttggccgcc ccagccccgc cttccccgcc       60
ccggggagcc cgcccctgc cccgcgtccc tgccgacagg aaacaggtga gcagattgcc      120
atcaagcagt gccggcagga gctcagcccc cggaaccgag agcggtggtg cctggagatc      180
cagatcatga gaaggctgac ccaccccaat gtggtggctg cccgagatgt ccctgagggg      240
atgcagaact ggcgcccaa tgacctgccc ctgctggcca tggagtactg ccaaggagga      300
gatctccgga gtacctgaa ccagtttgag aactgctgtg tctgcgggga aggtgccatc      360
ctcaccttgc tgagtgacat tgcctctgcg cttagatacc ttcatgaaaa cagaatcatc      420
```

-continued

```
catcgggatc taaagccaga aaacatcgtc ctgcagcaag gagaacagag gttaatacac        480
aaaattattg acctaggata tgccaaggag ctggatcagg gcagtctttg cacatcattc        540
gtggggaccc tgcagtacct ggccccagag ctactggagc agcagaagta cacagtgacc        600
gtcgactact ggagcttcgg caccctggcc tttgagtgca tcacgggctt ccggcccttc        660
ctccccaact ggcagcccgt gcagtggcat tcaaaagtgc ggcagaagag tgaggtggac        720
attgttgtta gcgaagactt gaatggaacg gtgaagtttt caagctcttt accctacccc        780
aataatctta acagtgtcct ggctgagcga ctggagaagt ggctgcaact gatgctgatg        840 tggcacccc gacagagggg cacggatccc acgtatgggc ccaatggctg cttcaaggcc        900
ctggatgaca tcttaaactt aaagctggtt catatcttga acatggtcac gggcaccatc        960
cacacctacc ctgtgacaga ggatgagagt ctgcagagct tgaaggccag aatccaacag       1020
gacacgggca tcccagagga ggaccaggag ctgctgcagg aagcgggcct ggcgttgatc       1080
cccgataagc ctgccactca gtgtatttca gacggcaagt aaatgaggg ccacacattg       1140 gacatggatc ttgtttttct ctttgacaac agtaaaatca cctatgagac tcagatctcc       1200
ccacggcccc aacctgaaag tgtcagctgt atccttcaag agcccaagag gaatctcgcc       1260
ttcttccagc tgaggaaggt gtggggccag gtctggcaca gcatccagac cctgaaggaa       1320
gattgcaacc ggctgcagca gggacagcga gccgccatga tgaatctcct ccgaaacaac       1380
agctgcctct ccaaaatgaa gaattccatg gcttccatgt ctcagcagct caaggccaag       1440
ttggatttct tcaaaaccag catccagatt gacctggaga gtacagcga gcaaaccgag       1500 tttgggatca catcagataa actgctgctg gcctggaggg aaatggagca ggctgtggag       1560
ctctgtgggc gggagaacga agtgaaactc ctggtagaac ggatgatggc tctgcagacc       1620
gacattgtgg acttacagag gagccccatg ggccggaagc aggggggaac gctggacgac       1680
ctagaggagc aagcaaggga gctgtacagg agactaaggg aaaaacctcg agaccagcga       1740
actgagggtg acagtcagga aatggtacgg ctgctgcttc aggcaattca gagcttcgag       1800
aagaaagtgc gagtgatcta tacgcagctc agtaaaactg tggtttgcaa gcagaaggcg       1860
ctggaactgt tgcccaaggt ggaagaggtg gtgagcttaa tgaatgagga tgagaagact       1920
gttgtccggc tgcaggagaa gcggcagaag gagctctgga atctcctgaa gattgcttgt       1980
agcaaggtcc gtggtcctgt cagtggaagc ccggatagca tgaatgcctc tcgacttagc       2040
cagcctgggc agctgatgtc tcagccctcc acggcctcca acagcttacc tgagccagcc       2100
aagaagagtg aagaactggt ggctgaagca cataacctct gcaccctgct agaaaatgcc       2160
atacaggaca ctgtgaggga acaagaccag agtttcacgg ccctagactg gagctggtta       2220
cagacggaag aagaagagca cagctgcctg gagcaggcct catga                      2265
```

<210> SEQ ID NO 42
<211> LENGTH: 771
<212> TYPE: DNA
<213> ORGANISM: Homo sapiens

<400> SEQUENCE: 42

```
atgagctggt caccttccct gacaacgcag acatgtgggg cctgggaaat gaaagagcgc         60
cttgggacag ggggatttgg aaatgtcatc cgatggcaca tcaggaaac aggtgagcag        120 attgccatca agcagtgccg gcaggagctc agcccccgga accgagagcg gtggtgcctg        180
gagatccaga tcatgagaag gctgacccac cccaatgtgg tggctgcccg agatgtccct        240
gaggggatgc agaacttggc gcccaatgac ctgccctgc tggccatgga gtactgccaa        300
```

-continued

```
ggaggagatc tccggaagta cctgaaccag tttgagaact gctgtggtct gcgggaaggt      360
gccatcctca ccttgctgag tgacattgcc tctgcgctta gataccttca tgaaaacaga      420
atcatccatc gggatctaaa gccagaaaac atcgtcctgc agcaaggaga acagaggtta      480
atacacaaaa ttattgacct aggatatgcc aaggagctgg atcagggcag tctttgcaca      540
tcattcgtgg ggaccctgca gtacctggcc ccagagctac tggagcagca gaagtacaca      600
gtgaccgtcg actactggag cttcggcacc ctggcctttg agtgcatcac gggcttccgg      660
cccttcctcc ccaactggca gcccgtgcag tgcgtaagaa tgtggccggg tacagtggct      720
cactcctgta tcccagcac tttgggaggc cgaggcaggt ggatcagttg a                771
```

<210> SEQ ID NO 43
<211> LENGTH: 2094
<212> TYPE: DNA
<213> ORGANISM: Homo sapiens

<400> SEQUENCE: 43

```
atgtcatccg atggcacaat caggctgacc caccccaatg tggtggctgc ccgagatgtc       60
cctgagggga tgcagaactt ggcgcccaat gacctgcccc tgctggccat ggagtactgc      120
caaggaggag atctccggaa gtacctgaac cagtttgaga actgctgtgg tctgcgggaa      180
ggtgccatcc tcaccttgct gagtgacatt gcctctgcgc ttagatacct tcatgaaaac      240
agaatcatcc atcgggatct aaagccagaa aacatcgtcc tgcagcaagg agaacagagg      300
ttaatacaca aaattattga cctaggatat gccaaggagc tggatcaggg cagtctttgc      360
acatcattcg tggggaccct gcagtacctg gccccagagc tactggagca gcagaagtac      420
acagtgaccg tcgactactg gagcttcggc accctggcct ttgagtgcat cacgggcttc      480
cggcccttcc tccccaactg gcagcccgtg cagtggcatt caaaagtgcg gcagaagagt      540
gaggtggaca ttgttgttag cgaagacttg aatggaacgg tgaagttttc aagctcttta      600
ccctacccca ataatcttaa cagtgtcctg gctgagcgac tggagaagtg gctgcaactg      660
atgctgatgt ggcaccccg acagaggggc acggatccca cgtatgggcc caatggctgc      720
ttcaaggccc tggatgacat cttaaactta aagctggttc atatcttgaa catggtcacg      780
ggcaccatcc acacctaccc tgtgacagag gatgagagtc tgcagagctt gaaggccaga      840
atccaacagg acacgggcat cccagaggag gaccaggagc tgctgcagga gcgggcctg       900 gcgttgatcc ccgataagcc tgccactcag tgtatttcag acggcaagtt aaatgagggc      960
cacacattgg acatggatct tgttttctc tttgacaaca gtaaaatcac ctatgagact     1020
cagatctccc cacggcccca acctgaaagt gtcagctgta tccttcaaga gcccaagagg     1080
aatctcgcct tcttccagct gaggaaggtg tggggccagg tctggcacag catccagacc     1140
ctgaaggaag attgcaaccg gctgcagcag ggacagcgag ccgccatgat gaatctcctc     1200
cgaaacaaca gctgcctctc caaaatgaag aattccatgg cttccatgtc tcagcagctc     1260
aaggccaagt ggattttctt caaaaccagc atccagattg acctggagaa gtacagcgag     1320
caaaccgagt ttgggatcac atcagataaa ctgctgctgg cctggaggga aatggagcag     1380
gctgtggagc tctgtgggcg ggagaacgaa gtgaaactcc tggtagaacg gatgatggct     1440
ctgcagaccg acattgtgga cttacagagg agccccatgg gccggaagca ggggggaacg     1500
ctggacgacc tagaggagca agcaagggag ctgtacagga gactaaggga aaaacctcga     1560
gaccagcgaa ctgagggtga cagtcaggaa atggtacggc tgctgcttca ggcaattcag     1620
```

-continued

```
agcttcgaga agaaagtgcg agtgatctat acgcagctca gtaaaactgt ggtttgcaag    1680
cagaaggcgc tggaactgtt gcccaaggtg aagaggtgg tgagcttaat gaatgaggat    1740
gagaagactg ttgtccggct gcaggagaag cggcagaagg agctctggaa tctcctgaag    1800
attgcttgta gcaaggtccg tggtcctgtc agtggaagcc cggatagcat gaatgcctct    1860
cgacttagcc agcctgggca gctgatgtct cagccctcca cggcctccaa cagcttacct    1920
gagccagcca agaagagtga agaactggtg gctgaagcac ataacctctg caccctgcta    1980
gaaaatgcca tacaggacac tgtgagggaa caagaccaga gtttcacggc cctagactgg    2040
agctggttac agacggaaga agaagagcac agctgcctgg agcaggcctc atga          2094

<210> SEQ ID NO 44
<211> LENGTH: 2220
<212> TYPE: DNA
<213> ORGANISM: Mus musculus

<400> SEQUENCE: 44
atgagctggt caccgtccct cccaacccag acatgtggag cctgggaaat gaaagaacgc      60
ctggggaccg ggggatttgg aaacgtcatc cggtggcaca tcaggcgac aggtgaacag     120 atcgccatca agcaatgccg acaggagctc agcccaaaga acagagaccg ctggtgcctc     180
gaaatccaga tcatgagaag gctgaaccat cccaatgtgg tggctgcccg ggatgtccca     240
gaggggatgc agaacctggc acccaatgat ttgccactgc tggccatgga gtactgccaa     300
ggaggagatc tccgaagata cttgaaccag ttcgagaact gctgtggcct gcgggaagga     360
gctgtcctta ccctgctgag tgacatcgca tcggctctta gataccttca cgaaaacaga     420
atcatccatc gagacctgaa gccagaaaac atcgttctgc agcaaggaga gaaaagatta     480
atacacaaaa ttattgatct aggatatgcc aaggagctgg atcagggcag tctgtgcacg     540
tcatttgtgg ggactctgca atacctggcg ccagagcttc tggagcagca gaagtacacc     600
gtgaccgttg actactggag cttcggcacc ctggccttcg agtgcatcac tggcttccgg     660
cccttcctcc ctaactggca gcctgtgcag tggcactcca agtccggca gaagagcgaa     720 gtggacatcg ttgttagtga agacttgaat ggagcagtga agttttcaag ttcgctaccc     780
ttccccaata atcttaacag tgtcttggct gaacggctgg agaagtggct gcagctgatg     840
cttatgtggc accctcggca aaggggcacg gatccccagt atggccccaa cggctgcttc     900
agagccctgg atgacatctt gaacttgaag ctggttcatg tcttgaacat ggtcacaggc     960
accgttcaca catacccccgt gacggaggat gagagtctgc agagcttaaa aaccagaatc    1020
caggaagaca cggggatcct ggagacagac caggagctgc tgcaagaggc agggctggtg    1080
ctgctccctg acaagcctgc tactcagtgc atctcagaca gcaagacaaa cgagggcctc    1140
acgttggaca tggatcttgt ttttctcttt gacaacagta aaatcaacta tgagactcag    1200 atcaccccc gacccccaacc ggaaagtgtc agctgtatcc ttcaggagcc caagcggaac    1260
ctctccttct tccagctgag gaaagtgtgg ggccaagtct ggcacagcat ccagacgctg    1320
aaggaagact gtaaccggct gcagcaggga cagcgagcag ccatgatgag tctcctccgg    1380
aataacagct gcctctctaa gatgaagaac gccatggcct ccacggccca gcagctcaag    1440
gccaagctgg acttcttcaa aaccagcatc cagatcgacc tggagaagta taaagagcag    1500
accgagtttg ggatcacctc agataaattg ctgctggctt ggcgggagat ggagcaggct    1560
gtggagcagt gtgggcggga gaatgacgtg aagcatctag tagagcggat gatggcactg    1620
cagactgaca ttgtggacct gcagaggagc ccgatgggtc ggaagcaggg gggcaccctg    1680
```

-continued

```
gatgacctag aggaacaagc gagggagctc taccgaagac tcagggagaa gccaagagac    1740
caaaggacag aaggtgacag ccaggagatg gtacggctgc tgcttcaggc aatccaaagc    1800
tttgagaaga aagttcgggt gatttataca cagctcagta agaccgtggt ttgtaagcag    1860
aaggcactgg agttgctgcc caaggtagaa gaggtagtga gccttatgaa cgaggacgag    1920
aggaccgtgg tccggcttca ggagaagcgg cagaaggaac tctggaacct cctgaagatc    1980
gcctgtagca aagtccgagg tcccgtgagt ggaagcccag acagcatgaa tgtgtctcga    2040
ctcagtcacc ctggtcagct aatgtcccag ccttccagtg cctgtgacag cttacctgaa    2100
tcagacaaga aaagtgaaga actggtggcc gaagcccacg ccctctgctc ccggctagaa    2160
agtgcgctgc aggacactgt gaaggagcaa gacagaagct tcacggtaac cgcctgataa    2220
```

<210> SEQ ID NO 45
<211> LENGTH: 11
<212> TYPE: PRT
<213> ORGANISM: Artificial Sequence
<220> FEATURE:
<223> OTHER INFORMATION: CDRH1 that binds CD206

<400> SEQUENCE: 45

Ser Gly Asn Ile Phe Ser Ile Asn Ala Ile Gly
1               5                   10

<210> SEQ ID NO 46
<211> LENGTH: 9
<212> TYPE: PRT
<213> ORGANISM: Artificial Sequence
<220> FEATURE:
<223> OTHER INFORMATION: CDRH2 that binds CD206

<400> SEQUENCE: 46

Thr Ile Thr Leu Ser Gly Ser Thr Asn
1               5

<210> SEQ ID NO 47
<211> LENGTH: 11
<212> TYPE: PRT
<213> ORGANISM: Artificial Sequence
<220> FEATURE:
<223> OTHER INFORMATION: CDRH3 that binds CD206

<400> SEQUENCE: 47

Asn Thr Tyr Ser Asp Ser Asp Val Tyr Gly Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: CDRH1 that binds CD206

<400> SEQUENCE: 48

Pro Gly Phe Lys Leu Asp Tyr Tyr Ala Ile Ala
1               5                   10

<210> SEQ ID NO 49
<211> LENGTH: 9
<212> TYPE: PRT
<213> ORGANISM: Artificial Sequence
<220> FEATURE:
<223> OTHER INFORMATION: CDRH2 that binds CD206

<400> SEQUENCE: 49

Ser Ile Asn Ser Ser Gly Gly Ser Thr
1               5

<210> SEQ ID NO 50
<211> LENGTH: 16
<212> TYPE: PRT
<213> ORGANISM: Artificial Sequence
<220> FEATURE:
<223> OTHER INFORMATION: CDRH3 that binds CD206

<400> SEQUENCE: 50

Leu Arg Arg Tyr Tyr Gly Leu Asn Leu Asp Pro Gly Ser Tyr Asp Tyr
1               5                   10                  15

<210> SEQ ID NO 51
<211> LENGTH: 10
<212> TYPE: PRT
<213> ORGANISM: Artificial Sequence
<220> FEATURE:
<223> OTHER INFORMATION: CDRH1 that binds CD206

<400> SEQUENCE: 51

Gly Phe Pro Phe Asn Ile Tyr Pro Met Ser
1               5                   10

<210> SEQ ID NO 52
<211> LENGTH: 9
<212> TYPE: PRT
<213> ORGANISM: Artificial Sequence
<220> FEATURE:
<223> OTHER INFORMATION: CDRH2 that binds CD206

<400> SEQUENCE: 52

Tyr Ile Ser His Gly Gly Thr Thr Thr
1               5

<210> SEQ ID NO 53
<211> LENGTH: 12
<212> TYPE: PRT
<213> ORGANISM: Artificial Sequence
<220> FEATURE:
<223> OTHER INFORMATION: CDRH3 that binds CD206

<400> SEQUENCE: 53

Gly Tyr Ala Arg Leu Met Thr Asp Ser Glu Leu Val
1               5                   10

<210> SEQ ID NO 54
<211> LENGTH: 9
<212> TYPE: PRT
<213> ORGANISM: Artificial Sequence
<220> FEATURE:
<223> OTHER INFORMATION: CDRL1 that binds CD163

<400> SEQUENCE: 54

Ala Ser Gln Ser Val Ser His Asp Val
1               5

<210> SEQ ID NO 55

<400> SEQUENCE: 55

000

<210> SEQ ID NO 56

```
<211> LENGTH: 8
<212> TYPE: PRT
<213> ORGANISM: Artificial Sequence
<220> FEATURE:
<223> OTHER INFORMATION: CDRL3 that binds CD163

<400> SEQUENCE: 56

Gln Asp Tyr Ser Ser Pro Arg Thr
1               5

<210> SEQ ID NO 57
<211> LENGTH: 8
<212> TYPE: PRT
<213> ORGANISM: Artificial Sequence
<220> FEATURE:
<223> OTHER INFORMATION: CDRH1 that binds CD163

<400> SEQUENCE: 57

Gly Tyr Ser Ile Thr Ser Asp Tyr
1               5

<210> SEQ ID NO 58

<400> SEQUENCE: 58

000

<210> SEQ ID NO 59
<211> LENGTH: 12
<212> TYPE: PRT
<213> ORGANISM: Artificial Sequence
<220> FEATURE:
<223> OTHER INFORMATION: CDRH3 that binds CD163

<400> SEQUENCE: 59

Cys Val Ser Gly Thr Tyr Tyr Phe Asp Tyr Trp Gly
1               5                   10

<210> SEQ ID NO 60
<211> LENGTH: 9
<212> TYPE: PRT
<213> ORGANISM: Artificial Sequence
<220> FEATURE:
<223> OTHER INFORMATION: CDRL1 that binds CD163

<400> SEQUENCE: 60

Ala Ser Gln Ser Val Ser Ser Asp Val
1               5

<210> SEQ ID NO 61

<400> SEQUENCE: 61

000

<210> SEQ ID NO 62
<211> LENGTH: 8
<212> TYPE: PRT
<213> ORGANISM: Artificial Sequence
<220> FEATURE:
<223> OTHER INFORMATION: CDRL3 that binds CD163

<400> SEQUENCE: 62

Gln Asp Tyr Thr Ser Pro Arg Thr
1               5

<210> SEQ ID NO 63
```

```
<211> LENGTH: 8
<212> TYPE: PRT
<213> ORGANISM: Artificial Sequence
<220> FEATURE:
<223> OTHER INFORMATION: CDRH1 that binds CD163

<400> SEQUENCE: 63

Gly Tyr Ser Ile Thr Ser Asp Tyr
1               5

<210> SEQ ID NO 64

<400> SEQUENCE: 64

000

<210> SEQ ID NO 65
<211> LENGTH: 12
<212> TYPE: PRT
<213> ORGANISM: Artificial Sequence
<220> FEATURE:
<223> OTHER INFORMATION: CDRH3 that binds CD163

<400> SEQUENCE: 65

Cys Val Ser Gly Thr Tyr Tyr Phe Asp Tyr Trp Gly
1               5                   10

<210> SEQ ID NO 66
<211> LENGTH: 16
<212> TYPE: PRT
<213> ORGANISM: Artificial Sequence
<220> FEATURE:
<223> OTHER INFORMATION: CDRL1 that bind CD23

<400> SEQUENCE: 66

Arg Ser Ser Lys Ser Leu Leu Tyr Lys Asp Gly Lys Thr Tyr Leu Asn
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: CDRL2 that bind CD23

<400> SEQUENCE: 67

Leu Met Ser Thr Arg Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: CDRL3 that bind CD23

<400> SEQUENCE: 68

Gln Gln Leu Val Glu Tyr Pro Phe Thr
1               5

<210> SEQ ID NO 69
<211> LENGTH: 5
<212> TYPE: PRT
<213> ORGANISM: Artificial Sequence
<220> FEATURE:
<223> OTHER INFORMATION: CDRH1 that bind CD23

<400> SEQUENCE: 69
```

```
Gly Tyr Trp Met Ser
1               5

<210> SEQ ID NO 70
<211> LENGTH: 19
<212> TYPE: PRT
<213> ORGANISM: Artificial Sequence
<220> FEATURE:
<223> OTHER INFORMATION: CDRH2 that bind CD23

<400> SEQUENCE: 70

Glu Ile Arg Leu Lys Ser Asp Asn Tyr Ala Thr His Tyr Ala Glu Ser
1               5                   10                  15

Val Lys Gly

<210> SEQ ID NO 71

<400> SEQUENCE: 71

000

<210> SEQ ID NO 72
<211> LENGTH: 8
<212> TYPE: PRT
<213> ORGANISM: Artificial Sequence
<220> FEATURE:
<223> OTHER INFORMATION: CDRL1 that bind CD38

<400> SEQUENCE: 72

Ser Ser Asn Ile Gly Asp Asn Tyr
1               5

<210> SEQ ID NO 73

<400> SEQUENCE: 73

000

<210> SEQ ID NO 74
<211> LENGTH: 10
<212> TYPE: PRT
<213> ORGANISM: Artificial Sequence
<220> FEATURE:
<223> OTHER INFORMATION: CDRL3 that bind CD38

<400> SEQUENCE: 74

Gln Ser Tyr Asp Ser Ser Leu Ser Gly Ser
1               5                   10

<210> SEQ ID NO 75
<211> LENGTH: 8
<212> TYPE: PRT
<213> ORGANISM: Artificial Sequence
<220> FEATURE:
<223> OTHER INFORMATION: CDRH1 that bind CD38

<400> SEQUENCE: 75

Gly Phe Thr Phe Asp Asp Tyr Gly
1               5

<210> SEQ ID NO 76
<211> LENGTH: 8
<212> TYPE: PRT
<213> ORGANISM: Artificial Sequence
<220> FEATURE:
<223> OTHER INFORMATION: CDRH2 that binds CD38
```

-continued

```
<400> SEQUENCE: 76

Ile Ser Trp Asn Gly Gly Lys Thr
1               5

<210> SEQ ID NO 77
<211> LENGTH: 16
<212> TYPE: PRT
<213> ORGANISM: Artificial Sequence
<220> FEATURE:
<223> OTHER INFORMATION: CDRH3 that binds CD38

<400> SEQUENCE: 77

Ala Arg Gly Ser Leu Phe His Asp Ser Ser Gly Phe Tyr Phe Gly His
1               5                   10                  15

<210> SEQ ID NO 78
<211> LENGTH: 8
<212> TYPE: PRT
<213> ORGANISM: Artificial Sequence
<220> FEATURE:
<223> OTHER INFORMATION: CDRL1 that binds CD38

<400> SEQUENCE: 78

Asn Ser Asn Ile Gly Ser Asn Thr
1               5

<210> SEQ ID NO 79

<400> SEQUENCE: 79

000

<210> SEQ ID NO 80
<211> LENGTH: 11
<212> TYPE: PRT
<213> ORGANISM: Artificial Sequence
<220> FEATURE:
<223> OTHER INFORMATION: CDRL3 that binds CD38

<400> SEQUENCE: 80

Gln Ser Tyr Asp Ser Ser Leu Ser Gly Ser Arg
1               5                   10

<210> SEQ ID NO 81
<211> LENGTH: 8
<212> TYPE: PRT
<213> ORGANISM: Artificial Sequence
<220> FEATURE:
<223> OTHER INFORMATION: CDRH1 that binds CD38

<400> SEQUENCE: 81

Gly Phe Thr Phe Asn Asn Tyr Gly
1               5

<210> SEQ ID NO 82
<211> LENGTH: 8
<212> TYPE: PRT
<213> ORGANISM: Artificial Sequence
<220> FEATURE:
<223> OTHER INFORMATION: CDRH2 that binds CD38

<400> SEQUENCE: 82

Ile Ser Tyr Asp Gly Ser Asp Lys
1               5
```

-continued

```
<210> SEQ ID NO 83
<211> LENGTH: 15
<212> TYPE: PRT
<213> ORGANISM: Artificial Sequence
<220> FEATURE:
<223> OTHER INFORMATION: CDRH3 that binds CD38

<400> SEQUENCE: 83

Ala Arg Val Tyr Tyr Tyr Gly Phe Ser Gly Pro Ser Met Asp Val
1               5                   10                  15

<210> SEQ ID NO 84
<211> LENGTH: 11
<212> TYPE: PRT
<213> ORGANISM: Artificial Sequence
<220> FEATURE:
<223> OTHER INFORMATION: CDRL1 that binds CD38

<400> SEQUENCE: 84

Arg Ala Ser Gln Ser Val Ser Ser Tyr Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: CDRL2 that binds CD38

<400> SEQUENCE: 85

Asp Ala Ser Asn Arg Ala Thr
1               5

<210> SEQ ID NO 86
<211> LENGTH: 10
<212> TYPE: PRT
<213> ORGANISM: Artificial Sequence
<220> FEATURE:
<223> OTHER INFORMATION: CDRL3 that binds CD38

<400> SEQUENCE: 86

Gln Gln Arg Ser Asn Trp Pro Pro Thr Phe
1               5                   10

<210> SEQ ID NO 87
<211> LENGTH: 5
<212> TYPE: PRT
<213> ORGANISM: Artificial Sequence
<220> FEATURE:
<223> OTHER INFORMATION: CDRH1 that binds CD38

<400> SEQUENCE: 87

Ser Phe Ala Met Ser
1               5

<210> SEQ ID NO 88
<211> LENGTH: 17
<212> TYPE: PRT
<213> ORGANISM: Artificial Sequence
<220> FEATURE:
<223> OTHER INFORMATION: CDRH2 that binds CD38

<400> SEQUENCE: 88

Ala Ile Ser Gly Ser Gly Gly Thr Tyr Tyr Ala Asp Ser Val Lys
1               5                   10                  15

Gly
```

<210> SEQ ID NO 89
<211> LENGTH: 13
<212> TYPE: PRT
<213> ORGANISM: Artificial Sequence
<220> FEATURE:
<223> OTHER INFORMATION: CDRH3 that binds CD38

<400> SEQUENCE: 89

Asp Lys Ile Leu Trp Phe Gly Glu Pro Val Phe Asp Tyr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: CDRL1 that binds CD64

<400> SEQUENCE: 90

Arg Ala Ser Gln Ser Val Ser Ser Tyr Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: CDRL2 that binds CD64

<400> SEQUENCE: 91

Asp Ala Ser Ser Arg Ala Thr
1               5

<210> SEQ ID NO 92
<211> LENGTH: 10
<212> TYPE: PRT
<213> ORGANISM: Artificial Sequence
<220> FEATURE:
<223> OTHER INFORMATION: CDRL3 that binds CD64

<400> SEQUENCE: 92

Gln Leu Arg Ser Asn Trp Pro Pro Tyr Thr
1               5                   10

<210> SEQ ID NO 93
<211> LENGTH: 5
<212> TYPE: PRT
<213> ORGANISM: Artificial Sequence
<220> FEATURE:
<223> OTHER INFORMATION: CDRH1 that binds CD64

<400> SEQUENCE: 93

Gly Tyr Gly Met His
1               5

<210> SEQ ID NO 94
<211> LENGTH: 17
<212> TYPE: PRT
<213> ORGANISM: Artificial Sequence
<220> FEATURE:
<223> OTHER INFORMATION: CDRH2 that binds CD64

<400> SEQUENCE: 94

Val Ile Trp Tyr Asp Gly Ser Asn Lys Tyr Tyr Ala Asp Ser Val Lys
1               5                   10                  15

Gly

-continued

<210> SEQ ID NO 95
<211> LENGTH: 9
<212> TYPE: PRT
<213> ORGANISM: Artificial Sequence
<220> FEATURE:
<223> OTHER INFORMATION: CDRH3 that binds CD64

<400> SEQUENCE: 95

Asp Thr Gly Asp Arg Phe Phe Asp Tyr
1               5

<210> SEQ ID NO 96
<211> LENGTH: 20
<212> TYPE: DNA
<213> ORGANISM: Artificial Sequence
<220> FEATURE:
<223> OTHER INFORMATION: Fw primer SerpinB2

<400> SEQUENCE: 96
actggggcag ttatgacagg                                              20

<210> SEQ ID NO 97
<211> LENGTH: 19
<212> TYPE: DNA
<213> ORGANISM: Artificial Sequence
<220> FEATURE:
<223> OTHER INFORMATION: Rv primer SerpinB2

<400> SEQUENCE: 97
gatgatcggc cacaaactg                                               19

<210> SEQ ID NO 98
<211> LENGTH: 21
<212> TYPE: DNA
<213> ORGANISM: Artificial Sequence
<220> FEATURE:
<223> OTHER INFORMATION: Fw primer Retnla

<400> SEQUENCE: 98
ttgttccctt ctcatctgca t                                           21

<210> SEQ ID NO 99
<211> LENGTH: 21
<212> TYPE: DNA
<213> ORGANISM: Artificial Sequence
<220> FEATURE:
<223> OTHER INFORMATION: Rv primer Retnla

<400> SEQUENCE: 99
ccttgacctt attctccacg a                                            21

<210> SEQ ID NO 100
<211> LENGTH: 19
<212> TYPE: DNA
<213> ORGANISM: Artificial Sequence
<220> FEATURE:
<223> OTHER INFORMATION: Fw primer Ccl5

<400> SEQUENCE: 100
cctactccca ctcggtcct                                               19

<210> SEQ ID NO 101
<211> LENGTH: 21
<212> TYPE: DNA
<213> ORGANISM: Artificial Sequence
<220> FEATURE:
<223> OTHER INFORMATION: Rv primer Ccl5

<400> SEQUENCE: 101
ctgatttctt gggtttgctg t                                                21

<210> SEQ ID NO 102
<211> LENGTH: 18
<212> TYPE: DNA
<213> ORGANISM: Artificial Sequence
<220> FEATURE:
<223> OTHER INFORMATION: Fw primer Ccl11

<400> SEQUENCE: 102
agagctccac agcgcttc                                                    18

<210> SEQ ID NO 103
<211> LENGTH: 18
<212> TYPE: DNA
<213> ORGANISM: Artificial Sequence
<220> FEATURE:
<223> OTHER INFORMATION: Rv primer Cdl11

<400> SEQUENCE: 103
cagcacctgg gaggtgaa                                                    18

<210> SEQ ID NO 104
<211> LENGTH: 26
<212> TYPE: DNA
<213> ORGANISM: Artificial Sequence
<220> FEATURE:
<223> OTHER INFORMATION: Fw primer Codon optimized IRF5

<400> SEQUENCE: 104
tcttaaagac cacatggtag aacagt                                           26

<210> SEQ ID NO 105
<211> LENGTH: 18
<212> TYPE: DNA
<213> ORGANISM: Artificial Sequence
<220> FEATURE:
<223> OTHER INFORMATION: Rv primer codon optimized IRF5

<400> SEQUENCE: 105
agctgctgtt gggattgc                                                    18

<210> SEQ ID NO 106
<211> LENGTH: 20
<212> TYPE: DNA
<213> ORGANISM: Artificial Sequence
<220> FEATURE:
<223> OTHER INFORMATION: Fw primer endogenous IRF5

<400> SEQUENCE: 106
gctgtgccct taacaaaagc                                                  20

<210> SEQ ID NO 107
<211> LENGTH: 18
<212> TYPE: DNA
<213> ORGANISM: Artificial Sequence
<220> FEATURE:
<223> OTHER INFORMATION: RV primer endogenous IRF5

<400> SEQUENCE: 107
ggctgaggtg gcatgtct                                                    18

<210> SEQ ID NO 108
<211> LENGTH: 19
<212> TYPE: DNA
<213> ORGANISM: Artificial Sequence
<220> FEATURE:
<223> OTHER INFORMATION: Fw primer GAPD

<400> SEQUENCE: 108
agccacatcg ctcagacac                                                                     19

<210> SEQ ID NO 109
<211> LENGTH: 19
<212> TYPE: DNA
<213> ORGANISM: Artificial Sequence
<220> FEATURE:
<223> OTHER INFORMATION: Rv primer GAPD

<400> SEQUENCE: 109
gcccaatacg accaaatcc                                                                     19

<210> SEQ ID NO 110
<211> LENGTH: 134
<212> TYPE: PRT
<213> ORGANISM: Homo sapiens

<400> SEQUENCE: 110

Met Asn Thr Glu Met Tyr Gln Thr Pro Met Glu Val Ala Val Tyr Gln
1               5                   10                  15

Leu His Asn Phe Ser Ile Ser Phe Phe Ser Ser Leu Leu Gly Gly Asp
                20                  25                  30

Val Val Ser Val Lys Leu Asp Asn Ser Ala Ser Gly Ala Ser Val Val
        35                  40                  45

Ala Ile Asp Asn Lys Ile Glu Gln Ala Met Asp Leu Val Lys Asn His
    50                  55                  60

Leu Met Tyr Ala Val Arg Glu Glu Val Glu Ile Leu Lys Glu Gln Ile
65                  70                  75                  80

Arg Glu Leu Val Glu Lys Asn Ser Gln Leu Glu Arg Glu Asn Thr Leu
                85                  90                  95

Leu Lys Thr Leu Ala Ser Pro Glu Gln Leu Glu Lys Phe Gln Ser Cys
            100                 105                 110

Leu Ser Pro Glu Glu Pro Ala Pro Glu Ser Pro Gln Val Pro Glu Ala
        115                 120                 125

Pro Gly Gly Ser Ala Val
    130

<210> SEQ ID NO 111
<211> LENGTH: 405
<212> TYPE: DNA
<213> ORGANISM: Homo sapiens

<400> SEQUENCE: 111
atgaacaccg aaatgtatca gacccccatg gaggtggcgg tctaccagct gcacaatttc    60
tccatctcct tcttctcttc tctgcttgga ggggatgtgg tttccgttaa gctggacaac   120
agtgcctccg gagccagcgt ggtggccata gacaacaaga tcgaacaggc catggatctg   180
gtgaagaatc atctgatgta tgctgtgaga gaggaggtgg agatcctgaa ggagcagatc   240

-continued

```
cgagagctgg tggagaagaa ctcccagcta gagcgtgaga acaccctgtt gaagaccctg      300
gcaagcccag agcagctgga gaagttccag tcctgtctga gccctgaaga gccagctccc      360
gaatccccac aagtgcccga ggcccctggt ggttctgcgg tgtaa                      405
```